United States Patent
Ali et al.

(10) Patent No.: US 8,334,290 B2
(45) Date of Patent: Dec. 18, 2012

(54) CETP INHIBITORS

(75) Inventors: Amjad Ali, Freehold, NJ (US); Julianne A. Hunt, Scotch Plains, NJ (US); Florida Kallashi, Laurence Harbor, NJ (US); Jennifer Kowalchick, Clark, NJ (US); Dooseop Kim, Westfield, NJ (US); Cameron J. Smith, Lawrenceville, NJ (US); Peter J. Sinclair, Scotch Plains, NJ (US); Ramzi F. Sweis, Franklin Park, NJ (US); Gayle E. Taylor, Jersey City, NJ (US); Christopher F. Thompson, Clark, NJ (US); Liya Chen, East Brunswick, NJ (US); Nazia Quraishi, Vienna, VA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 161 days.

(21) Appl. No.: 12/083,324

(22) PCT Filed: Oct. 30, 2006

(86) PCT No.: PCT/US2006/042208
§ 371 (c)(1),
(2), (4) Date: Apr. 8, 2008

(87) PCT Pub. No.: WO2007/070173
PCT Pub. Date: Jun. 21, 2007

(65) Prior Publication Data
US 2009/0264405 A1    Oct. 22, 2009

Related U.S. Application Data

(60) Provisional application No. 60/732,168, filed on Oct. 31, 2005.

(51) Int. Cl.
| | |
|---|---|
| A61K 31/496 | (2006.01) |
| A61K 31/497 | (2006.01) |
| A61K 31/443 | (2006.01) |
| A61K 31/421 | (2006.01) |
| C07D 239/42 | (2006.01) |
| C07D 413/14 | (2006.01) |
| C07D 211/32 | (2006.01) |
| C07D 213/26 | (2006.01) |
| C07D 263/57 | (2006.01) |

(52) U.S. Cl. ........... 514/253.1; 514/254.02; 514/318; 514/321; 514/375; 544/332; 544/368; 546/194; 546/198; 548/224

(58) Field of Classification Search .......... None
See application file for complete search history.

(56) References Cited

U.S. PATENT DOCUMENTS

| | | | |
|---|---|---|---|
| 4,025,636 A | | 5/1977 | Dunwell et al. |
| 4,032,503 A | * | 6/1977 | Kormany et al. ........ 252/301.23 |
| 5,104,960 A | | 4/1992 | Inbasekaran et al. |
| 5,665,737 A | | 9/1997 | Cavalla et al. |
| 5,744,127 A | * | 4/1998 | Giuseppe et al. ............... 424/59 |
| 6,372,770 B1 | | 4/2002 | Chasin et al. |
| 2005/0124497 A1 | * | 6/2005 | Fusslein et al. ............... 504/246 |

FOREIGN PATENT DOCUMENTS

| | | |
|---|---|---|
| WO | WO 96/26932 | 9/1996 |
| WO | 99/11627 A1 | 3/1999 |
| WO | WO 01/14354 | 3/2001 |
| WO | 01/74771 A1 | 10/2001 |
| WO | 02/12190 A2 | 2/2002 |
| WO | WO 02/036580 | 5/2002 |
| WO | 02/072090 A1 | 9/2002 |
| WO | 02/074296 A1 | 9/2002 |
| WO | 03/017994 A1 | 3/2003 |
| WO | WO 03/020698 | 3/2003 |
| WO | 03/032984 A1 | 4/2003 |
| WO | 03/075921 A2 | 9/2003 |
| WO | 2004/016611 A1 | 2/2004 |
| WO | WO 2004/032716 | 4/2004 |
| WO | WO 2004/046122 | 6/2004 |
| WO | 2005/033065 A1 | 4/2005 |
| WO | 2005/044807 A2 | 5/2005 |
| WO | 2005/049576 A1 | 6/2005 |
| WO | WO2005/100298 A1 | 10/2005 |
| WO | WO 2007/039170 | * 4/2007 |

OTHER PUBLICATIONS

CAPlus Accession No. 1997:581002. Abstract of Boreskov et al. Bioorganicheskaya Khimiya (1995), 21(10), pp. 795-801.*
Supplementary European Search Report for PCT/US2006/042208 from Munich; Completed Mar. 25, 2010; Performed by Authorized Officer, José Cortés.
"Remington, The Science and Practice of Pharmacy," 21st Edition, Lippincott, Williams and Wilkins, Philadelphia, 2005, p. 1452.
Arienti, K. L. et al., "Checkpoint Kinase Inhibitors: SAR and Radioprotective Properties of a Series of 2- Arylbenzimidazoles", Journal of Medicinal Chemistry, 2005, vol. 48, No. 6, pp. 1873-1885.

* cited by examiner

*Primary Examiner* — Rebecca Anderson
*Assistant Examiner* — Alicia L Otton
(74) *Attorney, Agent, or Firm* — James L. McGinnis; Catherine D. Fitch

(57) ABSTRACT

Compounds of Formula I, including pharmaceutically acceptable salts of the compounds, are CETP inhibitors, and are useful for raising HDL-cholesterol, reducing LDL-cholesterol, and for treating or preventing atherosclerosis.

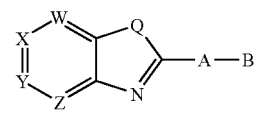

12 Claims, No Drawings

CETP INHIBITORS

CROSS REFERENCE TO RELATED APPLICATIONS

This application is a U.S. National Phase application under 35 U.S.C. §371 of PCT Application No. PCT/US2006/042208, filed Oct. 30, 2006, which claims priority under 35 U.S.C. §119(e) from U.S. Application No. 60/732,168, filed Oct. 31, 2005.

FIELD OF THE INVENTION

This invention relates to a class of chemical compounds that inhibit cholesterol ester transfer protein (CETP) and therefore may have utility in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoB lipoprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Conip. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies. No CETP inhibitors are currently being marketed. One CETP inhibitor, torcetrapib, is currently in clinical trials, and is being developed for use in combination with atorvastatin. It is not currently being developed as a drug for monotherapy. New compounds are needed so that additional pharmaceutical compounds can be found that are safe and effective, either alone or in combination with other drugs that are used for treatment of lipid disorders. The compounds described herein are very potent CETP inhibitors and may be suitable for use in monotherapy and/or combination therapy. Compounds that have structural similarities to some of the compounds disclosed herein are disclosed in the following documents: WO2004/032716, WO96/26932, WO02/036580, WO03/020698, WO01/14354, and WO2004/046122.

SUMMARY OF THE INVENTION

Compounds having Formula I, including pharmaceutically acceptable salts of the compounds, are CETP inhibitors, having the utilities described below:

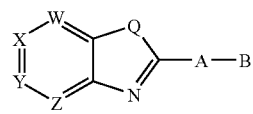

I

Three of the groups W, X, Y and Z represent =CH—, and the fourth of the groups W, X, Y, and Z represents =CH—, =N—, or =N(—O)—, wherein the H of each =CH— group optionally may be replaced with a substituent group $R^a$;

Q is selected from the group consisting of O, S, —CH=N—, and —(NR$^2$)—;

A is a difunctional cyclic group selected from 1,4-phenylene, 2,5-pyridinylene, 2,5-thienylene, 2,5-furylene, 2,5-pyrazinylene, 2,5-pyrimidinylene, and 1,4-bicyclo[2,2,2]octylene, wherein A is optionally substituted with 1-3 substituent groups $R^b$;

Each $R^a$ substituent is independently selected from the group consisting of halogen, —OH, —CN, —NO$_2$, —N(R$^9$)$_2$, C$_1$-C$_7$alkyl, OC$_1$-C$_7$alkyl, C$_2$-C$_7$alkenyl, C$_2$-C$_7$alkynyl, —C(=O)H, —C(=O)C$_1$-C$_5$alkyl, —N(R$^9$)C(=O)C$_1$-C$_5$alkyl, pyridinyl, N-oxidopyridinyl, phenyl, —OPhenyl, pyrimidinyl, C$_3$-C$_6$cycloalkyl, methyldioxolanyl, furyl, thienyl, oxazolyl, morpholinyl, isoxazolyl, —N(R$^9$)C(=O)OC$_1$-C$_5$alkyl, —C(=NH)NH$_2$, —C(=O)OC$_1$-C$_5$alkyl, —S(O)$_x$C$_1$-C$_7$alkyl, —CH$_2$S(O)$_x$C$_1$-C$_5$alkyl, —OC(=O)C$_1$-C$_5$alkyl, and —OCH$_2$C(=O)OCH$_2$-phenyl; wherein C$_1$-C$_7$alkyl, C$_1$-C$_5$alkyl, C$_2$-C$_7$alkenyl, and C$_2$-C$_7$ alkynyl in each occurrence is optionally substituted with 1-7 halogens and is optionally substituted with one substituent selected from the group consisting of —OH, —CN, —SH, —S(O)$_x$C$_1$-C$_3$alkyl, —N(R$^9$)$_2$, —OC$_1$-C$_3$alkyl, —OCF$_3$, —OC(=O)CH$_3$, phenyl, C$_3$-C$_6$cycloalkyl, —OC$_3$-C$_6$cycloalkyl, and —OCH$_2$-Phenyl; wherein when $R^a$ is phenyl or comprises a phenyl group, said phenyl group is optionally substituted with 1-3 substituents independently selected from halogen, C$_1$-C$_3$alkyl optionally substituted with 1-5 halogens, —OC$_1$-C$_5$alkyl optionally substituted with 1-5 halogens, —CN, and —C(=O)N(R$^9$)$_2$;

x is an integer from 0-2;

Each $R^b$ is independently selected from the group consisting of halogen, C$_1$-C$_3$alkyl, C$_2$-C$_3$alkenyl, C$_2$-C$_3$alkynyl, —OCH$_3$, and —OCF$_3$, wherein each alkyl, alkenyl, and alkynyl substituent is optionally substituted with 1-3 halogens;

$R^2$ is independently selected from H, C$_1$-C$_5$alkyl, C$_2$-C$_5$alkenyl, C$_2$-C$_5$alkynyl, —CH$_2$C$_3$-C$_6$cycloalkyl, and —CH$_2$-Phenyl, wherein each alkyl, alkenyl, and alkynyl substituent is optionally substituted with 1-7 halogens, and said phenyl and cycloalkyl groups are optionally substituted with 1-3 substituent groups independently selected from halogen, CH$_3$, CF$_3$, —OCH$_3$, and —OCF$_3$;

B is selected from the group consisting of:
—(NR$^9$)(C(=O))DR$^3$,
—(NR$^9$)(C(=O))DR$^7$,
—(NR$^9$)(C(=O)) R$^3$,
—(NR$^9$)(C(=O))R$^7$,
—(NR$^9$)(C(=O))OCH$_2$R$^3$,
—(NR$^9$)D(C(=O))R$^7$,
—(NR$^9$)DR$^3$,
—(NR$^9$)D$^2$R$^7$,
—OD$^2$R$^3$,
-D$^2$(C(=O))R$^7$,
-D$^2$R$^3$,
-D$^2$R$^7$, and
—R$^3$;

D is a difunctional group selected from C$_1$-C$_7$alkylene, C$_2$-C$_5$alkenylene, and C$_2$-C$_5$alkynylene, wherein said alkylene group optionally has one difunctional group O, —NH— or —N(C$_1$-C$_3$alkyl)-between two adjacent carbon atoms, and said alkylene, alkenylene, and alkynylene groups are optionally substituted with 1-9 substituents independently selected from 1-7 halogens and optionally 1-2-OH groups;

D$^2$ is a difunctional group selected from C$_2$-C$_7$alkylene, C$_2$-C$_5$alkenylene, and C$_2$-C$_5$alkynylene, wherein said alkylene group optionally has one difunctional group O, —NH— or —N(C$_1$-C$_3$alkyl)-between two carbon atoms, and said alkylene, alkenylene, and alkynylene groups are optionally substituted with 1-9 substituents independently selected from (a) 1-7 halogens, (b) 1-2 substituents independently selected from —N(R$^9$)$_2$, —CN, —NO$_2$, —C$_1$-C$_3$ alkyl optionally substituted with 1-3 halogens, —C(=O)OH, —C(=O)H, —C(=O)OC$_1$-C$_5$alkyl optionally substituted with 1-7 halogens, —C(=O)C$_1$-C$_5$alkyl optionally substituted with 1-7 halogens, —C(=O)N(R$^9$)$_2$, (c) 1-2-OH groups, and (d) an oxo group;

$R^3$ is selected from the group consisting of $R^4$, -T-R$^4$, and —R$^5$;

$R^7$ is selected from the group consisting of —OC$_1$-C$_7$alkyl, —CH$_2$S(O)$_2$C$_1$-C$_7$alkyl, C$_5$-C$_{10}$alkyl, —NR$^9$C$_1$-C$_7$alkyl, —NR$^9$C(=O)OC$_1$-C$_7$alkyl, —OC(=O)OC$_1$-C$_7$alkyl and —OSi(R$^8$)$_3$, wherein the C$_5$-C$_{10}$alkyl and C$_1$-C$_7$alkyl groups of R$^7$ are optionally substituted with 1-9 halogens and are optionally substituted with one group selected from —N(R$^9$)$_2$, —N(R$^9$)C(=O)OC$_1$-C$_7$alkyl, —N(R$^9$)C(=O)C$_1$-C$_7$alkyl, and —OH, wherein the C$_1$-C$_7$alkyl groups of the —N(R$^9$)C(=O)OC$_1$-C$_7$alkyl and —N(R$^9$)C(=O)C$_1$-C$_7$alkyl substituents on R$^7$ are optionally substituted with 1-9 halogens;

T is selected from —O—, —N(R$^9$)—, and —S—;

Each $R^8$ group is independently selected from C$_1$-C$_5$alkyl, which is optionally substituted with 1-7 halogens;

$R^4$ is a cyclic group selected from the group consisting of
(a) C$_3$-C$_8$Cycloalkyl which optionally comprises 1-2 double bonds;
(b) Bicyclic C$_6$-C$_{12}$Cycloalkyl optionally comprising 1-2 double bonds;
(c) A 4-8 membered saturated or partly unsaturated heterocyclic ring having 1-2 ring members independently selected from —O— and —N(R$^6$)—, said heterocyclic ring being connected to the left hand part of Formula I through a carbon atom of the heterocyclic ring, wherein said heterocyclic ring is optionally fused to an aromatic ring selected from phenyl and naphthyl or to a C$_5$-C$_7$Cycloalkyl;
(d) An aromatic ring selected from phenyl and naphthyl; and
(e) A 5-7 membered heteroaromatic ring having 1-3 heteroatoms independently selected from N, S, and O, and optionally having one —C(=O)— group as a ring member, said heteroaromatic ring being connected to the left hand part of formula I through a carbon atom of the heteroaromatic ring, wherein said heteroromatic group is optionally fused to an aromatic ring selected from phenyl and naphthyl;

Wherein said cyclic groups $R^4$ defined in (a)-(e), including optional fused rings, are optionally substituted with 1-7 substitutents independently selected from halogen, C$_1$-C$_5$alkyl, —OC$_1$-C$_5$alkyl, phenyl, —NO$_2$, —C(=O)C$_1$-C$_5$alkyl, —C(=O)OC$_1$-C$_5$alkyl, —C(=O)OH, and —NR$^9$C(=O)C$_1$-C$_5$alkyl, wherein C$_1$-C$_5$alkyl and OC$_1$-C$_5$alkyl in all uses are optionally substituted with 1-9 halogens, and said phenyl is optionally substituted with 1-5 substituents independently selected from halogen, CH$_3$, CF$_3$, —OCH$_3$, and —OCF$_3$;

$R^5$ is a saturated or partly unsaturated 5-8 membered monocyclic heterocyclic group or a saturated or partly unsaturated 6-10 membered bicyclic heterocyclic group, wherein said heterocyclic group has a heteroatom N connected to the left hand side of Formula I and optionally has a second heteroatom selected from O, S, and —N(R$^6$)—, wherein said heterocyclic group optionally has 1-2 double bonds and an optional carbonyl group and is optionally fused to a cyclic group selected from phenyl and a 5-7 membered heteroaromatic ring having 1-3 heteroatoms independently selected from O, N, and S, or is optionally connected through a spirolinkage of a carbon atom to a 5-6 membered cycloalkyl ring or to a 5-7 membered heterocyclic ring having one heteroatom selected from O, N and S(O)$_x$, said cycloalkyl and heterocyclic ring optionally having one double bond and optionally being fused to a phenyl ring;

wherein $R^5$ including the rings optionally fused to $R^5$ or connected to $R^5$ through a spiro linkage are optionally substituted with 1-9 halogen atoms and also are optionally substituted with 1-3 substituents independently selected from $C_1$-$C_5$alkyl; —$OC_1$-$C_5$alkyl; —$NO_2$; —$N(R^9)C(=O)$ $OCH_2$-phenyl; —$S(O)_2C_1$-$C_3$alkyl; $C_3$-$C_6$cycloalkyl; —$CO_2H$; —$C(=O)C_1$-$C_3$alkyl; —$C(=O)OC_1$-$C_3$alkyl; —$C(=O)N(R^9)_2$; —$C_1$-$C_3$alkyleneN($R^9)_2$; —$C_1$-$C_3$alkyleneC(=O)N($R^9)_2$; phenyl; —$C_1$-$C_3$alkylenePhenyl; a 5-10 membered heteroaromatic monocyclic or fused bicyclic group having 1-3 heteroatoms independently selected from N, O, and S; a 5-6 membered saturated or partly unsaturated heterocyclic ring having 1-3 heteroatoms independently selected from N, O, and S, optionally having a carbonyl group, optionally having one double bond, and optionally being fused to a phenyl ring; and a 5-6-membered heteroaromatic ring having 1-2 heteroatoms independently selected from N, S, and O, said heteroaromatic ring being fused to a 5-7 membered cycloalkyl or to a saturated or partly unsaturated heterocycle having 1-2 heteroatoms independently selected from N, S, and O; wherein all of said alkyl groups that are included in substituent groups on $R^5$ are optionally substituted with 1-9 halogens, and all of said phenyl groups that are substituents on $R^5$ or that are included in substituents on $R^5$ are optionally substituted with 1-5 substituents independently selected from halogen, —CN, —$NO_2$, $CH_3$, $CF_3$, —$OCH_3$, and —$OCF_3$;

$R^6$ is selected from the group consisting of $C_1$-$C_7$alkyl, —$C(=O)OC_1$-$C_7$alkyl, —$C(=O)C_1$-$C_7$alkyl, —$S(O)_x$ phenyl, —$S(O)_x$ $C_1$-$C_7$alkyl, —$C(=O)N(R^9)_2$, —$C(=O)$Phenyl, —$C(=O)$OPhenyl, —$C_1$-$C_3$alkylene-$C(=O)OC_1$-$C_6$alkyl, —$C_1$-$C_5$alkylene-$OC_1$-$C_5$alkyl, —$C(=O)C_3$-$C_7$cycloalkyl, —$C(=O)OC_3$-$C_7$cycloalkyl, and a cyclic group selected from (a) phenyl, (b) naphthyl, (c) biphenyl, (d) $C_3$-$C_8$cycloalkyl, (e) a saturated or partially unsaturated monocyclic or bicyclic 5-10 membered heterocycle having 1-2 heteroatoms independently selected from N, O, and S, said heterocycle optionally having 1-2 double bonds, and (f) a monocyclic or bicyclic 5-12 membered heteroaromatic group having 1-4 heteroatoms independently selected from N, S, and O and optionally having 1-2 carbonyl groups, wherein in all instances, each alkyl, alkenyl and alkynyl group included in $R^6$ is optionally substituted with 1-10 halogens and is also optionally substituted with 1-2 groups independently selected from phenyl, OH, biphenyl, —Ophenyl, and —$OC_1$-$C_3$alkylene-phenyl, wherein said phenyl substituents on the alkyl, alkenyl and alkynyl groups of $R^6$ are optionally substituted with 1-5 substituent groups independently selected from halogen, $CH_3$, $CF_3$, —$OCF_3$, —$NO_2$ and —$OCH_3$, and when $R^6$ is a cyclic group selected from (a) phenyl, (b) naphthyl, (c) biphenyl, (d) $C_3$-$C_8$cycloalkyl, (e) a saturated or partially unsaturated monocyclic or bicyclic 5-10 membered heterocycle having 1-2 heteroatoms independently selected from N, O, and S, said heterocycle optionally having 1-2 double bonds, and (f) a cyclic or bicyclic 5-12 membered heteroaromatic group having 1-4 heteroatoms independently selected from N, S, and O and optionally having 1-2 carbonyl groups, said cyclic group $R^6$ is optionally substituted with 1-3 groups independently selected from $C_1$-$C_5$alkyl, —$OC_1$-$C_5$alkyl, —$C(=O)C_1$-$C_3$alkyl, —$S(O)_x$ $C_1$-$C_3$alkyl, phenyl, halogen, —CN, and —$NO_2$, said $C_1$-$C_5$alkyl and —$OC_1$-$C_5$alkyl being optionally substituted with 1-7 halogens;

$R^9$ is selected from the group consisting of H, $C_1$-$C_5$alkyl, $C_2$-$C_5$alkenyl, and $C_2$-$C_5$alkynyl, wherein said $C_1$-$C_5$alkyl, $C_2$-$C_5$alkenyl, and $C_2$-$C_5$alkynyl are optionally substituted with 1-9 halogens;

With the proviso (I) that when (a) and (b) are as described below, where (a) the groups W, X, Y, and Z are each —CH= or —($CR^a$)=, where the substituent groups $R^a$ are each selected from Cl, $C_1$-$C_4$alkyl, —$OCH_3$, —$NH_2$, —N(H)C (=O)$OC_1$-$C_5$alkyl, or —N(H)C(=O)$C_1$-$C_5$alkyl, wherein the alkyl groups of —N(H)C(=O)$OC_1$-$C_5$alkyl and —N(H) C(=O)$C_1$-$C_5$alkyl are optionally substituted with 1-7 halogens; and (b) A is 1,4-phenylene, which is optionally substituted, then B is not (i) —NHC(=O)$CH_2$Ophenyl, (ii) —NHC(=O)$CH_2$Onaphthyl, (iii) —NHC(=O)benzofuryl, (iv) —NHC(=O)benzoxazolyl, (v) —NHC(=O)$CH_2R^5$ in which $R^5$ is a cyclic amine which is attached by a ring N atom and is selected from the group consisting of morpholinyl, piperidinyl, cbz-prolinyl and triazolyl, and (vi) —NHC(=O) $CH_2$— connected to the N of an amine group which is selected from the group consisting of dimethylamine, t-butylglycine, and n-butylglycine, wherein phenyl, naphthyl, benzofuryl, benzoxazolyl, morpholinyl, piperidinyl, prolinyl, and triazolyl are optionally substituted;

and with the further proviso (II) that when (a) and (b) are as described below, where (a) the groups W, X, Y, and Z are each —CH= or —($CR^a$)=, wherein $R^a$ is —$OCH_3$; and (b) A is unsubstituted 1,4-phenylene; then B is not —N(H)C(=O) ($CH_2)_5$NH(C(=O))$CF_3$, —N(H)C(=O)CH($NH_2)C_4$alkyl, or —N(H)C(=O)phenyl, wherein phenyl is optionally substituted.

DETAILED DESCRIPTION OF THE INVENTION

A subgroup of the compounds of this invention has the structure of Formula Ia, written below, or a pharmaceutically acceptable salt thereof:

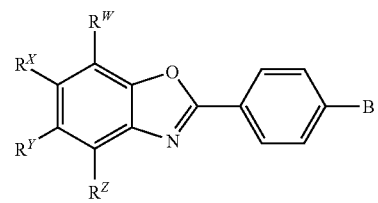

Ia

In the compound of Formula Ia:
$R^X$ and $R^Z$ are each H;
$R^W$ is selected from the group consisting of (a) $C_1$-$C_5$alkyl which is optionally substituted with 1-9 substituents independently selected from 1-7 halogens and 1-2 groups independently selected from —CN, —OH, —$OCH_3$, —$OCF_3$ and —N($R^9)_2$, (b) —C(=O)$C_1$-$C_3$alkyl which is optionally substituted with 1-7 halogens, (c) —C(=O)H, (d) —$NO_2$, (e) —$OC_1$-$C_3$ alkyl which is optionally substituted with 1-7 halogens, (f) $C_3$-$C_6$cycloalkyl, (g) phenyl, (h) a 5-6 membered saturated or partly unsaturated heterocyclic ring having 1-3 heteroatoms independently selected from N, S and O, and (i) a 5-7 membered heteroaromatic ring having 1-3 heteroatoms independently selected from N, S, and O, wherein said $C_3$-$C_6$cycloalkyl, phenyl, 5-6 membered saturated or partly unsaturated heterocyclic ring, and 5-7 membered heteroaromatic ring are optionally substituted with 1-5 substituents independently selected from halogen, $CH_3$, $CF_3$, —$OCH_3$, and —$OCF_3$; and $R^Y$ is selected from the group consisting of Br, —$OCH_3$, —CN, and pyridyl.

In subgroups of the compound of Formula Ia, proviso (I) stated previously with respect to Formula I does not apply to the definition of the compound of formula Ia, as defined immediately above.

In subgroups of the compounds having Formula I, at least one of the substituent groups $R^a$ is —CN.

In subgroups of the compounds of Formula Ia, $R^Y$ is —CN.

In subgroups of the compounds of Formula I and Ia, B is selected from the group consisting of:
- —(NH)(C(=O))CH$_2$R$^3$,
- —(NH)(C(=O))CH$_2$CH$_2$R$^3$,
- —(NH)(C(=O))CH$_2$O(CH$_2$)$_3$R$^7$,
- —(NH)(C(=O))OCH$_2$R$^4$,
- —C$_2$-C$_4$alkyleneR$^3$, wherein —C$_2$-C$_4$alkylene is optionally substituted with 1-8 substituents independently selected from (a) 1-7 halogens, (b) 1-2 substituents independently selected from —N(R$^9$)$_2$, —CN, —OC$_1$-C$_3$ alkyl optionally substituted with 1-3 halogens, —C(=O)OH, —C(=O)H, —C(=O)OC$_1$-C$_5$alkyl optionally substituted with 1-7 halogens, —C(=O)C$_1$-C$_5$alkyl optionally substituted with 1-7 halogens, —C(=O)N(R$^9$)$_2$, (c) 1-2-OH groups, and (d) an oxo group on a carbon atom between two other carbon atoms of the alkylene group;
- —C$_2$-C$_4$alkyleneR$^7$, wherein —C$_2$-C$_4$alkylene is optionally substituted with 1-8 substituents independently selected from (a) 1-7 halogens, (b) 1-2 substituents independently selected from —N(R$^9$)$_2$, —CN, —C(=O)OH, —C(=O)H, —C(=O)OC$_1$-C$_5$alkyl optionally substituted with 1-7 halogens, —C(=O)C$_1$-C$_5$alkyl optionally substituted with 1-7 halogens, —C(=O)N(R$^9$)$_2$, (c) 1-2-OH groups, and (d) an oxo group on a carbon atom between two other carbon atoms of the alkylene group;
- —CH=CHCH$_2$R$^3$,
- —CH=CHCH$_2$R$^7$,
- —C≡CCH$_2$R$^3$,
- —C≡CCH$_2$R$^7$,
- —NHCH$_2$CH$_2$R$^3$,
- —NHCH(CF$_3$)CH$_2$R$^7$,
- —NHCH$_2$C(=O)R$^5$, and
- —CH(OH)CH(OH)C(=O)OC$_1$-C$_4$alkyl.

In subgroups of the compound of Formula I or Ia, $R^3$ is selected from the group consisting of $R^4$, —OR$^4$, and —R$^5$.

In subgroups of the compound of Formula I or Ia, $R^4$ is a cyclic group selected from the group consisting of:
(a) Cyclohexyl,
(b) 2-quinolyl,
(c) 1-isoquinolyl,
(d) phenyl,
(e) 2-tetrahydropyranyl, (f)

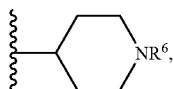

(g)

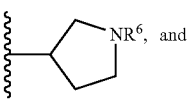

(h)

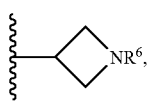

wherein $R^4$ is optionally substituted with 1-3 substituents independently selected from —CH$_3$, —CF$_3$, —OCH$_3$, —OCF$_3$, and halogen.

In subgroups of the compound of Formula I or Ia, $R^5$ is selected from the group consisting of:

(a)

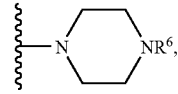

(b)

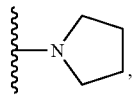

(c)

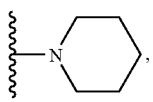

(d)

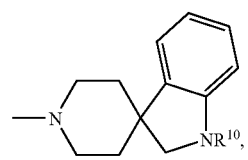

(e)

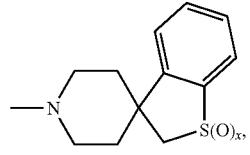

(f)

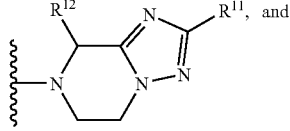

(g)

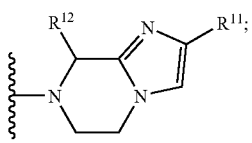

wherein $R^{10}$ is selected from the group consisting of —SO$_2$CF$_3$, —SO$_2$CH$_3$, and —C(=O)CH$_3$;

$R^{11}$ is selected from the group consisting of H, C$_1$-C$_5$alkyl, phenyl, and benzyl, wherein C$_1$-C$_5$alkyl is optionally substituted with 1-3 halogens, and wherein phenyl and benzyl are optionally substituted with 1-3 groups independently selected from halogen, —CH$_3$, —CF$_3$, —OCH$_3$, and —OCF$_3$;

$R^{12}$ is selected from the group consisting of H, C$_1$-C$_3$alkyl which is optionally substituted with 1-3 halogens, and —CH$_2$C(=O)N(R$^9$)$_2$;

wherein when $R^5$ is (a) or (d)-(g), then $R^5$ is optionally substituted with 1-3 substituent groups independently selected from halogen, —CH$_3$, —CF$_3$, —OCH$_3$, and —OCF$_3$; and when $R^5$ is (b) or (c), then $R^5$ is optionally substituted with 1-2 substituents independently selected from halogen, cyclohexyl, phenyl, —C(=O)N(R$^9$)C$_2$-C$_5$alkyl, —C(=O)OC$_1$-C$_4$alkyl, benzotriazole, pyrazolotetrahydropyridine, and —N(C$_2$-C$_3$alkenyl)(C(=O))Obenzyl, wherein alkyl and alkenyl are optionally substitued with 1-3 halogens, and phenyl and the phenyl of benzyl are optionally substituted with 1-3 halogens and 1 group selected from —CH$_3$, —CF$_3$, —OCH$_3$, —OCF$_3$, and —NO$_2$.

In subgroups of the compound of Formula I or Ia,
R$^6$ is selected from the group consisting of:
(a) phenyl,
(b) pyrimidinyl,
(c) pyrazinyl,
(d) pyridyl,
(e) naphthyl,
(f) C$_3$-C$_6$cycloalkyl,
(g) CH(phenyl)$_2$,
(h) —C(=O)OC$_1$-C$_5$alkyl,
(i) —C(=O)C$_1$-C$_5$alkyl,
(o) —SO$_2$C$_1$-C$_3$alkylene-phenyl,
(k) —SO$_2$C$_1$-C$_5$alkyl,
(l) —C(=O)OC$_3$-C$_5$alkylene-OH,
(m) —C(=O)OC$_3$-C$_5$alkylene-Obenzyl,
(n) —C(=O)O-phenyl,
(o) —C(=O)O-benzyl,
(p) —C(=O)N(R$^9$)C$_1$-C$_5$alkyl,
(q) —C(=O)OC$_5$-C$_6$cycloalkyl,
(r) —CH$_2$C(=O)OC$_1$-C$_5$alkyl,
(s) C$_1$-C$_3$alkylene-phenyl, and
(t) C$_4$-C$_6$alkyl,
wherein alkyl, alkylene, and cycloalkyl groups are optionally substituted with 1-3 halogens; phenyl, the phenyl groups of benzyl, and naphthyl are optionally substituted with 1-3 substituents independently selected from (i) halogen, (ii) C$_1$-C$_3$ alkyl optionally substituted with 1-3 halogens, (iii) —OCF$_3$, (iv) —OCH$_3$, (v) —NO$_2$, (vii) phenyl, (viii) —CN, (ix) —C(=O)CH$_3$, and (x) —SO$_2$CH$_3$; and pyridyl, pyrimidinyl and pyrazinyl are optionally substituted with 1-3 substituents independently selected from halogen, —CH$_3$, —CF$_3$, —OCH$_3$, —OCF$_3$, —NO$_2$, —CN, and phenyl.

In subgroups of the compound of Formula I or Ia,
R$^7$ is selected from the group consisting of —OC$_3$-C$_5$alkyl, —N(R$^9$)C(=O)OC$_3$-C$_5$alkyl, and —OSi(CH$_3$)$_2$C$_3$-C$_6$alkyl, wherein each alkyl group is optionally substituted with 1-3 halogens.

In subgroups of the compounds of formula I and Ia, each R$^9$ is independently selected from H and CH$_3$.

Specific examples of the compounds of this invention are provided in the examples, including Tables 1-18 in the examples. The specific embodiments include the compounds and pharmaceutically acceptable salts of the compounds.

DEFINITIONS

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—CH$_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocyclyl," "heterocycle," and "heterocyclic" means a saturated or partly unsaturated 5-6 membered ring containing 1-4 heteroatoms independently selected from N, S and O, unless otherwise stated. The heterocyclic ring may also be defined to include an optional carbonyl group or —N(O)- group as part of the ring structure.

Heteroaromatic means a 5-6 membered aromatic ring having 1-4 heteroatoms independently selected from N, S and O, unless otherwise stated. The heteroaromatic ring may also be defined to include an optional carbonyl group or —N(O)- group as part of the ring structure. An example of the latter is pyridine N-oxide.

"Benzoheterocycle" represents a phenyl ring fused to a 5-6-membered heterocyclic ring having 1-3 heteroatoms, each of which is O, N, or S, unless otherwise defined, where the heterocyclic ring may be saturated or unsaturated or aromatic (i.e. the heterocyclic ring may have 1-2 double bonds in addition to the double bond of the phenyl ring). Examples include indole, 2,3-dihydroindole, benzofuran, 2,3-dihydrobenzofuran, quinoline, and isoquinoline. When the fused heterocycle is aromatic, the benzoheterocycle may also be referred to as benzoheteroaromatic or benzoheteroaryl.

"Halogen" includes fluorine, chlorine, bromine and iodine. Halogen substitutents are most often fluorine or chlorine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to comprehend all such isomeric forms of the compounds of Formula I and of all structures provided herein.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of the Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the crystalline forms of compounds of the present invention may exist as polymorphs, and as such are intended to be included in the present invention. In addition, some of the compounds of the instant invention may form solvates with water or common organic solvents. Such solvates and hydrates are likewise encompassed within the scope of this invention.

Some of the biphenyl and biaryl compounds herein are observed as mixtures of atropisomers (rotamers) in the NMR spectra. The individual atropisomers as well as the mixtures are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also claimed.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, and diseases which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity and endotoxemia.

The compounds of this invention are expected to be particularly effective in raising HDL-C and/or increasing the ratio of HDL-C to LDL-C. They also may be effective in lowering LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate and bezafibrate, (v) cholesterol absorption inhibitors, such as ezetimibe, (vi) acyl CoA:cholesterol acyltransferase (ACAT) inhibitors, such as avasimibe, (vii) phenolic anti-oxidants, such as probucol, and (viii) a microsomal triglyceride transfer protein (MTP)/ApoB secretion inhibitor.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations with atorvastatin, ezetimibe, or both compounds.

Finally compounds of this invention can be used with compounds that are useful for treating other disease, such as diabetes and obesity, as well as other anti-atherosclerostic compounds.

Examples of other active ingredients that may be administered in combination with a compound of this invention include, but are not limited to:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-IB (PTP-1B) inhibitors, (d) dipeptidyl peptidase IV (DP-IV) inhibitors;

(e) insulin or insulin mimetics;

(f) sulfonylureas, such as tolbutamide and glipizide, or related materials;

(g) α-glucosidase inhibitors (such as acarbose);

(h) agents which improve a patient's lipid profile, as described previously;

(i) PPARcaly dual agonists, such as muraglitazar, tesaglitazar, farglitazar, and JT-501;

(j) PPARα/γ agonists such as those disclosed in WO97/28149;

(k) antiobesity compounds, including 5-HT(serotonin) inhibitors, neuropeptide Y5 (NPY5) inhibitors, melanocortin 4 receptor (Mc4r) agonists, cannabinoid receptor 1 (CB-1) antagonists/inverse agonists, and $β_3$ adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors, including etoricoxib and rofecoxib;

(n) glucagon receptor antagonists;

(o) GLP-1, (p) GIP-1, and (q) GLP-1 analogs, such as exendins, for example exenitide.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease.

CETP Assay

An in vitro continuous assay for determining $IC_{50}$'s to identify compounds that are CETP inhibitors was performed based on a modification of the method described by Epps et al. employing BODIPYS-CE as the cholesteryl ester lipid donor. See Epps et al. (1995) *Method for measuring the activities of cholesteryl ester transfer protein (lipid transfer protein)*, Chem. Phys. Lipids. 77, 51-63.

Particles used in the assay were created from the following sources: Synthetic donor HDL particles containing DOPC (Dioleoyl Phosphatidyl Choline), BODIPY®-CE (Molecular Probes C-3927), triolein (a triglyceride), and apoHDL were essentially created by probe sonication as described by Epps et al, but with the addition of a non-diffusable quencher molecule, dabcyl dicetylamide, in order to reduce background fluorescence. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat#7205). An assay cocktail containing CETP, 1×CETP buffer (50 mM Tris, pH 7.4, 100 mM NaCl, 1 mM EDTA), and half the final concentration of acceptor particles was prepared, and 100 μL of the assay cocktail was added to each well of the plate. Test compounds in DMSO were added in a volume of 3 μL. The plate was mixed on a plate shaker and then incubated at 25° C. for 1 hour. A second assay cocktail containing donor particles, the remaining acceptor particles and 1×CETP buffer was prepared. 47 μL of the second assay cocktail was added to the reaction wells to start the assay. Assays were performed at 25° C. in a final volume of 150 μL. Final concentrations of materials were: 5 ng/μL donor particles, 30 ng/μL acceptor particles (each expressed by protein content), 1×CETP buffer, 0.8 nM recombinant human CETP (expressed in CHO cells and partially purified), and up to 2% DMSO when testing compounds. The assay was followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well.

Data was evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate $IC_{50}$.

EXAMPLES

The following examples are provided so that the invention will be more fully appreciated and understood. They should not be construed as limiting the invention in any way. The scope of the invention is defined by the appended claims. Compounds described herein have an $IC_{50}$ value as measured using the assay described above of less than or equal to 50 µM. Preferred compounds have an $IC_{50}$ less than 1 µM, and more preferred compound have an $IC_{50}$<100 nm. The most potent compounds have an $IC_{50}$ of about 10 nm.

The following Schemes are provided to further teach how compounds claimed herein can be synthesized by one of ordinary skill in the art. Starting materials are made using known procedures or as illustrated. Some starting materials may also be available for purchase.

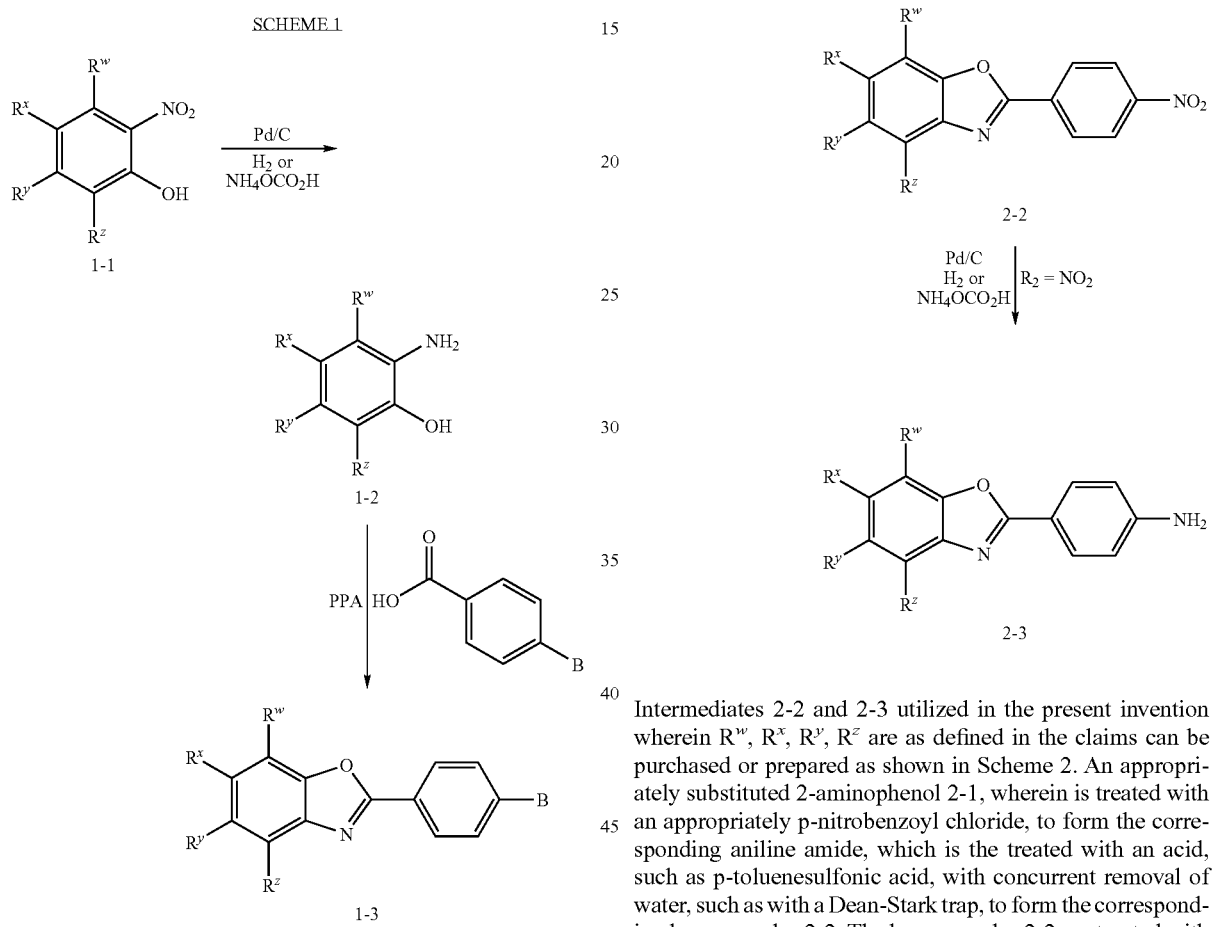

Compounds 1-3 claimed in the present invention can be prepared as shown in Scheme 1. An appropriately substituted 2-nitrophenol 1-1, which can be purchased or prepared according to known procedures by those skilled in the art, wherein $R^w$, $R^x$, $R^y$, $R^z$ and B are as defined in the claims, is treated with palladium on carbon in the presence of ammonium formate or hydrogen gas to afford the corresponding 2-aminophenol. Alternatively, the aminophenols can be prepared by reduction of 1-1 with Raney nickel, platinum oxide, or zinc in the presence of hydrogen gas, or tin chloride, or the like. Aminophenols 1-2 are treated with p-aminobenzoic acid and polyphosphoric acid to afford the corresponding benzoxazoles 1-3. Alternatively aminophenols and p-aminobenzoic acid can be treated with another acid, such as p-toluenesulfonic acid, with concurrent removal of water, such as with a Dean-Stark trap, to form the benzoxazoles.

Intermediates 2-2 and 2-3 utilized in the present invention wherein $R^w$, $R^x$, $R^y$, $R^z$ are as defined in the claims can be purchased or prepared as shown in Scheme 2. An appropriately substituted 2-aminophenol 2-1, wherein is treated with an appropriately p-nitrobenzoyl chloride, to form the corresponding aniline amide, which is the treated with an acid, such as p-toluenesulfonic acid, with concurrent removal of water, such as with a Dean-Stark trap, to form the corresponding benzoxazoles 2-2. The benzoxazoles 2-2 are treated with palladium on carbon in the presence of ammonium formate or hydrogen gas to afford the corresponding aniline 2-3. Alternatively, anilines 2-3 can be prepared by reduction of 2-2 with Raney nickel, platinum oxide, or zinc in the presence of hydrogen gas, or tin chloride, or the like.

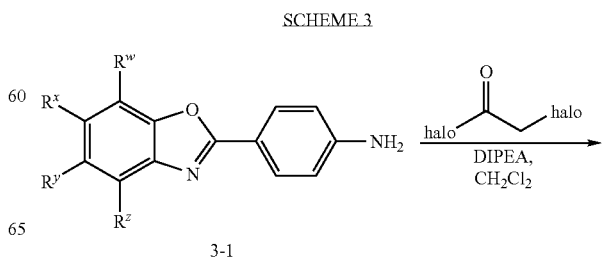

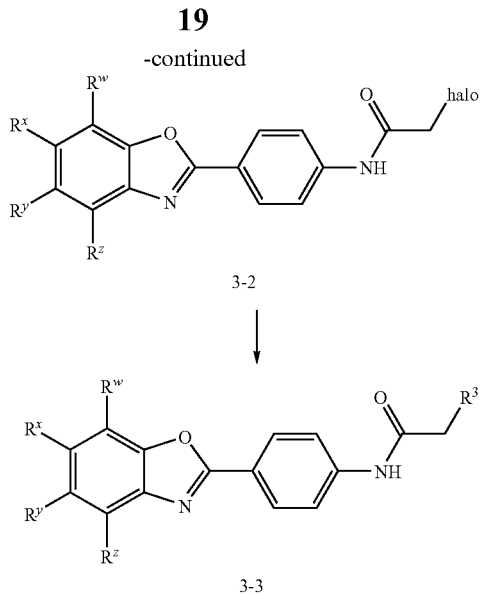

3-2

↓

3-3

Compounds 3-2 and 3-3 of the present invention wherein $R^w$, $R^x$, $R^y$, $R^z$ and $R^3$ are as defined in the claims can be prepared as shown in Scheme 3. An appropriately substituted aniline 3-1, is treated with an α-haloacetyl halide in the presence of a base such as diisopropylethylamine, triethylamine, potassium carbonate, cesium carbonate, or the like, to form the corresponding α-haloamide 3-2. Displacement of the halide with an appropriate reagent such as a primary or secondary amine to alcohol in the presence of a base such as potassium carbonate, diisopropylethylamine, sodium hydride and the like affords compounds 3-3.

SCHEME 4

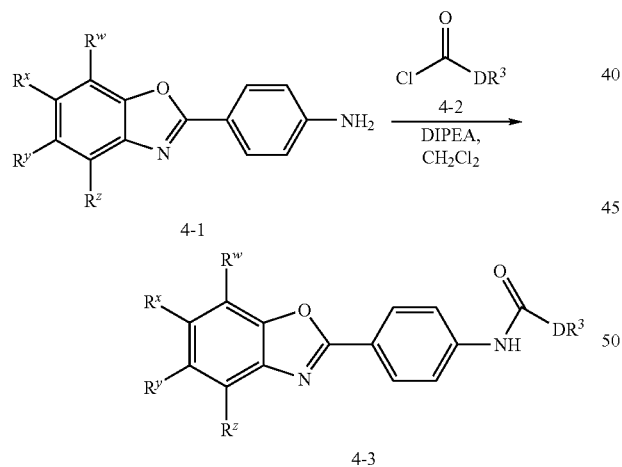

Compounds 4-3 of the present invention wherein $R^w$, $R^x$, $R^y$, $R^z$, D and $R^3$ are as defined in the claims can be prepared as shown in Scheme 4. An appropriately substituted aniline 4-1, is treated with an appropriately substituted acid chloride 4-2 in the presence of a base such as diisopropylethylamine, triethylamine, or the like, to form the corresponding amide 4-3. Acid chlorides 4-2 can be purchased or prepared from the corresponding acids by treatment with oxalyl chloride, thionyl chloride, phosphorus pentachloride, phosphorus oxychloride, phosgene, triphenyl phosphine and carbon tetrachloride, or the like. Alternatively, amides 4-2 can be prepared via standard amide formation between amine 4-1 and the corresponding acid using reagents such as DCC, HATU and the like.

SCHEME 5

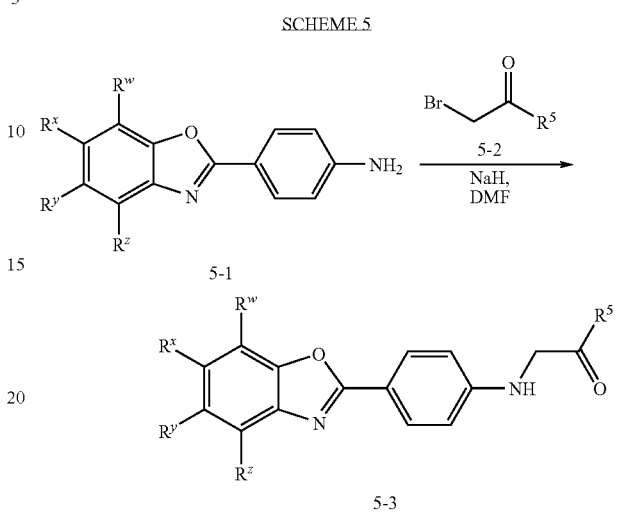

Compounds 5-2 of the present invention wherein $R^w$, $R^x$, $R^y$, $R^z$ and $R^5$ are as defined in the claims can be prepared as shown in Scheme 5. An appropriately substituted aniline 5-1, is treated with an appropriately substituted halide 5-2, wherein in the presence of a base such as sodium hydride, lithium, sodium, or potassium hexamethyldisilazide, diisopropylethylamine, triethylamine, potassium carbonate, cesium carbonate, or the like, to form the corresponding substituted aniline 5-3.

SCHEME 6

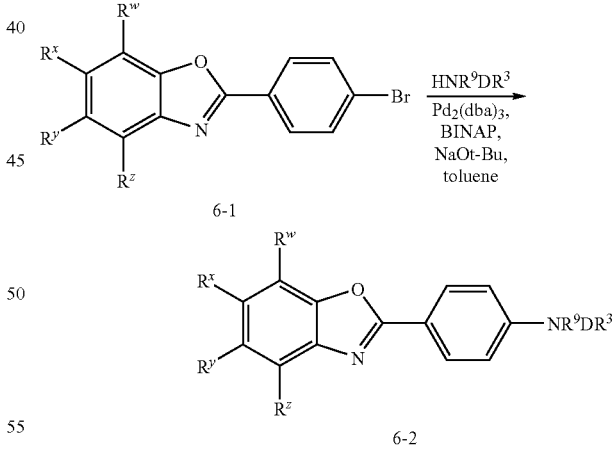

Compounds 6-2 of the present invention wherein $R^w$, $R^x$, $R^y$, $R^z$, D, $R^3$ and $R^9$ are as defined in the claims can be prepared as shown in Scheme 6 via a Hartwig-Buchwald reaction or variation thereof employing palladium- or nickel-catalyzed cross-coupling of an appropriately substituted bromide 6-1 with an amine as described in Smith, M. B. and March, J. "March's Advanced Organic Chemistry", 5$^{th}$ Ed., John Wiley and Sons, New York, pp. 502 and 864 (2001) and references cited therein, and as described in Palucki, M.; Wolfe, J. P.; and Buchwald, S. L., J. Am. Chem. Soc. 1997, 119, 3395. Alternatively, an alcohol could be employed giving compounds of the present invention wherein the $NR^9DR^3$ group is replaced by an $OD^2R^3$ group and wherein $D^2$ and $R^3$ are as defined in the claims.

SCHEME 7

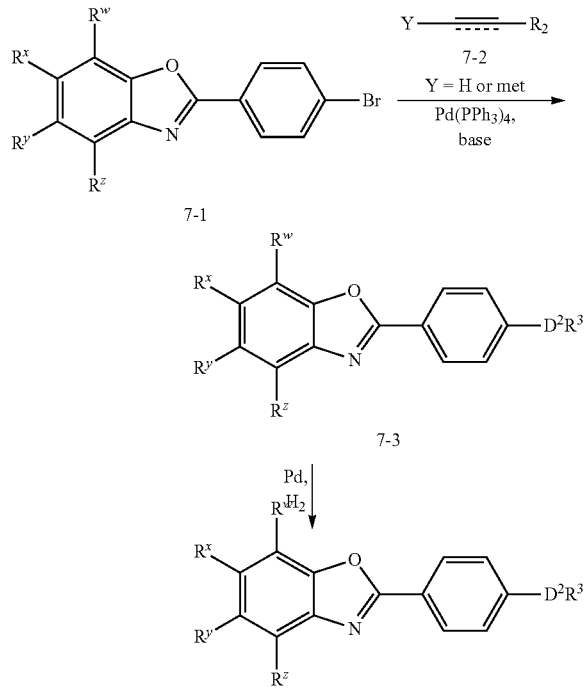

Compounds 7-3 of the present invention wherein $R^w$, $R^x$, $R^y$, $R^z$, $D^2$, and $R^3$ are as defined in the claims can be prepared as shown in Scheme 7. Compounds 7-3 are prepared via Suzuki, Stille, Sonogashira, or Heck reaction or variation thereof employing palladium-catalyzed cross-coupling of an appropriately substituted bromide 7-1 with an appropriately substituted alkynyl-, vinyl-, aryl- or heteroaryl-substituted boronic acid, boronate ester, or trialkyl tin reagent, or alkyne or alkene 7-2, as described in Miyaura et al., Chem. Rev. 95, 2457 (1995) and references cited within and as described in Smith, M. B. and March, J. "March's Advanced Organic Chemistry", 5$^{th}$ Ed., John Wiley and Sons, New York, pp. 868-869 and pp 930-932 (2001), and as described in Sonogashira, K.; Tohda, Y.; and Hagihara, N., Tetrahedron Lett. 1975, 50, 4467. Where D is an alkenylene or alkynylene, the compounds can be further reduced by hydrogenation using Pd on carbon, or the like.

SCHEME 8

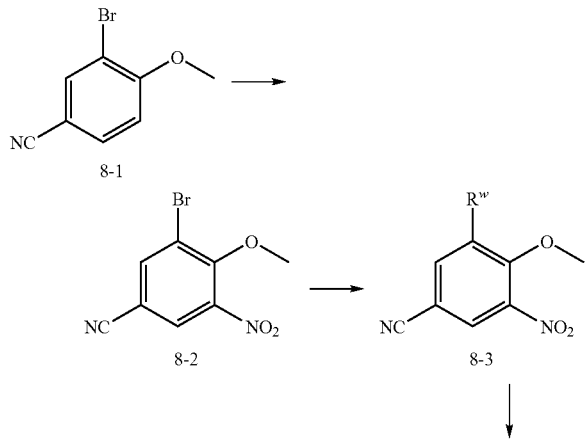

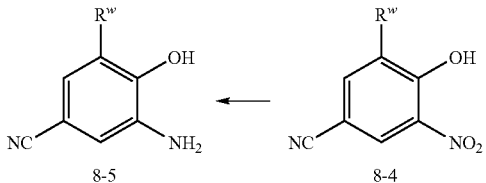

Intermediates 8-5 utilized in the present invention wherein $R^w$ is as defined in the claims can be prepared by standard aromatic substitution reactions starting with 1-bromo-5-cyano-2-methoxy benzene 8-1. Nitration with nitric acid affords nitro derivative 8-2. Pd catalyzed cross coupling with an appropriately substituted alkynyl-, vinyl-, aryl- or heteroaryl-substituted boronic acid, boronate ester, or trialkyl tin reagent, or alkyne or alkene as described in Miyaura et al., Chem. Rev. 95, 2457 (1995) and references cited within and as described in Smith, M. B. and March, J. "March's Advanced Organic Chemistry", 5$^{th}$ Ed., John Wiley and Sons, New York, pp. 868-869 and pp 930-932 (2001), and as described in Sonogashira, K.; Tohda, Y.; and Hagihara, N., Tetrahedron Lett. 1975, 50, 4467 affords nitro compound 8-3. Compound 8-4 can be prepared from 8-3 via demethylation using pyridinium chloride at elevated temperatures (150-200° C.). Compound 8-5 can be prepared from 8-4 via reduction with hydrogen gas over a palladium catalyst.

SCHEME 9

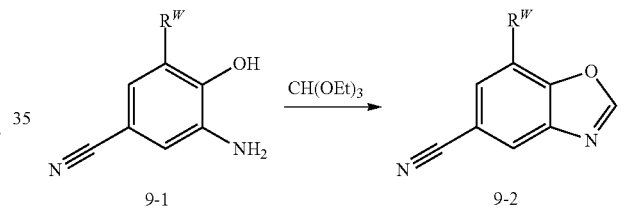

Intermediate 9-2 wherein $R^w$ is as defined in the claims cab be prepared as described in Scheme 9. Aminophenol intermediate 9-1 is heated with triethylorthoformate in the presence of catalytic amount of concentrated HCl to give the intermediate 9-2.

SCHEME 10

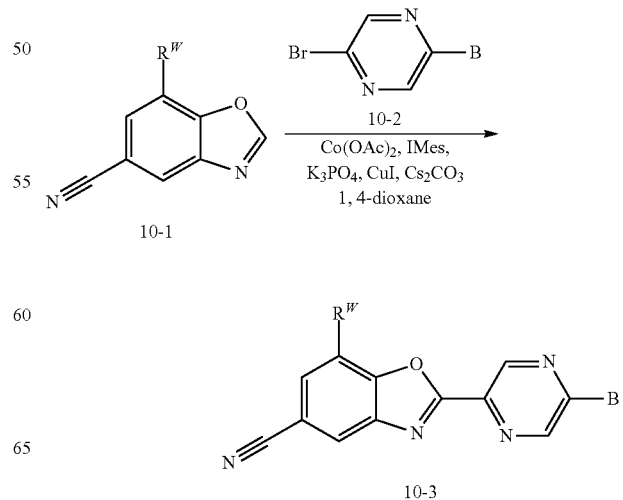

Compounds 10-3 of the present invention wherein $R^w$ and B are as defined in the claims may be prepared described in scheme 10. Benzoxazole 10-1 and bromopyrazine 10-2 are coupled according to the procedure of Sames et al, Organic Letters, 2003, 5 (20), 3607, to provide compounds 10-3.

ole formation can be found in Joule, J. A. and Mills, K. "Heterocyclic Chemistry", 4th Ed., Blackwell Science, Inc., Maiden, Mass., pp. 449-458 and references therein.

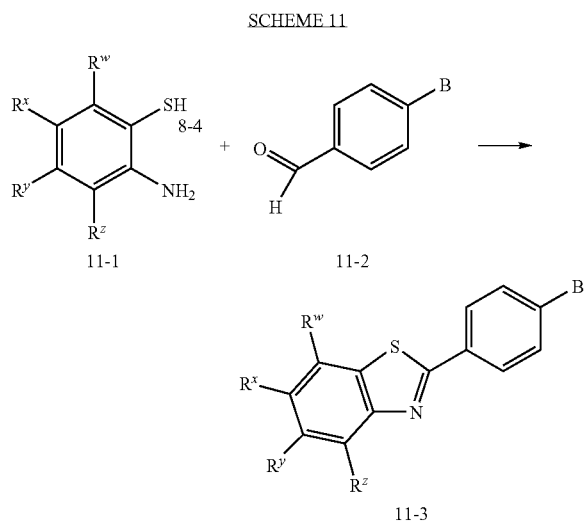

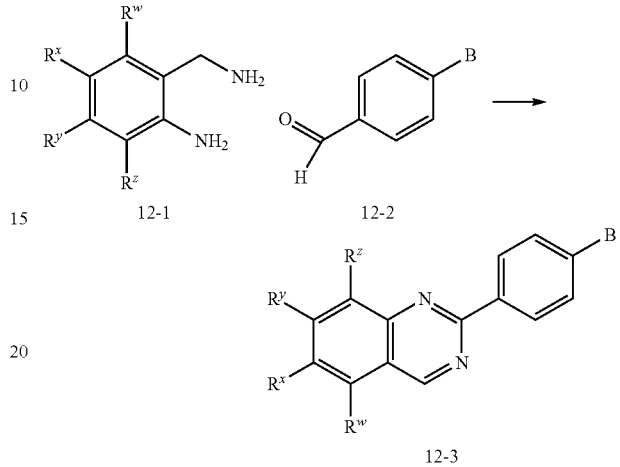

Compounds 12-3 of the present invention wherein $R^w$, $R^x$, $R^y$, $R^z$, and B are as defined in the claims can be prepared as shown in Scheme 12. Condensation of 12-2 with an appropriately substituted amino-benzylamine 12-1 under conditions of reflux with solvents such as DMSO and the like led to formation of quinazolines 12-3.

Compounds II-3 of the present invention wherein $R^w$, $R^x$, $R^y$, $R^z$, and B are as defined in the claims can be prepared as shown in Scheme 11. Aldehyde 11-2 can be condensed with an appropriately substituted aromatic amino-thiol 11-1 to give benzothiazole 11-3. Amino thiols 11-2 are either commercially available or prepared using standard literature procedures (see, for example Shi et. al., J. Med. Chem., 1996, 39, 3375 and references therein). Other methods for benzothiaz-

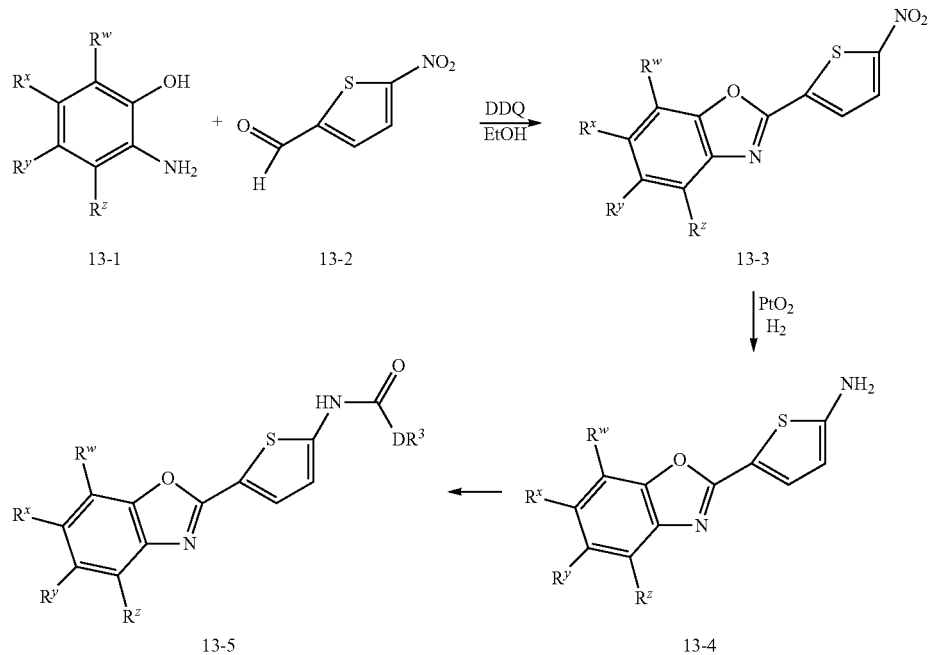

Compounds 13-5 of the present invention wherein $R^w$, $R^x$, $R^y$, $R^z$, D, and $R^3$ are as defined in the claims can be prepared as shown in Scheme 13. Commercially available 5-nitrothiophene-2-carbaldehyde 13-2 can be coupled with an appropriately substituted amino-phenol 13-1 according to the procedure of Chang, J. et. al., Tetrahedron Letters, 2002, 951.

Other methods for benzoxazole formation are available. For a leading reference on methods to form benzoxazoles, see Joule, J. A. and Mills, K. "Heterocyclic Chemistry", 4th Ed., Blackwell Science, Inc., Malden, Mass., pp. 449-458 and references therein. Amino-phenols 13-1 are commercially available or prepared using standard procedures. Intermediate 13-3 can be reduced to 13-4 using $H_2/PtO_2$ in THF. Other methods can be used to reduce nitro groups including $H_2$ and Pd/C in a variety of solvents and the like; for other methods, see: Smith, M. B. and March, J. "March's Advanced Organic Chemistry", 5th Ed., John Wiley and Sons, New York, pp. 1552 to 1554 (2001) and references cited therein. Intermediate 13-4 can be coupled to an appropriately activated carboxylic acid to form amide 13-5. Activation of the carboxylic acid can be accomplished via the acid chloride or by using standard coupling reagents such as HATU in the presence of a tertiary amine base such as DIPEA, triethylamine or the like. For leading references to amide bond formation, see: Smith, M. B. and March, J. "March's Advanced Organic Chemistry", 5th Ed., John Wiley and Sons, New York, pp. 506 to 512 (2001) and references cited therein.

therein. Amino-thiols (14-1) are commercially available or prepared using standard procedures. Intermediate 14-3 can be reduced to 14-4 using $PtO_2$, $H_2$ in THF. Other methods can be used to reduce nitro groups including $H_2$ and Pd/C in a variety of solvents and the like; for other methods, see: Smith, M. B. and March, J. "March's Advanced Organic Chemistry", 5th Ed., John Wiley and Sons, New York, pp. 1552 to 1554 (2001) and references cited therein. Intermediate 14-4 can be coupled to an appropriately activated carboxylic acid to form compounds 14-5. Activation of the carboxylic acid can be accomplished via the acid chloride or by using standard coupling reagents such as HATU in the presence of a tertiary amine base such as DIPEA, triethylamine or the like. For leading references to amide bond formation, see: Smith, M. B. and March, J. "March's Advanced Organic Chemistry", 5th Ed., John Wiley and Sons, New York, pp. 506 to 512 (2001) and references cited therein.

SCHEME 14

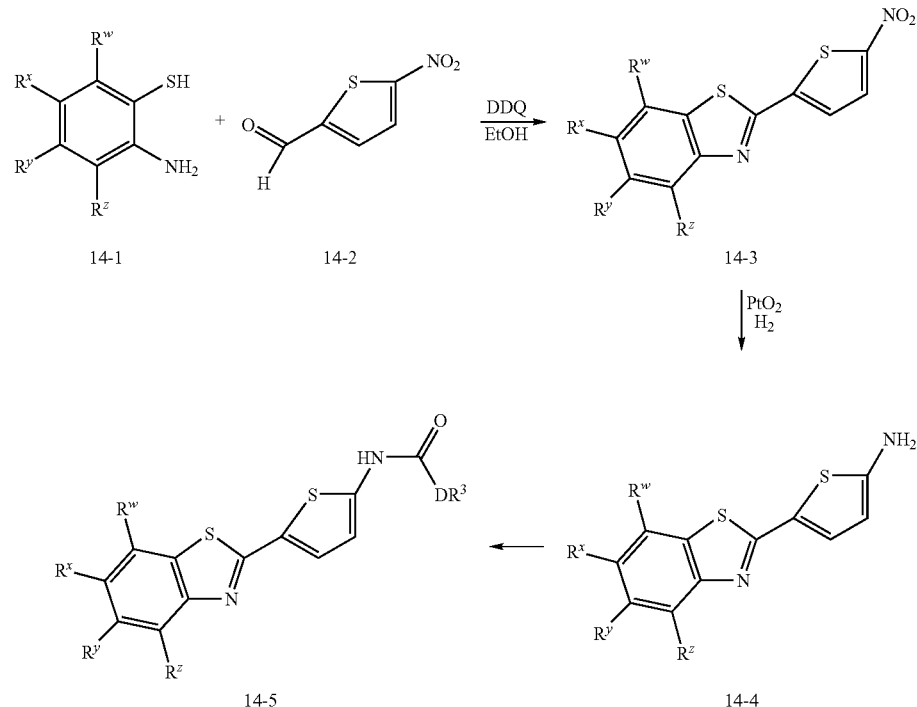

Compounds 14-5 of the present invention wherein $R^w$, $R^x$, $R^y$, $R^z$, D, and $R^3$ are as defined in the claims can be prepared as shown in Scheme 14. Commercially available 5-nitrothiophene-2-carbaldehyde 14-2 can be coupled with an appropriately substituted aromatic amino-thiol 14-1 under reflux in DMSO as described in Shi et. al., J. Med. Chem., 1996, 39, 3375 and references therein. Other methods for benzothiazole formation are available. For a leading reference on methods to form benzothiazoles, see Joule, J. A. and Mills, K. "Heterocyclic Chemistry", 4th Ed., Blackwell Science, Inc., Maiden, Mass., pp. 449-458 and references

SCHEME 15

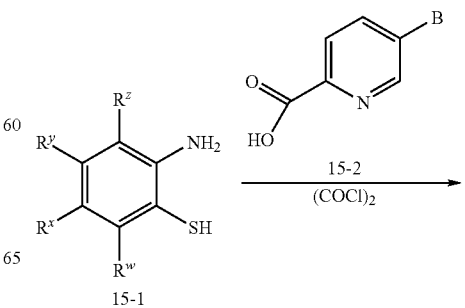

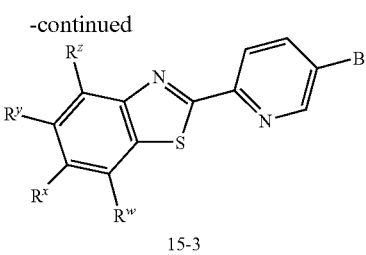

15-3

Compounds 15-3 of the present invention wherein $R^w$, $R^x$, $R^y$, $R^z$, and B are as defined in the claims can be prepared as shown in Scheme 15. Compounds 15-2 can be activated as the acid chloride using oxalyl chloride and catalytic DMF. Condensation of the acid chloride of 15-2 with aromatic amino-thiol 15-1 can afford benzothiazole 15-3. Amino-thiols 15-1 are commercially available or prepared using standard methods.

SCHEME 16

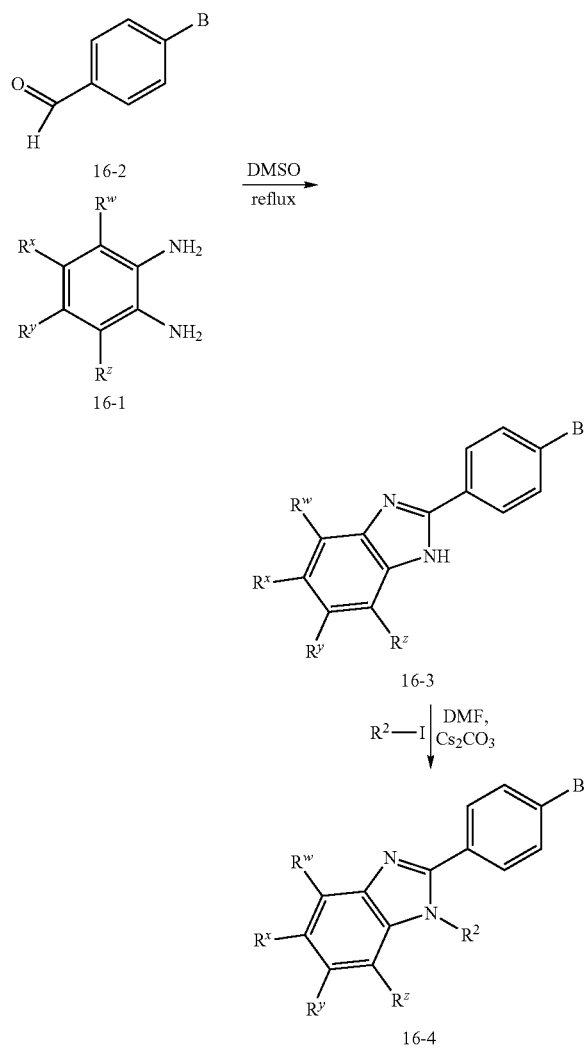

Compounds 16-3 and 16-4 of the present invention wherein $R^w$, $R^x$, $R^y$, $R^z$, $R^2$ and B are as defined in the claims can be prepared as shown in Scheme 16. Condensation of 16-2 with an appropriately substituted diamine 16-1 can afford benz-imidazoles 16-3. For a leading reference on methods to form benzimidazoles, see Joule, J. A. and Mills, K. "Heterocyclic Chemistry", 4th Ed., Blackwell Science, Inc., Maiden, Mass., pp. 449-458 and references therein. Alkylation of benzimidazole 16-3 with an appropriate alkyl iodide or bromide in DMF using $CS_2CO_3$ as a base afforded alkylated benzimidazoles 16-4 and can give rise to a mixture of regioisomers. Other alkylating reagents, bases, and solvents may be used to carry out this transformation.

SCHEME 17

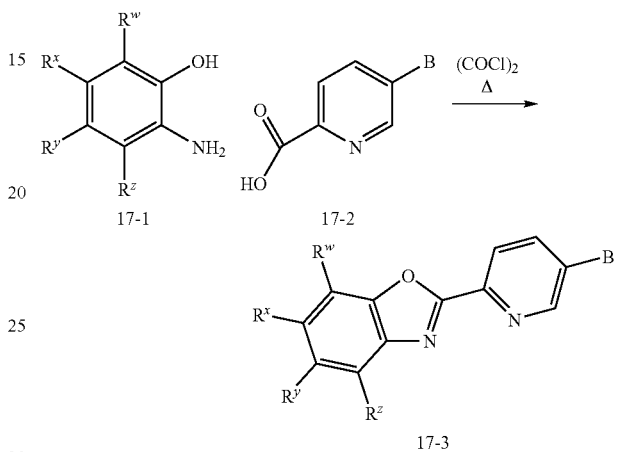

Compounds 17-3 of the present invention wherein $R^w$, $R^x$, $R^y$, $R^z$, and B are as defined in the claims can be prepared as shown in Scheme 17. Compound 17-2 can be activated as the acid chloride using oxalyl chloride and catalytic DMF which can then be condensed with an appropriately substituted amino-alcohol 17-1 to afford benzoxazoles 17-3. Amino-alcohols 17-1 are commercially available or prepared using standard methods.

Intermediate 1

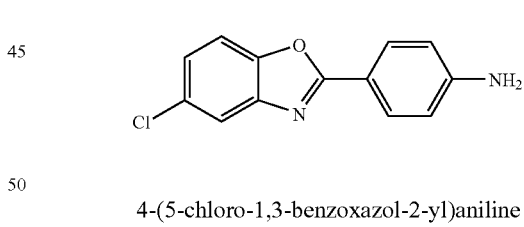

4-(5-chloro-1,3-benzoxazol-2-yl)aniline

Polyphosphoric acid (ca 50 g) was heated until it liquefied (ca. 50° C.). A mixture of 10.0 g of 2-amino-4-chlorophenol and 9.6 g of 4-aminobenzoic acid was added all at once, stirring with a spatula to dissolve solids. The mixture was heated to 150° C. for 15 min, and then poured into ca. 500 mL of ice water. The solid was filtered and washed with water, then resuspended in ca 70 mL of 1N $Na_2CO_3$ and filtered again, washing with water. The resulting gray solid was suspended in toluene and concentrated, then dried for 1 h under vacuum. The residue was preadsorbed onto ca 40 g of silica gel and purified by flash column chromatography on a Biotage Horizon, 65i column, eluting with 1 column volume of 1% EtOAc in $CH_2Cl_2$, followed by a linear gradient of EtOAc in $CH_2Cl_2$ from 1 to 100% over 10 column volumes to provide the title compound. Mass spectrum (ESI) 245.1

(M+1). $^1$H NMR (500 MHz, DMSO): δ 7.84 (d, J=8.5 Hz, 2H), 7.72 (d, J=2 Hz, 1H), 7.67 (dd, J=3.5, 8.5 Hz, 1H), 7.31 (dd, J=2, 8.5 Hz, 1H), 6.69 (dd, J=3.5, 9 Hz, 2H), 6.05 (s, 2H).

Intermediate 2

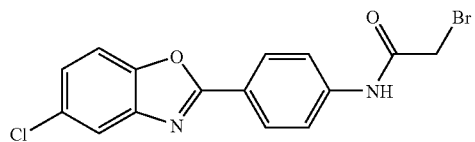

2-bromo-N-[4-(5-chloro-1,3-benzoxazol-2-yl)phenyl]acetamide

To a −78° C. suspension of 0.40 g of 4-(5-chloro-1,3-benzoxazol-2-yl)aniline (INTERMEDIATE 1) in 50 mL of CH$_2$Cl$_2$ was added 0.16 mL of bromoacetylbromide and 0.34 mL of diisopropylethylamine. The cooling bath was removed and the mixture was stirred overnight at r.t., and then diluted with 50 mL of EtOAc and washed with 50 mL of saturated NaHCO$_3$ solution and 50 mL of brine. The organic phase was dried over Na$_2$SO$_4$ and concentrated. The residue was preadsorbed onto 2 g of silica gel and purified by flash column chromatography on a Biotage Horizon, 40M column, eluting with 1 column volume of 1% EtOAc in CH$_2$Cl$_2$, followed by a linear gradient of EtOAc in CH$_2$Cl$_2$ from 1 to 100% over 10 column volumes to provide the title compound. Mass spectrum (ESI) 367.0 (M+1). $^1$H NMR (500 MHz, CDCl$_3$): δ 8.07 (d, J=9 Hz, 2H), 7.68 (d, J=9 Hz, 2H), 7.59 (d, J=2 Hz, 1H), 7.40 (d, J=8.5 Hz, 1H), 7.22 (dd, J=2, 8.5 Hz, 1H), 3.87 (s, 2H).

Example 1

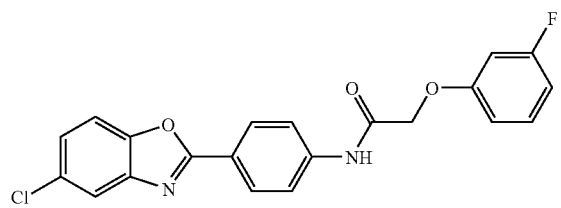

N-[4-(5-chloro-1,3-benzoxazol-2-yl)phenyl]-2-(3-fluorophenoxy)acetamide

A solution of 5.3 μL of 3-fluorophenol, 10.2 mg of potassium carbonate, and 18 mg of 2-bromo-N-[4-(5-chloro-1,3-benzoxazol-2-yl)phenyl]acetamide (INTERMEDIATE 2) in 1 mL of DMF was stirred overnight at r.t., and then diluted with 10 mL of water. The precipitate was collected by filtration, dissolved in chloroform, and purified by flash column chromatography on a Biotage Horizon, 25S column, eluting with 1 column volume of 1% EtOAc in CH$_2$Cl$_2$, followed by a linear gradient of EtOAc in CH$_2$Cl$_2$ from 1 to 100% over 10 column volumes to provide the title compound. Mass spectrum (ESI) 397.1 (M+1). $^1$H NMR (500 MHz, CDCl$_3$): δ 8.38, (s, 1H), 8.23 (dd, J=2, 7 Hz, 2H), 7.79 (dd, J=2, 7 Hz, 2H), 7.72 (s, 1H), 7.49 (d, J=8.5 Hz, 1H), 7.30-7.33 (m, 2H), 6.74-6.81 (m, 3H), 4.64 (s, 2H).

Example 2

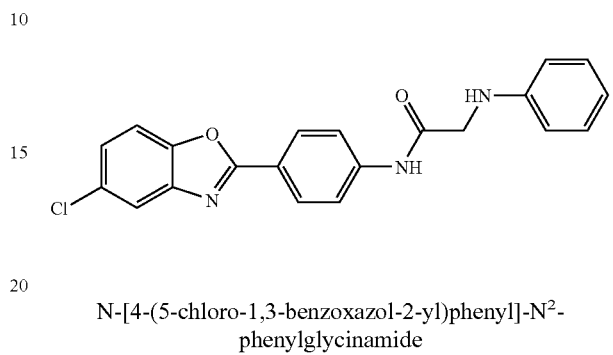

N-[4-(5-chloro-1,3-benzoxazol-2-yl)phenyl]-N$^2$-phenylglycinamide

A solution of 13 μL of aniline, 29 μL of diisopropylethylamine, and 47 mg of 2-bromo-N-[4-(5-chloro-1,3-benzoxazol-2-yl)phenyl]acetamide (INTERMEDIATE 2) in 1 mL of DMSO was stirred for 3 days at r.t., and then filtered and purified by reverse-phase HPLC on a Metachem Basic C8 21×100 mm column, eluting at 20 mL/min with a gradient of 30%) in water (0.1% TFA) to 100% acetonitrile (0.1% TFA over 8 min to yield the title compound. Mass spectrum (ESI) 378.1 (M+1). $^1$H NMR (500 MHz, CD$_3$OD): δ 8.18 (d, J=9 Hz, 2H), 7.82 (d, J=9 Hz, 2H), 7.70 (d, 2.5 Hz, 1H), 7.63 (d, J=8.5 Hz, 1H), 7.38 (dd, 2, 8.5 Hz, 1H), 7.18-7.22 (m, 2H), 6.77-6.82 (m, 3H), 4.00 (s, 2H).

Example 3

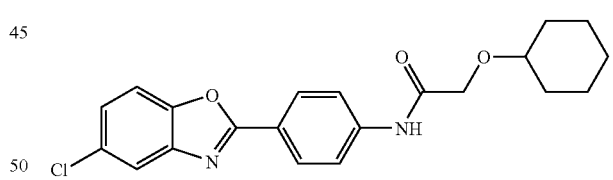

N-[4-(5-chloro-1,3-benzoxazol-2-yl)phenyl]-2-(cyclohexcyloxy)acetamide

Following the procedure described in EXAMPLE 8, 35 mg of (cyclohexyloxy)acetic acid, 89 μL of a 2M solution of oxalyl chloride in CH$_2$Cl$_2$, 54 mg of 4-(5-chloro-1,3-benzoxazol-2-yl)aniline (INTERMEDIATE 1) and 39 μL of diisopropylethylamine provided the title compound. Mass spectrum (ESI) 385.1 (M+1). $^1$H NMR (500 MHz, DMSO): δ 9.97, (s, 1H), 8.14 (d, J=9 Hz, 2H), 7.91 (d, J=9 Hz, 2H), 7.87 (d, J=2 Hz, 1H), 7.79 (d, J=8.5 Hz, 1H), 7.43 (dd, J=2.5, 9 Hz, 1H), 4.10 (s, 2H), 3.38 (m, 1H), 1.89-1.92 (m, 2H), 1.67-1.70 (m, 2H), 1.47-1.50 (m, 1H), 1.17-1.33 (m, 5H).

Intermediate 3

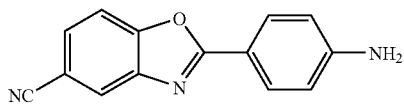

2-(4-aminophenyl)-1,3-benzoxazole-5-carbonitrile

Step A. 3-amino-4-hydroxybenzonitrile

To a suspension of 10.0 g of 4-hydroxy-3-nitrobenzonitrile and 19.0 g of ammonium formate in 150 mL of MeOH was added portionwise 1.0 g of 10% palladium on carbon. The mixture spontaneously refluxed after addition of the catalyst was complete, and was maintained at reflux with the use of a heating bath for a total of 1 h. The mixture was cooled, filtered through a pad of Celite, washing liberally with MeOH, and concentrated. The residue was preadsorbed onto ca. 25 g of silica gel and purified by flash column chromatography on a Biotage Horizon, 65i column, eluting with 1 column volume of 5% EtOAc in $CH_2Cl_2$, followed by a linear gradient of EtOAc in $CH_2Cl_2$ from 5 to 100% over 10 column volumes to provide the title compound. Mass spectrum (ESI) 135.0 (M+1).

Step B.
N-(5-cyano-2-hydroxyphenyl)-4-nitrobenzamide

A solution of 8.0 g of 3-amino-4-hydroxybenzonitrile (Step A) and 11.1 g of 4-nitrobenzoyl chloride in 500 mL of dioxane was heated to 100° C. and stirred overnight at this temperature. The mixture was then cooled and poured into 500 mL of 2 N NaOH, and extracted with 2×1000 mL of EtOAc. The aqueous phase was neutralized with concentrated HCl and extracted with 1000 mL of EtOAc. The combined extracts were washed with 1000 mL of brine, dried over $Na_2SO_4$, and concentrated. The residue was preadsorbed onto ca. 100 g of silica gel and purified by flash column chromatography on a Biotage Horizon, 2×65i column, eluting with 1 column volume of 5% EtOAc in $CH_2Cl_2$, followed by a linear gradient of EtOAc in $CH_2Cl_2$ from 5 to 100% over 10 column volumes, followed by 5 column volumes of 10% MeOH in $CH_2Cl_2$, followed by 5 column volumes of 100% MeOH in $CH_2Cl_2$, to provide the title compound. Mass spectrum (ESI) 284.1 (M+1).

Step C.
2-(4-nitrophenyl)-1,3-benzoxazole-5-carbonitrile

To a suspension of 9.5 g of N-(5-cyano-2-hydroxyphenyl)-4-nitrobenzamide (Step B) in 2 L of toluene in a round-bottom flask equipped with a reflux condenser and a Dean-Stark trap was added 3 g of p-toluenesulfonic acid. The mixture was heated to reflux and stirred at this temperature overnight, and the solids gradually went into solution. The solution was cooled and concentrated, and the resulting solid was recrystallized from EtOH to the title compound, mixed with a small amount of p-toluenesulfonic acid. This material was used in Step D without further purification. Mass spectrum (ESI) 254.1 (M+1).

Step D.
2-(4-aminophenyl)-1,3-benzoxazole-5-carbonitrile

To a suspension of ca. 9 g of 2-(4-nitrophenyl)-1,3-benzoxazole-5-carbonitrile (Step C) and 10.7 g of ammonium formate in 1.2 L of MeOH was added portionwise 500 mg of 10% palladium on carbon. The mixture was heated to reflux and stirred for 2 days at this temperature. The hot solution was then filtered through a pad of Celite and concentrated. The residue was purified by trituration with hot MeOH to provide the title compound. Mass spectrum (ESI) 236.1 (M+1). $^1$H NMR (500 MHz, DMSO): δ 8.20 (d, 1.5 Hz, 1H) 8.87 (m, 3H), 7.76 (dd, J=1.5, 8 Hz, 1H), 6.69 (d, J=8.5 Hz, 2H), 6.13 (s, 2H).

Intermediate 4

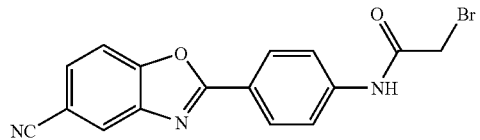

2-bromo-N-[4-(5-cyano-1,3-benzoxazol-2-yl)phenyl] acetamide

Following the procedure described in INTERMEDIATE 2, 0.46 g of 2-(4-aminophenyl)-1,3-benzoxazole-5-carbonitrile (INTERMEDIATE 3), 0.41 mL of diisopropylethylamine, and 0.19 mL of bromoacetylbromide provided the title compound. Mass spectrum (ESI) 358.0 (M+1). $^1$H NMR (500 MHz, DMSO): δ 10.7 (s, 1H), 8.37 (s, 1H), 8.30 (d, J=8.5 Hz, 2H), 7.99 (d, 8.5 Hz, 1H), 7.87 (dd, J=1.5, 8.5 Hz, 1H), 7.84 (d, J=9 Hz, 2H), 4.09 (s, 2H).

Intermediate 5

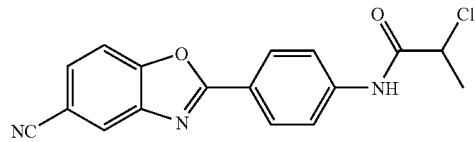

2-chloro-N-[4-(5-cyano-1,3-benzoxazol-2-yl)phenyl] propanamide

Following the procedure described in INTERMEDIATE 2, 0.1 g of 2-(4-aminophenyl)-1,3-benzoxazole-5-carbonitrile (INTERMEDIATE 3), 45 μL of diisopropylethylamine, and 54 μL of 2-chloropropionyl chloride provided the title compound. Mass spectrum (ESI) 326.2 (M+1). $^1$H NMR (500

MHz, CDCl₃): δ 8.45 (s, 1H), 8.28 (d, J=8.5 Hz, 2H), 8.05 (s, 1H), 7.80 (d, J=8.5 Hz, 2H), 7.65 (m, 2H), 4.61 (q, J=5 Hz, 1H), 1.90 (d, J=5 Hz, 1H).

Example 4

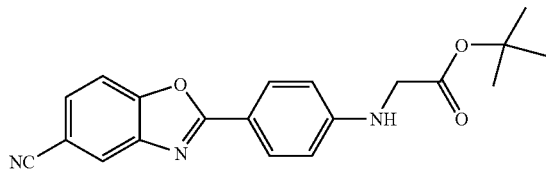

tert-Butyl
N-[4-(5-cyano-1,3-benzoxazol-2-yl)phenyl]glycinate

To a solution of 50 mg of 2-(4-aminophenyl)-1,3-benzoxazole-5-carbonitrile (INTERMEDIATE 3) in 1 mL of DMF was added 10 mg of NaH (60% dispersion in oil). After stirring 30 min at r.t., this solution was added by syringe to a solution of 50 mg of tert-butylbromoacetate in 0.5 mL of DMF and the resulting mixture was stirred overnight at r.t. The mixture was quenched by addition of 0.5 mL of MeOH, then concentrated, diluted with minimal CH₂Cl₂, and purified by preparative thin-layer chromatography on a 1000-μM plate, eluting with 1% MeOH in CH₂Cl₂ to provide the title compound. (ESI) 350.2 (M+1). ¹H NMR (500 MHz, CDCl₃): δ 8.06 (dd, J=2, 7 Hz, 2H), 7.96 (s, 1H), 7.57 (m, 2H), 6.67 (dd, J=2, 7 Hz, 2H), 4.84 (m, 2H), 3.88 (d, J=5 Hz, 2H), 1.51 (s, 9H).

Example 5

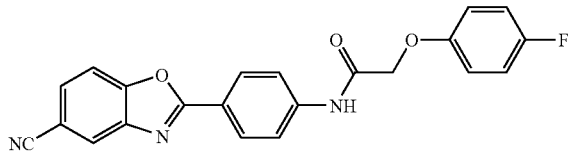

N-[4-(5-cyano-1,3-benzoxazol-2-yl)phenyl]-2-(4-fluorophenoxy)acetamide

Following the procedure described in EXAMPLE 1, 13.5 mg of 4-fluorophenol, 19 mg of potassium carbonate, and 33 mg of 2-bromo-N-[4-(5-cyano-1,3-benzoxazol-2-yl)phenyl]acetamide (INTERMEDIATE 4) gave the title compound. (ESI) 388.1 (M+1). ¹H NMR (500 MHz, CDCl₃): δ 8.65, (s, 1H), 8.23 (d, J=9 Hz, 2H), 8.03 (s, 1H), 7.80 (d, J=9 Hz, 2H), 7.63 (m, 2H), 7.03 (m, 2H), 6.90-6.96 (m, 21H), 4.59 (s, 2H).

Example 6

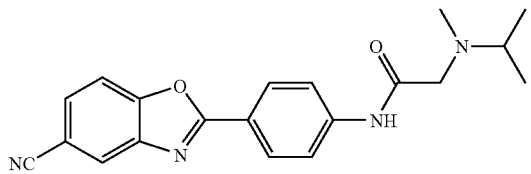

N¹-[4-(5-cyano-1,3-benzoxazol-2-yl)phenyl]-N²-isopropyl-N²-methylglycinamide

Following the procedure described in EXAMPLE 2, 11 μL of N-methylcyclohexanamine, 14 μL of isopropylmethylamine, and 25 mg of 2-bromo-N-[4-(5-cyano-1,3-benzoxazol-2-yl)phenyl]acetamide (INTERMEDIATE 4) gave the title compound. Mass spectrum (ESI) 349.3 (M+1). ¹H NMR (500 MHz, DMSO): δ 10.02, (s, 1H), 8.36 (s, 1H), 8.17 (d, J=8.5 Hz, 2H), 7.98 (d, J=8.5 Hz, 1H), 7.95 (d, J=8.5 Hz, 2H), 7.87 (dd, J=1.5, 8.5 Hz, 1H), 3.16 (s, 2H), 2.88 (m, 1H) 2.25 (s, 3H), 1.01 (d, J=7 Hz, 6H).

Intermediate 6

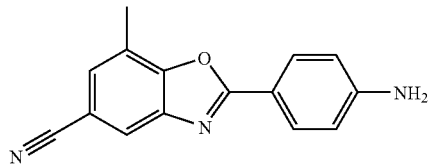

2-(4-aminophenyl)-7-methyl-1,3-benzoxazole-5-carbonitrile

Step A: 4-bromo-2-methyl-6-nitrophenol

To a stirred mixture of 4-bromo-2-methylphenol (10.0 g, 53.5 mmol) in 53 ml acetic acid at 0° C. was added dropwise over 30 minutes a solution of fuming HNO₃ (3.24 ml, 69.6 mmol) in 16 ml acetic acid. The reaction mixture was stirred for an additional 15 minutes, then poured into 200 ml ice/water. A yellow solid precipitated, which was washed with water. The solid was then diluted with dichloromethane, dried over sodium sulfate, and concentrated under reduced pressure to give 11 g of crude, which was separated in 3 batches. Each batch was purified by flash column chromatography on a Biotage Horizon, 65I Si column, eluting with 1 column volume of hexanes, followed by a linear gradient of dichloromethane in hexanes from 23% to 100% over 10 column volumes. The three batches of pure product were combined to provide the title compound. ¹H NMR (500 MHz, CDCl₃): δ 2.33 (s, 3H); 7.55 (d, J=1.4 Hz, 1H); 8.10 (d, J=2.6 Hz, 1H); 10.82 (s, 1H).

Step B: 2-amino-4-bromo-6-methylphenol

To a stirred mixture of 4-bromo-2-methyl-6-nitrophenol (Step A) (640 mg, 2.76 mmol) in 12 ml of methanol was added 6.6 ml of concentrated HCl. The resulting mixture was chilled in an ice bath and tin chloride bishydrate (2.98 g, 13.2 mmol) was added. The ice bath was removed after 10 minutes and the reaction mixture was stirred at room temperature for ca. 24 hours. Ethyl acetate and saturated aqueous sodium bicarbonate (till pH~7) were then added to the reaction. The resulting white, milky mixture was filtered through a pad of celite washing with ethyl acetate. The layers of the filtrate were separated and the aqueous layer was extracted with ethyl acetate. The combined organics were washed with brine, dried over sodium sulfate, and concentrated under reduced pressure to provide the title compound, which was used without further purification. Mass spectrum (ESI) 202.0 (M+1);

204.0 (M+3). ¹H NMR (400 MHz, CDCl₃): δ 2.19 (s, 3H); 3.63 (br s, 2H); 4.60 (br s, 1H); 6.72 (d, J=2.1 Hz, 1H); 6.76 (d, J=2.2 Hz, 1H).

Step C:
5-bromo-7-methyl-2-(4-nitrophenyl)-1,3-benzoxazole

To a stirred mixture of 2-amino-4-bromo-6-methylphenol (Step B) (500 mg, 2.47 mmol) in 40 ml of 1,4-dioxane was added 4-nitrobenzoyl chloride (458 mg, 2.47 mmol). The resulting mixture was heated to reflux for 14.5 hrs, then, concentrated under reduced pressure, and added 100 ml of toluene and a catalytic amount of p-toluenesulfonic acid monohydrate. The resulting mixture was refluxed using a Dean-Stark trap for 6 hours, then, concentrated under reduced pressure to provide the title compound, which was used without further purification. Mass spectrum (ESI) 333.0 (M+1); 335.0 (M+3). ¹H NMR (400 MHz, CDCl₃): δ 2.60 (s, 3H); 7.37 (d, J=0.7 Hz, 1H); 7.78 (d, J=1.4 Hz, 1H); 8.41 (m, 4H).

Step D:
4-(5-bromo-7-methyl-1,3-benzoxazol-2-yl)aniline

To a stirred mixture of 5-bromo-7-methyl-2-(4-nitrophenyl)-1,3-benzoxazole (Step C) (213 mg, 0.64 mmol) in 10 ml dichloromethane was added 10% Pd/C (64 mg). The resulting mixture was flushed with nitrogen, degassed and then flushed 3 times with hydrogen from a double balloon. The reaction was stirred under hydrogen atmosphere for 1.5 hours, then, diluted with dichloromethane and the catalyst was filtered. The filtrate was concentrated, dissolved with dichloromethane/methanol, preadsorbed on silica gel, and purified by flash column chromatography on a Biotage Horizon, 40M Si column, eluting with 1 column volume of CH₂Cl₂, followed by a linear gradient of EtOAc in CH₂Cl₂ from 0% to 100% over 10 column volumes to provide the title compound. Mass spectrum (ESI) 303.0 (M+1); 305.0 (M+3). ¹H NMR (500 MHz, CDCl₃): δ 2.53 (s, 3H); 4.07 (br s, 2H); 6.76 (d, J=8.5 Hz, 2H); 7.21 (s, 1H); 7.64 (s, 1H); 8.04 (d, J=8.7 Hz, 2H).

Step E: 2-(4-aminophenyl)-7-methyl-1,3-benzoxazole-5-carbonitrile

To a stirred mixture of 4-(5-bromo-7-methyl-1,3-benzoxazol-2-yl)aniline (Step D) (1.97 g, 6.50 mmol) in 32 ml NMP was added CuCN (699 mg, 7.80 mmol) and the resulting mixture was heated at 190° C. under nitrogen for ca. 20 hours. The reaction was then cooled to room temperature, added 200 ml EtOAc and 200 ml of water, and stirred the resulting mixture vigorously for ca. 40 hours. The layers were separated adding saturated aqueous sodium bicarbonate and brine to help with emulsion. The aqueous layer was extracted 5 times with EtOAc and the combined organics were washed with brine, dried over sodium bicarbonate and concentrated under reduced pressure. The crude (2.39 g) was preadsorbed on silica gel and purified by flash column chromatography on a Biotage Horizon, 651 Si column, eluting with 1 column volume of CH₂Cl₂, followed by a linear gradient of EtOAc in CH₂Cl₂ from 0% to 100% over 10 column volumes to provide the title compound. Mass spectrum (ESI) 250.1 (M+1). ¹H NMR (500 MHz, CDCl₃): δ 2.59 (s, 3H); 4.13 (br s, 2H); 6.77 (d, J=8.4 Hz, 2H); 7.38 (s, 1H); 7.82 (s, 1H); 8.06 (d, J=8.4 Hz, 2H).

Example 7

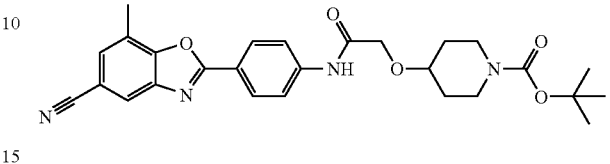

tert-butyl 4-(2-{[4-(5-cyano-7-methyl-1,3-benzoxazol-2-yl)phenyl]amino}-2-oxoethoxy)piperidine-1-carboxylate Step A: {[1-(tert-butoxycarbonyl)piperidin-4-yl]oxy}acetic acid To a stirred solution of N-Boc-4-hydroxypiperidine(5.60 g, 27.8 mmol) in 50 ml THF at 0° C. under nitrogen was added NaH (60% in mineral oil, 2.34 g, 58.4 mmol). The resulting mixture was stirred at room temperature for ca. 2 hours. Then, cooled again to 0° C. and bromoacetic acid (3.86 g, 27.8 mmol) was added and the resulting mixture was stirred under nitrogen for ca. 20 hours. The mixture was made basic with 1M aqueous NaOH and extracted 2 times with ethyl ether. The aqueous layer was acidified with dilute HCl and extracted 3 times with EtOAc. The combined EtOAc layers were washed with brine, dried over sodium sulfate, and concentrated under reduced pressure to provide the title compound, which was used without further purification. ¹H NMR (500 MHz, CDCl₃): δ 1.45 (s, 9H); 1.58 (m, 2H); 1.87 (m, 2H); 3.08 (m, 2H); 3.60 (m, 11H); 3.80 (m, 2H); 4.16 (s, 2H).

Step B: tert-butyl 4-(2-{[4-(5-cyano-7-methyl-1,3-benzoxazol-2-yl)phenyl]amino}-2-oxoethoxy)piperidine-1-carboxylate To a solution of {[1-(tert-butoxycarbonyl)piperidin-4-yl]oxy}acetic acid (Step A) (427 mg, 1.65 mmol) in 5 ml CH₂Cl₂, at room temperature under nitrogen, was added oxalyl chloride (2M solution in CH₂Cl₂, 910 μl, 1.82 mmol) followed by 1 drop of DMF. The resulting mixture was stirred under N₂ until the gas evolution ceased, then, concentrated and azeotroped with toluene. It was then diluted with 10 ml THF and, under nitrogen, 2-(4-aminophenyl)-7-methyl-1,3-benzoxazole-5-carbonitrile (INTERMEDIATE 6) (200 mg, 0.802 mmol) was added followed by diisopropylethyl amine (698 μl, 4.01 mmol). After 5 minutes the reaction mixture was concentrated under reduced pressure, dissolved in hot ethanol and kept at room temperature for 5 days. 279 mg of product crystallized as a yellowish solid. The solids were filtered and washed with ethanol. The filtrate was concentrated, dissolved in hot EtOH and kept at room temperature for 1 day. 81 mg of product was collected which was combined with the first batch to provide the title compound. Mass spectrum (ESI) 491.4 (M+1). ¹H NMR (400 MHz, CDCl₃): δ 1.48 (s, 9H); 1.63 (m, 2H); 1.95 (m, 2H); 2.63 (s, 3H); 3.11 (m, 2H); 3.65

(m, 1H); 3.87 (m, 2H); 4.15 (s, 2H); 7.44 (s, 1H); 7.79 (d, J=8.8 Hz, 2H); 7.88 (s, 1H); 8.25 (d, J=8.8 Hz, 2H); 8.49 (s, 1H).

Example 8

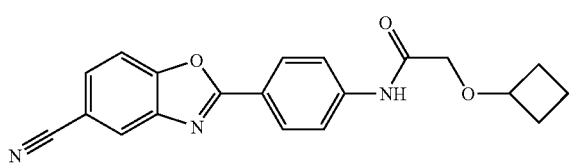

N-[4-(5-cyano-1,3-benzoxazol-2-yl)phenyl]-2-(cyclobutyloxy)acetamide

Step A: (cyclobutyloxy)acetic acid

The title compound was prepared from cyclobutanol and bromoacetic acid by a procedure analogous to that described in EXAMPLE 7, Step A. $^1$H NMR (500 MHz, CDCl$_3$): δ 1.52 (m, 1H); 1.74 (m, 1H); 2.01 (m, 2H); 2.24 (m, 2H); 4.03 (s, 2H); 4.06 (m, 1H).

Step B: N-[4-(5-cyano-1,3-benzoxazol-2-yl)phenyl]-2-(cyclobutyloxy)acetamide

To a solution of (cyclobutyloxy)acetic acid (Step A) (24 mg, 0.18 mmol) in 2 ml CH$_2$Cl$_2$ under nitrogen was added oxalyl chloride (2M solution in CH$_2$Cl$_2$, 100 μl, 0.20 mmol) followed by 1 drop of DMF. After ca. 1 hour 2-(4-aminophenyl)-1,3-benzoxazole-5-carbonitrile (INTERMEDIATE 3) (20 mg, 0.085 mmol) was added followed by diisopropylethyl amine (76 μl, 0.44 mmol). The resulting mixture was stirred at room temperature overnight. The product was purified by flash column chromatography on a Biotage Horizon, 25M Si column, eluting with 1 column volume of 2% EtOAc in CH$_2$Cl$_2$, followed by a linear gradient of EtOAc in CH$_2$Cl$_2$ from 2% to 100% over 10 column volumes. A second purification was necessary using thin layer chromatography (2×1000 μm plates), eluting with 10% EtOAc in CH$_2$Cl$_2$ to provide the title compound. Mass spectrum (ESI) 348.2 (M+1). $^1$H NMR (500 MHz, CDCl$_3$): δ 1.58 (m, 1H); 1.79 (m, 1H); 2.04 (m, 2H); 2.30 (m, 2H); 4.00 (s, 2H); 4.09 (m, 1H); 7.65 (m, 2H); 7.81 (m, 2H); 8.05 (s, 1H); 8.24 (m, 2H); 8.51 (s, 1H).

Intermediate 7

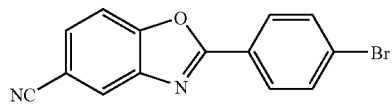

2-(4-bromophenyl)-1,3-benzoxazole-5-carbonitrile

A solution of 5.5 g of 3-amino-4-hydroxybenzonitrile (INTERMEDIATE 3, Step A) and 9.0 g of 4-bromobenzoyl chloride in 350 mL of dioxane was heated to reflux and stirred overnight at this temperature. The mixture was then cooled and concentrated and the residue dissolved in 400 mL of toluene in a round-bottom flask equipped with a reflux condenser and a Dean-Stark trap. p-Toluenesulfonic acid (ca. 0.1 g) was added and the mixture was heated to reflux and stirred at this temperature for 4 h. The solution was cooled and concentrated, and the resulting solid was triturated with 2×100 mL of hot MeOH. The solids were collected by filtration and dried overnight under vacuum to provide the title compound. Mass spectrum (ESI) 301.1 (M+1). $^1$H NMR (500 MHz, DMSO): δ 8.41 (s, 1H) 8.13 (d, J=8.5 Hz, 2H), 8.01 (d, J=8.5 Hz, 1H), 7.90 (dd, J=1, 8 Hz, 1H), 7.84 (d, J=8.5 Hz, 2H).

Intermediate 8

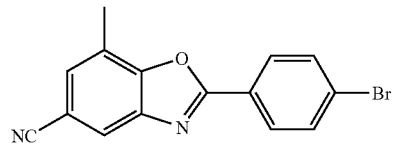

2-(4-bromophenyl)-7-methyl-1,3-benzoxazole-5-carbonitrile

Step A: 4-hydroxy-3-methyl-5-nitrobenzonitrile

The title compound was prepared from 4-bromo-2-methyl-6-nitrophenol (INTERMEDIATE 6, Step A) and CuCN by a procedure analogous to that described in INTERMEDIATE 6, Step E. $^1$H NMR (400 MHz, CDCl$_3$): δ 2.39 (s, 3H); 7.68 (s, 1H); 8.33 (d, J=1.9 Hz, 1H); 11.24 (s, 1H).

Step B: 3-amino-4-hydroxy-5-methylbenzonitrile

The title compound was prepared from 4-hydroxy-3-methyl-5-nitrobenzonitrile (Step A), Pd/C, and ammonium formate by procedure analogous to that described in INTERMEDIATE 3, Step A. $^1$H NMR (400 MHz, CD$_3$OD): δ 2.19 (s, 3H); 6.81 (s, 1H); 6.84 (d, J=1.9 Hz, 1H).

Step C: 2-(4-bromophenyl)-7-methyl-3-benzoxazole-5-carbonitrile

Following the procedure described in INTERMEDIATE 7, 0.75 g of 3-amino-4-hydroxy-5-methylbenzonitrile and 1.10 g of 4-bromobenzoyl chloride provided the title compound. Mass spectrum (ESI) 315.1 (M+1). $^1$H NMR (500 MHz, CDCl$_3$): δ 8.13 (d, J=8.5 Hz, 2H), 7.91 (s, 1H), 7.70 (d, J=8.5 Hz, 2H), 7.46 (s, 1H), 2.63 (s, 3H).

Example 9

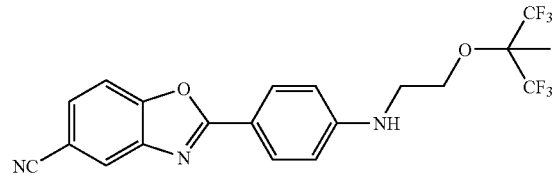

2-[4-({2-[2,2,2-trifluoro-1-methyl-1-(trifluoromethyl)ethoxy]ethyl}amino)phenyl]-1,3-benzoxazole-5-carbonitrile A mixture of 1.11 g of 2-(4-bromophenyl)-1,3-benzoxazole-5-carbonitrile (INTERMEDIATE 7), 1.00 g of 2-[2,2,2-trifluoro-1-methyl-1-(trifluoromethyl)ethoxy]ethanamine (INTERMEDIATE 11), and 498 mg of sodium t-butoxide in 1 mL of toluene was purged and flushed with argon. Tris(dibenzylideneacetone)dipalladium (102 mg) and racemic BINAP (115 mg) were added and the mixture was heated to 80° C. and stirred overnight at this temperature. The reaction mixture was cooled and concentrated, then diluted with CH$_2$Cl$_2$ and filtered, washing with more CH$_2$Cl$_2$. The filtrate was concentrated and purified by flash column chromatography on a Biotage Horizon, 65i column, eluting with 1 column volume of 2% EtOAc in CH$_2$Cl$_2$, followed by a linear gradient of EtOAc in CH$_2$Cl$_2$ from 2 to 100% over 10 column volumes to provide the title compound. Mass spectrum (ESI) 444.2 (M+1). $^1$H NMR (500 MHz, CDCl$_3$): δ 8.07 (d, J=9 Hz, 2H), 7.98 (s, 1H), 7.58 (m, 2H), 6.71 (d, J=8.5 Hz, 2H), 3.93 (t, J=5.5 Hz, 2H), 3.49 (t, J=5.5 Hz, 2H), 1.61 (s, 3H),

Example 10

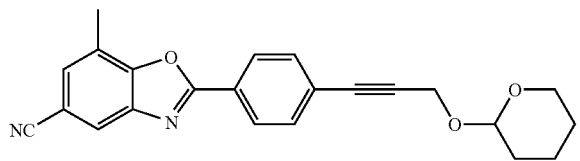

7-methyl-2-{4-[3-(tetrahydro-2H-pyran-2-yloxy)prop 1-yn-1-yl]phenyl}-1,3-benzoxazole-5-carbonitrile To a suspension of 409 mg of 2-(4-bromophenyl)-7-methyl-1,3-benzoxazole-5-carbonitrile in 14 mL of THF and 2 mL of diethylamine was added 10 mg of copper(I) iodide, 30 mg of tetrakis(triphenylphosphine)palladium, and 201 mg of 2-(prop-2-yn-1-yloxy)tetrahydro-2H-pyran. The mixture was heated to 60° C. and stirred for 6 h at this temperature. The reaction mixture was cooled and concentrated. The residue was purified by flash column chromatography on a Biotage Horizon, 40M column, eluting with 1 column volume of CH$_2$Cl$_2$, followed by a linear gradient of EtOAc in CH$_2$Cl$_2$ from 0 to 100% over 10 column volumes to provide unreacted bromide and the title compound. Mass spectrum (ESI) 373.2 (M+1). $^1$H NMR (500 MHz, CDCl$_3$): δ 8.21 (d, J=8.5 Hz, 2H), 7.89 (s, 1H), 7.62 (d, J=8 Hz, 2H), 7.46 (s, 1H), 4.91 (m, 1H), 4.53 (m, 2H). 3.90 (m, 1H), 3.59 (m, 1H), 2.63 (s, 3H), 1.55-1.92 (m, 6H).

Example 11

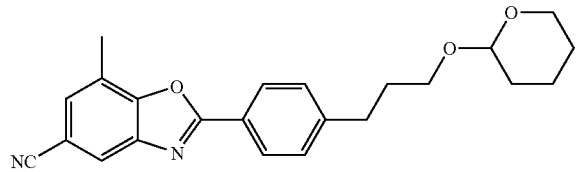

7-methyl-2-{4-[3-(tetrahydro-2H-pyran-2-yloxy)propyl]phenyl}-1,3-benzoxazole-5-carbonitrile A mixture of 50 mg of 7-methyl-2-{4-[3-(tetrahydro-2H-pyran-2-yloxy)prop-1-yn-1-yl]phenyl}-1,3-benzoxazole-5-carbonitrile (EXAMPLE 10) and 15 mg of Lindlar's catalyst in 1 mL of benzene was purged and flushed with argon, and then purged and flushed with hydrogen. The mixture was stirred for 4 h at r.t., and then filtered through Celite, washing liberally with benzene. The filtrate was concentrated to provide the title compound. Mass spectrum (ESI) 377.2 (M+1). $^1$H NMR (500 MHz, CDCl$_3$): δ 8.18 (d, J=8 Hz, 2H), 7.89 (s, 1H), 7.44 (s, 1H), 7.39 (d, J=8.5 Hz, 2H), 4.59 (t, J=3 Hz, 1H), 3.88 (m, 1H). 3.80 (m, 1H), 3.50 (m, 1H), 3.44 (m, 1H), 2.82 (m, 1H), 2.63 (s, 3H), 1.98 (m, 1H), 1.86 (m, 1H), 1.74 (m, 1H), 1.50-1.63 (m, 4H).

Intermediate 9

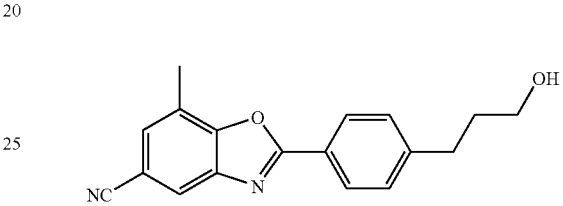

2-[4-(3-hydroxypropyl)phenyl]-7-methyl-1,3-benzoxazole-5-carbonitrile

A solution of 40 mg of 7-methyl-2-{4-[3-(tetrahydro-2H-pyran-2-yloxy)propyl]phenyl}-1,3-benzoxazole-5-carbonitrile (EXAMPLE 11) and ca. 5 mg of p-toluenesulfonic acid in 1 mL of 1:1 methanol-THF was stirred for 15 min at r.t., at which point a precipitate formed. The mixture was concentrated and then redissolved in CH$_2$Cl$_2$, washed twice with water and once with brine, dried over Na$_2$SO$_4$ and concentrated to provide the title compound. Mass spectrum (ESI) 293.2 (M+1). $^1$H NMR (500 MHz, CDCl$_3$): δ 8.19 (d, J=8.5 Hz, 2H), 7.89 (s, 1H), 7.44 (s, 1H), 7.40 (d, J=8 Hz, 2H), 3.72 (t, J=6.5 Hz, 2H), 2.83 (t, J=7.5 Hz, 2H), 2.62 (s, 3H), 1.96 (m, 2H).

Example 12

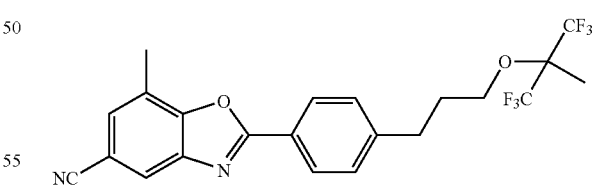

7-methyl-2-(4-{3-[2,2,2-trifluoro-1-methyl-1-(trifluoromethyl)ethoxy]propyl}phenyl)-1,3-benzoxazole-5-carbonitrile To a solution of 29 mg of 2-[4-(3-hydroxypropyl)phenyl]-7-methyl-1,3-benzoxazole-5-carbonitrile (INTERMEDIATE 9), and 50 mg of 1,1'-(azodicarbonyl)dipiperidine in 1 mL of benzene was added 40 mg of tributylphosphine. After stirring for 15 min at r.t., 36 mg of 1,1,1,3,3,3-hexafluoro-2-methylpropan-2-ol was added and the mixture was stirred at r.t. for 2 h. The mixture was then concentrated, diluted with minimal CH$_2$Cl$_2$, and purified by preparative thin-layer chromatography on a 1000-μM plate, eluting with 1% MeOH in CH$_2$Cl$_2$ to provide the title compound. Mass spectrum (ESI) 457.2 (M+1). $^1$H NMR (500 MHz, CDCl$_3$): δ 8.19 (d, J=8 Hz, 2H), 7.89 (s, 1H), 7.44 (s, 1H), 7.38 (d, J=8 Hz, 2H), 3.71 (t, J=5.5 Hz, 2H), 2.83 (t, J=8.0 Hz, 2H), 2.63 (s, 3H), 2.00 (m, 2H), 1.58 (s, 3H).

Example 13

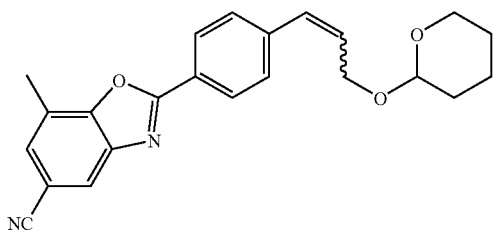

7-methyl-2-{4-[(1Z)-3-(tetrahydro-2H-pyran-2-yloxy)prop-1-en-1-yl]phenyl}-1,3-benzoxazole-5-carbonitrile A mixture of 24 mg of 7-methyl-2-{4-[3-(tetrahydro-2H-pyran-2-yloxy)prop-1-yn-1-yl]phenyl}-1,3-benzoxazole-5-carbonitrile (EXAMPLE 10) and 2 mg of Lindlar's catalyst in 0.5 mL of benzene was purged and flushed with argon, and then purged and flushed with hydrogen. The mixture was stirred for 2.5 h at r.t., and then filtered through Celite, washing liberally with benzene. The filtrate was concentrated and the residue was purified by preparative thin-layer chromatography on a 1000-μM plate, eluting with 5% EtOAc in CH$_2$Cl$_2$ to provide the title compound as a 93:7 mixture of cis and trans isomers. Mass spectrum (ESI) 273.2 (M-THP). $^1$H NMR (500 MHz, CDCl$_3$): δ 8.23 (d, J=8 Hz, 2H), 7.89 (s, 1H), 7.43 (s, 1H), 7.41 (d, J=8.5 Hz, 2H), 6.63 (d, 13.5 Hz, 1H), 6.03 (m, 1H), 4.69 (t, J=3.5 Hz, 1H), 4.54 (ddd, J=1.5, 6, 13 Hz, 1H), 4.31 (ddd, J=2, 7, 13.5 Hz, 1H), 3.88 (m, 1H), 3.52 (m, 1H), 2.62 (s, 3H), 1.50-1.92 (m, 6H).

Intermediate 10

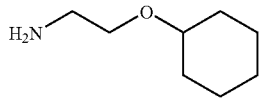

2-(cyclohexyloxy)ethanamine

To a solution of 50 mg of (cyclohexyloxy)acetic acid in 1 mL of CH$_2$Cl$_2$ was added 0.24 mL of oxalyl chloride (2.0M solution in CH$_2$Cl$_2$), and then a drop (ca. 10 μL) of DMF. The mixture was stirred for 45 min at r.t., and then concentrated and co-concentrated with 2 mL of toluene. The residue was dissolved in 1 mL of dioxane and 1 mL of concentrated ammonium hydroxide was added. The mixture was stirred for 2 h at r.t., and then diluted with 5 mL of 1N NaOH and extracted with 3×5 mL of EtOAc. The combined organics were washed with brine, dried (Na$_2$SO$_4$), and concentrated. The residue was dissolved in 1 mL of THF and 1 mL of lithium aluminum hydride (1.0M solution in Et$_2$O) was added dropwise. The mixture was stirred for 2 h at r.t., and then quenched by addition 35 mL of water, 35 mL of 15% NaOH, and then 105 mL of water. The solids were filtered off, washing liberally with Et$_2$O, and the filtrate was concentrated to provide the title compound. $^1$H NMR (500 MHz, CDCl$_3$): δ 3.44 (t, J=4.5 Hz, 2H), 2.69 (t, 4.5 Hz, 2H), 3.20-3.26 (m, 1H), 1.80-1.90 (m, 2H), 1.64-1.72 (m, 2H), 1.46-1.52 (m, 1H), 1.12-1.34 (m, 5H).

Intermediate 11

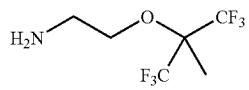

2-[2,2,2-trifluoro-1-methyl-1-(trifluoromethyl)ethoxy]ethanamine

To a solution of 1.79 g of bromoacetamide, 1.6 mL of 1,1,1,3,3,3-hexafluoro-2-methylpropan-2-ol, and 2.15 g of potassium carbonate in 10 mL of DMF was stirred overnight at r.t., and then diluted with 20 mL of water and extracted with 3×10 mL of Et$_2$O. The combined organics were washed with brine, dried (Na$_2$SO$_4$), and concentrated. The residue was dissolved in 10 mL of Et$_2$O and cooled to 0° C., and then 39 mL of lithium aluminum hydride (1.0M solution in Et$_2$O) was added dropwise via addition funnel. The mixture was stirred overnight at r.t., and then recooled to 0° C. and quenched by addition 1.4 mL of water, 1.4 mL of 15% NaOH, and then 4.4 mL of water. The solids were filtered off, washing liberally with Et$_2$O. The filtrate was concentrated to a volume of about 5 mL, and then distilled under reduced pressure to provide the title compound. Mass spectrum (ESI) 358.0 (M+1). $^1$H NMR (500 MHz, CDCl$_3$): δ 3.72 (t, J=5 Hz, 2H), 2.90 (t, 5 Hz, 2H), 1.61 (s, 3H).

Intermediate 12

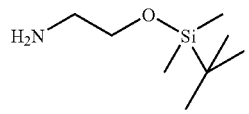

2-{[tert-butyl(dimethyl)silyl]oxy}ethanamine

To a 0° C. solution of 0.1 g of ethanolamine and 0.28 g of imidazole in 0.5 mL of DMF was added 0.3 g of t-butyldimethylsilyl chloride. The mixture was allowed to warm to r.t. and stirred overnight at this temperature. The mixture was then diluted with 5 mL of water and extracted with 3×5 mL of Et$_2$O. The combined organics were washed with brine, dried (Na$_2$SO$_4$), and concentrated. The residue was purified by flash column chromatography on a Biotage Horizon, 25M column, eluting with 1 column volume of 2% MeOH in CH$_2$Cl$_2$, followed by a linear gradient of MeOH in CH$_2$Cl$_2$ from 2 to 40% over 10 column volumes to provide the title compound. ¹H NMR (500 MHz, CDCl₃): δ 3.95 (m, 2H), 3.19 (m, 2H), 0.90 (s, 9H), 0.08 (s, 6H).

Intermediate 13

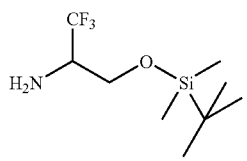

3-{[tert-Butyl(dimethyl)silyl]oxy}-1,1,1-trifluoro-propan-2-amine

Step A. Ethyl N-[(benzyloxy)carbonyl]-3,3,3-trifluoroalaninate

To a solution of 1.5 g of ethyl 2-diazo-3,3,3-trifluoropropanoate (prepared according to Shi & Xu, J. Org. Chem. 1990, 35, 3383) and 1.25 g of benzyl carbamate in 15 mL of CH₂Cl₂ was added 0.1 g of rhodium acetate dimmer. The mixture was stirred overnight at r.t., and then diluted with 50 mL of Et₂O and washed with 50 mL of water. The aqueous phase was extracted with 2×25 ml of Et₂O. The combined organics were washed with brine, dried (Na₂SO₄), and concentrated. The residue was purified by flash column chromatography on a Biotage Horizon, 40S column, eluting with 1 column volume of 1% EtOAc in hexanes, followed by a linear gradient of EtOAc in hexanes from 1 to 100% over 10 column volumes to provide the title compound. ¹H NMR (500 MHz, CDCl₃): δ 7.64 (m, 4H), 5.62 (br d, J=9.5 Hz, 1H), 5.16 (m, 2H), 5.03 (m, 1H), 4.32 (m, 2H), 1.32 (t, J=7 Hz, 3H).

Step B. Benzyl[2,2,2-trifluoro-1-(hydroxymethyl)ethyl]carbamate

To a solution of 0.1 g of ethyl N-[(benzyloxy)carbonyl]-3,3,3-trifluoroalaninate in 1 mL of THF was added 0.084 g of calcium borohydride. The mixture was stirred for 1 h at r.t., and then diluted with 10 mL of water and extracted with 10 mL of EtOAc. The aqueous phase was extracted with 2×10 ml of EtOAc. The combined organics were washed with brine, dried (Na₂SO₄), and concentrated. The residue was purified by flash column chromatography on a Biotage Horizon, 25M column, eluting with 1 column volume of 5% EtOAc in hexanes, followed by a linear gradient of EtOAc in hexanes from 5 to 100% over 10 column volumes to provide the title compound. Mass spectrum H NMR (500 MHz, CDCl₃): δ 7.36 (m, 4H), 5.44 (m, 1H), 5.16 (m, 2H), 4.38 (m, 1H), 3.98 (m, 1H), 3.86 (m, 1H), 1.83 (m, 1H).

Step C. Benzyl[1-({[tert-butyl(dimethyl)silyl]oxy}methyl)-2,2,2-trifluoroethyl]carbamate To a solution of 0.25 g of benzyl[2,2,2-trifluoro-1-(hydroxymethyl)ethyl]carbamate in 2 mL of DMF was added 0.16 g of t-butyldimethylsilyl chloride and 0.12 g of imidazole. The mixture was stirred overnight at r.t., and then co-concentrated with 100 mL of toluene. The residue was diluted with 25 mL of water and extracted with 30 mL of EtOAc. The aqueous phase was extracted with 2×20 ml of EtOAc. The combined organics were washed with brine, dried (Na₂SO₄), and concentrated. The residue was purified by flash column chromatography on a Biotage Horizon, 40Scolumn, eluting with 1 column volume of 1% EtOAc in hexanes, followed by a linear gradient of EtOAc in hexanes from 1 to 100% over 10 column volumes to provide the title compound. ¹H NMR (500 MHz, CDCl₃): δ 7.38 (m, 4H), 5.36 (br d, J=9.5 Hz, 1H), 5.16 (m, 2H), 4.34 (m, 1H), 3.94 (m, 1H), 3.79 (m, 1H), 0.88 (s, 9H), 0.06 (s, 6H).

Step D. 3-{[tert-Butyl(dimethyl)silyl]oxy}-1,1,1-trifluoropropan-2-amine

To a solution of 0.27 g of benzyl[1-({[tert-butyl(dimethyl)silyl]oxy}methyl)-2,2,2-trifluoroethyl]carbamate in 5 mL of MeOH was added 25 mg of 10% palladium on carbon. The mixture was purged and flushed with argon, and then purged and flushed with hydrogen. The mixture was stirred overnight at r.t., and then filtered through Celite, washing with MeOH. The filtrate was concentrated to provide the title compound. ¹H NMR (500 MHz, CDCl₃): δ 3.82 (m, 1H), 3.75 (dd, J=5.5, 10 Hz, 1H), 3.30 (m, 1H), 1.68 (m, 2H), 0.90 (s, 9H), 0.08 (s, 6H).

Example 14

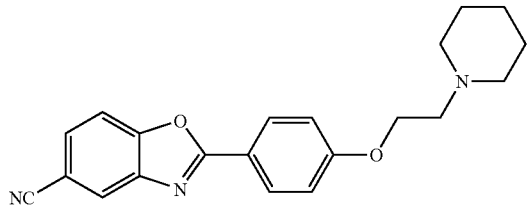

2-[4-(2-piperidin-1-ylethoxy)phenyl]-1,3-benzoxazole-5-carbonitrile

A mixture of 20 mg of 2-(4-bromophenyl)-1,3-benzoxazole-5-carbonitrile (INTERMEDIATE 7), 17 mg of 2-piperidin-1-ylethanol, and 8 mg of sodium hydride (60% dispersion in oil) in 1 mL of toluene was purged and flushed with argon. Tris(dibenzylideneacetone)dipalladium (3 mg) and racemic BINAP (3 mg) were added and the mixture was heated to 80° C. and stirred overnight at this temperature. The reaction mixture was cooled and added directly to a 1000-μM thin-layer chromatography plate, eluting with 4% isopropanol in CH₂Cl₂ to provide 3.4 mg (15%) of the title compound. Mass spectrum (ESI) 348.3 (M+1). ¹H NMR (500 MHz, CDCl₃): δ 8.18 (d, J=8.5 Hz, 2H), 8.02 (s, 1H), 7.63 (m, 2H), 7.05 (d, J=9 Hz, 2H), 4.26 (t, J=6 Hz, 2H), 3.48 (d, J=3 Hz, 1H), 2.88 (br t, J=5.5 Hz, 2H), 2.61 (m, 3H), 1.68 (m, 5H), 1.49 (m, 1H).

Example 15

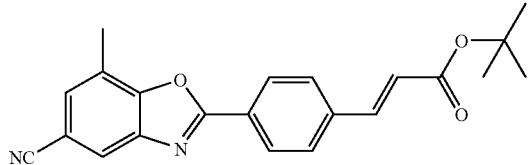

tert-butyl (2E)-3-[4-(5-cyano-7-methyl-1,3-benzoxazol-2-yl)phenyl]acrylate

A mixture of 40 mg of 2-(4-bromophenyl)-7-methyl-1,3-benzoxazole-5-carbonitrile (INTERMEDIATE 8), 24 µL of t-butylacrylate, 8 mg of palladium acetate, 14 mg of tri-o-tolylphosphine, and 23 µL of triethylamine in 1 mL of DMF was purged and flushed with argon, and then heated to 90° C. and stirred overnight at this temperature. Another 24 µL of t-butylacrylate, 8 mg of palladium acetate, 14 mg of tri-o-tolylphosphine, and 23 µL of triethylamine were added and stirring at 90° C. was continued for 20 h. The reaction mixture was cooled and added directly to a Biotage Horizon 12M column, eluting with 10 column volumes of CH2Cl2, followed by 10 column volumes of 10% methanol in CH2Cl2 to provide the title compound. (ESI) 361.2 (M+1). $^1$H NMR (500 MHz, CDCl$_3$): δ 8.24 (d, J=8.5 Hz, 2H), 7.89 (s, 1H), 7.66 (d, J=8.5 Hz, 2H), 7.61 (d, J=15.5 Hz, 1H), 7.43 (s, 1H), 6.48 (d, J=16.5 Hz, 1H), 2.62 (s, 3H), 1.55 (s, 9H).

Example 16

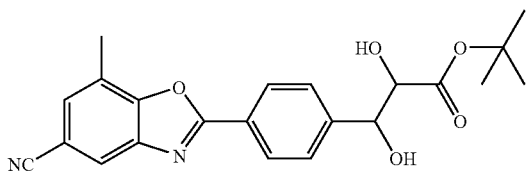

tert-Butyl 3-[4-(5-cyano-7-methyl-1,3-benzoxazol-2-yl)phenyl]-2,3-dihydroxypropanoate To a solution of 19 mg of tert-butyl (2E)-3-[4-(5-cyano-7-methyl-1,3-benzoxazol-2-yl)phenyl]acrylate (EXAMPLE 15) in 1 mL of acetone and 1.3 mL of THF was added 16 µL of osmium peroxide (4% aqueous solution). The mixture was stirred over the weekend at r.t.; then another 16 µL of osmium tetraoxide was added and the mixture was stirred for 3 h at r.t. The reaction mixture was quenched with 2 mL of saturated sodium sulfite solution, and extracted twice with EtOAc. The combined organic extracts were washed with water and brine, dried over Na$_2$SO$_4$, and concentrated. The residue was purified by preparative thin-layer chromatography on a 1000-µM plate, eluting with 5% isopropanol in CH$_2$Cl$_2$ to provide the title compound. Mass spectrum (ESI) 395.2 (M+1). $^1$H NMR (500 MHz, CDCl$_3$): δ 8.25 (d, J=8 Hz, 2H), 7.89 (s, 1H), 7.61 (d, J=8.5 Hz, 2H), 7.44 (s, 1H), 5.03 (d, J=3 Hz, 1H), 4.31 (d, J=3.5 Hz, 1H), 2.62 (s, 3H), 1.48 (s, 9H).

Example 17

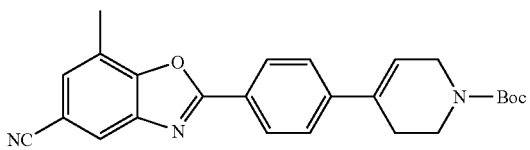

tert-butyl 4-[4-(5-cyano-7-methyl-1,3-benzoxazol-2-yl)phenyl]-3,6-dihydropyridine-1(2H)-carboxylate A mixture of 50 mg of 2-(4-bromophenyl)-7-methyl-1,3-benzoxazole-5-carbonitrile (INTERMEDIATE 8), 61 mg of tert-butyl 4-(trimethylstannyl)-3,6-dihydropyridine-1(2H)-carboxylate, and 10 mg of tetrakis(triphenylphosphine) palladium in 1 mL of dioxane was purged and flushed with argon, and then heated to reflux and stirred overnight at this temperature. The reaction mixture was cooled and added directly to a Biotage Horizon, 12M column, eluting with 1 column volume of CH$_2$Cl$_2$, followed by a linear gradient of EtOAc in CH$_2$Cl$_2$ from 0 to 100% over 10 column volumes to provide the title compound. Mass spectrum (ESI) 416.3 (M+1). $^1$H NMR (500 MHz, CDCl$_3$): δ 8.23 (d, J=8.5 Hz, 2H), 7.90 (s, 1H), 7.56 (d, J=8.5 Hz, 2H), 7.45 (s, 1H), 6.23 (br s, 1H), 4.14 (d, J=3 Hz, 2H), 3.68 (t, J=5.5 Hz, 2H), 2.63 (s, 3H), 2.59 (br s, 2H), 1.51 (s, 9H).

Example 18

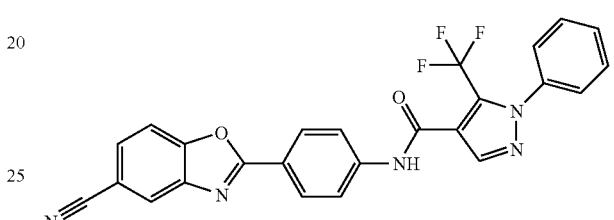

N-[4-(5-cyano-1,3-benzoxazol-2-yl)phenyl]-1-phenyl-5-(trifluoromethyl)-1H-pyrazole-4-carboxamide The title compound was prepared from 2-(4-aminophenyl)-1,3-benzoxazole-5-carbonitrile (INTERMEDIATE 3) and 1-phenyl-5-(trifluoromethyl)-1H-pyrazole-4-carboxylic acid by a procedure analogous to that described in EXAMPLE 8, Step B. Mass spectrum (ESI) 474.2 (M+1). $^1$H NMR (500 MHz, CDCl$_3$): δ 7.48 (m, 2H); 7.54 (m, 3H); 7.67 (m, 2H); 7.78 (s, 1H); 7.85 (m, 2H); 8.07 (s, 1H); 8.29 (m, 2H).

Example 19

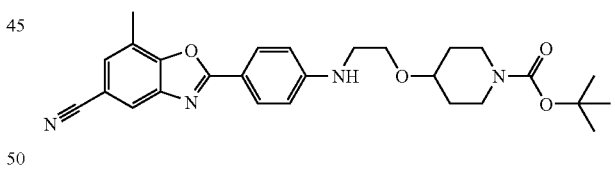

tert-butyl 4-(2-{[4-(5-cyano-7-methyl-1,3-benzoxazol-2-yl)phenyl]amino}ethoxy)piperidine-1-carboxylate

Step A: tert-butyl 4-(allyloxy)piperidine-1-carboxylate

To a solution of N-Boc-4-hydroxypiperidine (2.00 g, 9.93 mmol) in 20 ml THF under nitrogen was added NaH (60% in mineral oil, 417 mg, 10.4 mmol) and, after stirring for 10 minutes, allyl bromide (858 µl, 9.93 mmol) was added. The resulting mixture was stirred for ca. 72 hours, then, added water and extracted 3 times with ethyl ether. The combined organics were washed with brine, dried over sodium sulfate, and concentrated to provide 2.55 g of crude. 507 mg of crude were used without further purification, while the rest was purified by flash column chromatography on a Biotage Horizon, 40M Si column, eluting with 1 column volume of 2% EtOAc in hexanes, followed by a linear gradient of EtOAc in hexanes from 2% to 100% over 10 column volumes to provide the pure title compound. $^1$H NMR (400 MHz, CDCl$_3$): δ 1.45 (s, 9H); 1.53 (m, 2H); 1.83 (m, 2H); 3.08 (m, 2H); 3.50 (m, 1H); 3.77 (m, 2H); 4.01 (d, J=5.6 Hz, 2H); 5.17 (dd, J=1.4 Hz, 10.4 Hz, 1H); 5.28 (dd, J=1.7 Hz, 17.2 Hz, 1H); 5.92 (m, 1H).

Step B: tert-butyl 4-(2-oxoethoxy)piperidine-1-carboxylate

To a mixture of tert-butyl 4-(allyloxy)piperidine-1-carboxylate (Step A) (550 mg, 2.28 mmol) in 15 ml of 1,4-dioxane and 5 ml of water under nitrogen was added OSO$_4$ (4% by weight solution in water, 139 □l, 0.023 mmol) and, after stirring for 15 minutes, NaIO$_4$ (1.03 g, 4.79 mmol) was added. White solids slowly precipitated and, after stirring for 2 hours, the solids were filtered and washed with dichloromethane. The filtrate was dried over sodium sulfate, concentrated, and purified by flash column chromatography on a Biotage Horizon, 40S Si column, eluting with 1 column volume of 10% EtOAc in hexanes, followed by a linear gradient of EtOAc in hexanes from 10% to 100% over 10 column volumes to provide the title compound. $^1$H NMR (400 MHz, CDCl$_3$): δ 1.46 (s, 9H); 1.57 (m, 2H); 1.86 (m, 2H); 3.10 (m, 2H); 3.54 (m, 1H); 3.79 (m, 2H); 4.11 (s, 2H); 9.74 (s, 1H).

Step C: tert-butyl 4-(2-{[4-(5-cyano-7-methyl-1,3-benzoxazol-2-yl)phenyl]amino}ethoxy)piperidine-1-carboxylate To a slurry of 2-(4-aminophenyl)-7-methyl-1,3-benzoxazole-5-carbonitrile (INTERMEDIATE 6) (125 mg, 0.501 mmol) in 8 ml 1,2-dichloroethane was added tert-butyl 4-(2-oxoethoxy)piperidine-1-carboxylate (Step B) (166 mg, 0.682 mmol) followed immediately by AcOH (29 μl, 0.501 mmol) and NaBH(OAc)$_3$ (212 mg, 1.00 mmol). After 30 minutes saturated aqueous sodium bicarbonate was added and extracted 3 times with dichloromethane. The combined organics were washed with brine, dried over sodium sulfate, and concentrated. The product was purified by flash column chromatography on a Biotage Horizon, 25M Si column, eluting with 1 column volume of 5% EtOAc in CH$_2$Cl$_2$, followed by a linear gradient of EtOAc in CH$_2$Cl$_2$ from 5% to 100% over 10 column volumes. A second purification was necessary using thin layer chromatography (4×1000 μm plates), eluting with 30% EtOAc in CH$_2$Cl$_2$ to provide the title compound. Mass spectrum (ESI) 477.2 (M+1). $^1$H NMR (500 MHz, CDCl$_3$): δ 1.46 (s, 9H); 1.53 (m, 2H); 1.84 (m, 2H); 2.59 (s, 3H); 3.09 (m, 2H); 3.40 (m, 2H); 3.51 (m, 1H); 3.71 (m, 2H); 3.76 (m, 2H); 4.56 (m, 1H); 6.71 (d, J=9.0 Hz, 2H); 7.36 (s, 1H); 7.80 (s, 1H); 8.07 (d, J=9.0 Hz, 2H).

Example 20

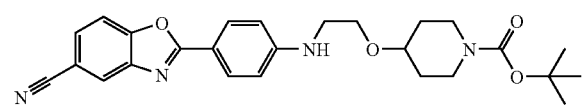

tert-butyl 4-(2-{[4-(5-cyano-1,3-benzoxazol-2-yl)phenyl]amino}ethoxy)piperidine-1-carboxylate The title compound was prepared from 2-(4-aminophenyl)-1,3-benzoxazole-5 carbonitrile (INTERMEDIATE 3) and tert-butyl 4-(2-oxoethoxy)piperidine-1-carboxylate (EXAMPLE 19, Step B) by a procedure analogous to that described in EXAMPLE 19, Step C. Mass spectrum (ESI) 463.2 (M+1). $^1$H NMR (500 MHz, CDCl$_3$): δ 1.46 (s, 9H); 1.53 (m, 2H); 1.85 (m, 2H); 3.09 (m, 2H); 3.40 (m, 2H); 3.51 (m, 1H); 3.71 (m, 2H); 3.77 (m, 2H); 4.57 (m, 1H); 6.71 (d, J=8.7 Hz, 2H); 7.58 (m, 2H); 7.97 (s, 1H); 8.06 (d, J=8.7 Hz, 2H).

Example 21

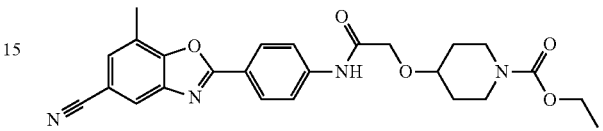

ethyl 4-(2-{[4-(5-cyano-7-methyl-1,3-benzoxazol-2-yl)phenyl]amino}-2-oxoethoxy)piperidine-1-carboxylate To a solution of tert-butyl 4-(2-{[4-(5-cyano-7-methyl-1,3-benzoxazol-2-yl)phenyl]amino}-2-oxoethoxy)piperidine-1-carboxylate (EXAMPLE 7) (31 mg, 0.063 mmol) in 2 ml of CH$_2$Cl$_2$ was added 1 ml of TFA and the resulting solution was stirred at RT for ca. 60 minutes, then, concentrated, azeotroped with toluene, and dried under reduced pressure for 1 hour. 5 ml of pyridine was then added under N$_2$ followed by ethyl chloroformate (12 μl, 0.13 mmol). After 15 minutes the reaction mixture was concentrated, azeotroped with heptane, and dried under reduced pressure overnight. The product was purified by flash column chromatography on a Biotage Horizon, 25M Si column, eluting with 1 column volume of CH$_2$Cl$_2$, followed by a linear gradient of EtOAc in CH$_2$Cl$_2$ from 0% to 100% over 10 column volumes. It was then lyophilized from benzene to provide the title compound. Mass spectrum (ESI) 463.3 (M+1). $^1$H NMR (500 MHz, CDCl$_3$): δ 1.28 (t, J=7.1 Hz, 3H); 1.65 (m, 2H); 1.97 (m, 2H); 2.63 (s, 3H); 3.18 (m, 2H); 3.67 (m, 1H); 3.91 (m, 2H); 4.15 (s, 2H); 4.15 (q, J=7.1 Hz, 2H); 7.44 (s, 1H); 7.79 (d, J=8.7 Hz, 2H); 7.88 (s, 1H); 8.25 (d, J=8.7 Hz, 2H); 8.49 (s, 1H).

Example 22

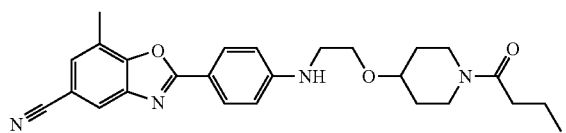

ethyl 4-(2-{[4-(5-cyano-7-methyl-1,3-benzoxazol-2-yl)phenyl]amino}-2-oxoethoxy)piperidine-1-carboxylate To a solution of tert-butyl 4-(2-{[4-(5-cyano-7-methyl-1,3-benzoxazol-2-yl)phenyl]amino}-ethoxy)piperidine-1-carboxylate (EXAMPLE 19) (16 mg, 0.034 mmol) in 1 ml of CH$_2$Cl$_2$ was added 1 ml of TFA and the resulting solution was stirred at RT for ca. 30 minutes, then, concentrated and dried under reduced pressure overnight. 2 ml of CH$_2$Cl$_2$ was then added under N$_2$ followed by butyryl chloride (3.5 μl, 0.034 mmol) and diisopropylethyl amine (18 μl, 0.10 mmol). Reaction was complete in 10 minutes. The product was purified by thin layer chromatography (2×500 μm plates), eluting with 5% NH₃ (2M solution in MeOH) in CH₂Cl₂ to provide the title compound. Mass spectrum (ESI) 447.2 (M+1). ¹H NMR (500 MHz, CDCl₃): δ 0.97 (t, J=7.3 Hz, 3H); 1.56-1.67 (br m, 3H); 1.88 (m, 2H); 2.31 (m, 2H); 2.59 (s, 3H); 3.25 (m, 2H); 3.41 (br d, J=4.4 Hz, 2H); 3.59 (m, 1H); 3.71 (m, 4H); 3.99 (m, 1H); 4.54 (br s, 1H); 6.72 (d, J=9.0 Hz, 2H); 7.37 (s, 1H); 7.80 (s, 1H); 8.07 (d, J=8.7 Hz, 2H).

Example 23

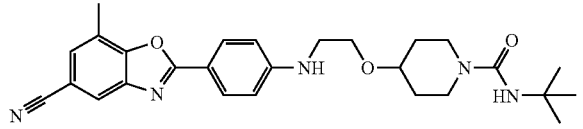

N-(tert-butyl)-4-(2-{[4-(5-cyano-7-methyl-1,3-benzoxazol-2-yl)phenyl]amino}ethoxy)piperidine-1-carboxamide The title compound was prepared from tert-butyl 4-(2-{[4-(5-cyano-7-methyl-1,3-benzoxazol-2-yl)phenyl]amino}ethoxy)piperidine-1-carboxylate (EXAMPLE 19) and t-butyl isocyanate by a procedure analogous to that described in EXAMPLE 22. Mass spectrum (ESI) 476.2 (M+1). ¹H NMR (500 MHz, CDCl₃): δ 1.35 (s, 9H); 1.57 (m, 2H); 1.88 (m, 2H); 2.59 (s, 3H); 3.04 (m, 2H); 3.40 (m, 2H); 3.52 (m, 1H); 3.63 (m, 2H); 3.71 (m, 2H); 4.31 (br s, 1H); 4.55 (br t, J=5.8 Hz, 1H); 6.71 (d, J=9.0 Hz, 2H); 7.36 (s, 1H); 7.80 (s, 1H); 8.06 (d, J=8.9 Hz, 2H).

Example 24 benzenesulfonyl chloride by a procedure analogous to that described in EXAMPLE 22. Mass spectrum (ESI) 531.1 (M+1). ¹H NMR (500 MHz, CDCl₃): δ 1.84 (m, 2H); 2.04 (m, 2H); 2.63 (s, 3H); 2.90 (m, 2H); 3.94 (m, 2H); 3.54 (m, 1H); 4.06 (s, 2H); 7.44 (s, 1H); 7.56 (m, 2H); 7.63 (m, 1H); 7.70 (d, J=8.5 Hz, 2H); 7.79 (d, J=7.6 Hz, 2H); 7.89 (s, 1H); 8.23 (d, J=8.7 Hz, 2H); 8.32 (s, 1H).

Example 25

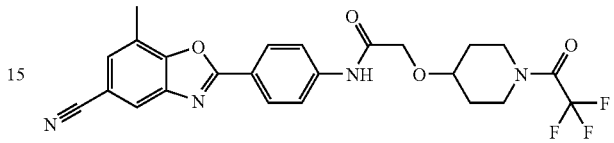

N-[4-(5-cyano-7-methyl-1,3-benzoxazol-2-yl)phenyl]-2-{[1-(trifluoroacetyl)piperidin-4-yl]oxy}acetamide The title compound was obtained from the reaction of tert-butyl 4-(2-{[4-(5-cyano-7-methyl-1,3-benzoxazol-2-yl)phenyl]amino}-2-oxoethoxy)piperidine-1-carboxylate (EXAMPLE 7) and phenethylsulfonyl chloride by a procedure analogous to that described in EXAMPLE 21. The formation of the trifluoroacetamide is attributed to mixed anhydride formation between trifluoroacetate and sulfonyl chloride followed by preferential acylation with the trifluoroactyl group. Mass spectrum (ESI) 487.2 (M+1). ¹H NMR (500 MHz, CDCl₃): δ 1.81 (m, 2H); 2.06 (m, 2H); 2.62 (s, 3H); 3.48 (m, 2H); 3.82 (m, 1H); 3.88 (m, 1H); 4.04 (m, 1H); 4.17 (s, 2H); 7.44 (s, 1H); 7.79 (d, J=8.7 Hz, 2H); 7.88 (s, 1H); 8.25 (d, J=8.7 Hz, 2H); 8.41 (s, 1H).

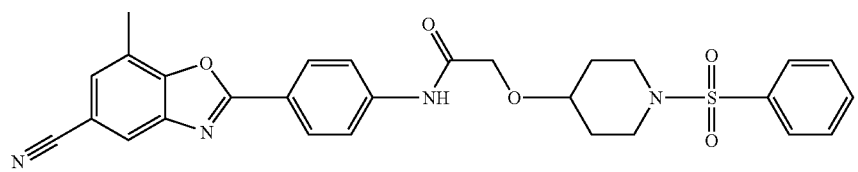

N-[4-(5-cyano-7-methyl-1,3-benzoxazol-2-yl)phenyl]-2-{[1-(phenylsulfonyl)piperidin-4-yl]oxy}acetamide The title compound was prepared from tert-butyl 4-(2-{[4-(5-cyano-7-methyl-1,3-benzoxazol-2-yl)phenyl]amino}-2-oxoethoxy)piperidine-1-carboxylate (EXAMPLE 7) and

Example 26

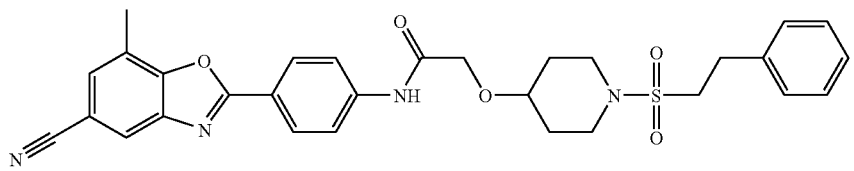

N-[4-(5-cyano-7-methyl-1,3-benzoxazol-2-yl)phenyl]-2-({1-[(2-phenylethyl)sulfonyl]piperidin-4-yl}oxy)acetamide To a solution of tert-butyl 4-(2-{[4-(5-cyano-7-methyl-1,3-benzoxazol-2-yl)phenyl]amino}-2-oxoethoxy)piperidine-1-carboxylate (EXAMPLE 7) (35 mg, 0.071 mmol) in 2 ml of $CH_2Cl_2$ was added 1 ml of TFA and the resulting solution was stirred at room temperature for ca. 60 minutes, then, concentrated and azeotroped with toluene. The residue was shaken with EtOAc and sat. aq. $NaHCO_3$. The layers were separated and the aqueous extracted 2 times with dichloromethane. The combined organics were dried over $Na_2SO_4$, and concentrated to give 23 mg of free amine, which was taken up in 5 ml of pyridine and, under $N_2$, 178 mg of by phenethylsulfonyl chloride were added in portions over ca. 24 hours while the reaction temperature was increased up to 100° C. to get most of the starting material consumed. The reaction mixture was concentrated, azeotroped with heptane, and dried under reduced pressure. The product was purified by thin layer chromatography (3×1000 μm plates), eluting with 20% EtOAc in $CH_2Cl_2$, followed by a second thin layer chromatography purification (2×1000 μm plates) eluting 3 times same as above. The product was lyophilized from benzene to provide the title compound. Mass spectrum (ESI) 559.3 (M+1). $^1$H NMR (500 MHz, $CDCl_3$): δ 1.82 (m, 2H); 2.04 (m, 2H); 2.63 (s, 3H); 3.12-3.22 (br m, 6H); 3.59 (m, 2H); 3.67 (m, 1H); 4.13 (s, 2H); 7.24 (m, 3H); 7.33 (m, 2H); 7.44 (s, 1H); 7.78 (d, J=8.7 Hz, 2H); 7.89 (s, 1H); 8.25 (d, J=8.9 Hz, 2H); 8.42 (s, 1H).

Example 27

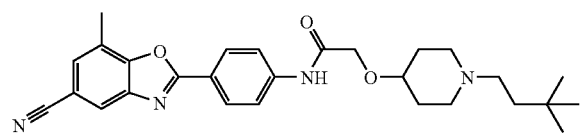

N-[4-(5-cyano-7-methyl-1,3-benzoxazol-2-yl)phenyl]-2-{[1-(3,3-dimethylbutyl)piperidin-4-yl]oxy}acetamide To a solution of tert-butyl 4-(2-{[4-(5-cyano-7-methyl-1,3-benzoxazol-2-yl)phenyl]amino}-2-oxoethoxy)piperidine-1-carboxylate (EXAMPLE 7) (28 mg, 0.057 mmol) in 2 ml of $CH_2Cl_2$ was added 1 ml of TFA and the resulting solution was stirred at RT for ca. 30 minutes, then, concentrated and dried under reduced pressure for 30 min. 8 ml of 1,2-dichloroethane was then added under $N_2$ followed by 3,3-dimethyl butyraldehyde (7.9 μl, 0.063 mmol) and $NaBH(OAc)_3$ (28 mg, 0.13 mmol). The resulting mixture was stirred at room temperature overnight. Only ca. 25% of starting material was converted to product. Another 110 μl of 3,3-dimethyl butyraldehyde, 30 mg of $NaBH(OAc)_3$, 5 ml of 1,2-dichloroethane, and 1 drop of acetic acid were added over 5 days while the temperature of the reaction was increased to 50° C. The product was purified by thin layer chromatography (2×1000 μm plates), eluting first with 2% $NH_3$ (2M solution in MeOH) in $CH_2Cl_2$, followed by a second elution with 5% $NH_3$ (2M solution in MeOH) in $CH_2Cl_2$, then, lyophilized from benzene to provide the title compound. Mass spectrum (ESI) 475.3 (M+1). $^1$H NMR (500 MHz, $CDCl_3$): selected peaks δ 7.44 (s, 1H); 7.79 (d, J=8.5 Hz, 2H); 7.88 (s, 1H); 8.25 (d, J=8.4 Hz, 2H); 8.53 (br s, 1H).

Example 28

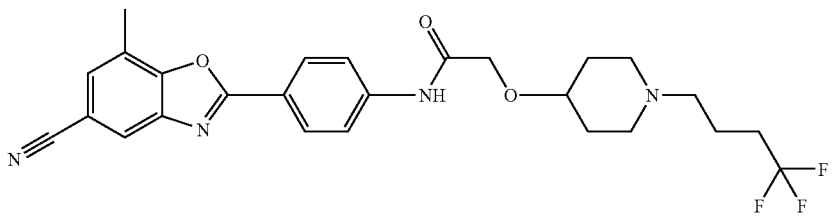

N-[4-(5-cyano-7-methyl-1,3-benzoxazol-2-yl)phenyl]-2-{[1-(4,4,4-trifluorobutyl)piperidin-4-yl]oxy}acetamide The title compound was prepared from tert-butyl 4-(2-{[4-(5-cyano-7-methyl-1,3-benzoxazol-2-yl)phenyl]amino}-2-oxoethoxy)piperidine-1-carboxylate (EXAMPLE 7) and 4,4,4-trifluorobutyrylaldehyde by a procedure analogous to that described in EXAMPLE 27. Mass spectrum (ESI) 501.4 (M+1). $^1$H NMR (500 MHz, CDCl$_3$): selected peaks δ 7.44 (s, 1H); 7.77 (d, J=8.5 Hz, 1H); 7.84 (d, J=8.4 Hz, 1H); 7.88 (s, 1H); 8.25 (m, 2H); 8.43 (s, 1H).

Example 29

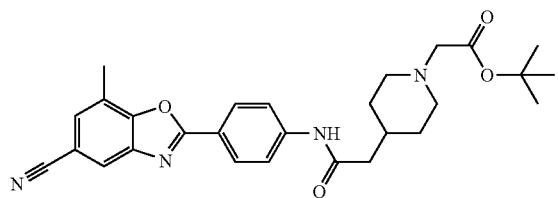

tert-butyl[4-(2-{[4-(5-cyano-7-methyl-1,3-benzoxazol-2-yl)phenyl]amino}-2-oxoethyl)piperidin-1-yl]acetate The title compound was prepared from tert-butyl 4-(2-{[4-(5-cyano-7-methyl-1,3-benzoxazol-2-yl)phenyl]amino}-2-oxoethyl)piperidine-1-carboxylate (EXAMPLE 163) and t-butyl bromoacetate by a procedure analogous to that described in EXAMPLE 22. Mass spectrum (ESI) 489.3 (M+1). $^1$H NMR (500 MHz, CDCl$_3$): δ 1.47 (s, 9H); 1.54 (m, 2H); 1.82 (m, 2H); 1.99 (m, 1H); 2.33 (m, 4H); 2.61 (s, 3H); 3.03 (br d, J=11.4 Hz, 2H); 3.18 (s, 2H); 7.43 (s, 1H); 7.57 (s, 1H); 7.76 (d, J=8.4 Hz, 2H); 7.87 (s, 1H); 8.21 (d, J=8.4 Hz, 2H).

Example 30

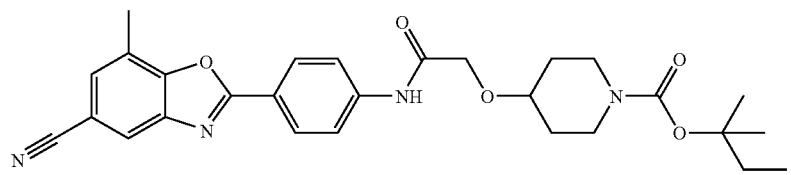

1,1-dimethylpropyl 4-(2-{[4-(5-cyano-7-methyl-1,3-benzoxazol-2-yl)phenyl]amino}-2-oxoethoxy)piperidine-1-carboxylate The title compound was prepared from tert-butyl 4-(2-{[4-(5-cyano-7-methyl-1,3-benzoxazol-2-yl)phenyl]amino}-2-oxoethoxy)piperidine-1-carboxylate (EXAMPLE 7), di-t-amyl dicarbonate, and triethylamine by a procedure analogous to that described in EXAMPLE 22. Mass spectrum (ESI) 505.3 (M+1). $^1$H NMR (500 MHz, CDCl$_3$): selected peaks δ 0.90 (t, J=7.5 Hz, 3H); 1.44 (s, 6H); 1.79 (q, J=7.5 Hz, 2H); 2.62 (s, 3H); 4.14 (s, 2H).

Example 31

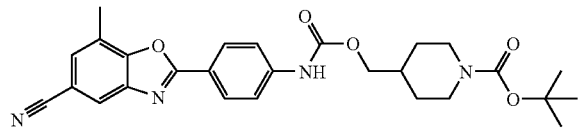

tert-butyl 4-{[({[4-(5-cyano-7-methyl-1,3-benzoxazol-2-yl)phenyl]amino}carbonyl)oxy]methyl}piperidine-1-carboxylate To slurry of 2-(4-aminophenyl)-7-methyl-1,3-benzoxazole-5-carbonitrile (INTERMEDIATE 6) (176 mg, 0.71 mmol) in 10 ml CH$_2$Cl$_2$ under N$_2$ was added in portions over 2 days 16.4 ml of phosgene (20% in toluene), while the reaction temperature was increased from room temperature to 40° C. The reaction mixture was then concentrated, azeotroped with toluene, and dried under reduced pressure to provide 485 mg of crude 2-(4-isocyanatophenyl)-7-methyl-1,3-benzoxazole-5-carbonitrile, 110 mg of which was refluxed overnight with 100 mg of t-butyl 4-(hydroxymethyl)piperidine-1-carboxylate in 6 ml of toluene. The mixture was then concentrated and purified by flash column chromatography on a Biotage Horizon, 25M Si column, eluting with 1 column volume of CH$_2$Cl$_2$, followed by a linear gradient of EtOAc in CH$_2$Cl$_2$ from 0% to 100% over 10 column volumes. A second purifi cation was necessary using thin layer chromatography (2×1000 μm plates), eluting with 20% EtOAc in CH$_2$Cl$_2$ to provide the title compound. Mass spectrum (ESI) 491.2 (M+1). $^1$H NMR (600 MHz, CDCl$_3$): δ 1.25 (m, 2H); 1.46 (s, 9H); 1.73 (m, 2H); 1.87 (m, 1H); 2.61 (s, 3H); 2.72 (m, 2H); 4.08 (m, 2H); 4.15 (m, 2H); 7.00 (s, 1H); 7.42 (s, 1H); 7.59 (d, J=8.5 Hz, 2H); 7.86 (s, 1H); 8.20 (d, J=8.8 Hz, 2H).

Example 32

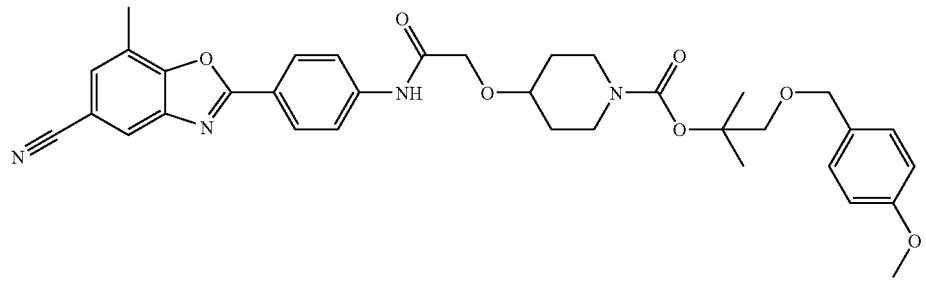

2-[(4-methoxybenzyl)oxy]-1,1-dimethylethyl 4-(2-{[4-(5-cyano-7-methyl-1,3-benzoxazol-2-yl)phenyl]amino}-2-oxoethoxy)piperidine-1-carboxylate Step A: 1-[(4-methoxybenzal)oxy]-2-methylpropan-2-ol To a slurry of NaH (60% in mineral oil, 1.33 g, 33.3 mmol) in 12 ml DMF at room temperature under N$_2$ was added in portions over 25 min a solution of 1-chloro-2-methyl-2 propanol (1.03 ml, 10.0 mmol) in 2 ml DMF and, after stirring the resulting mixture for 2 hrs, a solution of 4-methoxy-benzylalcohol (1.38 g, 10.0 mmol) in 2 ml DMF was added over 25 min. The reaction mixture was stirred at room temperature overnight, then, heated to 60° C. for 3.5 hours, made acidic with dilute HCl, and extracted 3 times with ethyl ether. The combined organics were washed with brine, dried over Na$_2$SO$_4$, and concentrated under reduced pressure. The crude was purified by flash column chromatography on a Biotage Horizon, 40M Si column, eluting with 3600 ml of CH$_2$Cl$_2$, followed by 1200 ml of EtOAc to provide the title compound as a yellow oil. $^1$H NMR (400 MHz, CDCl$_3$): δ 1.21 (s, 6H); 3.28 (s, 2H); 3.81 (s, 3H); 4.50 (s, 2H); 6.89 (m, 2H); 7.26 (m, 2H).

Step B: 2-[(4-methoxybenzyl)oxy]-1,1-dimethylethyl 1,2,2,2-tetrachloroethyl carbonate To a solution of 1-[(4-methoxybenzyl)oxy]-2-methylpropan-2-ol (Step A) (413 mg, 1.96 mmol) in 2 ml of CH$_2$Cl$_2$ under nitrogen at 0° C. was added 1,2,2,2-tetrachloroethyl chloroformate (330 μl, 2.16 mmol) followed by pyridine (175 μl, 2.16 mmol) and the resulting mixture was stirred at room temperature overnight. Another 100 μl of 1,2,2,2-tetrachloroethyl chloroformate and 100 μl pyridine were added and the reaction solidified. It was kept like this overnight, then, diluted with CH$_2$Cl$_2$ and washed 2 times with water and once with brine, dried over Na$_2$SO$_4$, and concentrated. The product was purified by flash column chromatography on a Biotage Horizon, 40M Si column, eluting with CH$_2$Cl$_2$ to provide the title compound. $^1$H NMR (400 MHz, CDCl$_3$): δ 1.53 (d, J=2.0 Hz, 6H); 3.58 (d, J=2.0 Hz, 2H); 3.81 (s, 3H); 4.50 (s, 2H); 6.65 (s, 1H); 6.87 (m, 2H); 7.25 (m, 2H).

Step C: 2-[(4-methoxybenzyl)oxy]-1,1'-dimethylethyl 4-(2-{[4-(5-cyano-7-methyl-1,3-benzoxazol-2-yl)phenyl]amino}-2-oxoethoxy)piperidine-1-carboxylate The title compound was prepared from tert-butyl 4-(2-{[4-(5-cyano-7-methyl-1,3-benzoxazol-2-yl)phenyl]amino}-2-oxoethoxy)piperidine-1-carboxylate (EXAMPLE 7) and 2-[(4-methoxybenzyl)oxy]-1,1-dimethylethyl 1,2,2,2-tetrachloroethyl carbonate (Step B) by a procedure analogous to that described in EXAMPLE 21. Mass spectrum (ESI) 627.3 (M+1). $^1$H NMR (500 MHz, CDCl$_3$): δ 1.47 (s, 6H); 1.62 (m, 2H); 1.93 (m, 2H); 2.62 (s, 3H); 3.12 (m, 2H); 3.60 (s, 2H); 3.64 (m, 1H); 3.79 (s, 2H); 3.86 (m, 2H); 4.13 (s, 2H); 4.49 (s, 2H); 6.87 (d, J=8.7 Hz, 2H); 7.25 (d, J=7.1 Hz, 2H); 7.43 (s, 1H); 7.78 (d, J=8.7 Hz, 2H); 7.88 (s, 1H); 8.24 (d, J=8.7 Hz, 2H); 8.49 (s, 1H).

Example 33

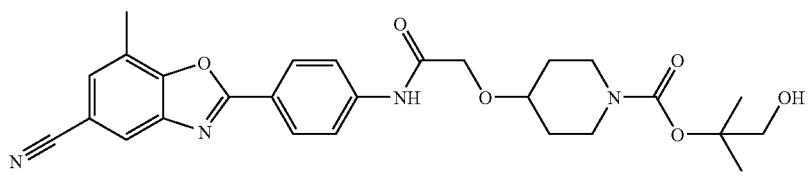

2-hydroxy-1,1-dimethylethyl 4-(2-{[4-(5-cyano-7-methyl-1,3-benzoxazol-2-yl)phenyl]amino}-2-oxoethoxy)piperidine-1-carboxylate To a solution of 2-[(4-methoxybenzyl)oxy]-1,1-dimethylethyl 4-(2-{[4-(5-cyano-7-methyl-1,3-benzoxazol-2-yl)phenyl]amino}-2-oxoethoxy)piperidine-1-carboxylate (EXAMPLE 32) in 2 ml $CH_2Cl_2$ under $N_2$ at room temperature was added water (40 μl) and 2,3-dichloro-5,6-dicyano-1,4-benzoquinone (27 mg, 0.12 mmol). The resulting mixture was stirred for 1 hour, then, diluted with $CH_2Cl_2$, filtered, and concentrated under reduced pressure. The product was purified by flash column chromatography on a Biotage Horizon, 25M Si column, eluting with EtOAc. A second purification was necessary using thin layer chromatography (2×1000 μm plates), eluting with 20% EtOAc in $CH_2Cl_2$. The product was lyophilized from benzene to provide the title compound. Mass spectrum (ESI) 507.2 (M+1). $^1$H NMR (500 MHz, $CDCl_3$): δ 1.42 (s, 6H); 1.66 (m, 2H); 1.97 (m, 2H); 2.63 (s, 3H); 3.19 (m, 2H); 3.67 (s, 2H); 3.68 (m, 1H); 3.86 (br s, 2H); 4.15 (s, 2H); 4.68 (br s, 1H); 7.44 (s, 1H); 7.79 (d, J=8.7 Hz, 2H); 7.89 (s, 1H); 8.25 (d, J=8.9 Hz, 2H); 8.47 (s, 1H).

Example 34

$CDCl_3$): selected peaks δ 7.44 (s, 1H); 7.79 (d, J=8.8 Hz, 2H); 7.89 (s, 1H); 8.25 (d, J=8.7 Hz, 2H); 8.50 (s, 1H).

Example 35

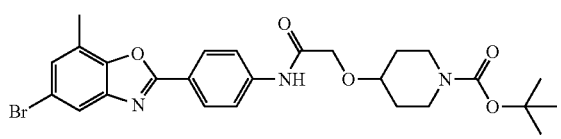

tert-butyl 4-(2-{[4-(5-bromo-7-methyl-1,3-benzoxazol-2-yl)phenyl]amino}-2-oxoethoxy)piperidine-1-carboxylate The title compound was prepared from 4-(5-bromo-7-methyl-1,3-benzoxazol-2-yl)aniline (INTERMEDIATE 6, Step D) and {[1-(tert-butoxycarbonyl)piperidin-4-yl]oxy}acetic acid (EXAMPLE 7, Step A) by a procedure analogous to that described in EXAMPLE 7, Step B. Mass spectrum (ESI) 544 (M+1); 546.1 (M+3). $^1$H NMR (500 MHz, $CDCl_3$): δ 1.48 (s, 9H); 1.63 (m, 2H); 1.95 (m, 2H); 2.56 (s, 3H); 3.12 (m, 2H);

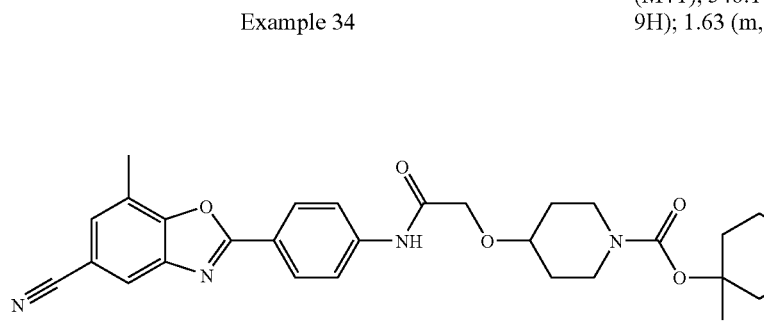

1-methylcyclohexyl 4-(2-{[4-(5-cyano-7-methyl-1,3-benzoxazol-2-yl)phenyl]amino}-2-oxoethoxy)piperidine-1-carboxylate The title compound was prepared from tert-butyl 4-(2-{[4-(5-cyano-7-methyl-1,3-benzoxazol-2-yl)phenyl]amino}-2-oxoethoxy)piperidine-1-carboxylate (EXAMPLE 7) and 1-methylcyclohexyl 1,2,2,2-tetrachloroethyl carbonate by a procedure analogous to that described in EXAMPLE 32. Mass spectrum (ESI) 531.4 (M+1). $^1$H NMR (400 MHz, 3.65 (m, 1H); 3.86 (m, 2H); 4.14 (s, 2H); 7.28 (s, 1H); 7.70 (s, 1H); 7.76 (d, J=8.7 Hz, 2H); 8.23 (d, J=8.5 Hz, 2H); 8.47 (s, 1H).

Example 36

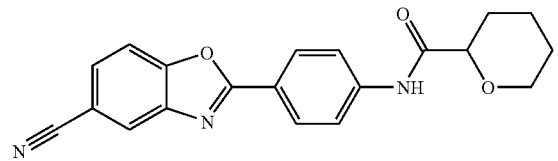

N-[4-(5-cyano-1,3-benzoxazol-2-yl)phenyl]tetrahydro-2H-pyran-2-carboxamide

To a solution of tetrahydro-2H-pyran-2-ylmethanol (116 mg, 1 mmol) in 10 ml acetone was added 5 ml of Jones Reagent. After 20 minutes, 5 ml of isopropanol were added and the resulting mixture was concentrated under reduced pressure, diluted with EtOAc, and filtered through a pad of celite. 2M HCl was added to the filtrate and extracted 3 times with EtOAc. The combined organics were washed with brine, dried over sodium sulfate, and concentrated under reduced pressure to provide 60 mg of tetrahydro-2H-pyran-2-carboxylic acid, which was dissolved in 3 ml $CH_2Cl_2$ and, to the mixture under nitrogen, was added 275 µl of oxalyl chloride (2M solution in $CH_2Cl_2$) followed by 1 drop of DMF. After ca. 1 hour 2-(4-aminophenyl)-1,3-benzoxazole-5-carbonitrile (INTERMEDIATE 3) (20 mg, 0.085 mmol) was added followed by diisopropylethyl amine (191 µl, 1.1 mmol) and the resulting mixture was stirred at room temperature overnight. The product was purified by thin layer chromatography (2×1000 µm plates), eluting with 10% EtOAc in $CH_2Cl_2$ to provide the title compound. Mass spectrum (ESI) 348.2 (M+1). $^1$H NMR (500 MHz, CDCl$_3$): δ 1.47-1.67 (m, 4H); 1.98 (m, 1H); 2.22 (m, 1H); 3.58 (m, 1H); 3.93 (m, 1H); 4.16 (m, 1H); 7.65 (m, 2H); 7.81 (m, 2H); 8.05 (s, 1H); 8.23 (m, 2H); 8.57 (s, 1H).

Example 37

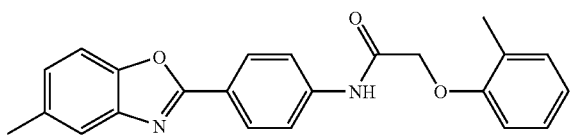

N-[4-(5-methyl-1,3-benzoxazol-2-yl)phenyl]-2-(2-methylphenoxy)acetamide

Step A: 4-{[(2-methylphenoxy)acetyl]amino}benzoic acid

The title compound was prepared from (2-methylphenoxy)acetic acid and 4-aminobenzoic acid by a procedure analogous to that described in EXAMPLE 8, Step B. Mass spectrum (ESI) 286.2 (M+1).

Step B: N-[4-(5-methyl-1,3-benzoxazol-2-yl)phenyl]-2-(2-methylphenoxy)acetamide The title compound was prepared from 4-{[(2-methylphenoxy)acetyl]amino}benzoic acid (Step A) and 2-amino-p-cresol by a procedure analogous to that described in INTERMEDIATE 6, Step C. Mass spectrum (ESI) 373.1 (M+1). $^1$H NMR (500 MHz, CDCl$_3$): δ 2.40 (s, 3H); 2.49 (s, 3H); 4.65 (s, 2H); 6.86 (d, J=8.0 Hz, 1H); 7.00 (t, J=7.5 Hz, 1H); 7.15 (d, J=8.0 Hz, 1H); 7.23 (m, 2H); 7.44 (d, J=8.2 Hz, 1H); 7.54 (s, 1H); 7.77 (d, J=8.7 Hz, 2H); 8.24 (d, J=8.7 Hz, 2H); 8.51 (s, 1H).

Example 38

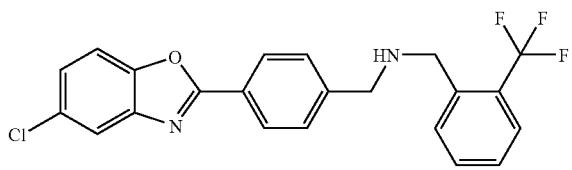

[4-(5-chloro-1,3-benzoxazol-2-yl)benzyl][2-(trifluoromethyl)benzyl]amine

StepA: 5-chloro-2-[4-(chloromethyl)phenyl]-1,3-benzoxazole

The title compound was prepared from 5-chloro-2-hydroxyaniline and 4-chloromethylbenzoyl chloride by a procedure analogous to that described in INTERMEDIATE 6, Step C. Mass spectrum (ESI) 296.0 (M+1).

StepB: [4-(5-chloro-1,3-benzoxazol-2-yl)benzyl][2-(trifluoromethyl)benzyl]amine A mixture of 5-chloro-2-[4-(chloromethyl)phenyl]-1,3-benzoxazole (Step A) (23 mg, 0.083 mmol), [2-(trifluoromethyl)benzyl]amine (13 µl, 0.091 mmol), and diisopropylethyl amine (18 µl, 0.10 mmol) in 1 ml DMF was heated to 100° C. overnight. The product was purified by RP HPLC, Waters XTerra C8 19×50 mm column, eluting with a linear gradient of MeCN (0.06% TFA) in water (0.06% TFA) from 10% to 100% over 12 minutes at 20 ml/minute to provide the TFA salt of the title compound. Mass spectrum (ESI) 417.2 (M+1). $^1$H NMR (500 MHz, CD$_3$OD): δ 4.47 (d, J=5.0 Hz, 4H); 7.45 (dd, J=2 Hz, 8.7 Hz, 1H); 7.65-7.78 (br m, 7H); 7.84 (d, J=8.0 Hz, 1H); 8.35 (d, J=8.4 Hz, 2H).

Following the procedures described in EXAMPLES 1-38, the compounds listed in Tables 1-4 were prepared:

TABLE 1

| EXAMPLE | R₁ | R₂ | R₃ | MS (M+1) |
|---|---|---|---|---|
| 39 | CH₂-O-(2-CF₃-phenyl) | H | Cl | 447.1 |
| 40 | CH₂-O-(3-CF₃-phenyl) | H | Cl | 447.1 |
| 41 | CH₂-O-(4-CF₃-phenyl) | H | Cl | 447.1 |
| 42 | CH₂-O-(2-Cl-phenyl) | H | Cl | 413.2 |
| 43 | CH₂-O-(3-Cl-phenyl) | H | Cl | 413.0 |
| 44 | CH₂-O-(4-Cl-phenyl) | H | Cl | 413.0 |
| 45 | CH₂-O-(3-methylphenyl) | H | Cl | 393.1 |
| 46 | CH₂-O-(4-methylphenyl) | H | Cl | 393.1 |
| 47 | CH₂-O-(2-ethylphenyl) | H | Cl | 407.1 |

TABLE 1-continued

| EXAMPLE | R₁ | R₂ | R₃ | MS (M + 1) |
|---|---|---|---|---|
| 48 | (2-propylphenoxy)methyl | H | Cl | 421.1 |
| 49 | (2-fluorophenoxy)methyl | H | Cl | 397.1 |
| 50 | (4-fluorophenoxy)methyl | H | Cl | 397.1 |
| 51 | phenoxymethyl | H | Cl | 393.1 |
| 52 | (3-methoxyphenoxy)methyl | H | Cl | 409.1 |
| 53 | (4-methoxyphenoxy)methyl | H | Cl | 409.1 |
| 54 | (3-nitrophenoxy)methyl | H | Cl | 424.1 |
| 55 | (4-nitrophenoxy)methyl | H | Cl | 424.1 |

TABLE 1-continued
| EXAMPLE | R₁ | R₂ | R₃ | MS (M + 1) |
|---|---|---|---|---|
| 56 | 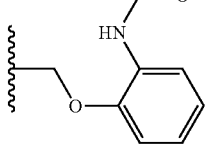 | H | Cl | 490.1 |
| 57 | 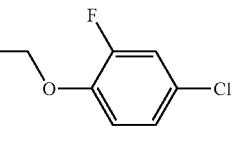 | H | Cl | 431.1 |
| 58 | 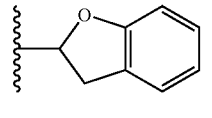 | H | Cl | 391.1 |
| 59 | 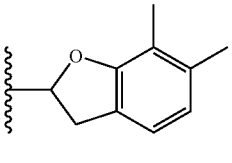 | H | Cl | 419.1 |
| 60 | 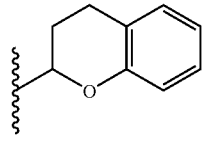 | H | Cl | 405.1 |
| 61 | 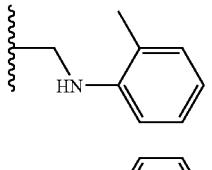 | H | Cl | 392.2 |
| 62 | 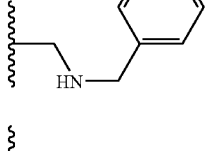 | H | Cl | 392.2 |
| 63 | 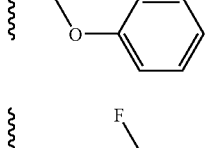 | H | CN | 370.1 |
| 64 | 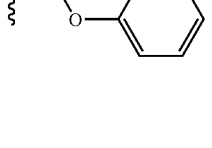 | H | CN | 388.2 |

TABLE 1-continued

| EXAMPLE | R₁ | R₂ | R₃ | MS (M + 1) |
|---|---|---|---|---|
| 65 | -CH₂-O-C₆H₄-F (4-F) | H | CN | 388.1 |
| 66 | -CH₂-O-C₆H₄-CF₃ (2-CF₃) | H | CN | 438.0 |
| 67 | -CH₂-O-C₆H₄-CF₃ (3-CF₃) | H | CN | 438.1 |
| 68 | -CH₂-O-C₆H₄-Et (2-Et) | H | CN | 398.2 |
| 69 | -CH₂-O-C₆H₄-nPr (2-nPr) | H | CN | 412.2 |
| 70 | -CH₂-O-C₆H₄-Cl (2-Cl) | H | CN | 404.1 |
| 71 | -CH₂-O-C₆H₄-Cl (3-Cl) | H | CN | 404.0 |
| 72 | -CH₂-O-C₆H₄-Cl (4-Cl) | H | CN | 404.1 |
| 73 | -CH₂-O-C₆H₄-OCF₃ (4-OCF₃) | H | CN | 454.1 |

TABLE 1-continued
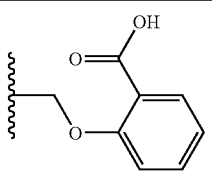
| EXAMPLE | R₁ | R₂ | R₃ | MS (M + 1) |
|---|---|---|---|---|
| 74 | 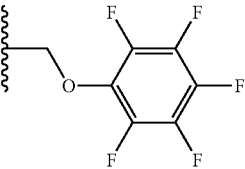 | H | CN | 414.1 |
| 75 | 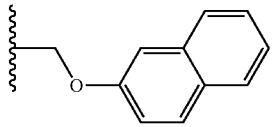 | H | CN | 460.1 |
| 76 | 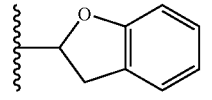 | H | CN | 420.2 |
| 77 | 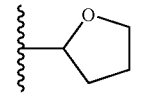 | H | CN | 382.2 |
| 78 | 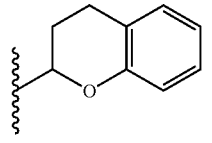 | H | CN | 334.2 |
| 79 | 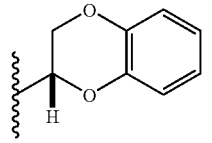 | H | CN | 396.1 |
| 80 | 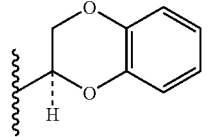 | H | CN | 398.2 |
| 81 | 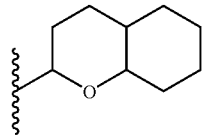 | H | CN | 398.2 |
| 82 |  | H | CN | 402.2 |

TABLE 1-continued

| EXAMPLE | R₁ | R₂ | R₃ | MS (M + 1) |
|---------|----|----|----|------------|
| 83 | -CH₂-O-cyclohexyl | H | CN | 385.1 |
| 84 | -CH₂-O-CH(CF₃)₂ | H | CN | 444.1 |
| 85 | -CH(CH₃)-O-CH(CF₃)₂ | H | CN | 458.2 |
| 86 | -CH₂-O-C(CF₃)₃ | H | CN | 512.0 |
| 87 | -CH₂-O-C(CH₃)(CF₃)₂ | H | CN | 458.0 |
| 88 | -CH(CH₃)-O-C(CH₃)(CF₃)₂ | H | CN | 472.2 |
| 89 | -CH₂-S(O)₂-CH(CH₃)₂ | H | CN | 384.1 |
| 90 | -CH₂-NH-phenyl | H | CN | 369.2 |
| 91 | -CH₂-NH-CH₂-phenyl | H | CN | 383.2 |
| 92 | -CH₂-N(CH₃)-CH₂-phenyl | H | CN | 397.2 |

TABLE 1-continued

| EXAMPLE | R₁ | R₂ | R₃ | MS (M + 1) |
|---------|----|----|----|------------|
| 93 | (CH₂-NH-CH₂-(2-CF₃-phenyl)) | H | CN | 451.2 |
| 94 | (CH₂-NH-cyclohexyl) | H | CN | 375.2 |
| 95 | (CH₂-N(CH₃)-cyclohexyl) | H | CN | 389.3 |
| 96 | (CH₂-NH-decahydronaphthalen-1-yl) | H | CN | 429.3 |
| 97 | (CH₂-NH-decahydronaphthalen-2-yl) | H | CN | 429.3 |
| 98 | (CH₂-piperidin-1-yl) | H | CN | 361.3 |
| 99 | (CH₂-2-azabicyclo[2.2.1]heptan-2-yl) | H | CN | 373.2 |
| 100 | (CH₂-NH-bicyclo[2.2.2]octyl) | H | CN | 415.3 |
| 101 | (CH₂-decahydroquinolin-1-yl) | H | CN | 415.3 |

TABLE 1-continued

| EXAMPLE | R₁ | R₂ | R₃ | MS (M+1) |
|---|---|---|---|---|
| 102 | CH₂-decahydroisoquinolinyl | H | CN | 415.3 |
| 103 | CH₂-NH-cyclopentyl | H | CN | 361.3 |
| 104 | CH₂-pyrrolidinyl | H | CN | 347.3 |
| 105 | CH₂-NH-cycloheptyl | H | CN | 389.3 |
| 106 | CH₂-azepanyl | H | CN | 375.2 |
| 107 | CH₂-NH-cyclobutyl | H | CN | 347.2 |
| 108 | CH₂-NH-cyclopropyl | H | CN | 333.2 |
| 109 | CH₂-NH-C(CH₃)₃ | H | CN | 349.3 |
| 110 | CH₂-NH-CH(CH₃)₂ | H | CN | 335.3 |
| 111 | CH₂-N(Et)-CH(CH₃)₂ | H | CN | 363.3 |

TABLE 1-continued

| EXAMPLE | R₁ | R₂ | R₃ | MS (M + 1) |
|---|---|---|---|---|
| 112 | -CH₂-N(iPr)₂ | H | CN | 377.3 |
| 113 | -CH₂-NH-CH₂-iPr | H | CN | 349.3 |
| 114 | -CH₂-NH-CH₂-CH(Et)₂ | H | CN | 363.3 |
| 115 | -CH₂-N(CH₃)₂ | H | CN | 321.2 |
| 116 | -CH₂-O-(4-methylcyclohexyl) | H | CN | 390.3 |
| 117 | -CH₂-O-(3-methylcyclohexyl) | H | CN | 390.3 |
| 118 | -CH₂-O-(2-methylcyclohexyl) | H | CN | 390.3 |
| 119 | -CH₂-O-(4-trifluoromethylcyclohexyl) | H | CN | 444.2 |
| 120 | -CH₂-CH₂-CH(CH₃)₂ | H | CN | 334.2 |
| 121 | -CH(OH)-CH₂-CH(CH₃)₂ | H | CN | 350.2 |

TABLE 1-continued
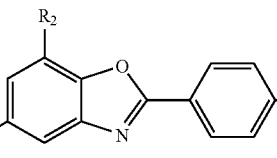
| EXAMPLE | R₁ | R₂ | R₃ | MS (M + 1) |
|---|---|---|---|---|
| 122 | 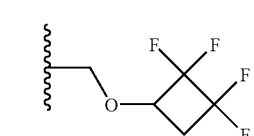 | H | CN | 447.3 |
| 123 | 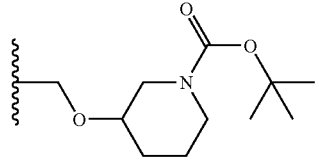 | H | CN | 420.2 |
| 124 | 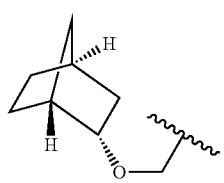 | H | CN | 477.3 |
| 125 | 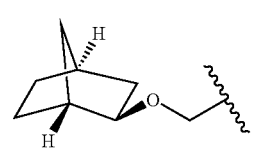 | H | CN | 388.3 |
| 126 | 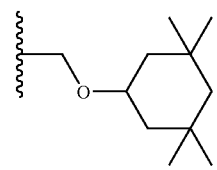 | H | CN | 388.3 |
| 127 | 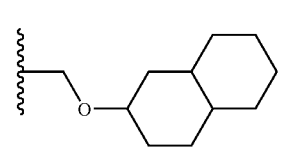 | H | CN | 432.3 |
| 128 | 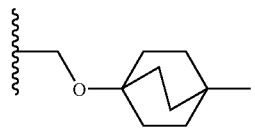 | H | CN | 430.3 |
| 129 | 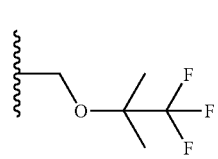 | H | CN | 416.3 |
| 130 | | H | CN | 404.2 |

TABLE 1-continued

| EXAMPLE | R₁ | R₂ | R₃ | MS (M + 1) |
|---|---|---|---|---|
| 131 | -CH₂-O-cycloheptyl | H | CN | 390.3 |
| 132 | -CH₂-O-CH₂-cyclohexyl | H | CN | 390.3 |
| 133 | -CH₂-O-CH(CH₃)-cyclohexyl | H | CN | 404.3 |
| 134 | -CH₂-O-cyclopentyl | H | CN | 362.2 |
| 135 | -CH₂-O-(tetrahydropyran-4-yl) | H | CN | 378.3 |
| 136 | -CH₂-O-C(CH₃)₃ | H | CN | 350.3 |
| 137 | -CH₂-O-n-hexyl | H | CN | 378.3 |
| 138 | -CH₂-O-CH(CH₃)-phenyl | H | CN | 398.2 |
| 139 | -CH₂-O-CH(C₂H₅)₂ | H | CN | 364.2 |
| 140 | -CH₂-O-CH₂-CH(CH₃)₂ | H | CN | 350.2 |

TABLE 1-continued

| EXAMPLE | R₁ | R₂ | R₃ | MS (M + 1) |
|---|---|---|---|---|
| 141 | (CH₂O-piperidine-N-Boc) | H | CN | 477.2 |
| 142 | (CH₂O-menthyl) | H | CN | 432.3 |
| 143 | (CH₂OEt) | H | CN | 322.2 |
| 144 | (CH₂OCH₂-4-Cl-Ph) | H | CN | 418.2 |
| 145 | (CH₂OCH(CF₃)Ph) | H | CN | 452.2 |
| 146 | (CH₂O-iPr) | H | CN | 336.2 |
| 147 | (CH₂O-cyclohexyl) | H | CN | 376.2 |
| 148 | (CH₂OCH₂-4-CF₃-Ph) | H | CN | 452.1 |
| 149 | (CH₂OCH₂-3-CF₃-Ph) | H | CN | 452.1 |

TABLE 1-continued

| EXAMPLE | R₁ | R₂ | R₃ | MS (M + 1) |
|---|---|---|---|---|
| 150 | (CH₂-O-CH₂-[2-(CF₃)phenyl]) | H | CN | 452.1 |
| 151 | (CH₂-O-CH₂-[4-F-phenyl]) | H | CN | 402.1 |
| 152 | (CH₂-O-CH₂-[3-F-phenyl]) | H | CN | 402.2 |
| 153 | (CH₂-O-CH₂-[2-F-phenyl]) | H | CN | 402.2 |
| 154 | (CH₂-O-CH₂-[4-CH₃-phenyl]) | H | CN | 398.2 |
| 155 | (CH₂-O-CH₂-[2-CH₃-phenyl]) | H | CN | 398.2 |
| 156 | (CH₂-O-CH₂-phenyl) | H | CN | 384.2 |
| 157 | (CH₂-O-(3S)-N-Boc-pyrrolidinyl) | CH₃ | CN | 477.2 |
| 158 | (CH₂-O-(3R)-N-Boc-pyrrolidinyl) | CH₃ | CN | 477.2 |

TABLE 1-continued

[Structure: R2 and R3 substituted benzoxazole linked to phenyl-NH-C(=O)-R1]

| EXAMPLE | R₁ | R₂ | R₃ | MS (M + 1) |
|---|---|---|---|---|
| 159 | CH₂-O-azetidine-N-C(=O)-O-tBu | CH₃ | CN | 463.3 |
| 160 | CH₂-O-CH₂CH₂CH₂-NH-C(=O)-O-tBu | CH₃ | CN | 465.3 |
| 161 | CH₂-(4-piperidinyl)-N-C(=O)-O-CH₃ | CH₃ | CN | 447.2 |
| 162 | CH₂-(4-piperidinyl)-N-C(=O)-O-tBu | CH₃ | CN | 489.2 |
| 163 | CH₂-(4-piperidinyl)-N-C(=O)-O-tBu | CH₃ | CN | 475.2 |

TABLE 2

[Structure: R2 and R3 substituted benzoxazole linked to phenyl-R1]

| EXAMPLE | R₁ | R₂ | R₃ | LC/MS Data (M + 1) |
|---|---|---|---|---|
| 165 | N-(imidazolidinone)-N'-cycloheptyl | H | CN | 401.3 |
| 166 | NH-CH₂CH₂-O-iPr | H | CN | 322.3 |
| 167 | NH-CH₂CH₂-O-Si(CH₃)₂-tBu | H | CN | 394.3 |

TABLE 2-continued
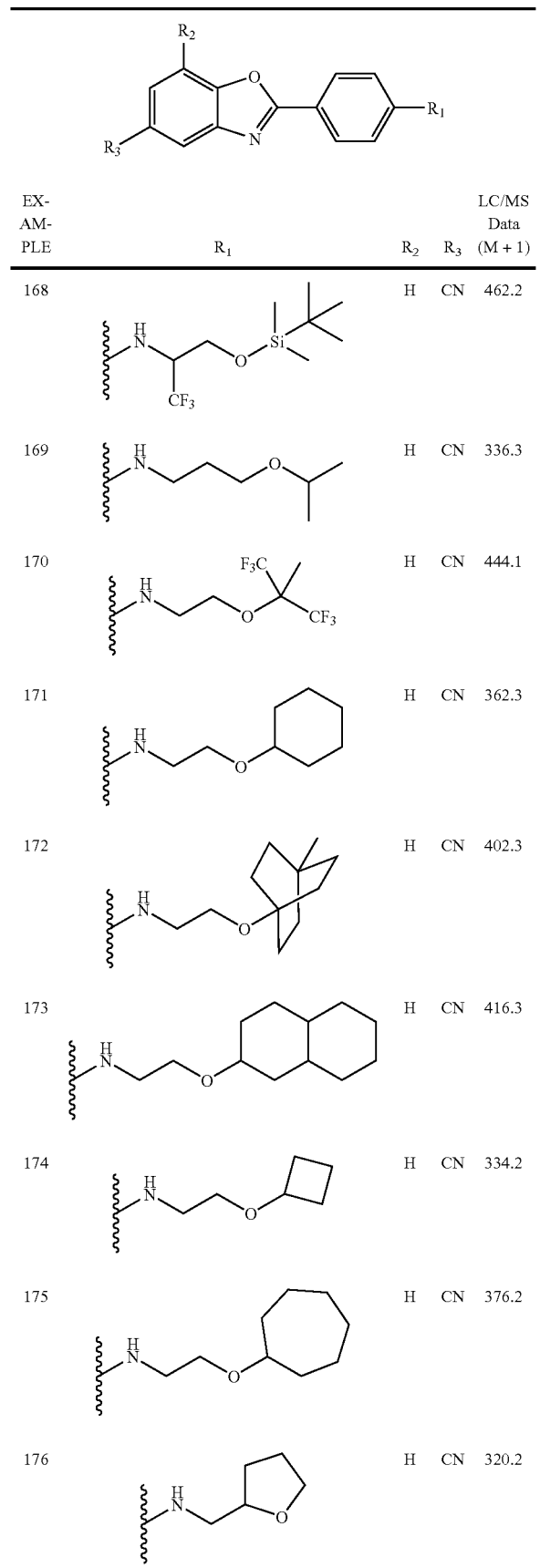
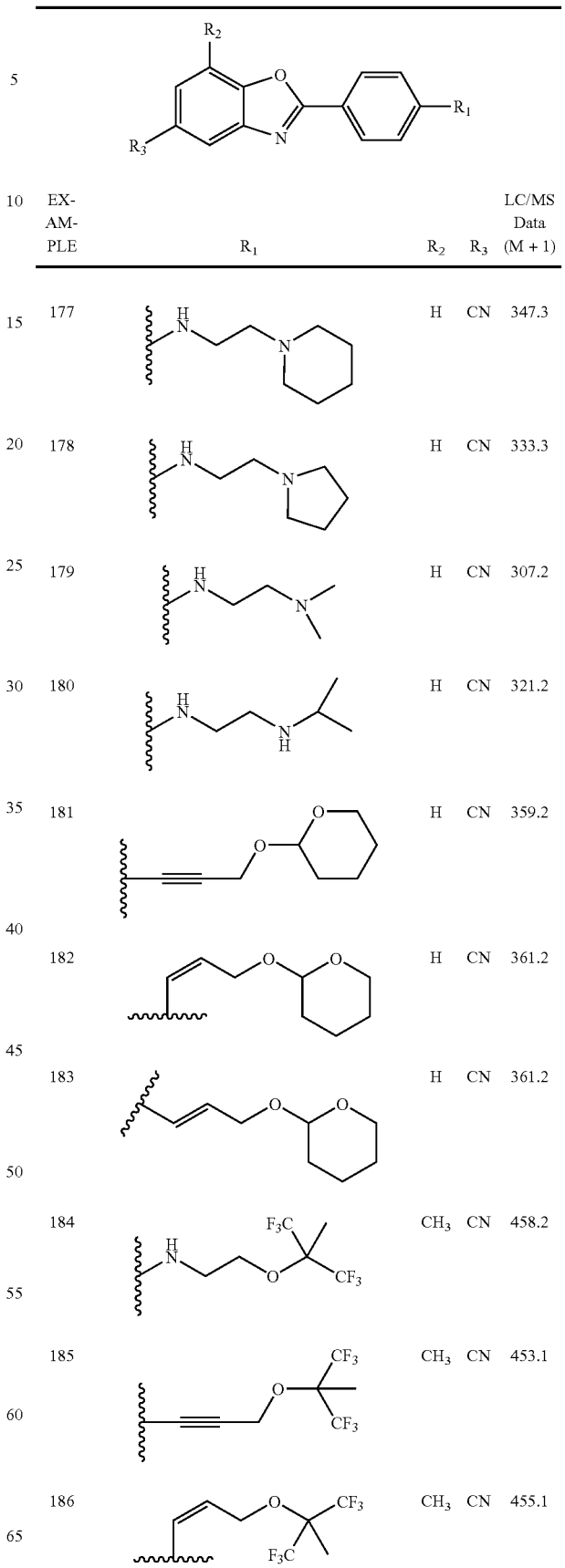

TABLE 2-continued

[Structure: R2, R3-substituted benzoxazole connected to phenyl-R1]

| EXAMPLE | R1 | R2 | R3 | LC/MS Data (M + 1) |
|---|---|---|---|---|
| 187 | ~NH-CH2CH2-O-CH(CH3)2 | CH3 | Br | 391.2 |
| 188 | ~NH-CH2CH2-O-C(CF3)2-CH3 (with F3C and CF3 groups) | CH3 | Br | 513.1 |

TABLE 3

[Structure: 7-methyl-5-cyano-benzoxazole connected to 2-(4-NHR-phenyl)]

| EXAMPLE | R | MS (M + 1) |
|---|---|---|
| 189 | -C(=O)-CH2-O-(piperidine)-N-C(=O)-O-CH3 | 449.1 |
| 190 | -C(=O)-CH2-O-(piperidine)-N-C(=O)-O-CH2-C(CH3)3 | 505.3 |
| 191 | -CH2CH2-O-(piperidine)-N-C(=O)-C(CH3)3 | 461.2 |
| 192 | -CH2CH2-O-(piperidine)-N-C(=O)-CH2-C(CH3)3 | 475.2 |
| 193 | -C(=O)-CH2-O-(piperidine)-N-C(=O)-CH2-C(CH3)3 | 489.2 |
| 194 | -C(=O)-CH2-O-(piperidine)-N-C(=O)-NH-C(CH3)3 | 490.1 |

TABLE 3-continued
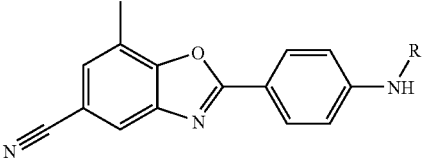
| EXAMPLE | R | MS (M + 1) |
|---|---|---|
| 195 | 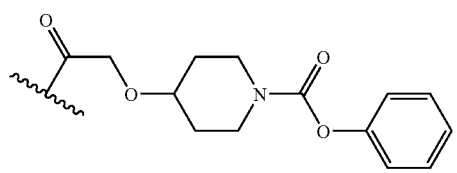 | 511.1 |
| 196 | 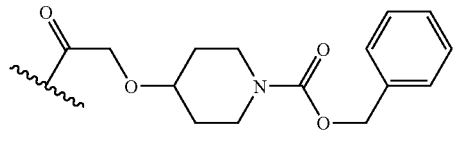 | 511.1 |
| 197 | 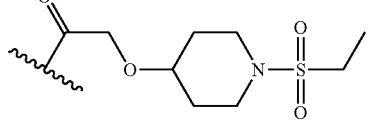 | 525.2 |
| 198 | 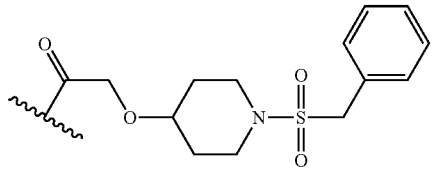 | 483.1 |
| 199 | 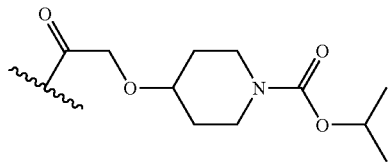 | 545.2 |
| 200 | 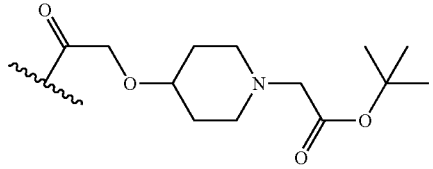 | 477.2 |
| 201 | | 505.3 |

TABLE 4

| EXAMPLE | R | MS (M + 1) |
|---|---|---|
| 202 | ![N-CH2-phenyl-CF3 (meta)] | 417.2 |
| 203 | ![N-CH2-phenyl-CF3 (para)] | 417.1 |
| 204 | ![NH-CH2CH2-O-iPr] | 345.2 |

Example 205

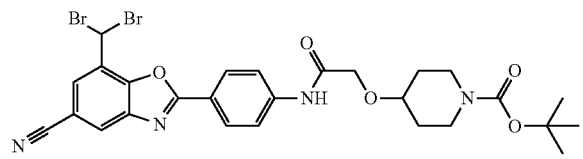

tert-butyl 4-[2-({4-[5-cyano-7-(dibromomethyl)-1,3-benzoxazol-2-yl]phenyl}amino)-2-oxoethoxy]piperidine-1-carboxylate Step A: tert-butyl[4-(5-cyano-7-methyl-1,3-benzoxazol-2-yl)phenyl]carbamate To a slurry of 2-(4-aminophenyl)-7-methyl-1,3-benzoxazole-5-carbonitrile (INTERMEDIATE 6) (500 mg, 2.00 mmol) in 20 ml $CH_2Cl_2$ was added 10 ml of phosgene (20% in toluene) in two portions under $N_2$ and the resulting mixture was stirred at room temperature for 3 days. Another 5 ml of phosgene were added and the resulting mixture was stirred for 4 hours and concentrated under reduced pressure azeotroping with toluene. 10 ml of toluene and 10 ml of t-butanol were added to the crude isocyanate and the resulting mixture was refluxed for ca. 1.5 hours, concentrated under reduced pressure, and purified by flash column chromatography on a Biotage Horizon, 40M Si column, eluting with 1 column volume of $CH_2Cl_2$, followed by a linear gradient of EtOAc in $CH_2Cl_2$ from 0% to 50% over 10 column volumes to provide the title compound and unreacted starting material. Mass spectrum (ESI) 350.3 (M+1). $^1$H NMR (400 MHz, $CDCl_3$): δ 1.55 (s, 9H); 2.61 (s, 3H); 6.70 (s, 1H); 7.42 (s, 1H); 7.56 (d, J=8.8 Hz, 2H); 7.86 (s, 1H); 8.19 (d, J=8.8 Hz, 2H).

Step B: tert-butyl {4-[5-cyano-7-(dibromomethyl)-1,3-benzoxazol-2-yl]phenyl}carbamate Benzoyl peroxide (14 mg, 0.057 mmol) was added to a refluxing solution of tert-butyl[4-(5-cyano-7-methyl-1,3-benzoxazol-2-yl)phenyl]carbamate (Step A) (200 mg, 0.57 mmol) in 40 ml of carbon tetrachloride. 32 μl of bromine were added and the reaction mixture was irradiated with an infrared heat lamp for 2 hours, then, another 32 μl of bromine were added and after 1 hour the reaction was stopped. The mixture was concentrated under reduced pressure and purified by RP HPLC at pH=10 on a Kromacil 21×100 mm C18, 5 micron column eluting with 65% MeCN (0.1% TEA) in water (0.1% TEA) at 25 ml/min for 20 minutes to provide tert-butyl {4-[7-(bromomethyl)-5-cyano-1,3-benzoxazol-2-yl]phenyl}carbamate and the title compound. Mass spectrum (ESI) 506 (M+1); 508.1 (M+3); 510.1 (M+5). $^1$H NMR (500 MHz, $CDCl_3$): δ 1.55 (s, 9H); 6.75 (s, 1H); 7.04 (s, 1H); 7.36 (s, 1H); 7.59 (d, J=8.7 Hz, 2H); 7.95 (dd, J=1.4 Hz, 30.9 Hz, 1H); 8.22 (d, J=8.7 Hz, 2H).

Step C: tert-butyl 4-[2-({4-[5-cyano-7-(dibromomethyl)-1,3-benzoxazol-2-yl]phenyl}amino)-2-oxoethoxy]piperidine-1-carboxylate The title compound was prepared from tert-butyl {4-[5-cyano-7-(dibromomethyl)-1,3-benzoxazol-2-yl]phenyl}carbamate (Step B) and {[1-(tert-butoxycarbonyl)piperidin-4-yl]oxy}acetic acid (EXAMPLE 7, Step A) by a procedure analogous to that described in EXAMPLE 7, Step B.

Mass spectrum (ESI) 647 (M+1); 649.3 (M+3); 651 (M+5). $^1$H NMR (500 MHz, $CDCl_3$): δ 1.48 (s, 9H); 1.63 (m, 2H); 1.96 (m, 2H); 3.11 (m, 2H); 3.66 (m, 1H); 3.87 (m, 2H); 4.15 (s, 2H); 7.05 (s, 1H); 7.82 (d, J=8.7 Hz, 21H); 7.94 (d, J=1.4 Hz, 1H); 8.01 (d, J=1.2 Hz, 1H); 8.28 (d, J=8.7 Hz, 2H); 8.53 (s, 1H).

Example 206

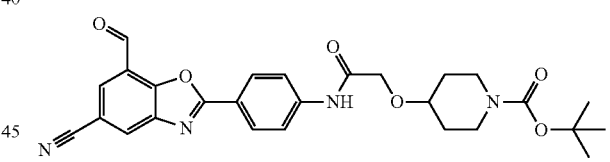

tert-butyl 4-(2-{[4-(5-cyano-7-formyl-1,3-benzoxazol-2-yl)phenyl]amino}-2-oxoethoxy)piperidine-1-carboxylate A mixture of tert-butyl 4-[2-({4-[5-cyano-7-(dibromomethyl)-1,3-benzoxazol-2-yl]phenyl}amino)-2-oxoethoxy]piperidine-1-carboxylate(EXAMPLE 205) (30 mg, 0.046 mmol), $AgNO_3$ (24 mg, 0.14 mmol), and water (300 μl) in 3 ml THF was refluxed under nitrogen for 5 hours, cooled to room temperature, diluted with $CH_2Cl_2$, filtered washing with $CH_2Cl_2$, and concentrated under reduced pressure. The product was purified by flash column chromatography on a Biotage Horizon, 25M Si column, eluting with 1 column volume of $CH_2Cl_2$, followed by a linear gradient of EtOAc in from 0% to 100% over 10 column volumes to provide the title compound. Mass spectrum (ESI) 505.4 (M+1). $^1$H NMR (500 MHz, $CDCl_3$): δ 1.48 (s, 9H); 1.63 (m, 2H); 1.96 (m, 2H); 3.11 (m, 2H); 3.66 (m, 1H); 3.87 (m, 2H); 4.15 (s, 2H); 7.82

(d, J=8.7 Hz, 2H); 8.13 (d, J=1.4 Hz, 1H); 8.25 (d, J=1.4 Hz, 1H); 8.31 (d, J=8.9 Hz, 2H); 8.53 (s, 1H); 10.45 (s, 1H).

Example 207

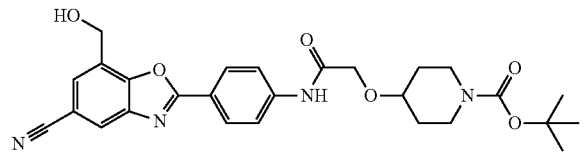

tert-butyl 4-[2-({4-[5-cyano-7-(hydroxymethyl)-1,3-benzoxazol-2-yl]phenyl}amino)-2-oxoethoxy]piperidine-1-carboxylate A mixture of tert-butyl 4-(2-{[4-(5-cyano-7-formyl-1,3-benzoxazol-2-yl)phenyl]amino-}-2-oxoethoxy)piperidine-1-carboxylate (EXAMPLE 206) (22 mg, 0.044 mmol) and NaBH$_4$ (1.8 mg, 0.048 mmol) in 2 ml THF was stirred at room temperature under N$_2$ for 15 minutes. The product was purified by thin layer chromatography (2×1000 μm plates) eluting with 40% EtOAc in CH$_2$Cl$_2$ to provide the title compound. Mass spectrum (ESI) 507.4 (M+1). $^1$H NMR (500 MHz, CDCl$_3$): δ 1.48 (s, 9H); 1.62 (m, 2H); 1.95 (m, 2H); 3.11 (m, 2H); 3.65 (m, 1H); 3.87 (m, 2H); 4.14 (s, 2H); 5.10 (s, 2H); 7.73 (s, 1H); 7.78 (d, J=8.7 Hz, 2H); 7.98 (s, 1H); 8.23 (d, J=8.5 Hz, 2H); 8.50 (s, 1H).

Example 208

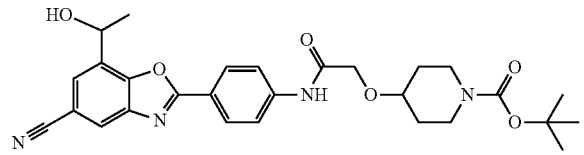

tert-butyl 4-[2-({4-[5-cyano-7-(1-hydroxyethyl)-1,3-benzoxazol-2-yl]phenyl}amino)-2-oxoethoxy]piperidine-1-carboxylate To a mixture of tert-butyl 4-(2-{[4-(5-cyano-7-formyl-1,3-benzoxazol-2-yl)phenyl]amino}-2-oxoethoxy)piperidine-1-carboxylate (EXAMPLE 206) (37 mg, 0.073 mmol) in 2 ml THF under nitrogen at room temperature were added in portions 312 μl of methylmagnesium bromide (1.4M in toluene/THF 75:25) over 2 hours 20 minutes. The reaction mixture was quenched with water, added EtOAc, and the biphasic mixture was filtered. The filtrate was extracted 3 times with EtOAc and the combined organics were washed with brine, dried over sodium sulfate, and concentrated under reduced pressure. The product was purified 2 times by thin layer chromatography (2×1000 μm plates) eluting with 40% EtOAc in CH$_2$Cl$_2$ to provide the title compound. Mass spectrum (ESI) 521.4 (M+1). $^1$H NMR (500 MHz, CDCl$_3$): δ 1.47 (s, 9H); 1.63 (m, 2H); 1.71 (d, J=6.6 Hz, 3H); 1.96 (m, 2H); 3.11 (m, 2H); 3.65 (m, 1H); 3.87 (m, 2H); 4.14 (s, 2H); 5.43 (q, J=6.7 Hz, 1H); 7.75 (s, 1H); 7.78 (d, J=8.7 Hz, 2H); 7.96 (d, J=1.4 Hz, 1H); 8.23 (d, J=8.7 Hz, 2H); 8.50 (s, 1H).

Example 209

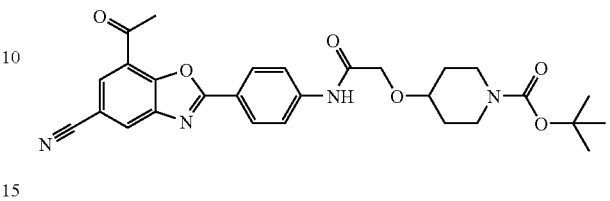

tert-butyl 4-(2-{[4-(7-acetyl-5-cyano-1,3-benzoxazol-2-yl)phenyl]amino}-2-oxoethoxy)piperidine-1-carboxylate A mixture of 20 mg of tert-butyl 4-[2-({4-[5-cyano-7-(1-hydroxyethyl)-1,3-benzoxazol-2-yl]phenyl}amino)-2-oxoethoxy]piperidine-1-carboxylate (EXAMPLE 208) and 18 mg of Dess-Martin periodinane in 5 ml dichloromethane was stirred under nitrogen at room temperature for 4 hours. 9 mg of Dess-Martin periodinane were added and, after stirring overnight, the resulting mixture was diluted with dichloromethane and filtered washing with dichloromethane and concentrated. The product was purified by thin layer chromatography (2×1000 μm plates) eluting with 20% EtOAc in CH$_2$Cl$_2$ to provide the title compound. Mass spectrum (ESI) 519.4 (M+1). $^1$H NMR (400 MHz, CDCl$_3$): δ 1.47 (s, 9H); 1.63 (m, 2H); 1.96 (m, 2H); 2.93 (s, 3H); 3.11 (m, 2H); 3.66 (m, 1H); 3.87 (m, 2H); 4.15 (s, 2H); 7.82 (d, J=8.8 Hz, 2H); 8.20 (dd, J=1.5 Hz, 5.5 Hz, 1H); 8.27 (d, J=8.7 Hz, 2H); 8.53 (s, 1H).

Example 210

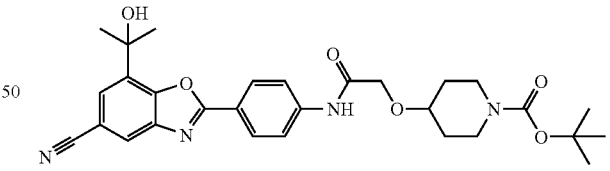

tert-butyl 4-[2-({4-[5-cyano-7-(1-hydroxy-1-methylethyl)-1,3-benzoxazol-2-yl]phenyl}amino)-2-oxoethoxy]piperidine-1-carboxylate The title compound was prepared from tert-butyl 4-(2-{[4-(7-acetyl-5-cyano-1,3-benzoxazol-2-yl)phenyl]amino}-2-oxoethoxy)piperidine-1-carboxylate (EXAMPLE 209) and methylmagnesium bromide by a procedure analogous to that described in EXAMPLE 208. Mass spectrum (ESI) 535.5 (M+1). $^1$H NMR (500 MHz, CDCl$_3$): δ 1.47 (s, 9H); 1.63 (m, 2H); 1.82 (s, 6H); 1.95 (m, 2H); 3.11 (m, 2H); 3.65 (m, 1H);

3.87 (m, 2H); 4.15 (s, 2H); 7.79 (d, J=9.0 Hz, 2H); 7.84 (d, J=1.3 Hz, 1H); 7.95 (d, J=1.6 Hz, 1H); 8.22 (d, J=8.6 Hz, 2H); 8.51 (s, 1H).

Example 211

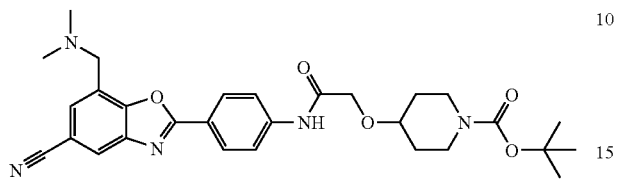

tert-butyl 4-{2-[(4-{5-cyano-7-[(dimethylamino) methyl]-1,3-benzoxazol-2-yl}phenyl)amino]-2-oxoethoxy}piperidine-1-carboxylate To a mixture of 43 mg of tert-butyl 4-(2-{[4-(5-cyano-7-formyl-1,3-benzoxazol-2-yl)phenyl]amino}-2-oxoethoxy) piperidine-1-carboxylate (EXAMPLE 206), 85 μl of dimethylamine, and 5 μl of AcOH in 5 ml of 1,2-dichloroethane were added 36 mg of NaBH(OAc)$_3$ and the resulting mixture was stirred under nitrogen at room temperature for 40 minutes, diluted liberally with CH$_2$Cl$_2$, filtered and concentrated. The product was purified by thin layer chromatography (2×1000 μm plates) eluting with 5% MeOH in CH$_2$Cl$_2$ to provide the title compound. Mass spectrum (ESI) 534.5 (M+1). $^1$H NMR (500 MHz, CDCl$_3$): δ 1.47 (s, 9H); 1.63 (m, 2H); 1.95 (m, 2H); 2.35 (s, 6H); 3.11 (m, 2H); 3.65 (m, 1H); 3.81 (s, 2H); 3.87 (m, 2H); 4.14 (s, 2H); 7.67 (s, 1H); 7.78 (d, J=8.7 Hz, 2H); 7.95 (d, J=1.4 Hz, 1H); 8.24 (d, J=8.7 Hz, 2H); 8.50 (s, 1H).

Intermediate 14

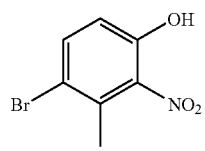

4-bromo-3-methyl-2-nitrophenol

A solution of bromine (3.03 g, 0.971 mL, 18.9 mmol) in AcOH (2.3 mL) was added dropwise to a stirred solution of 3-methyl-2-nitrophenol (3.06 g, 20.0 mmol) in AcOH (11 mL) and CHCl$_3$ (3 mL) at 0° C. The mixture was stirred at 0° C. for 1.5 h then poured into ice (40 mL) and extracted with CHCl$_3$ (3×10 mL). The combined organic extracts were washed with H$_2$O and brine, dried (Na$_2$SO$_4$) then concentrated under reduced pressure to afford the crude product. This was purified by flash column chromatography (Si, 40×230 mm, 0-25% EtOAc in hexanes gradient) to afford 4-bromo-3-methyl-2-nitrophenol as a yellow solid. $^1$H NMR (500 MHz, CDCl$_3$) δ 9.31 (s, 1H), 7.68 (d, J=9.0 Hz, 1H), 6.94 (d, J=9.0 Hz, 1H), 2.65 (s, 3H).

Intermediate 15

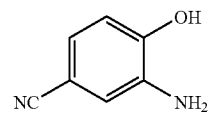

3-amino-4-hydroxybenzonitrile

A mixture of 4-hydroxy-3-nitrobenzonitrile (328 mg, 2.00 mmol), NH$_4$O$_2$CH (631 mg, 10 mmol) and 10% Pd/C (55 mg) in MeOH (5 mL) was stirred at room temperature overnight. The mixture was concentrated under reduced pressure and diluted with EtOAc and brine. The aqueous layer was extracted with EtOAc (3×) and the combined organic extracts were dried (MgSO$_4$) and concentrated under reduced pressure to afford the crude product. This was purified by flash column chromatography (Si, 40×230 mm, 0-30% EtOAc in CH$_2$Cl$_2$ gradient) to afford 2-amino-4-bromo-6-methylphenol as a solid. LCMS calc.=135.03; found=135.06 (M+1)$^+$. $^1$H NMR (500 MHz, CD$_3$OD) δ 6.97 (d, J=2.0 Hz, 1H), 6.92 (dd, J=8.0, 2.0 Hz, 1H), 6.77 (d, J=8.0 Hz, 1H).

Intermediate 16

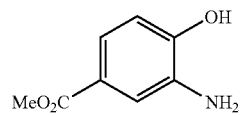

methyl 3-amino-4-hydroxybenzoate (Trimethylsilyl)diazomethane (3.48 mL, 2M in hexanes, 6.97 mmol) was added to a stirred solution of 3-amino-4-hydroxybenzoic acid (820 mg, 5.36 mmol) in MeOH (20 mL) and the resulting solution was stirred at room temperature for 20 min. The solution was concentrated under reduced pressure and diluted with EtOAc and brine. The aqueous layer was extracted with EtOAc (3×) and the combined organic extracts were dried (MgSO$_4$) and concentrated under reduced pressure to afford the crude product. This was purified by flash column chromatography (Si, 30×130 mm, 0-30% EtOAc in CH$_2$Cl$_2$ gradient) to afford a byproduct methyl 4-hydroxy-3-(methylamino)benzoate and the desired product methyl 3-amino-4-hydroxybenzoate as solids. LCMS calc.=168.07;

found=168.1 (M+1)⁺. ¹H NMR (500 MHz, CDCl₃) δ 7.49 (d, J=2.0 Hz, 1H), 7.45 (dd, J=8.0, 2.0 Hz, 1H), 6.79 (d, J=8.0 Hz, 1H), 3.91 (s, 3H).

Intermediate 17

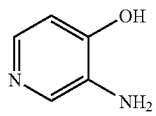

3-aminopyridin-4-ol

A suspension of PtO₂ (8.1 mg, 0.036 mmol) in a solution of 3-nitropyridin-4-ol (100 mg, 0.714 mmol) in EtOH (5 mL) was stirred under a balloon of H₂ overnight. The reaction mixture was filtered through Celite and the filtrate was concentrated under reduced pressure to afford 3-aminopyridin-4-ol as a brown solid. LCMS calc.=111.06; found=110.9 (M+1)⁺.

Example 212

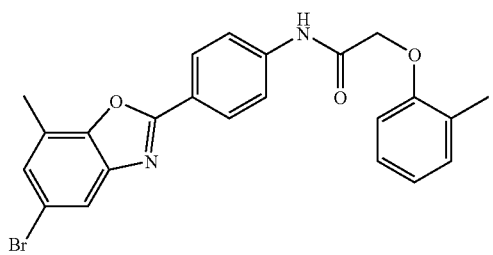

N-[4-(5-bromo-7-methyl-1,3-benzoxazol-2-yl)phenyl]-2-(2-methylphenoxy)acetamide

Step A: 4-bromo-2-methyl-6-nitrophenol

A solution of 90% HNO₃ (0.49 g, 324 µL, 6.95 mmol) and AcOH (1.6 mL) was added dropwise to a stirred solution of 4-bromo-2-methylphenol (1.00 g, 5.35 mmol) in AcOH (5.3 mL) at 40° C. The mixture was stirred for 1 h after which time the reaction was poured into ice/water (30 mL). The mixture was neutralized with saturated NaHCO₃ and acidified to pH 4 with 6N HCl. The mixture was extracted with EtOAc (4×100 mL) and CH₂Cl₂ (2×100 mL) and the combined organic extracts were dried (MgSO₄) and concentrated under reduced pressure to afford the crude product. This was purified by flash column chromatography (Si, 40×230 mm, 0-20% EtOAc in CHCl₃ gradient) to afford 2-amino-4-bromo-6-methylphenol as a yellow solid. ¹H NMR (500 MHz, CDCl₃) δ 10.81 (s, 1H), 8.09 (d, J=2.3 Hz, 1H), 7.55 (d, J=1.8 Hz, 1H), 2.33 (s, 3H).

Step B: 2-amino-4-bromo-6-methylphenol

A mixture of SnCl₂.2H₂O (4.04 g, 17.9 mmol) and concentrated HCl (8.9 mL) in MeOH (16.2 mL) was cooled to 15° C. and treated with 4-bromo-2-methyl-6-nitrophenol (0.865 g, 3.73 mmol) in one portion. After the addition was complete, the reaction was warmed to room temperature and stirred overnight. After this time the reaction mixture was diluted with EtOAc and the pH was adjusted to 7 with saturated NaHCO₃. The mixture was filtered through Celite and the filter cake was washed with EtOAc. The organic phase was separated and the aqueous phase was extracted with EtOAc. The combined organic extracts were dried (MgSO₄) and concentrated under reduced pressure to afford 2-amino-4-bromo-6-methylphenol as a colorless solid. LCMS calc.=204.1; found=203.98 (M+1)⁺. ¹H NMR (500 MHz, DMSO-d₆) δ 8.09 (br s, 1H), 6.60 (d, J=2.6 Hz, 1H), 6.43 (d, J=2.6 Hz, 1H), 4.81 (br s, 2H), 2.06 (s, 3H).

Step C: N-[4-(5-bromo-7-methyl-1,3-benzoxazol-2-yl)phenyl]-2-(2-methylphenoxy)acetamide A mixture of 4-{[(2-methylphenoxy)acetyl]amino}benzoic acid (300 mg, 1.05 mmol), 2-amino-4-bromo-6-methylphenol (213 mg, 1.05 mmol) and boric acid (84.6 mg, 1.37 mmol) in o-xylene (60 mL) was heated at reflux under a Dean-Stark apparatus overnight. After this time the reaction mixture was diluted with EtOAc (50 mL), washed successively with saturated NaHCO₃ (50 mL), H₂O (50 mL), and brine (50 mL), dried (Na₂SO₄) and concentrated under reduced pressure to afford the crude product. This was purified by flash column chromatography (Si, 30×130 mm, 0-10% EtOAc in CHCl₃ gradient) to afford a byproduct 5-bromo-7-methyl-2-[(2-methylphenoxy)methyl]-1,3-benzoxazole and the desired product N-[4-(5-bromo-7-methyl-1,3-benzoxazol-2-yl)phenyl]-2-(2-methylphenoxy)acetamide as colorless solids. LCMS calc.=453.06; found=453.1 (M+1)⁺. ¹H NMR (500 MHz, CDCl₃) δ 8.52 (s, 1H), 8.22 (d, J=8.7 Hz, 2H), 7.76 (d, J=8.7 Hz, 2H), 7.68 (d, J=1.6 Hz, 1H), 7.26-7.21 (m, 3H), 7.12-7.04 (t, J=7.4 Hz, 1H), 6.85 (d, J=8.2 Hz, 1H), 4.63 (s, 2H), 2.55 (s, 3H), 2.40 (s, 3H).

Example 213

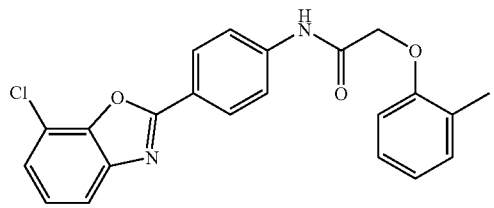

N-[4-(7-chloro-1,3-benzoxazol-2-yl)phenyl]-2-(2-methylphenoxy)acetamide

Step A: 2-amino-6-chlorophenol

A suspension of 10% Pd/C (10 mg) in a solution of 2-chloro-6-nitrophenol (100 mg, 0.576 mmol) in EtOH (5 mL) was stirred under a balloon of H₂ for 5 h. The reaction mixture was filtered through Celite and the filtrate was concentrated under reduced pressure to afford 2-amino-6-chlorophenol as a brown solid. ¹H NMR (500 MHz, CDCl₃) δ 6.73 (dd, J=8.0, 1.6 Hz, 1H), 6.69 (t, J=8.0 Hz, 1H), 6.62 (dd, J=7.6, 1.6 Hz, 1H).

Step B: N-[4-(7-chloro-1,3-benzoxazol-2-yl)phenyl]-2-(2-methylphenoxy)acetamide

A mixture of 4-{[(2-methylphenoxy)acetyl]amino}benzoic acid (87.6 mg, 0.307 mmol), 2-amino-6-chlorophenol (61.8 mg, 0.430 mmol) and boric acid (26.6 mg, 0.430 mmol) in o-xylene (2.5 mL) was subjected to microwave irradiation (300 W, 270° C., 60 min). The reaction mixture was diluted with EtOAc (25 mL), washed successively with saturated NaHCO₃ (25 mL), H₂O (25 mL), and brine (25 mL), dried (MgSO₄) and concentrated under reduced pressure to afford the crude product. This was purified by flash column chromatography (Si, 20×75 mm, 0-30% EtOAc in hexanes gradient) and reversed phase HPLC (C18, 20×150 mm, 0.1% TFA, 20-100% MeCN in H₂O gradient) to afford N-[4-(7-chloro-1,3-benzoxazol-2-yl)phenyl]-2-(2-methylphenoxy)acetamide as a colorless solid. LCMS calc.=393.10; found=393.15 (M+1)⁺. ¹H NMR (500 MHz, CDCl₃) δ 8.54 (s, 1H), 8.29 (d, J=8.7 Hz, 2H), 7.80 (d, J=8.7 Hz, 2H), 7.66 (dd, J=7.7, 1.2 Hz, 1H), 7.34 (dd, J=8.0, 1.1 Hz, 1H), 7.29 (t, J=7.8 Hz, 1H), 7.23 (m, 2H), 7.00 (t, J=7.4 Hz, 1H), 6.87 (d, J=8.1 Hz, 1H), 4.66 (s, 2H), 2.55 (s, 3H), 2.40 (s, 3H).

Example 214

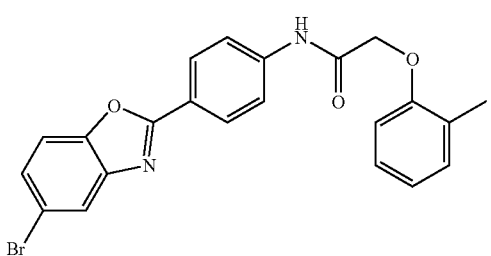

N-[4-(5-bromo-1,3-benzoxazol-2-yl)phenyl]-2-(2-methylphenoxy)acetamide

Step A: 2-amino-4-bromophenol

Synthesized from the appropriately substituted commercially available o-nitrophenol using SnCl₂.2H₂O as in EXAMPLE 212, Step B.

Step B: N-[4-(5-bromo-1,3-benzoxazol-2-yl)phenyl]-2-(2-methylphenoxy)acetamide

A solution of oxalyl chloride (702 μL, 2 M in CH₂Cl₂, 1.40 mmol) was added to a stirred suspension of 4-{[(2-methylphenoxy)acetyl]amino}benzoic acid (200 mg, 0.702 mmol) in CH₂Cl₂ (11 mL) followed by a few drops of DMF at room temperature under N₂. The reaction was stirred at room temperature for 4 h after which time the suspension dissolved. The reaction mixture was concentrated under reduced pressure and azeotroped with toluene (10 mL). The crude acid chloride and 2-amino-4-bromophenol (198 mg, 1.05 mmol) were dissolved in 1,4-dioxane (20 mL) and heated at reflux for 4 h under N₂. The reaction was diluted with EtOAc (50 mL) and water (50 mL) and the aqueous layer was extracted with EtOAc (2×50 mL). The combined organic extracts were washed with brine (50 mL), dried (Na₂SO₄) and concentrated under reduced pressure to afford the crude amide product. A mixture of the crude amide and pyridinium p-toluenesulfonate (17.6 mg, 0.0702 mmol) in o-xylene (30 mL) was heated at reflux under a Dean-Stark apparatus overnight under N₂. The reaction was diluted with EtOAc (100 mL) and washed successively with saturated NaHCO₃ (50 mL), water (50 mL) and brine (50 mL), dried (Na₂SO₄) and concentrated under reduced pressure to afford the crude product. This was purified by flash column chromatography (Si, 30×130 mm, 0-30% EtOAc in hexanes gradient) to afford N-[4-(5-bromo-1,3-benzoxazol-2-yl)phenyl]-2-(2-methylphenoxy)acetamide as a colorless solid. LCMS calc.=439.05; found=439.03 (M+1)⁺. ¹H NMR (500 MHz, CDCl₃) δ 8.53 (s, 1H), 8.23 (d, J=8.7 Hz, 2H), 7.88 (br s, 1H), 7.78 (d, J=8.7 Hz, 1H), 7.45 (br s, 2H), 7.25-7.19 (m, 2H), 7.00 (t, J=7.3 Hz, 1H), 6.86 (d, J=8.2 Hz, 1H), 4.64 (s, 2H), 2.40 (s, 3H).

Example 215

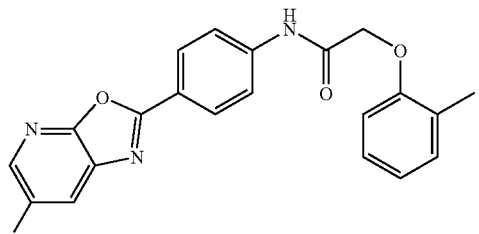

N-[4-(6-chloro[1,3]oxazolo[5,4-b]pyridin-2-yl)phenyl]-2-(2-methylphenoxy)acetamide A solution of oxalyl chloride (351 μL, 2 M in CH₂Cl₂, 0.702 mmol) was added to a stirred suspension of 4-{[(2-methylphenoxy)acetyl]amino}benzoic acid (100 mg, 0.351 mmol) in CH₂Cl₂ (20 mL) followed by a few drops of DMF at room temperature under N₂. The reaction was stirred at room temperature for 2 h after which time the suspension dissolved. The reaction mixture was concentrated under reduced pressure and azeotroped with toluene (10 mL). A mixture of the crude acid chloride, 2,5-dichloropyridin-3-amine (63 mg, 0.386 mmol) and 1,4-dioxane (10 mL) was heated at reflux overnight under N₂. The reaction mixture was concentrated under reduced pressure to afford the crude amide product. Separately, a mixture of P₂O₅ (109.5 mg, 0.386 mmol), hexamethyldisilane (245 mg, 321 μL, 1.51 mmol) and 1,2-dichlorobenzene (1 mL) was heated at reflux for 10 min under N₂ until the reaction became clear. The mixture was transferred by cannula to a suspension of the crude amide above in 1,2-dichlorobenzene (2 mL). The resulting mixture was heated at reflux under N₂ for 2 days. The reaction mixture was cooled, diluted with CH₂Cl₂ (25 mL) and washed with saturated NaHCO₃ (25 mL). The aqueous layer was extracted with CH₂Cl₂ (2×25 mL) and EtOAc (25 mL) and the combined organic extracts were washed with brine (10 mL), dried (Na₂SO₄) and concentrated under reduced pressure to afford the crude product. This was purified by flash column chromatography (Si, 30×130 mm, 0-10% EtOAc in CHCl₃ gradient) to afford N-[4-(6-chloro[1,3]oxazolo[5,4-b]pyridin-2-yl)phenyl]-2-(2-methylphenoxy)acetamide as a colorless solid. LCMS calc.=394.10; found=394.1 (M+1)⁺. ¹H NMR (500 MHz, DMSO-d₆) δ 10.49 (s, 1H), 8.43 (d, J=2.3 Hz, 1H), 8.40 (d, J=2.3 Hz, 1H), 8.19 (d, J=8.7 Hz, 2H), 7.90 (d, J=8.7 Hz, 2H), 7.19-7.12 (m, 2H), 6.87 (m, 2H), 4.78 (s, 2H), 2.25 (s, 3H).

Example 216

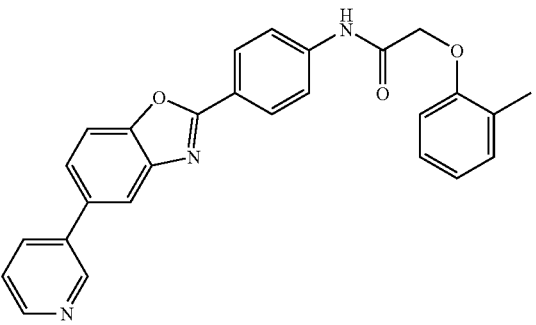

2-(2-methylphenoxy)-N-[4-(5-pyridin-3-yl-1,3-benzoxazol-2-yl)phenyl]acetamide

A mixture of N-[4-(5-bromo-1,3-benzoxazol-2-yl)phenyl]-2-(2-methylphenoxy)acetamide (40 mg, 0.0915 mmol), pyridin-3-ylboronic acid (41.4 mg, 0.274 mmol), (Ph$_3$P)$_4$Pd (10.6 mg, 0.00914 mmol), Na$_2$CO$_3$ (57 mg, 0.687 mmol) in benzene/EtOH/H$_2$O (1.4 mL/0.2 mL/0.6 mL) was heated at reflux overnight under N$_2$. The reaction was diluted with CH$_2$Cl$_2$ (10 mL) and water (10 mL) and the aqueous layer was extracted with CH$_2$Cl$_2$ (2×10 mL). The combined organic extracts were washed with brine, dried (Na$_2$SO$_4$) and concentrated under reduced pressure to afford the crude product. This was purified by flash column chromatography (Si, 20×75 mm, 0-100% EtOAc in CHCl$_3$ gradient) to afford 2-(2-methylphenoxy)-N-[4-(5-pyridin-3-yl-1,3-benzoxazol-2-yl)phenyl]acetamide as a colorless solid. LCMS calc.=436.17; found=436.2 (M+1)$^+$. $^1$H NMR (500 MHz, DMSO-d$_6$) δ 10.44 (s, 1H), 8.97 (br s, 1H), 8.59 (br d, J=4.5 Hz, 1H), 8.19 (d, J=8.7 Hz, 2H), 8.16 (m, 1H), 8.13 (d, J=1.7 Hz, 1H), 7.90 (d, J=6.9 Hz, 1H), 7.89 (t, J=6.9 Hz, 2H), 7.75 (dd, J=8.4, 1.8 Hz, 1H), 7.51 (dd, J=7.8, 4.7 Hz, 1H), 7.16 (m, 2H), 6.88 (m, 2H), 4.78 (s, 2H), 2.26 (s, 3H).

Example 217

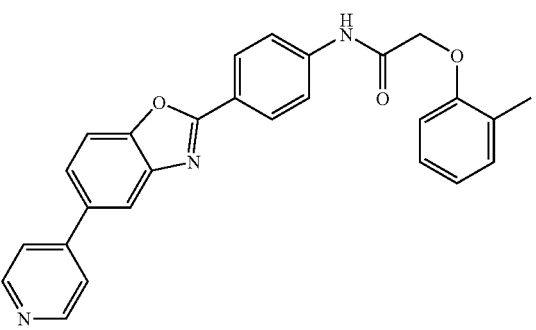

2-(2-methylphenoxy)-N-[4-(5-pyridin-4-yl-1,3-benzoxazol-2-yl)phenyl]acetamide A mixture of N-[4-(5-bromo-1,3-benzoxazol-2-yl)phenyl]-2-(2-methylphenoxy)acetamide (40 mg, 0.0915 mmol), pyridin-4-ylboronic acid (13.8 mg, 0.0915 mmol), (Ph$_3$P)$_4$Pd (10.6 mg, 0.00914 mmol), Na$_2$CO$_3$ (91 μL, 2 M aqueous solution, 0.183 mmol) in DME/EtOH/H$_2$O (0.75 mL/0.18 mL/0.24 mL) was degassed and subjected to microwave irradiation (60 W, 150° C., 10 min). The reaction was diluted with CH$_2$Cl$_2$ (10 mL) and water (10 mL) and the aqueous layer was extracted with CH$_2$Cl$_2$ (2×10 mL). The combined organic extracts were washed with brine (10 mL), dried (Na$_2$SO$_4$) and concentrated under reduced pressure to afford the crude product. This was purified by flash column chromatography (Si, 20×75 mm, 0-100% EtOAc in CHCl$_3$ gradient) and reversed phase HPLC(C18, 20×150 mm, 0.1% TFA, 20-100% MeCN in H$_2$O gradient) to afford the desired product as its corresponding TFA salt. A solution of the salt in CH$_2$Cl$_2$ was washed with saturated NaHCO$_3$. The organic layer was dried (Na$_2$SO$_4$) and concentrated under reduced pressure to afford 2-(2-methylphenoxy)-N-[4-(5-pyridin-4-yl-1,3-benzoxazol-2-yl)phenyl]acetamide as a colorless solid. LCMS calc.=436.17; found=436.2 (M+1)$^+$. $^1$H NMR (500 MHz, DMSO-d$_6$) δ 8.69 (br s, 2H), 8.56 (s, 1H), 8.27 (d, J=8.7 Hz, 2H), 8.00 (s, 1H), 7.80 (d, J=8.7 Hz, 2H), 7.67 (m, 1H), 7.62 (dd, J=8.4, 1.4 Hz, 1H), 7.56 (br d, J=4.7 Hz, 2H), 7.25-7.19 (m, 2H), 6.99 (t, J=7.4 Hz, 1H), 6.86 (d, J=8.2 Hz, 1H), 4.64 (s, 2H), 2.40 (s, 3H).

Example 218

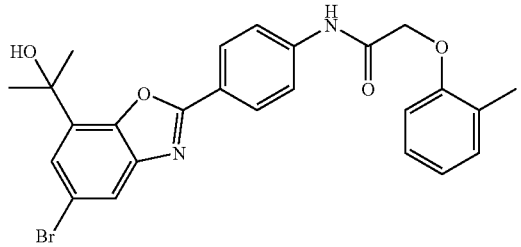

N-{4-[5-bromo-7-(1-hydroxy-1-methylethyl)-1,3-benzoxazol-2-yl]phenyl}-2-(2-methylphenoxy)acetamide Methyl magnesium chloride (333 μL, 3 M in THF, 1.00 mmol) was added to a stirred solution of N-[4-(7-acetyl-5-bromo-1,3-benzoxazol-2-yl)phenyl]-2-(2-methylphenoxy)acetamide (240 mg, 0.5 mmol) in dry THF at −20° C. under N$_2$. The reaction was allowed to warm to −10° C. over 3 h then was stirred at room temperature for 2 h. The reaction was quenched with saturated NH$_4$Cl and extracted with EtOAc (2×). The combined organic extracts were concentrated under reduced pressure to afford the crude product. This was purified by flash column chromatography (Si, 30×130 mm, EtOAc/hexanes gradient) to afford N-{4-[5-bromo-7-(1-hydroxy-1-methylethyl)-1,3-benzoxazol-2-yl]phenyl}-2-(2-methylphenoxy)acetamide as a colorless solid. LCMS calc.=497.09; found=497.2 (M+1)$^+$. $^1$H NMR (500 MHz, DMSO-d$_6$) δ 10.50 (s, 1H), 8.19 (d, J=8.5 Hz, 2H), 7.91 (d, J=9.0 Hz, 2H), 7.87 (d, J=1.5 Hz, 1H), 7.63 (d, J=2.0 Hz, 1H), 7.21-7.14 (m, 2H), 6.89 (m, 2H), 5.58 (s, 1H), 4.80 (s, 2H), 2.27 (s, 3H), 1.67 (s, 6H).

Example 219

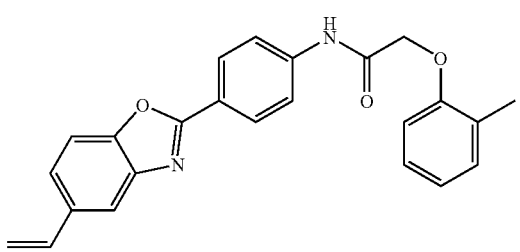

2-(2-methylphenoxy)-N-[4-(5-vinyl-1,3-benzoxazol-2-yl)phenyl]acetamide (Ph$_3$P)$_4$Pd (4.0 mg, 0.00343 mmol) and tributylvinyl tin (13 mg, 12 µL, 0.0412 mmol) were added to a stirred solution of N-[4-(5-bromo-1,3-benzoxazol-2-yl)phenyl]-2-(2-methylphenoxy)acetamide (15.0 mg, 0.0343 mmol) in dry DMF (1 mL) under N$_2$. The mixture was degassed with N$_2$ and heated at 80° C. for 12 h. The reaction was diluted with CH$_2$Cl$_2$ (10 mL) and water (10 mL). The aqueous layer was extracted with CH$_2$Cl$_2$ (2×10 mL) and the combined organic extracts were washed with brine (10 mL), dried (Na$_2$SO$_4$) and concentrated under reduced pressure to afford the crude product. This was purified by flash column chromatography (Si, 20×75 mm, 0-30% EtOAc in hexanes gradient) to afford 2-(2-methylphenoxy)-N-[4-(5-vinyl-1,3-benzoxazol-2-yl)phenyl]acetamide as a colorless solid. LCMS calc.=385.16; found=385.2 (M+1)$^+$. $^1$H NMR (500 MHz, CDCl$_3$) δ 8.52 (s, 1H), 8.26 (d, J=8.4 Hz, 2H), 7.78 (m, 3H), 7.51 (d, J=8.4 Hz, 1H), 7.43 (t, J=8.4 Hz, 1H), 7.22 (m, 2H), 7.00 (t, J=7.4 Hz, 1H), 6.86 (d, J=8.1 Hz, 1H), 6.83 (dd, J=17.5, 10.9 Hz, 1H), 5.78 (d, J=17.5 Hz, 1H), 5.28 (d, J=10.9 Hz, 1H), 4.65 (s, 2H), 2.40 (s, 2H).

Example 220

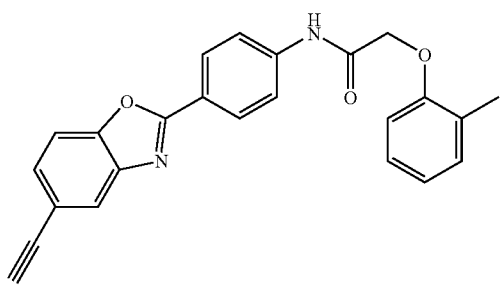

N-[4-(5-ethynyl-1,3-benzoxazol-2-yl)phenyl]-2-(2-methylphenoxy)acetamide

A solution of N-[4-(5-bromo-1,3-benzoxazol-2-yl)phenyl]-2-(2-methylphenoxy)acetamide (15 mg, 0.0343 mmol), trimethylsilylacetylene (13.9 mg, 20 µL, 0.142 mmol), (Ph$_3$P)$_2$PdCl$_2$ (2.4 mg, 0.00343 mmol), CuI (5.0 mg, 0.0263 mmol), Ph$_3$P (1.8 mg, 0.00686 mmol) and Et$_2$NH (37.6 mg, 53.8 µL, 0.515 mmol) in dry DMF (0.5 mL) was subjected to microwave irradiation (75 W, 120° C., 75 min). The reaction was diluted with CH$_2$Cl$_2$ (10 mL) and 0.1M HCl (10 mL). The aqueous layer was extracted with CH$_2$Cl$_2$ (2×10 mL) and the combined organic extracts were washed with saturated NaHCO$_3$ (10 mL) and water (10 mL), dried (Na$_2$SO$_4$) and concentrated under reduced pressure to afford the crude product. A solution of the crude product in 0.1M NaOH (4 mL) and THF (10 mL) was stirred at room temperature for 1 h. The reaction was diluted with CH$_2$Cl$_2$ (15 mL) and water (15 mL). The aqueous layer was extracted with CH$_2$Cl$_2$ (2×15 mL) and the combined organic extracts were washed with brine (15 mL), dried (Na$_2$SO$_4$) and concentrated under reduced pressure to afford the crude product. This was purified by flash column chromatography (Si, 20×75 mm, 0-5% EtOAc in CHCl$_3$ gradient) to afford recovered starting material (6.8 mg), dehalogenated starting material (0.8 mg) and N-[4-(5-ethynyl-1,3-benzoxazol-2-yl)phenyl]-2-(2-methylphenoxy)acetamide as a colorless solid. LCMS calc.=383.14; found=383.2 (M+1)$^+$. $^1$H NMR (500 MHz, CDCl$_3$) δ 8.53 (s, 1H), 8.24 (d, J=8.7 Hz, 2H), 7.88 (s, 1H), 7.78 (d, J=8.7 Hz, 2H), 7.51-7.44 (m, 2H), 7.21 (m, 2H), 7.00 (t, J=7.4 Hz, 1H), 6.86 (d, J=8.1 Hz, 1H), 4.65 (s, 2H), 3.08 (s, 1H), 2.40 (s, 3H).

Example 221

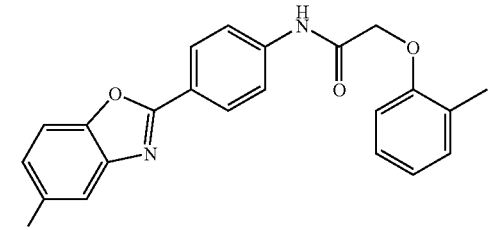

N-[4-(5-amino-1,3-benzoxazol-2-yl)phenyl]-2-(2-methylphenoxy)acetamide

A suspension of 10% Pd/C (200 mg) in a solution of 2-(2-methylphenoxy)-N-[4-(5-nitro-1,3-benzoxazol-2-yl)phenyl]acetamide (620 mg, 1.54 mmol) in CH$_2$Cl$_2$ (10 mL) and MeOH (10 mL) was shaken under an atmosphere of H$_2$ (50 psi) for 3 days. After this time the mixture was filtered through a plug of Celite and the filtrate was concentrated under reduced pressure to afford the crude product. This was purified by reversed phase HPLC(C18, 20×150 mm, 0.1% TFA, 10-100% MeCN in H$_2$O gradient) to afford N-[4-(5-amino-1,3-benzoxazol-2-yl)phenyl]-2-(2-methylphenoxy)acetamide as a colorless solid. LCMS calc.=374.15; found=374.2 (M+1)$^+$. $^1$H NMR (500 MHz, DMSO-d$_6$) δ 8.10 (d, 2H), 7.85

(d, 2H), 7.40 (d, 1H), 7.21-7.10 (m, 2H), 6.89 (m, 3H), 6.68 (d, 1H), 4.79 (s, 2H), 2.28 (s, 3H).

Example 222

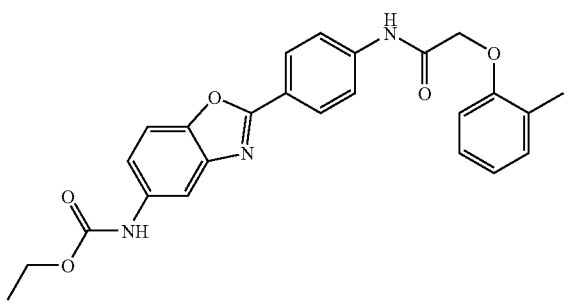

ethyl[2-(4-{[(2-methylphenoxy)acetyl]amino}phenyl)-1,3-benzoxazol-5-yl]carbamate A solution of N-[4-(5-amino-1,3-benzoxazol-2-yl)phenyl]-2-(2-methylphenoxy)acetamide (25 mg, 0.067 mmol) in ethyl chloroformate (3 mL) was stirred at 90° C. for 2 h. The reaction mixture was concentrated under reduced pressure to afford the crude product. This was purified by flash column chromatography (Si, 20×75 mm, 0-30% EtOAc in CHCl$_3$ gradient) to afford ethyl[2-(4-{[(2-methylphenoxy)acetyl]amino}phenyl)-1,3-benzoxazol-5-yl]carbamate as a colorless solid. LCMS calc.=446.17; found=446.2 (M+1)$^+$. $^1$H NMR (500 MHz, DMSO-d$_6$) δ 9.76 (br s, (d, 2H), 7.94 (s, 1H), 7.86 (d, 2H), 7.66 (d, 1H), 7.40 (d, 1H), 7.21-7.11 (m, 2H), 6.89 (m, 2H), 4.79 (s, 2H), 4.15 (q, 2H), 2.27 (s, 3H), 1.27 (t, 3H).

Example 223

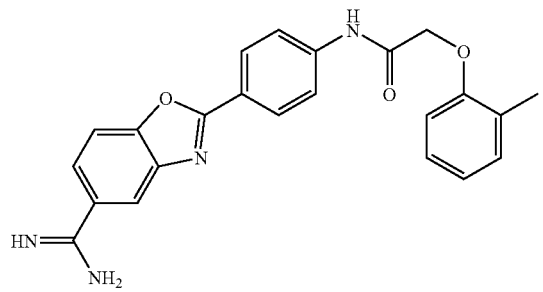

N-(4-{5-[amino(imino)methyl]-1,3-benzoxazol-2-yl}phenyl)-2-(2-methylphenoxy)acetamide Dry HCl was bubbled through a stirred solution of N-[4-(5-cyano-1,3-benzoxazol-2-yl)phenyl]-2-(2-methylphenoxy)acetamide (20 mg, 0.052 mmol) in MeOH (5 mL) at 0° C. for 30 min. Ammonium formate (8.0 mg, 0.13 mmol) was added to the solution and the mixture was stirred for 3 days. The reaction mixture was concentrated under reduced pressure to afford the crude product. This was purified by reversed phase HPLC(C18, 20×150 mm, 0.1% TFA, 10-100% MeCN in H$_2$O gradient) to afford N-(4-{5-[amino(imino)methyl]-1,3-benzoxazol-2-yl}phenyl)-2-(2-methylphenoxy)acetamide (TFA salt) as a colorless solid. LCMS calc.=401.16; found=401.2 (M+1)$^+$.

Example 224

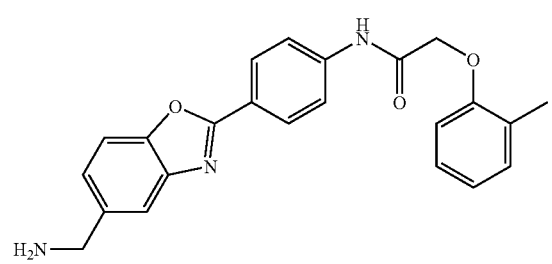

N-{4-[5-(aminomethyl)-1,3-benzoxazol-2-yl]phenyl}-2-(2-methylphenoxy)acetamide

A suspension of Raney Ni (10 mg) in a solution of N-[4-(5-cyano-1,3-benzoxazol-2-yl)phenyl]-2-(2-methylphenoxy)acetamide (30 mg, 0.078 mmol) in DMF (7 mL) was hydrogenated at 35 atm, at room temperature for 48 h. The mixture was filtered through Celite and the filtrate was concentrated under reduced pressure to afford the crude product. This was purified by reversed phase HPLC(C18, 20×150 mm, 0.1% TFA, 10-100% MeCN in H$_2$O gradient) to afford N-{4-[5-(aminomethyl)-1,3-benzoxazol-2-yl]phenyl}-2-(2-methylphenoxy)acetamide as a colorless solid. LCMS calc.=388.17; found=388.3 (M+1)$^+$. $^1$H NMR (500 MHz, DMSO-d$_6$) δ 10.46 (s, 1H), 8.17 (d, J=9.0 Hz, 2H), 7.89 (d, J=9.0 Hz, 2H), 7.83 (d, J=8.5 Hz, 1H), 7.49 (dd, J=8.0, 1.5 Hz, 1H), 7.18-7.12 (m, 2H), 6.88 (m, 2H), 4.77 (s, 2H), 4.17 (s, 2H), 2.26 (s, 3H).

Example 225

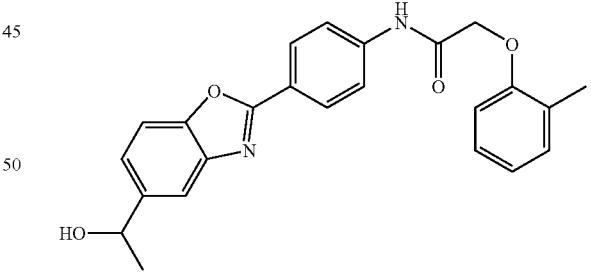

N-{4-[5-(1-hydroxyethyl)-1,3-benzoxazol-2-yl]phenyl}-2-(2-methylphenoxy)acetamide NaBH$_4$ (9.0 mg, 0.150 mmol) was added to a stirred suspension of N-[4-(5-acetyl-1,3-benzoxazol-2-yl)phenyl]-2-(2-methylphenoxy)acetamide (20.0 mg, 0.0500 mmol) in MeOH (3 mL). After 1 h the reaction was diluted with EtOAc (20 mL) and water (20 mL). The aqueous layer was extracted with EtOAc (2×20 mL). The combined organic extracts were dried (Na$_2$SO$_4$) and concentrated under reduced pressure to afford N-{4-[5-(1-hydroxyethyl)-1,3-benzoxazol-2-yl]phenyl}-2-(2-methylphenoxy)acetamide as a colorless solid. LCMS calc.=403.17; found=403.2 (M+1)+. ¹H NMR (500 MHz, CDCl₃) δ 8.52 (s, 1H), 8.25 (d, J=8.7 Hz, 2H), 7.78 (d, J=8.7 Hz, 2H), 7.76 (m, 1H), 7.54 (d, J=8.3 Hz, 1H), 7.39 (dd, J=8.4, 1.6 Hz, 1H), 7.22 (m, 2H), 7.00 (t, J=7.1 Hz, 1H), 6.86 (d, J=8.0 Hz, 1H), 5.05 (q, J=6.4 Hz, 1H), 4.65 (s, 2H), 2.40 (s, 3H), 1.94 (s, 1H), 1.56 (d, J=6.4 Hz, 3H).

Example 226

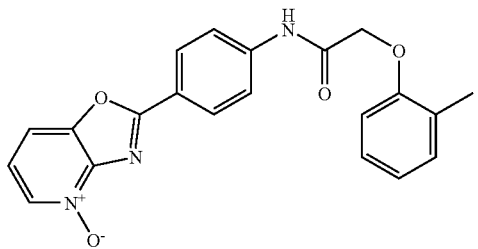

2-(2-methylphenoxy)-N-[4-(4-oxido[1,3]oxazolo[4,5-b]pyridin-2-yl)phenyl]acetamide A solution of 2-(2-methylphenoxy)-N-(4-[1,3]oxazolo[4,5-b]pyridin-2-ylphenyl)acetamide (70.9 mg, 0.197 mmol) and 30% H₂O₂ (135 μL, 1.19 mmol) in AcOH (2 mL) was heated at 90° C. for 36 h. The reaction mixture was concentrated under reduced pressure to afford the crude product. This was purified by reversed phase HPLC(C18, 20×150 mm, 0.1% TFA, 10-100% MeCN in H₂O gradient) to afford 2-(2-methylphenoxy)-N-[4-(4-oxido[1,3]oxazolo[4,5-b]pyridin-2-yl)phenyl]acetamide as a colorless solid. LCMS calc.=376.13; found=376.2 (M+1)+. ¹H NMR (500 MHz, DMSO-d₆) δ 10.52 (s, 1H), 8.31 (d, J=6.5 Hz, 1H), 8.19 (d, J=8.7 Hz, 2H), 7.91 (d, J=8.7 Hz, 2H), 7.80 (d, J=8.3 Hz, 1H), 7.39 (dd, J=8.3, 6.6 Hz, 1H), 7.15 (m, 2H), 6.89-6.85 (m, 2H), 4.78 (s, 2H), 2.25 (s, 3H).

Example 227

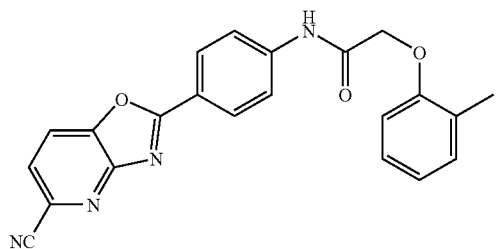

N-[4-(5-cyano[1,3]oxazolo[4,5-b]pyridin-2-yl)phenyl]-2-(2-methylphenoxy)acetamide A solution of benzoyl chloride (12.0 mg., 9.9 μL., 0.0855 mmol) in CHCl₃ (1.3 mL) was added to a mixture of KCN (9.9 mg, 0.153 mmol) in H₂O (532 μL) and 2-(2-methylphenoxy)-N-[4-(4-oxido[1,3]oxazolo[4,5-b]pyridin-2-yl)phenyl]acetamide (22.0 mg, 0.0611 mmol) in CHCl3 (1.3 mL) at 0° C. The reaction was stirred vigorously at room temperature overnight. The reaction was diluted with CHCl₃ (10 mL) and water (10 mL) and the aqueous layer was extracted with CHCl₃ (2×10 mL). The combined organic extracts were dried (Na₂SO₄) and concentrated under reduced pressure to afford the crude product. This was purified by flash column chromatography (Si, 20×75 mm, 0-10% EtOAc in CHCl₃ gradient) to afford N-[4-(5-cyano[1,3]oxazolo[4,5-b]pyridin-2-yl)phenyl]-2-(2-methylphenoxy)acetamide as a colorless solid. LCMS calc.=385.13; found=385.1 (M+1)+. ¹H NMR (500 MHz, DMSO-d₆) δ 10.55 (s, 1H), 8.43 (d, J=8.3 Hz, 1H), 8.24 (d, J=8.8 Hz, 2H), 8.09 (d, J=8.2 Hz, 1H), 7.93 (d, J=8.8 Hz, 2H), 7.15 (m, 2H), 6.87 (m, 2H), 4.79 (s, 2H), 2.25 (s, 3H).

Example 228

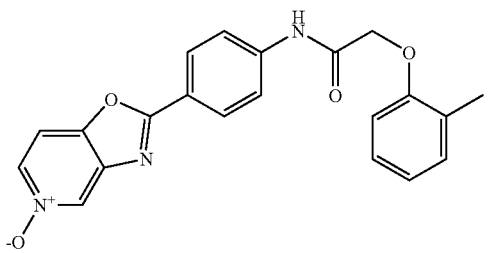

2-(2-methylphenoxy)-N-[4-(5-oxido[1,3]oxazolo[4,5-c]pyridin-2-yl)phenyl]acetamide m-CPBA (77%, 62 mg, 0.278 mmol) was added to a stirred solution/suspension of 2-(2-methylphenoxy)-N-(4-[1,3]oxazolo[4,5-c]pyridin-2-ylphenyl)acetamide (20.0 mg, 0.0557 mmol) in CH₂Cl₂ (0.84 mL) and the reaction was stirred overnight at room temperature. The mixture was diluted with EtOAc (20 mL) and washed with saturated NaHSO₃ (20 mL), saturated NaHCO₃ (20 mL) and brine (20 mL), dried (Na₂SO₄) and concentrated under reduced pressure to afford the crude product. This was purified by reversed phase HPLC (C18, 20×150 mm, 0.1% TFA, 10-100% MeCN in H₂O gradient) to afford 2-(2-methylphenoxy)-N-[4-(5-oxido[1,3]oxazolo[4,5-c]pyridin-2-yl)phenyl]acetamide as a colorless solid. LCMS calc.=376.13; found=376.2 (M+1)+. ¹H NMR (500 MHz, DMSO-d₆) δ 10.54 (s, 1H), 9.10 (s, 1H), 8.44 (d, J=6.8 Hz, 1H), 8.17 (d, J=8.7 Hz, 2H), 8.03 (d, J=6.9 Hz, 1H), 7.91 (d, J=8.7 Hz, 2H), 7.15 (m, 2H), 6.87 (m, 2H), 4.78 (s, 2H), 2.24 (d, J=6.2 Hz, 3H).

Example 229

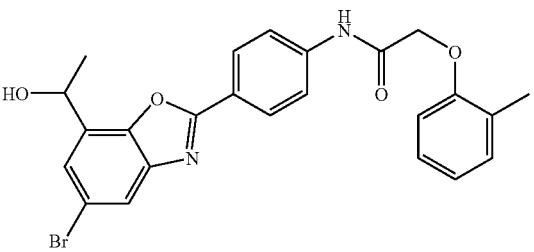

N-{4-[5-bromo-7-(1-hydroxyethyl)-1,3-benzoxazol-2-yl]phenyl}-2-(2-methylphenoxy)acetamide BF$_3$·Et$_2$O (188 μL, 1.50 mmol) was added to a stirred solution of N-[4-(7-acetyl-5-bromo-1,3-benzoxazol-2-yl)phenyl]-2-(2-methylphenoxy)acetamide (240 mg, 0.500 mmol) and NaCNBH$_3$ (63 mg, 1.0 mmol) in dry THF (1.5 mL) at 0° C. under N$_2$. The solution was stirred at room temperature overnight, then diluted with saturated NaHCO$_3$ and extracted with EtOAc (2×). The combined organic extracts were dried (MgSO$_4$) and concentrated under reduced pressure to afford the crude product. This was purified by flash column chromatography (Si, 20×75 mm, 0-10% EtOAc in CHCl$_3$ gradient) to afford N-{4-[5-bromo-7-(1-hydroxyethyl)-1,3-benzoxazol-2-yl]phenyl}-2-(2-methylphenoxy)acetamide as a colorless solid. LCMS calc.=481.08; found=481.1 (M+1)$^+$. $^1$H NMR (500 MHz, DMSO-d$_6$) δ 10.46 (s, 1H), 8.19 (d, J=8.5 Hz, 2H), 7.90 (d, J=8.5 Hz, 2H), 7.88 (d, J=2.0 Hz, 1H), 7.56 (d, J=1.5 Hz, 1H), 7.21-7.15 (m, 2H), 6.90 (m, 2H), 5.63 (d, J=5 Hz, 1H), 5.21 (pentet, J=6.0 Hz, 1H), 4.80 (s, 2H), 2.28 (s, 3H), 1.55 (d, J=6 Hz, 3H).

Example 230

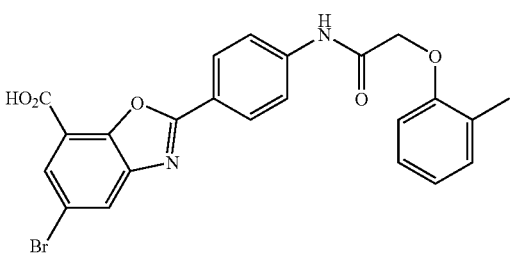

5-bromo-2-(4-{[(2-methylphenoxy)acetyl]amino}phenyl)-1,3-benzoxazole-7-carboxylic acid A sodium hypobromite solution was prepared by adding Br$_2$ (300 mg, 96 μL, 1.88 mmol) to a stirred solution of NaOH (300 mg, 7.51 mmol) in water (1.85 mL) at 0° C. An aliquot (185 μL) of the above solution was added to a stirred suspension of N-[4-(7-acetyl-5-bromo-1,3-benzoxazol-2-yl)phenyl]-2-(2-methylphenoxy)acetamide (20.0 mg, 0.0417 mmol) in 1,4-dioxane (0.37 mL) at room temperature and the mixture was stirred for 2 h. Saturated NaHSO$_4$ (1 mL) was added and the reaction mixture was diluted with water (15 mL) and acidified with 1N HCl to approximately pH 2. The mixture was extracted with EtOAc (3×20 mL) and the combined extracts were dried (Na$_2$SO$_4$) and concentrated under reduced pressure to afford 5-bromo-2-(4-{[(2-methylphenoxy)acetyl]amino}phenyl)-1,3-benzoxazole-7-carboxylic acid as a colorless solid. LCMS calc.=483.04; found=483.1 (M+1)$^+$. $^1$H NMR (500 MHz, DMSO-d$_6$) δ 10.49 (s, 1H), 8.26 (d, J=2.0 Hz, 1H), 8.16 (d, J=8.8 Hz, 3H), 7.93 (d, J=2.0 Hz, 1H), 7.90 (d, J=8.8 Hz, 2H), 7.17-7.13 (m, 2H), 6.87 (m, 2H), 4.78 (s, 2H), 2.25 (s, 3H).

Example 231

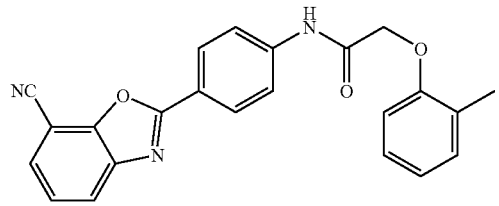

N-[4-(7-cyano-1,3-benzoxazol-2-yl)phenyl]-2-(2-methylphenoxy)acetamide

A solution of N-[4-(7-chloro-1,3-benzoxazol-2-yl)phenyl]-2-(2-methylphenoxy)acetamide (12.8 mg, 0.0326 mmol), tris(dibenzylideneacetone)dipalladium (3.0 mg, 0.326 mmol), 1,1'-bis(diphenylphosphino)ferrocene (3.6 mg, 0.00652 mmol) and Zn(CN)$_2$ (3.8 mg, 0.0326 mmol) in dimethylacetamide (1 mL) was degassed, flushed with N$_2$ and subjected to microwave irradiation (60 W, 200° C., 60 min). The reaction mixture was diluted with CH$_2$Cl$_2$ (10 mL) and water (10 mL). The aqueous layer was extracted with CH$_2$Cl$_2$ (2×10 mL) and the combine organic extracts were washed with brine, dried (Na$_2$SO$_4$) and concentrated under reduced pressure to afford the crude product. This was purified by flash column chromatography (Si, 20×75 mm, 0-5% EtOAc in hexanes gradient) to afford N-[4-(7-cyano-1,3-benzoxazol-2-yl)phenyl]-2-(2-methylphenoxy)acetamide as a colorless solid. LCMS calc.=384.13; found=384.2 (M+1)$^+$. $^1$H NMR (500 MHz, CDCl$_3$) δ 8.56 (s, 1H), 8.28 (d, J=9.7 Hz, 2H), 7.97 (d, J=7.9 Hz, 1H), 7.80 (d, J=9.8 Hz, 2H), 7.62 (d, J=7.6 Hz, 1H), 7.43 (t, J=7.9 Hz, 1H), 7.21 (m, 2H), 6.99 (t, J=7.4 Hz, 1H), 6.86 (d, J=8.1 Hz, 1H), 4.65 (s, 2H), 2.40 (s, 3H).

Examples 232, 233, 234

232

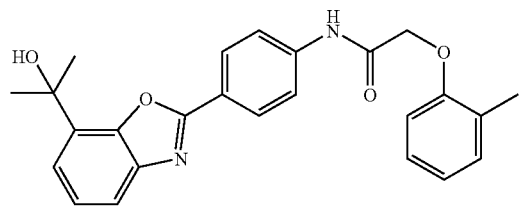

233

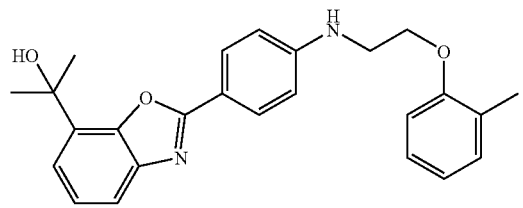

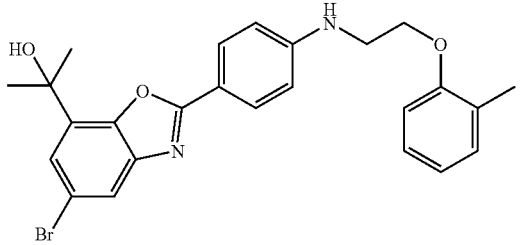

N-{4-[7-(1-hydroxy-1-methylethyl)-1,3-benzoxazol-2-yl]phenyl}-2-(2-methylphenoxy)acetamide, 2-[2-(4-{[2-(2-methylphenoxy)ethyl]amino}phenyl)-1,3-benzoxazol-7-yl]propan-2-ol, and 2-[5-bromo-2-(4-{[2-(2-methylphenoxy)ethyl]amino}phenyl)-1,3-benzoxazol-7-yl]propan-2-ol LiAlH$_4$ (100 μL, 1M in THF, 0.100 mmol) was added to a stirred solution of N-{4-[5-bromo-7-(1-hydroxy-1-methylethyl)-1,3-benzoxazol-2-yl]phenyl}-2-(2-methylphenoxy)acetamide (26 mg, 0.050 mmol) in dry THF (11 mL) at room temperature under N$_2$. The reaction was stirred at room temperature for 15 h then diluted with saturated NH$_4$Cl and extracted with EtOAc (2×). The combined organic extracts were dried and concentrated under reduced pressure to afford the crude product. This was purified by reversed phase HPLC (C18, 20×150 mm, 0.1% TFA, 10-100% MeCN in H$_2$O gradient) to afford as colorless solids, N-{4-[7-(1-hydroxy-1-methylethyl)-1,3-benzoxazol-2-yl]phenyl}-2-(2-methylphenoxy)acetamide, LCMS calc.=417.18; found=417.3 (M+1)$^+$, 2-[2-(4-{[2-(2-methylphenoxy)ethyl]amino}phenyl)-1,3-benzoxazol-7-yl]propan-2-ol, LCMS calc.=403.20; found=403.3 (M+1)$^+$, and the desired product 2-[5-bromo-2-(4-{[2-(2-methylphenoxy)ethyl]amino}phenyl)-1,3-benzoxazol-7-yl]propan-2-ol, LCMS calc.=483.11; found=483.2 (M+1)$^+$. $^1$H NMR (500 MHz, CDCl$_3$) δ 8.04 (d, J=8.7 Hz, 2H), 7.79 (d, J=1.8 Hz, 1H), 7.59 (d, J=1.8 Hz, 1H), 7.16 (m, 2H), 6.90 (t, J=7.3 Hz, 1H), 6.84 (t, J=8.7 Hz, 1H); 6.77 (d, J=8.8 Hz, 2H), 4.21 (t, J=5.2 Hz, 2H), 4.11 (br s, 1H), 3.67 (t, J=5.2 Hz, 2H), 2.75 (s, 1H), 2.25 (s, 3H), 1.79 (s, 6H).

Example 235

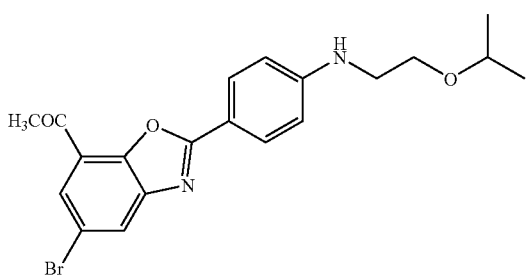

1-(5-bromo-2-{4-[(2-isopropoxyethyl)amino]phenyl}-1,3-benzoxazol-7-yl)ethanone

Step A: methyl 4-[(2-isopropoxyethyl)amino]benzoate

A flask was charged with Cs$_2$CO$_3$ (5.72 g, 17.6 mmol), tris(dibenzylideneacetone)dipalladium (0.230 g, 0.251 mmol) and racemic-2,2'-bis(diphenylphoshino)-1,1'-binaphyl (0.235 g, 0.377 mmol) and purged with nitrogen. Methyl 4-bromobenzoate (2.70 g, 12.6 mmol), (2-isopropoxyethyl)amine (1.55 g, 15.0 mmol) and dry toluene (50 mL) were added and the mixture was heated to 100° C. with stirring. After 24 h the mixture was diluted with Et$_2$O, filtered through Celite and concentrated under reduced pressure to afford the crude product. This was purified by flash column chromatography (Si, 40×230 mm, 0-20% EtOAc in hexanes gradient) to afford methyl 4-[(2-isopropoxyethyl)amino]benzoate. LCMS calc.=238.14; found=238.3 (M+1)$^+$. $^1$H NMR (500 MHz, CDCl$_3$) δ 7.85 (d, J=8.8 Hz, 2H), 6.57 (d, J=8.8 Hz, 2H), 4.50 (m, 1H), 3.84 (s, 3H), 3.64-3.58 (m, 3H), 3.31 (q, J=5.4 Hz, 1H), 1.17 (d, J=6.1 Hz, 3H).

Step B: methyl 4-[(tert-butoxycarbonyl)(2-isopropoxyethyl)amino]benzoate

Four aliquots of KHMDS (2.03 mL of a 0.5 M solution in toluene, 1.01 mmol) were added dropwise to a stirred solution of methyl 4-[(2-isopropoxyethyl)amino]benzoate (482 mg, 2.03 mmol) and di-tert-butyl dicarbonate (2.21 g, 10.1 μmol) in dry THF (20 mL) at room temperature under N$_2$ until the red coloration persisted. After this time the reaction was poured into water (50 mL) and extracted with EtOAc (3×30 mL). The combined organic extracts were washed with brine (30 mL), dried (MgSO$_4$) and concentrated under reduced pressure to afford the crude product. This was purified by flash column chromatography (Si, 30×130 mm, 0-20% EtOAc in hexanes gradient) to afford methyl 4-[(tert-butoxycarbonyl)(2-isopropoxyethyl)amino]benzoate. LCMS calc.=360.18; found=360.3 (M+Na)$^+$. $^1$H NMR (500 MHz, CDCl$_3$) δ 7.98 (d, J=8.6 Hz, 1H), 7.37 (d, J=8.6 Hz, 1H), 3.90 (s, 3H), 3.80 (t, J=5.9 Hz, 2H), 3.58 (t, J=6.0 Hz, 2H), 3.54 (pentet, J=6.1 Hz, 1H), 1.45 (s, 9H), 1.10 (d, J=6.1 Hz, 3H).

Step C: 4-[(tert-butoxycarbonyl)(2-isopropoxyethyl)amino]benzoic acid

A mixture of methyl 4-[(tert-butoxycarbonyl)(2-isopropoxyethyl)amino]benzoate (647 mg, 1.92 mmol) and 1N NaOH (3.84 mL, 3.84 mmol) in H$_2$O (8.6 mL) and EtOH (7.1 mL) was stirred at room temperature overnight. The reaction was acidified with 1N HCl and extracted with EtOAc (3×30 mL). The combined organic extracts were dried and concentrated under reduced pressure to afford 4-[(tert-butoxycarbonyl)(2-isopropoxyethyl)amino]benzoic acid. LCMS calc.=346.16; found=346.3 (M+Na)$^+$.

Step D: 1-(5-bromo-2-[4-[(2-isopropoxyethyl)amino]phenyl]-1,3-benzoxazol-7-yl)ethanone A solution of oxalyl chloride (1.5 mL, 2 M in CH$_2$Cl$_2$, 2.99 mmol) was added to a stirred suspension of 4-[(tert-butoxycarbonyl)(2-isopropoxyethyl)amino]benzoic acid (644 mg, 1.99 mmol) in CH$_2$Cl$_2$ (90 mL) followed by a few drops of DMF at room temperature under N$_2$. The reaction was stirred at room temperature for 2 h after which time the suspension dissolved. The reaction mixture was concentrated under reduced pressure and azeotroped with toluene (2×30 mL). The crude acid chloride and 1-(3-amino-5-bromo-2-hydroxyphenyl)ethanone (550 mg, 2.39 mmol) were dissolved in 1,4-dioxane (90 mL) and heated at reflux for 2 h under N$_2$. The reaction was concentrated under reduced pressure to afford the crude amide product. A mixture of the crude amide and pyridinium p-toluenesulfonate (601 mg, 2.39 mmol) in o-xylene (90 mL) was heated at reflux under a Dean-Stark apparatus for 22 h under N₂. The reaction was concentrated under reduced pressure to afford the crude product. This was purified by flash column chromatography (Si, 30×130 mm, 0-10% EtOAc in hexanes gradient) to afford 1-(5-bromo-2-{4-[(2-isopropoxyethyl)amino]phenyl}-1,3-benzoxazol-7-yl)ethanone as a yellow solid. LCMS calc.=419.08; found=419.2 (M+1)⁺. ¹H NMR (500 MHz, CDCl₃) δ 8.04 (d, J=8.1 Hz, 2H), 7.95 (d, J=2.0 Hz, 1H), 7.94 (d, J=2.0 Hz, 1H), 6.70 (d, J=8.9 Hz, 2H), 4.62 (m, 1H), 3.68-3.62 (m, 3H), 3.38-3.34 (m, 2H), 2.88 (s, 3H), 1.19 (d, J=6.1 Hz, 6H).

Example 236

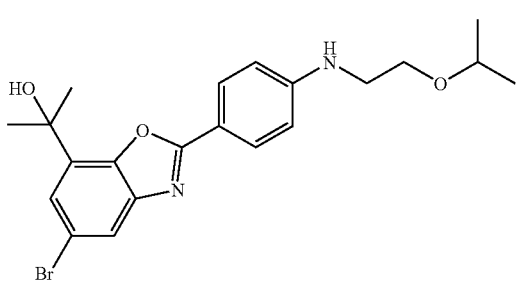

2-(5-bromo-2-{4-[(2-isopropoxyethyl)amino]phenyl}-1,3-benzoxazol-7-yl)propan-2-ol Methyl magnesium bromide (3.0M in Et₂O, 240 μL, 0.720 mmol) was added dropwise to a stirred solution of 1-(5-bromo-2-{4-[(2-isopropoxyethyl)amino]phenyl}-1,3-benzoxazol-7-yl)ethanone (50.0 mg, 0.120 mmol) in dry THF at −78° C. under N₂. After 2 h saturated NH₄Cl (4 mL) was added and the reaction was diluted with water (15 mL) and EtOAc (20 mL). The aqueous layer was extracted with EtOAc (2×20 mL) and the combined organic extracts were dried (Na₂SO₄) and concentrated under reduced pressure to afford the crude product. This was purified by flash column chromatography (Si, 20×75 mm, 0-20% EtOAc in hexanes gradient) to afford 2-(5-bromo-2-{4-[(2-isopropoxyethyl)amino]phenyl}-1,3-benzoxazol-7-yl)propan-2-ol. LCMS calc.=435.11; found=435.2 (M+1)⁺. ¹H NMR (500 MHz, CDCl₃) δ 8.01 (d, J=8.7 Hz, 2H), 7.70 (d, J=1.8 Hz, 1H), 7.55 (d, J=1.9 Hz, 1H), 6.69 (d, J=8.7 Hz, 2H), 3.67-3.61 (m, 3H), 3.35 (t, J=5.2 Hz, 2H), 1.78 (s, 6H), 1.19 (d, J=6.1 Hz, 6H).

Example 237

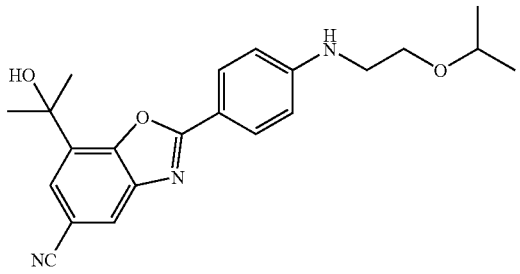

7-(1-hydroxy-1-methylethyl)-2-{4-[(2-isopropoxyethyl)amino]phenyl}-1,3-benzoxazole-5-carbonitrile A solution of 2-(5-bromo-2-{4-[(2-isopropoxyethyl)amino]phenyl}-1,3-benzoxazol-7-yl)propan-2-ol (28.0 mg, 0.0646 mmol), tris(dibenzylideneacetone)dipalladium (5.9 mg, 0.00646 mmol), 1,1'-bis(diphenylphosphino)ferrocene (7.2 mg, 0.00129 mmol) and Zn(CN)₂ (7.6 mg, 0.0646 mmol) in dimethylacetamide (2 mL) was degassed, flushed with N₂ and subjected to microwave irradiation (60 W, 150° C., 130 min). The reaction mixture was diluted with CH₂Cl₂ (10 mL) and water (10 mL). The aqueous layer was filtered through a plug of Celite and washed through with EtOAc. The filtrate was concentrated under reduced pressure to afford the crude product. This was purified by reversed phase HPLC(C18, 20×150 mm, 0.1% TFA, 10-100% MeCN in H₂O gradient) to afford 7-(1-hydroxy-1-methylethyl)-2-{4-[(2-isopropoxyethyl)amino]phenyl}-1,3-benzoxazole-5-carbonitrile. LCMS calc.=380.20; found=380.4 (M+1)⁺. ¹H NMR (500 MHz, CDCl₃) δ 8.01 (d, J=8.7 Hz, 2H), 7.87 (d, J=1.4 Hz, 1H), 7.76 (d, J=1.4 Hz, 2H), 6.70 (d, J=8.7 Hz, 2H), 3.68-3.62 (m, 3H), 3.37 br (s, 2H), 2.69 (s, 2H), 1.80 (s, 6H), 1.19 (d, J=6.1 Hz, 6H).

Example 238

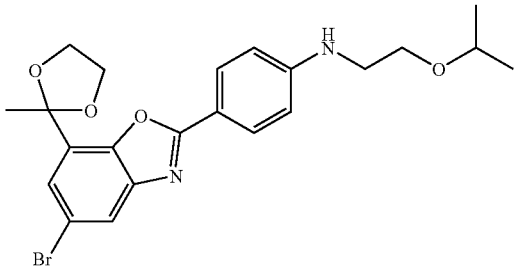

{4-[5-bromo-7-(2-methyl-1,3-dioxolan-2-yl)-1,3-benzoxazol-2-yl]phenyl}(2-isopropoxyethyl)amine Step A: 1-[5-bromo-2-(4-iodophenyl)-1,3-benzoxazol-7-yl]ethanone This compound was synthesized in an analogous procedure to that for EXAMPLE 235 Step D from 4-iodobenzoic acid and 1-(3-amino-5-bromo-2-hydroxyphenyl)ethanone. LCMS calc.=443.89; found=444.0 (M+1)⁺. ¹H NMR (500 MHz, CDCl₃) δ 8.11 (d, J=1.9 Hz, 1H), δ 8.09 (d, J=1.9 Hz, 1H), 8.02 (d, J=8.6 Hz, 2H), 7.96 (d, J=8.6 Hz, 2H), 2.93 (s, 3H).

Step B: 5-bromo-2-(4-iodophenyl)-7-(2-methyl-1,3-dioxolan-2-yl)-1,3-benzoxazole

A solution of 1-[5-bromo-2-(4-iodophenyl)-1,3-benzoxazol-7-yl]ethanone (980 mg, 2.22 mmol), ethylene glycol (688 mg, 618 μL, 11.1 mmol) and TsOH (42.0 mg, 0.222 mmol) in benzene (150 mL) was heated at reflux under a Dean Stark apparatus overnight under N₂. The reaction was diluted with EtOAc (150 mL) and washed with saturated NaHCO₃ (100 mL), H₂O (100 mL), and brine (100 mL). The organic layer was dried (MgSO₄) and concentrated under reduced pressure to afford 5-bromo-2-(4-iodophenyl)-7-(2-methyl-1,3-dioxolan-2-yl)-1,3-benzoxazole. LCMS calc.=487.92;

found=488.0 (M+1)⁺. ¹H NMR (500 MHz, CDCl₃) δ 7.97 (d, J=8.4 Hz, 2H), 7.88 (d, J=8.4 Hz, 2H), 7.83 (d, J=2.0 Hz, 1H), 7.57 (d, J=2.0 Hz, 1H), 4.17-4.10 (m, 2H), 3.94-3.87 (m, 2H), 1.87 (s, 3H).

Step C: {4-[5-bromo-7-(2-methyl-1,3-dioxolan-2-yl)-1,3-benzoxazol-2-yl]phenyl}(2-isopropoxyethyl)amine A solution of 5-bromo-2-(4-iodophenyl)-7-(2-methyl-1,3-dioxolan-2-yl)-1,3-benzoxazole (1.05 g, 2.16 mmol), 18-crown-6 (799 mg, 3.02 mmol), racemic-2,2'-bis(diphenylphoshino)-1,1'-binaphyl (202 mg, 0.324 mmol), NaOtBu (291 mg, 3.02 mmol), tris(dibenzylideneacetone)dipalladium (99 mg, 0.108 mmol), and (2-isopropoxyethyl)amine (267 mg, 318 μL, 2.59 mmol) in dry THF was stirred at room temperature for 24 h under N₂. The reaction mixture was filtered through a plug of Celite® and the filtrate was concentrated under reduced pressure to afford the crude product. This was purified by flash column chromatography (Si, 40×230 mm, 0-20% EtOAc in hexanes gradient) to afford {4-[5-bromo-7-(2-methyl-1,3-dioxolan-2-yl)-1,3-benzoxazol-2-yl]phenyl}(2-isopropoxyethyl)amine. LCMS calc.=463.11; found=463.2 (M+1)⁺. ¹H NMR (500 MHz, CDCl₃) δ 8.06 (d, J=8.7 Hz, 2H), 7.74 (d, J=1.9 Hz, 1H), 7.47 (d, J=1.9 Hz, 1H), 6.69 (d, J=8.7 Hz, 2H), 4.15-4.08 (m, 2H), 3.94-3.87 (m, 2H), 3.67-3.61 (m, 3H), 3.35 (t, J=5.2 Hz, 2H), 1.88 (s, 3H), 1.19 (d, J=6.1 Hz, 6H).

Following the procedures outlined in EXAMPLES 212-238, the compounds listed in Tables 5 and 6 were prepared

TABLE 5

| EXAMPLE | R₄ | R₅ | R₆ | R₇ | LC-MS (M + 1) |
|---|---|---|---|---|---|
| 239 | H | Ph | H | H | Calc. = 435.17 Found = 435.2 |
| 240 | H | H | CO2CH3 | H | Calc. = 417.15 Found = 417.2 |
| 241 | H | CO2CH3 | H | H | Calc. = 417.15 Found = 417.1 |
| 242 | H | CN | H | H | Calc. = 384.13 Found = 384.1 |
| 243 | H | Cl | CH3 | H | Calc. = 407.12 Found = 407.1 |
| 244 | CH3 | Br | H | H | Calc. = 453.06 Found = 453.0 |
| 245 | H | F | H | H | Calc. = 477.13 Found = 377.1 |
| 246 | H | SCH3 | H | H | Calc. = 405.13 Found = 405.2 |
| 247 | H | Br | H | F | Calc. = 457.04 Found = 457.0 |
| 248 | H | Cl | H | Cl | Calc. = 427.06 Found = 427.1 |
| 249 | H | H | F | H | Calc. = 377.13 Found = 376.9 |
| 250 | H | H | H | Cl | Calc. = 393.10 Found = 393.1 |
| 251 | H | OCH3 | H | H | Calc. = 389.15 Found = 389.2 |
| 252 | H | H | NO2 | H | Calc. = 404.12 Found = 403.9 |
| 253 | H | NO2 | H | H | Calc. = 404.12 Found = 404.2 |
| 254 | CH3 | H | H | H | Calc. = 373.16 Found = 373.2 |
| 255 | H | COCH3 | H | H | Calc. = 401.15 Found = 401.2 |
| 256 | H | OH | H | H | Calc. = 375.13 Found = 375.2 |
| 257 | H | Cl | H | NO2 | Calc. = 438.09 Found = 438.1 |
| 258 | H | Br | H | COCH3 | Calc. = 481.06 Found = 481.1 |

TABLE 5-continued
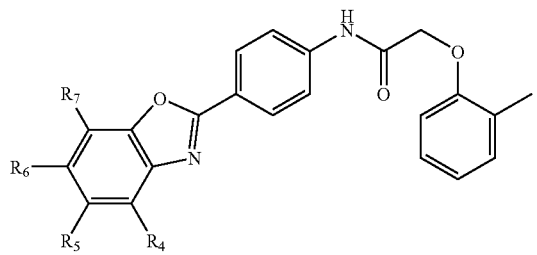
| EXAMPLE | $R_4$ | $R_5$ | $R_6$ | $R_7$ | LC-MS (M + 1) |
|---|---|---|---|---|---|
| 259 | H | 3-pyridyl | H | H | Calc. = 436.17<br>Found = 436.2 |
| 260 | H | 4-pyridyl | H | H | Calc. = 436.17<br>Found = 436.2 |
| 261 | H | 3,5-bis(trifluoromethyl)phenyl | H | H | Calc. = 571.15<br>Found = 571.2 |
| 262 | H | 3-pyridyl | H | CH3 | Calc. = 450.18<br>Found = 450.2 |
| 263 | H | 5-pyrimidinyl | H | H | Calc. = 437.16<br>Found = 437.2 |
| 264 | H | 2-cyanophenyl | H | H | Calc. = 460.17<br>Found = 460.2 |
| 265 | H | 2-carbamoylphenyl | H | H | Calc. = 478.18<br>Found = 478.2 |
| 266 | H | 4-methoxyphenyl | H | H | Calc. = 465.18<br>Found = 465.2 |

TABLE 5-continued
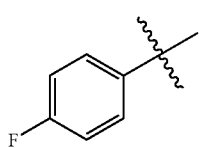
| EXAMPLE | R₄ | R₅ | R₆ | R₇ | LC-MS (M + 1) |
|---|---|---|---|---|---|
| 267 | H | 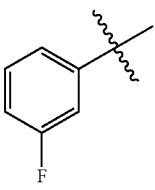 | H | H | Calc. = 453.18<br>Found = 453.2 |
| 268 | H | 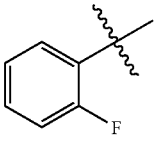 | H | H | Calc. = 453.18<br>Found = 453.2 |
| 269 | H | 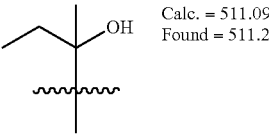 | H | H | Calc. = 453.16<br>Found = 453.2 |
| 270 | H | Br | H | 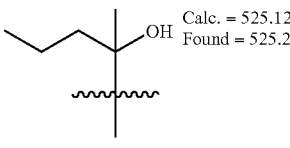 | Calc. = 511.09<br>Found = 511.2 |
| 271 | H | Br | H | 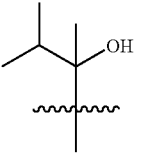 | Calc. = 525.12<br>Found = 525.2 |
| 272 | H | Br | H | 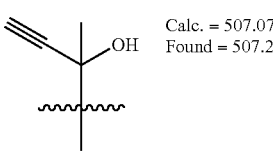 | Calc. = 525.12<br>Found = 525.3 |
| 273 | H | Br | H | 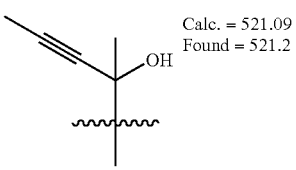 | Calc. = 507.07<br>Found = 507.2 |
| 274 | H | Br | H |  | Calc. = 521.09<br>Found = 521.2 |

TABLE 5-continued

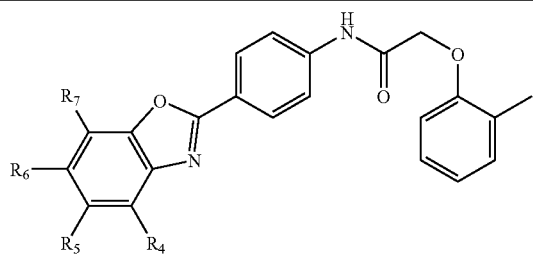

| EXAMPLE | R₄ | R₅ | R₆ | R₇ | LC-MS (M + 1) |
|---|---|---|---|---|---|
| 275 | H | H | CN | H | Calc. = 384.13<br>Found = 384.2 |
| 276 | H | CN | H | CH3 | Calc. = 398.15<br>Found = 398.2 |
| 277 | H | CN | H | CO2H | Calc. = 428.12<br>Found = 428.2 |
| 278 | H | CN | CH3 | H | Calc. = 398.15<br>Found = 398.2 |
| 279 | CH3 | CN | H | H | Calc. = 398.15<br>Found = 398.2 |
| 280 | H | CN | H | CN | Calc. = 409.13<br>Found = 409.1 |
| 281 | H | CN | H | F | Calc. = 402.13<br>Found = 402.2 |
| 282 | H | CN | H | COCH3 | Calc. = 426.15<br>Found = 426.2 |
| 283 | H | CN | H | ⟨CH(OH)CH3⟩ | Calc. = 428.16<br>Found = 428.2 |
| 284 | H | CN | H | ⟨C(CH3)2OH⟩ | Calc. = 442.18<br>Found = 442.3 |
| 285 | H | CN | H | ⟨C(Et)(CH3)OH⟩ | Calc. = 456.19<br>Found = 456 |
| 286 | H | CN | H | ⟨C(Pr)(CH3)OH⟩ | Calc. = 470.21<br>Found = 470.3 |
| 287 | H | CN | H | ⟨C(iPr)(CH3)OH⟩ | Calc. = 470.21<br>Found = 470.3 |
| 288 | H | CN | H | ⟨C(C≡CH)(CH3)OH⟩ | Calc. = 466.18<br>Found = 466.3 |

TABLE 6

| Example | Molecular structure | LCMS (M + 1)+ |
|---|---|---|
| 289 | 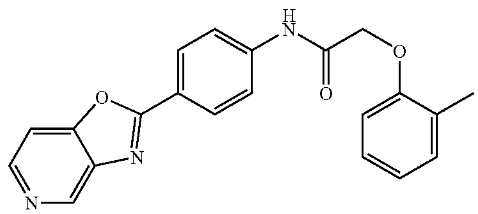 | Calc. = 360.13<br>Found = 360.2 |
| 290 | 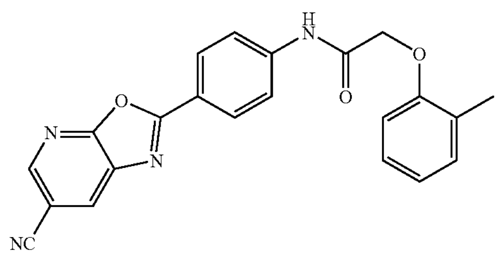 | Calc. = 385.13<br>Found = 385.2 |
| 291 | 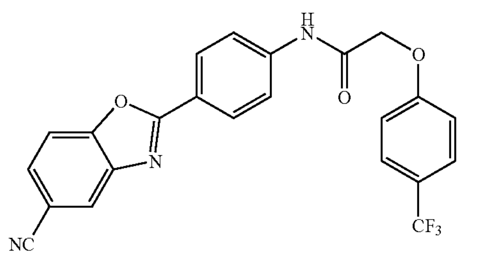 | Calc. = 438.11<br>Found = 438.1 |
| 292 | 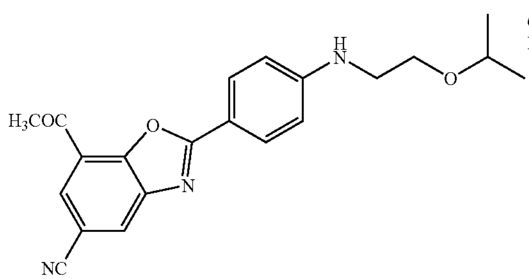 | Calc. = 364.17<br>Found = 364.4 |

Example 293

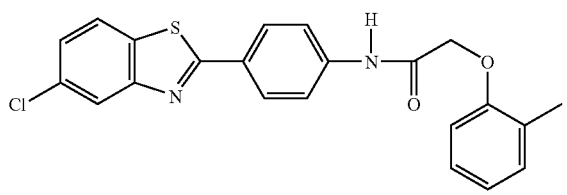

N-[4-(5-chloro-1,3-benzothiazol-2-yl)phenyl]-2-(2-methylphenoxy)acetamide

Step A:
N-(4-formylphenyl)-2-(2-methylphenoxy)acetamide

To a 0° C. suspension of (2-methylphenoxy)acetic acid (1.00 g, 6.01 mmol) in CH$_2$Cl$_2$ was added oxalyl chloride (787 µL, 9.02 mmol) and DMF (2 drops). The reaction was warmed to room temperature and stirred at room temperature for 1 hour. The reaction was then concentrated under reduced pressure and the residue was azeotroped with toluene. The residue was then dissolved (not completely soluble) in CH$_2$Cl$_2$ and 4-aminobenzaldehyde (2.3 g, 9.46 mmol) was added followed by DIPEA (3 mL, 17.2 mmol). The reaction was stirred at room temperature for 30 minutes. Next, the reaction was filtered to remove solids. The filtrate was diluted with EtOAc (150 mL) and washed with 1N HCl, brine, saturated NaHCO$_3$, and brine (30 mL each). The organic layer was dried over Na$_2$SO$_4$, filtered, and concentrated. Purification of the residue by flash column chromatography with 25% EtOAc/hexanes gave impure product. Further purification by flash column chromatography with 5/4/1 hexanes/CH$_2$Cl$_2$/Et$_2$O afforded pure N-(4-formylphenyl)-2-(2-methylphenoxy)acetamide. R$_f$=0.22 (25% EtOAc/hexanes). LCMS=269.9 (M+1)+. $^1$H NMR (CDCl$_3$, 500 MHz) δ 9.95 (s, 1H), 8.58 (s, 1H), 7.90 (d, J=8.7 Hz, 2H), 7.79 (d, J=8.5 Hz, 2H), 7.20-7.24 (m, 2H), 7.00 (t, J=7.3 Hz, 1H), 6.85 (d, J=8.0 Hz, 1H), 4.65 (s, 2H), 2.39 (s, 3H).

Step B: N-[4-(5-chloro-1,3-benzothiazol-2-yl)phenyl]-2-(2-methylphenoxy)acetamide 2-amino-4-chlorobenzenethiol (160.8 mg, 1.01 mmol) and N-(4-formylphenyl)-2-(2-methylphenoxy)acetamide (271.0 mg, 1.01 mmol) were dissolved in DMSO (10 mL) and heated to 180° C. After 30 minutes, the reaction was diluted with EtOAc (100 mL) and washed with water and brine (25 mL each). The organic layer was dried over $Na_2SO_4$, filtered, and concentrated. Recrystallization from EtOAc afforded N-[4-(5-chloro-1,3-benzothiazol-2-yl)phenyl]-2-(2-methylphenoxy)acetamide. $R_f$=0.31 (25% EtOAc/hexanes). LCMS=409.1 (M+1)$^+$. $^1$H NMR (CDCl$_3$, 500 MHz) δ 8.51 (s, 1H), 8.08 (d, J=8.5 Hz, 2H), 8.03 (d, J=2.0 Hz, 1H), 7.80 (d, J=8.5 Hz, 1H), 7.75 (d, J=8.5 Hz, 2H), 7.35 (dd, J=8.5, 2.1 Hz, 1H), 7.20-7.24 (m, 1H), 7.00 (t, J=7.5 Hz, 1H), 6.86 (d, J=8.3 Hz, 1H), 4.65 (s, 2H), 2.40 (s, 3H).

Example 294

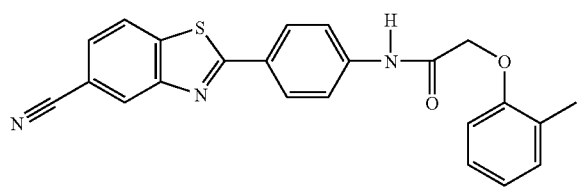

N-[4-(5-cyano-1,3-benzothiazol-2-yl)phenyl]-2-(2-methylphenoxy)acetamide

A solution of N-[4-(5-chloro-1,3-benzothiazol-2-yl)phenyl]-2-(2-methylphenoxy)acetamide (29.4 mg, 0.072 mmol), Zn(CN)$_2$ (5.3 mg, 0.045 mmol), and dppf (8.2 mg, 0.015 mmol) in DMA (1.2 mL) was degassed with N$_2$ in a microwave tube. Pd$_2$(dba)$_3$ (7 mg, 0.0076 mmol) was added and the reaction was heated in a microwave at 60 W and 200° C. for 60 minutes. The reaction was then diluted with EtOAc (100 mL) and washed with aqueous NH$_3$, water, and brine (20 mL each). The organic layer was dried over Na$_2$SO$_4$, filtered and concentrated. The residue was purified by flash column chromatography with 100% CH$_2$Cl$_2$ followed by Oct. 50, 1940 Et$_2$O/CH$_2$Cl$_2$/hexanes to afford N-[4-(5-cyano-1,3-benzothiazol-2-yl)phenyl]-2-(2-methylphenoxy)acetamide. $R_f$=0.12 (25% EtOAc/hexanes). LCMS=400.1 (M+1)$^+$. $^1$H NMR (DMSO, 500 MHz) δ 10.44 (s, 1H), 8.54 (s, 1H), 8.37 (d, J=8.4 Hz, 1H), 8.10 (d, J=8.7 Hz, 2H), 7.86 (d, J=8 Hz, 2H), 7.83 (dd, J=7.3, 1.5 Hz, 1H), 7.13-7.18 (m, 2H), 6.86-6.89 (m, 2H), 4.77 (s, 2H), 2.25 (s, 3H).

Example 295

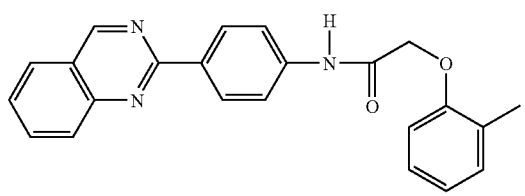

2-(2-methylphenoxy)-N-(4-quinazolin-2-ylphenyl)acetamide

A solution of 2-aminobenzylamine (17.5 mg, 0.143 mmol) and N-(4-formylphenyl)-2-(2-methylphenoxy)acetamide (38.6 mg, 0.143 mmol) were dissolved in DMSO (1.5 mL) and heated to 180° C. After 4 hours, the reaction was cooled to room temperature, diluted with EtOAc (40 mL), and washed with H$_2$O and brine (10 mL each). The organic layer was dried over Na$_2$SO$_4$, filtered, and concentrated. The residue was purified by flash column chromatography with 5 to 40% EtOAc/hexanes to afford 2-(2-methylphenoxy)-N-(4-quinazolin-2-ylphenyl)acetamide. $R_f$=0.17 (25% EtOAc/hexanes). LCMS=370.1 (M+1)$^+$. $^1$H NMR (CDCl$_3$, 500 MHz) δ 9.47 (s, 1H), 8.66 (d, J=8.7 Hz, 2H), 8.51 (s, 1H), 8.11 (d, J=8.4 Hz, 1H), 7.90-7.94 (m, 2H), 7.78 (d, J=8.7 Hz, 2H), 7.62 (t, J=8.0 Hz, 1H), 7.21-7.25 (m, 2H), 6.99 (t, J=7.3 Hz, 1H), 6.88 (d, J=8.0 Hz, 1H), 4.66 (s, 2H), 2.41 (s, 3H).

Example 296

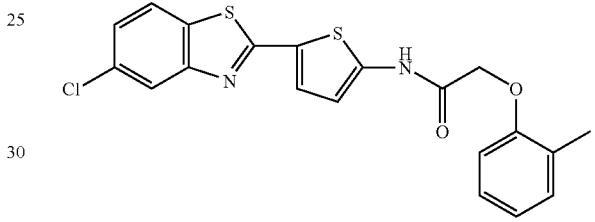

N-[5-(5-chloro-1,3-benzothiazol-2-yl)-2-thienyl]-2-(2-methylphenoxy)acetamide

Step A: 5-chloro-2-(5-nitro-2-thienyl)-1,3-benzothiazole 2-amino-4-chlorobenzenethiol (40.2 mg, 0.252 mmol) and 5-nitrothiophene-2-carbaldehyde (39.6 mg, 0.252 mmol) were dissolved in DMSO (2 mL) and heated to 180° C. After 30 minutes, the reaction was diluted with EtOAc (40 mL) and washed with water and brine (10 mL each). The organic layer was dried over Na$_2$SO$_4$, filtered, and concentrated. Purification of the residue by flash column chromatography with 5 to 25% EtOAc/hexanes afforded 5-chloro-2-(5-nitro-2-thienyl)-1,3-benzothiazole. Minor impurities present. $R_f$=0.35 (25% EtOAc/hexanes). LCMS=297.0 (M+1)$^+$. $^1$H NMR (DMSO, 500 MHz) δ 8.21-8.26 (m, 3H), 7.99 (d, J=4.6 Hz, 1H), 7.59 (dd, J=8.7, 2.0 Hz, 1H).

Step B: N-[5-(5-chloro-1,3-benzothiazol-2-yl)-2-thienyl]-2-(2-methylphenoxy)acetamide 5-chloro-2-(5-nitro-2-thienyl)-1,3-benzothiazole (60.0 mg, 0.203 mmol) was dissolved in THF (6 mL) and PtO$_2$ (10 mg, 0.044 mmol) was added. The reaction was placed under H$_2$ and stirred vigorously. After 25 minutes, the catalyst was removed by filtration and the filtrate was concentrated the crude material was added to a reaction containing (2-methylphenoxy)acetic acid (61.2 mg, 0.368 mmol), DIPEA (128 μL, 0.736 mmol), and HATU (140 mg, 0.368 mmol). After 30 minutes, the reaction was filtered through a plug of silica gel with 40% EtOAc/hexanes and the filtrate was concentrated.

LCMS showed a mixture of starting material and product and the coupling process was repeated. The reaction was then filtered again through a plug of silica gel and concentrated. The residue was purified, first by preparative thin layer chromatography with 25% EtOAc/hexanes, then by flash column chromatography with 5 to 25% EtOAc/hexanes, then by preparative thin layer chromatography with 40/40/20 $CH_2Cl_2$/hexanes/$Et_2O$ to afford N-[5-(5-chloro-1,3-benzothiazol-2-yl)-2-thienyl]-2-(2-methylphenoxy)acetamide. $R_f$=0.27 (25% EtOAc/hexanes). LCMS=415.0 $(M+1)^+$. $^1H$ NMR ($CD_2Cl_2$, 500 MHz) δ 9.11 (s, 1H), 7.94 (d, J=2.1 Hz, 1H), 7.78 (d, J=8.5 Hz, 1H), 7.50 (d, J=4.1 Hz, 1H), 7.33 (dd, J=8.7, 2.0 Hz, 1H), 7.19-7.24 (m, 2H), 6.99 (t, J=7.0 Hz, 1H), 6.88 (d, J=8.0 Hz, 1H), 6.79 (d, J=4.1 Hz, 1H), 4.73 (s, 2H), 2.38 (s, 3H).

Example 297

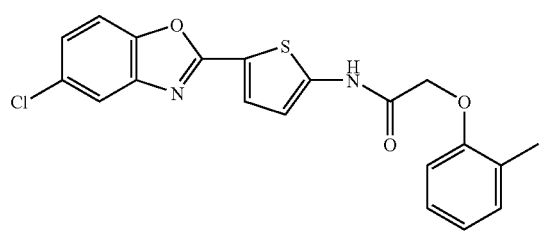

N-[5-(5-chloro-1,3-benzoxazol-2-yl)-2-thienyl]-2-(2-methylphenoxy)acetamide

Step A: 5-chloro-2-(5-nitro-2-thienyl)-1,3-benzoxazole 2-amino-4-chlorophenol (67.7 mg, 0.472 mmol) and 5-nitrothiophene-2-carbaldehyde (74.1 mg, 0.472 mmol) were dissolved in EtOH (5 mL) and heated to reflux. After 30 minutes, the reaction was cooled to room temperature and concentrated. To the residue was added $CH_2Cl_2$ (3 mL) and THF (3 mL). Next, DDQ (107 mg, 0.472 mmol) was added. After 30 minutes, additional DDQ (20 mg, 0.088 mmol) was added. After an additional 30 minutes, the reaction was filtered through silica gel with 50/50 $CH_2Cl_2$/hexanes. The filtrate was concentrated, and the residue was purified by flash column chromatography with 50% EtOAc/hexanes to afford 5-chloro-2-(5-nitro-2-thienyl)-1,3-benzoxazole. $R_f$=0.56 (40% EtOAc/hexanes). LCMS=281.0 $(M+1)^+$. $^1H$ NMR (DMSO, 600 MHz) δ 8.25 (d, J=4.4 Hz, 1H), 8.00 (d, J=4.3 Hz, 1H), 7.99 (d, J=2.0 Hz, 1H), 7.88 (dd, J=8.6 Hz, 1H), 7.55 (dd, J=8.8, 2.2 Hz, 1H).

Step B: N-[5-(5-chloro-1,3-benzoxazol-2-yl)-2-thienyl]-2-(2-methylphenoxy)acetamide 5-chloro-2-(5-nitro-2-thienyl)-1,3-benzoxazole (47.8 mg, 0.171 mmol) was dissolved in THF (5 mL). $PtO_2$ (10.2 mg, 0.045 mmol) was added and the reaction was placed under $H_2$. After 1 hour, the catalyst was removed by filtration, and the filtrate was treated with a $CH_2Cl_2$ (10 mL) solution of (2-methylphenoxy)acetyl chloride (1.5 mmol, prepared from the corresponding acid with oxalyl chloride and catalytic DMF). DIPEA (1 mL, 5.74 mmol) was added and the reaction was stirred for 30 minutes. The reaction was quenched with saturated $NaHCO_3$ (15 mL) and the mixture was extracted with EtOAc (50 mL). The organic layer was washed with brine (20 mL), dried over $Na_2SO_4$, filtered through a plug of silica gel with 40% EtOAc/hexanes, and concentrated. The residue was purified by flash column chromatography with 5 to 25% EtOAc/hexanes, then by preparative thin layer chromatography with 25% EtOAc/hexanes, then by preparative thin layer chromatography with 100% $CH_2Cl_2$ (2 elutions) to afford N-[5-(5-chloro-1,3-benzoxazol-2-yl)-2-thienyl]-2-(2-methylphenoxy)acetamide. $R_f$=0.27 (100% $CH_2Cl_2$). LCMS=399.0 $(M+1)^+$. $^1H$ NMR ($CD_2Cl_2$, 600 MHz) δ 9.18 (s, 1H), 7.74 (d, J=4.1 Hz, 1H), 7.66 (d, J=2.1 Hz, 1H), 7.47 (d, J=8.6 Hz, 1H), 7.29 (dd, J=8.0, 2.0 Hz, 1H), 7.20-7.24 (m, 2H), 7.00 (t, J=7.4 Hz, 1H), 6.88 (d, J=8.1 Hz, 1H) 6.83 (d, J=4.1 Hz, 1H), 4.74 (s, 2H), 2.38 (s, 3H).

Example 298

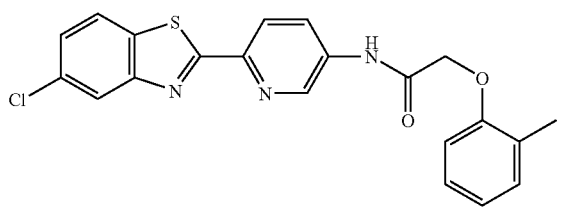

N-[6-(5-chloro-1,3-benzothiazol-2-yl)pyridin-3-yl]-2-(2-methylphenoxy)acetamide

Step A: tert-butyl[6-(5-chloro-1,3-benzothiazol-2-yl)pyridin-3-yl]carbamate

A solution of 5-[(tert-butoxycarbonyl)amino]pyridine-2-carboxylic acid (60 mg, 0.25 mmol) in $CH_2Cl_2$ (3 mL) was cooled to 0° C. and oxalyl chloride (40 μL, 0.45 mmol) was added followed by DMF (1 drop). The reaction was warmed to room temperature, stirred at room temperature for 1.5 hour and then concentrated. The crude acid chloride was dissolved in THF (2 mL) and added to a solution of 2-amino-4-chlorobenzenethiol (40 mg, 0.25 mmol) in THF (4 mL). Next, $Et_3N$ (35 μL, 0.25 mmol) was added to the reaction. The reaction was stirred at room temperature for 1.5 hours, diluted with EtOAc (40 mL), washed with saturated $NaHCO_3$ and brine (15 mL each), dried over $Na_2SO_4$, filtered, and concentrated. Purification of the residue by flash column chromatography (0 to 20% EtOAc/hexanes) afforded tert-butyl[6-(5-chloro-1,3-benzothiazol-2-yl)pyridin-3-yl]carbamate. LCMS=362.2 $(M+1)^+$. $^1H$ NMR (DMSO, 500 MHz) δ 10.01 (s, 1H), 8.71 (d, J=2.0 Hz, 1H), 8.11-8.24 (m, 4H), 7.49 (dd, J=8.5, 2.0 Hz, 1H), 1.50 (s, 9H).

Step B: 6-(5-chloro-1,3-benzothiazol-2-yl)pyridin-3-amine

To a solution of tert-butyl[6-(5-chloro-1,3-benzothiazol-2-yl)pyridin-3-yl]carbamate (40.1 mg, 0.111 mmol) in $CH_2Cl_2$ (3 mL) was added TFA (3 mL). The reaction was stirred at room temperature for 20 minutes and then diluted with EtOAc (40 mL). The organic layer was neutralized with saturated $NaHCO_3$ and the organic layer was separated. The organic layer was then washed with additional saturated $NaHCO_3$ (2×15 mL), water, and brine (15 mL each). The organic layer was dried over $Na_2SO_4$, filtered, and concentrated to dryness to afford crude 6-(5-chloro-1,3-benzothiazol-2-yl)pyridin-3-amine that was used in the next reaction without further purification. LCMS=262.2 (M+1)+.

Step C: N-[6-(5-chloro-1,3-benzothiazol-2-yl)pyridin-3-yl]-2-(2-methylphenoxy)acetamide To a solution of 6-(5-chloro-1,3-benzothiazol-2-yl)pyridin-3-amine (0.111 mmol based on previous reaction) in $CH_2Cl_2$ (1.5 mL) was added (2-methylphenoxy)acetyl chloride (444 μL of a 0.5 M solution in $CH_2Cl_2$, 0.222 mmol; prepared from the corresponding carboxylic acid with oxalyl chloride and catalytic DMF) followed by DIPEA (100 μL, 0.574 mmol). After 30 minutes, and additional aliquot of (2-methylphenoxy)acetyl chloride (200 uL of 0.5M solution in $CH_2Cl_2$, 0.1 mmol) was added. After another 30 minutes, the reaction was diluted with EtOAc (40 mL), and washed with water, saturated $NaHCO_3$, and brine (15 mL each). The organic layer was dried over $Na_2SO_4$, filtered, and concentrated. Recrystallization of the crude material from MeOH afforded N-[6-(5-chloro-1,3-benzothiazol-2-yl)pyridin-3-yl]-2-(2-methylphenoxy)acetamide. LCMS=410.1 (M+1)+. $^1$HNMR (DMSO, 500 MHz) δ 10.66 (s, 1H), 8.92 (d, J=2.5 Hz, 1H), 8.35 (dd, J=8.5, 2.5 Hz, 1H), 8.30 (d, J=8.5 Hz, 1H), 8.18 (d, J=8.5 Hz, 1H), 8.14 (d, J=2.0 Hz, 1H), 7.52 (dd, J=8.5, 2.0 Hz, 1H), 7.13-7.19 (m, 2H), 6.87-6.91 (m, 2H), 4.81 (s, 2H), 2.26 (s, 3H).

The EXAMPLES in Table 7 were prepared following the procedures outlined in EXAMPLES 293-298 amine (191 mg, 1.34 mmol) in DMSO (12 mL) was heated to 180° for 30 minutes. The reaction was then cooled to room temperature and diluted with EtOAc (100 mL). The organic layer was washed with water and brine (20 mL each) and then concentrated onto silica gel. Purification by flash column chromatography (15 to 75% EtOAc/hexanes) afforded N-[4-(5-chloro-1H-benzimidazol-2-yl)phenyl]-2-(2-methylphenoxy)acetamide. $R_f$=0.38 (60% EtOAc/hexanes). LCMS=392.0 (M+1)+.

$^1$H NMR (DMSO, 500 MHz, tautomers present) δ 13.0 (s), 12.97 (s), 10.29 (s, 1H), 8.11 (d, J=8.3 Hz, 2H), 7.81 (d, J=8.5 Hz, 2H), 7.67 (s), 7.63 (d, J=8.0 Hz), 7.50-7.51 (m), 7.13-7.21 (m), 6.86-6.89 (m), 4.76 (s, 2H), 2.26 (s, 3H).

Example 302 and 303

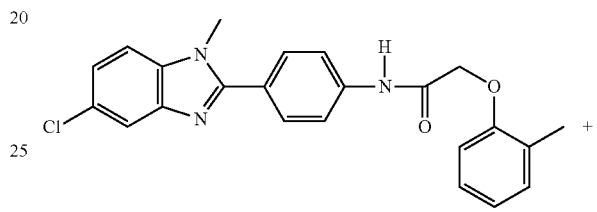
+

TABLE 7

| EXAMPLE | Molecular structure | LCMS (M + 1)+ |
|---|---|---|
| 299 | 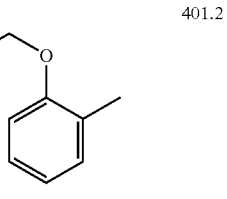 | 375.0 |
| 300 | 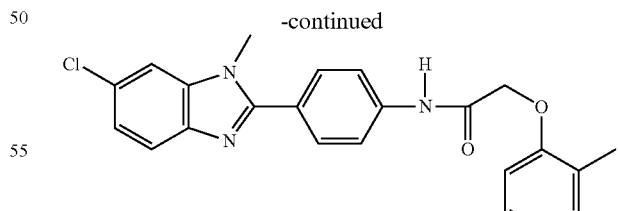 | 401.2 |

Example 301

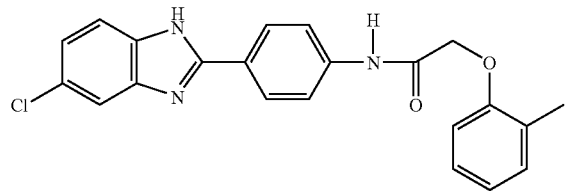

N-[4-(5-chloro-1H-benzimidazol-2-yl)phenyl]-2-(2-methylphenoxy)acetamide

A solution of N-(4-formylphenyl)-2-(2-methylphenoxy)acetamide (360 mg, 1.34 mmol) and 4-chlorobenzene-1,2-di- -continued

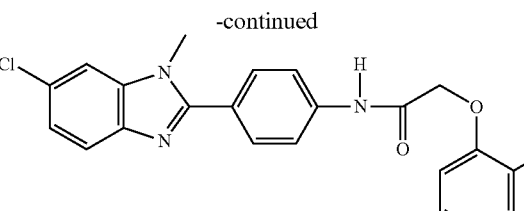

N-[4-(5-chloro-1-methyl-1H-benzimidazol-2-yl)phenyl]-2-(2-methylphenoxy)acetamide and N-[4-(6-chloro-1-methyl-1H-benzimidazol-2-yl)phenyl]-2-(2-methylphenoxy)acetamide A solution of N-[4-(5-chloro-1H-benzimidazol-2-yl)phenyl]-2-(2-methylphenoxy)acetamide (20.7 mg, 0.0529 mmol) in DMF (3 mL) was treated with Cs₂CO₃ (26 mg, 0.0794 mmol) and MeI (5 µL, 0.0794 mmol). After 30 minutes, additional Cs₂CO₃ (10 mg, 0.031 mmol) and MeI (2 µL, 0.032 mmol) were added. After 30 more minutes, the reaction was diluted with EtOAc (40 mL) and washed with H₂O and brine (15 mL each). The organic layer was dried over Na₂SO₄, filtered, and concentrated. The residue was purified by flash column chromatography with 5 to 75% EtOAc/hexanes to afford N-[4-(5-chloro-1-methyl-1H-benzimidazol-2-yl)phenyl]-2-(2-methylphenoxy)acetamide and N-[4-(6-chloro-1-methyl-1H-benzimidazol-2-yl)phenyl]-2-(2-methylphenoxy)acetamide as separable isomers. Data for less polar isomer: R$_f$=0.32 (50% EtOAc/hexanes). LCMS=406.2 (M+1)⁺. ¹H NMR (DMSO, 600 MHz) δ 10.33 (s, 1H), 7.84 (s, 4H), 7.71 (d, J=2.0 Hz, 1H), 7.64 (d, J=8.5 Hz, 1H), 7.30 (dd, J=8.7, 2.0 Hz, 1H), 7.14-7.18 (m, 2H), 6.86-6.89 (m, 2H), 4.77 (s, 2H), 3.88 (s, 3H), 2.26 (s, 3H). Data for more polar isomer: R$_f$=0.28 (50% EtOAc/hexanes). LCMS=406.2 (M+1)⁺. ¹H NMR (DMSO, 600 MHz) δ 10.33 (s, 1H), 7.83 (s, 4H), 7.77 (d, J=1.9 Hz, 1H), 7.65 (d, J=8.5 Hz, 1H), 7.24 (dd, J=8.5, 1.9 Hz, 1H), 7.14-7.18 (m, 2H), 6.86-6.89 (m, 2H), 4.76 (s, 2H), 3.86 (s, 3H), 2.26 (s, 3H).

The EXAMPLES in Table 8 were prepared following the general procedures outlined in EXAMPLES 301-303.

TABLE 8

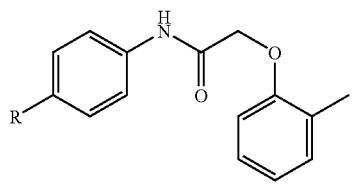

| EXAMPLE | Molecular structure | LCMS (M + 1)⁺ |
|---|---|---|
| 304 | | 432.2 |
| 305 | | 432.2 |
| 306 | | 420.2 |
| 307 | | 420.2 |
| 308 | 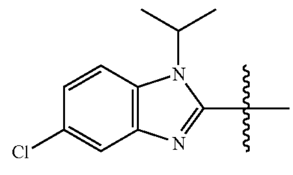 | 434.1 |
| 309 | 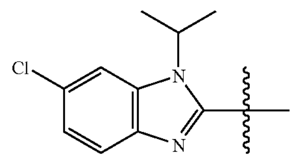 | 434.1 |
| 310 | 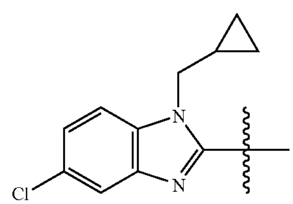 | 446.2 |
| 311 | 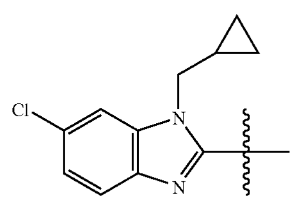 | 446.2 |
| 312 | 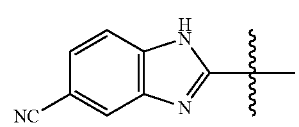 | 383.2 |
| 313 | 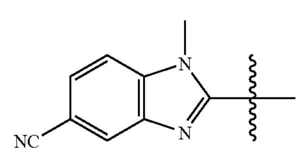 | 397.2 |
| 314 | 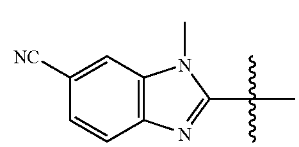 | 397.2 |

Example 315

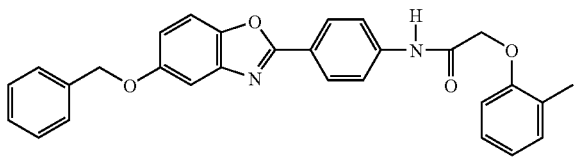

N-{4-[5-(benzyloxy)-1,3-benzoxazol-2-yl]phenyl}-
2-(2-methylphenoxy)acetamide

Step A: 4-(benzyloxy)-2-nitrophenol 4-(benzyloxy)phenol (6.0 g, 30 mmol) was suspended in HOAc (30 mL) and a solution of fuming $HNO_3$ (630 μL) in HOAc (4.5 mL) was added over 30 minutes by addition funnel while maintaining the temperature of the reaction below 30° C. The reaction was then poured into ice water (100 mL) and extracted with $Et_2O$ (200 mL). The $Et_2O$ layer was dried over $Na_2SO_4$, filtered, and concentrated onto celite. The celite was placed on top of a silica gel column, and the product was purifed by flash column chromatography with 0 to 10% EtOAc/hexanes to afford 4-(benzyloxy)-2-nitrophenol. $R_f$=0.44 (15% EtOAc/hexanes). $^1H$ NMR (DMSO, 500 MHz) δ 7.49 (d, J=3.0 Hz, 1H), 7.31-7.44 (m, 5H), 7.27 (dd, J=9.0, 3.0 Hz, 1H), 7.07 (d, J=8.9 Hz, 1H), 5.09 (s, 2H).

Step B: 2-amino-4-(benzyloxy)phenol

To a solution of 4-(benzyloxy)-2-nitrophenol (1.7 g, 6.94 mmol) in THF/MeOH (1:1, 40 mL total) was added $SnCl_2.2H_2O$ (6.3 g, 27.75 mmol) followed by concentrated HCl (11.2 mL). The reaction was allowed to stir overnight at room temperature. The reaction was then diluted with water (100 mL) and EtOAc (200 ml). The mixture was neutralized with $Na_2CO_3$ and filtered through celite to remove precipitates. The layers were separated, and the organic layer was filtered through a plug of silica gel. The filtrate was concentrated to afford 2-amino-4-(benzyloxy)phenol. $R_f$=0.07 (40% EtOAc/hexanes). LCMS=216.2 $(M+1)^+$.

Step C: N-{4-[5-(benzyloxy)-1,3-benzoxazol-2-yl]phenyl}-2-(2-methylphenoxy)acetamide N-(4-formylphenyl)-2-(2-methylphenoxy)acetamide (450 mg, 1.67 mmol) and 2-amino-4-(benzyloxy)phenol (430 mg, 2.01 mmol) were refluxed in EtOH (20 mL) for 2 hours. The reaction was cooled to room temperature, and concentrated. The residue was dissolved in $CH_2Cl_2$ (20 mL) and THF (10 mL) and DDQ (456 mg, 2.01 mmol) was added. The reaction was stirred at room temperature for 1 hour, and then diluted with EtOAc (125 mL). The organic layer was washed with 10% aqueous $K_2CO_3$ (3×25 mL), and then concentrated onto celite. The celite was placed on top of a silica gel column, and the column was eluted with 5 to 100% EtOAc/hexanes. Fractions containing the desired product were combined and concentrated. Repurification with 10/50/40 EtOAc/$CH_2Cl_2$/hexanes afforded N-{4-[5-(benzyloxy)-1,3-benzoxazol-2-yl]phenyl}-2-(2-methylphenoxy)acetamide. $R_f$=0.31(10/50/40 EtOAc/$CH_2Cl_2$/hexanes). LCMS=465.3 $(M+1)^+$. $^1H$ NMR ($CD_2Cl_2$, 600 MHz) δ 8.53 (s, 1H), 8.21 (m, 2H), 7.79 (m, 2H), 7.48-7.49 (m, 3H), 7.41 (t, J=7.8 Hz, 2H), 7.35 (m, 1H), 7.30 (d, J=2.4 Hz, 1H), 7.20-7.25 (m, 2H), 7.02 (dd, J=9.0, 2.4 Hz, 1H), 6.98 (t, J=7.2 Hz, 1H), 6.89 (d, J=8.4 Hz, 1H), 5.13 (s, 2H), 4.64 (s, 2H), 2.40 (s, 3H).

Example 316

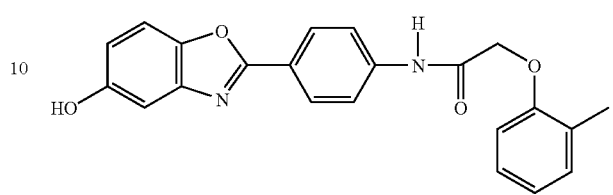

N-[4-(5-hydroxy-1,3-benzoxazol-2-yl)phenyl]-2-(2-methylphenoxy)acetamide

To a solution of N-{4-[5-(benzyloxy)-1,3-benzoxazol-2-yl]phenyl}-2-(2-methylphenoxy)acetamide (358.0 mg, 0.772 mmol) in THF/MeOH (1:1, 30 mL total) was added 10% Pd/C (100 mg). The reaction was placed under an atmosphere of $H_2$ and stirred vigorously for 24 hours. The catalyst was removed by filtration, and the reaction was concentrated to provide N-[4-(5-hydroxy-1,3-benzoxazol-2-yl)phenyl]-2-(2-methylphenoxy)acetamide. $R_f$=0.43 (60% EtOAc/hexanes). LCMS=375.3 $(M+1)^+$. $^1H$ NMR (DMSO, 600 MHz) δ 10.40 (s, 1H), 9.49 (s, 1H), 8.11 (d, J=9.0 Hz, 2H), 7.85 (d, J=9.0 Hz, 2H), 7.52 (d, J=9.0 Hz, 1H), 7.13-7.18 (m, 2H), 7.05 (d, J=2.4 Hz, 1H), 6.86-6.88 (m, 2H), 6.81 (dd, J=9.0, 2.4 Hz, 1H), 4.76 (s, 2H), 2.25 (s, 3H).

Example 317

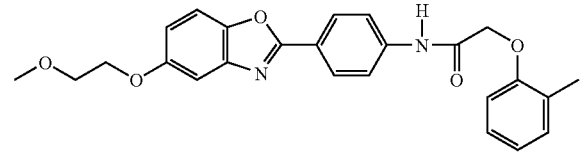

N-{4-[5-(2-methoxyethoxy)-1,3-benzoxazol-2-yl]phenyl}-2-(2-methylphenoxy)acetamide N-[4-(5-hydroxy-1,3-benzoxazol-2-yl)phenyl]-2-(2-methylphenoxy)acetamide (11.0 mg, 0.0294 mmol) was dissolved in DMF (1.0 mL). $Cs_2CO_3$ (11.5 mg, 0.0353 mmol) and 2-bromoethyl methyl ether (3 μL, 0.0323 mmol) mmol were added to the reaction. Over the next hour, two more additions of $Cs_2CO_3$ and bromoethyl methyl ether (same amounts as first time) were made. The reaction was then diluted with EtOAc (20 mL) and washed with $H_2O$ and brine (5 mL each). The organic layer was dried over $Na_2SO_4$, filtered, and concentrated. Purification of the residue by preparative thin layer chromatography (0.5% MeOH/$CH_2Cl_2$) afforded 7.6 mg (60%) of N-{4-[5-(2-methoxyethoxy)-1,3-benzoxazol-2-yl]phenyl}-2-(2-methylphenoxy)acetamide. $R_f$=0.21 (40% EtOAc/hexanes). LCMS=433.3 $(M+1)^+$. $^1H$ NMR ($CDCl_3$, 500 MHz) δ 8.22 (d, J=8.2 Hz, 2H), 7.76 (d, J=8.5 Hz, 2H), 7.44 (d, J=8.9 Hz, 1H), 7.19-7.26 (m, 3H), 6.98-7.00 (m, 2H), 6.85 (d, J=8.0 Hz, 1H), 4.64 (s, 2H), 4.17 (t, J=4.8 Hz, 2H), 3.79 (t, J=4.5 Hz, 2H), 3.47 (s, 3H), 2.39 (s, 3H).

Example 318

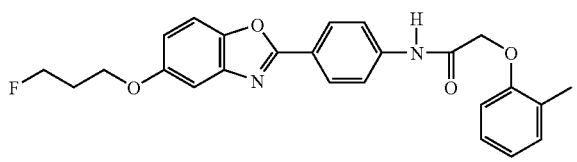

N-{4-[5-(3-fluoropropoxy)-1,3-benzoxazol-2-yl]phenyl}-2-(2-methylphenoxy)acetamide To a 0° C. solution of N-{4-[5-(3-hydroxypropoxy)-1,3-benzoxazol-2-yl]phenyl}-2-(2-methylphenoxy)acetamide (10 mg, 0.0231 mmol) in $CH_2Cl_2$ (150 µL) was added DAST (6.1 µL, 0.0463 mmol). The reaction was warmed to room temperature. After 30 minutes more DAST (6.1 µL, 0.0463 mmol) was added. After 30 more minutes, the reaction was quenched with saturated $NaHCO_3$ (5 mL) and extracted with EtOAc (25 mL). The organic layer was washed with brine (10 mL), dried over $Na_2SO_4$, filtered and concentrated. Purification of the residue by preparative thin layer chromatography (1% MeOH/$CH_2Cl_2$) afforded 3.0 mg (30%) of N-{4-[5-(3-fluoropropoxy)-1,3-benzoxazol-2-yl]phenyl}-2-(2-methylphenoxy)acetamide. LCMS=435.3 (M+1)$^+$. $^1$H NMR ($CD_2Cl_2$, 500 MHz) δ 8.53 (s, 1H), 8.22 (d, J=8.5 Hz, 2H), 7.79 (d, J=9.0 Hz, 2H), 7.47 (d, J=9.0 Hz, 1H), 7.20-7.24 (m, 3H), 6.94-7.00 (m, 2H), 6.89 (d, J=8.0 Hz, 1H), 4.67 (dt, J=47, 6.0 Hz, 2H), 4.64 (s, 2H), 4.15 (t, J=6.0 Hz, 2H), 2.40 (s, 3H), 2.20 (m, 2H).

Example 319

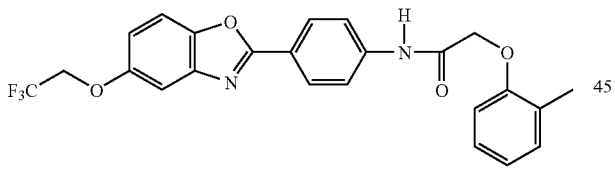

2-(2-methylphenoxy)-N-{4-[5-(2,2,2-trifluoroethoxy)-1,3-benzoxazol-2-yl]phenyl}acetamide To a solution of N-[4-(5-hydroxy-1,3-benzoxazol-2-yl)phenyl]-2-(2-methylphenoxy)acetamide (15.0 mg, 0.040 mmol) in DMF (1 mL) was added $Cs_2CO_3$ (19.5 mg, 0.06 mmol) and 1,1,1-trifluoro-2-iodoethane. The reaction was irradiated in a microwave for 10 minutes at 60 W and 150° C. The reaction was then diluted with EtOAc (25 mL) and washed with water and brine (5 mL each). The organic layer was dried over $Na_2SO_4$, filtered, and concentrated. Purification of the residue by preparative thin layer chromatography (5% acetone/hexanes) afforded 2-(2-methylphenoxy)-N-{4-[5-(2,2,2-trifluoroethoxy)-1,3-benzoxazol-2-yl]phenyl}acetamide. LCMS=457.2 (M+1)$^+$. $^1$H NMR ($CD_2Cl_2$, 500 MHz) δ 8.54 (s, 1H), 8.23 (d, J=9.0 Hz, 2H), 7.80 (d, J=9.0 Hz, 2H), 7.53 (d, J=8.5 Hz, 1H), 7.29 (d, J=2.5 Hz, 1H), 7.20-7.25 (m, 2H), 7.03 (dd, J=9.0, 2.5 Hz, 1H), 6.98 (t, J=7.5 Hz, 1H), 6.89 (d, J=8.0 Hz, 1H), 4.64 (s, 2H), 4.45 (q, J=8.0 Hz, 2H), 2.40 (s, 3H).

EXAMPLES in Table 9 were prepared following the general procedures outlined in EXAMPLES 315-319

TABLE 9

![General structure with R group on benzoxazole]

| Compound | R | LCMS (M + 1)$^+$ |
|---|---|---|
| 320 | phenyl-O- | 451.3 |
| 321 | HO-(CH2)3-O- | 433.3 |
| 322 | CH3-O-CH2-O- | 419.2 |
| 323 | ethyl-O- | 403.3 |
| 324 | isopropyl-O- | 417.3 |
| 325 | cyclopropylmethyl-O- | 429.3 |
| 326 | NC-CH2-O- | 414.2 |
| 327 | CH3-S-CH2-O- | 435.3 |
| 328 | CH3-S-CH2CH2-O- | 449.3 |
| 329 | benzyl-O-C(O)-CH2-O- | 523.3 |
| 330 | F-CH2CH2-O- | 421.3 |

TABLE 9-continued

| Compound | R | LCMS (M + 1)+ |
|---|---|---|
| 331 | HO—CH2CH2CH2—O—⟨⟩ | 433.3 |
| 332 | F3C—CH2—O—⟨⟩ | 439.4 |

Example 333

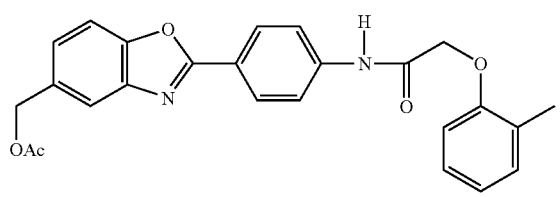

[2-(4-{[2-(2-methylphenoxy)acetyl]amino}phenyl)-1,3-benzoxazol-5-yl]methyl acetate

Step A: 4-hydroxy-3-nitrobenzyl acetate

To a solution of 4-(hydroxymethyl)-2-nitrophenol (200 mg, 1.18 mmol) in $CH_2Cl_2$ (12 mL) was added pyridine (478 μL) and $Ac_2O$ (134 μL, 1.42 mmol). After 4.5 hours, catalytic DMAP (15 mg, 0.12 mmol) was added. After 2 more hours, additional $Ac_2O$ (100 uL, 1.05 mmol) was added to the reaction. The reaction was stirred at room temperature for 15 more hours. Next, the reaction was diluted with EtOAc (100 mL), and washed with $H_2O$, 1N HCl, and brine (25 mL each). The organic layer was dried over $Na_2SO_4$, filtered, and concentrated. Purification of the residue by flash column chromatography (5 to 40% EtOAc/hexanes) afforded 4-hydroxy-3-nitrobenzyl acetate. $R_f$=0.5 (40% EtOAc/hexanes).

Step B: 3-amino-4-hydroxybenzyl acetate $PtO_2$ (7.3 mg, 0.032 mmol) was added to a solution of 4-hydroxy-3-nitrobenzyl acetate (69.3 mg, 0.33 mmol) in EtOH. The reaction was placed under an atmosphere of $H_2$ and stirred for 30 minutes. The reaction was then filtered to remove the catalyst and concentrated. Purification of the residue by flash column chromatography (10 to 50% EtOAc/hexanes) afforded 3-amino-4-hydroxybenzyl acetate. $R_f$=0.13 (40% EtOAc/hexanes). $^1$H NMR ($CDCl_3$, 500 MHz) δ 6.76 (s, 1H), 6.65-6.69 (m, 2H), 4.96 (s, 2H), 4.11 (bs, 2H), 2.07 (s, 3H).

Step C: [2-(4-{[2-(2-methylphenoxy)acetyl]amino}phenyl)-1,3-benzoxazol-5-yl]methyl acetate N-(4-formylphenyl)-2-(2-methylphenoxy)acetamide (61 mg, 0.227 mmol) and 3-amino-4-hydroxybenzyl acetate (41 mg, 0.227 mmol) were refluxed in EtOH (4 mL) for 45 minutes. The reaction was cooled to room temperature, and concentrated. The residue was dissolved in $CH_2Cl_2$ (5 mL) and DDQ (52 mg, 0.227 mmol) was added. The reaction was stirred at room temperature for 1 hour, and then diluted with EtOAc (50 mL). The organic layer was washed with 10% aqueous $K_2CO_3$ (3×15 mL) and brine (15 mL), dried over $Na_2SO_4$, filtered and concentrated. Purification of the residue by flash column chromatography with 0 to 2% acetone/$CH_2Cl_2$ afforded [2-(4-{[2-(2-methylphenoxy)acetyl]amino}phenyl)-1,3-benzoxazol-5-yl]methyl acetate. $R_f$=0.35 (40% EtOAc/hexanes). LCMS=431.4 (M+1)$^+$. $^1$H NMR (DMSO, 500 MHz) δ 10.44 (s, 1H), 8.16 (d, J=8.7 Hz, 2H), 7.87 (d, J=8.9 Hz, 2H), 7.74-7.77 (m, 2H), 7.41 (dd, J=8.3, 1.4 Hz, 1H), 7.13-7.18 (m, 2H), 6.86-6.89 (m, 2H), 5.18 (s, 2H), 4.77 (s, 2H), 2.25 (s, 3H), 2.07 (s, 3H).

Example 334

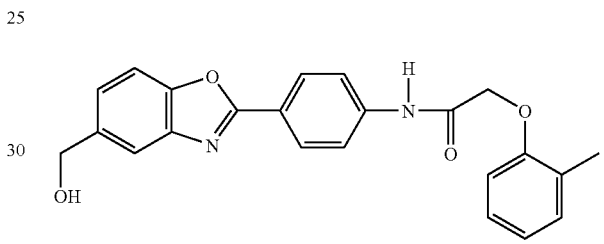

N-{4-[5-(hydroxymethyl)-1,3-benzoxazol-2-yl]phenyl}-2-(2-methylphenoxy)acetamide To a solution of [2-(4-{[2-(2-methylphenoxy)acetyl]amino}phenyl)-1,3-benzoxazol-5-yl]methyl acetate (15.7 mg, 0.036 mmol) in THF (4 mL) was added MeOH (500 μL), $H_2O$ (500 μL), and 10% $K_2CO_3$ (50 μL). The reaction was stirred overnight at room temperature and then diluted with EtOAc (30 mL), and washed with water and brine (10 mL each). The organic layer was dried over $Na_2SO_4$, filtered, and concentrated. Purification of the residue by flash column chromatography with 5% MeOH/$CH_2Cl_2$ afforded N-{4-[5-(hydroxymethyl)-1,3-benzoxazol-2-yl]phenyl}-2-(2-methylphenoxy)acetamide. $R_f$=0.40 (75% EtOAc/hexanes). LCMS=389.3 (M+1)$^+$. $^1$H NMR (DMSO, 500 MHz) δ 10.42 (s, 1H), 8.15 (d, J=8.7 Hz, 2H), 7.86 (d, J=8.7 Hz, 2H), 7.68-7.70 (m, 2H), 7.35 (d, J=9.2 Hz, 1H), 7.13-7.18 (m, 2H), 6.86-6.89 (m, 2H), 4.77 (s, 2H), 4.61 (s, 2H), 2.25 (s, 3H).

Example 335

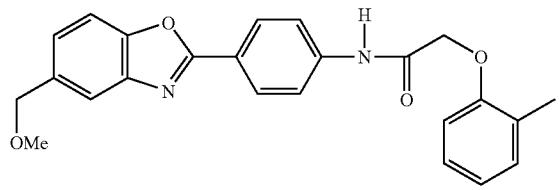

N-{4-[5-(methoxymethyl)-1,3-benzoxazol-2-yl]phenyl}-2-(2-methylphenoxy)acetamide

Step A: {4-[(4-methoxybenzyl)oxy]-3-nitrophenyl}methanol

To a solution of 4-(hydroxymethyl)-2-nitrophenol (200 mg, 1.18 mmol) in DMF (10 mL) was added $Cs_2CO_3$ (769 mg, 2.36 mmol) followed by PMBCl (240 uL, 1.77 mmol). After 30 minutes, additional PMBCl (200 uL, 1.48 mmol) and $Bu_4NI$ (200 mg, 0.54 mmol) were added. The reaction was stirred at room temperature for 3 hours and then diluted with EtOAc (100 mL), and washed with $H_2O$, aq. 10% $K_2CO_3$, and brine (25 mL each). The organic layer was dried over $Na_2SO_4$, filtered, and concentrated. Purification of the residue by flash column chromatography with 50% EtOAc/hexanes afforded {4-[(4-methoxybenzyl)oxy]-3-nitrophenyl}methanol. $R_f$=0.15 (40% EtOAc/hexanes). $^1$H NMR ($CDCl_3$, 500 MHz) δ 7.85 (d, J=1.8 Hz, 1H), 7.49 (dd, J=8.5, 2.0 Hz, 1H), 7.37 (d, J=8.5 Hz, 2H), 7.11 (d, J=8.7 Hz, 1H), 6.91 (d, J=8.7 Hz, 2H), 5.17 (s, 2H), 4.77 (s, 2H), 3.81 (s, 3H).

Step B: 1-[(4-methoxybenzyl)oxy]-4-(methoxymethyl)-2-nitrobenzene

To a solution of {4-[(4-methoxybenzyl)oxy]-3-nitrophenyl}methanol (290 mg, 1.00 mmol) in THF (10 mL) was added MeI (228 μL, 1.5 mmol) followed by KHMDS (3 mL of a 0.5 M solution in toluene, 1.5 mmol). After 20 minutes, the reaction was diluted with EtOAc (100 mL) and washed with $H_2O$ and brine (25 mL each). The organic layer was dried over $Na_2SO_4$, filtered, and concentrated. Purification of the residue by flash column chromatography with 40% EtOAc/hexanes afforded 1-[(4-methoxybenzyl)oxy]-4-(methoxymethyl)-2-nitrobenzene. $R_f$=0.36 (40% EtOAc/hexanes). $^1$H NMR ($CDCl_3$, 500 MHz) δ 7.82 (d, J=1.9 Hz, 1H), 7.46 (dd, J=8.7, 1.9 Hz, 1H), 7.37 (d, J=8.7 Hz, 2H), 7.10 (d, J=8.7 Hz, 1H), 6.91 (d, J=8.5 Hz, 2H), 5.17 (s, 2H), 4.41 (s, 2H), 3.81 (s, 3H), 3.39 (s, 3H).

Step C: 4-(methoxymethyl)-2-nitrophenol

To a solution of 1-[(4-methoxybenzyl)oxy]-4-(methoxymethyl)-2-nitrobenzene (92.6 mg, 0.0306 mmol) in $CH_2Cl_2$ (3 mL) was added TFA (300 μL). The reaction was stirred at room temperature for 10 minutes and then poured into saturated $NaHCO_3$ (15 mL). The aqueous solution was extracted with EtOAc (30 mL) and then the aqueous layer was acidified with 1N HCl. The aqueous layer was extracted again with EtOAc (30 mL), and the combined organic extracts were washed with brine, dried over $Na_2SO_4$, filtered, and concentrated. Purification of the residue by flash column chromatography with 5 to 40% EtOAc/hexanes afforded 4-(methoxymethyl)-2-nitrophenol. $R_f$=0.55 (40% EtOAc/hexanes). $^1$H NMR ($CDCl_3$, 500 MHz) δ 10.57 (s, 1H), 8.08 (d, J=2.2 Hz, 1H), 7.57 (dd, J=8.5, 2.1 Hz, 1H), 7.15 (d, J=8.6 Hz, 1H), 4.42 (s, 2H), 3.41 (s, 3H).

Step D: 2-amino-4-(methoxymethyl)phenol

To a solution of 4-(methoxymethyl)-2-nitrophenol (58.8 mg, 0.32 mmol) in EtOH (6 mL) and THF (2 mL) was added $PtO_2$ (7 mg, 0.031 mmol). The reaction was placed under an atmosphere of H2 and stirred at room temperature. After 45 minutes, the reaction was filtered through a plug of silica gel with EtOAc to remove the catalyst and the filtrate was concentrated to provide 2-amino-4-(methoxymethyl)phenol. $R_f$=0.17 (40% EtOAc/hexanes). LCMS=154.1 $(M+1)^+$.

Step E: N-{4-[5-(methoxymethyl)-1,3-benzoxazol-2-yl]phenyl}-2-(2-methylphenoxy)acetamide N-(4-formylphenyl)-2-(2-methylphenoxy)acetamide (93.5 mg, 0.348 mmol) and 2-amino-4-(methoxymethyl)phenol (53.2 mg, 0.348 mmol) were refluxed in EtOH (5 mL) for 45 minutes. The reaction was cooled to room temperature, and concentrated. The residue was dissolved in $CH_2Cl_2$ (5 mL) and DDQ (79 mg, 0.348 mmol) was added. The reaction was stirred at room temperature for 1 hour, and then diluted with EtOAc (50 mL). The organic layer was washed with 10% aqueous $K_2CO_3$ (3×15 mL) and brine (15 mL), dried over $Na_2SO_4$, filtered, and concentrated. Purification of the residue by flash column chromatography with 0 to 4% acetone/$CH_2Cl_2$ afforded N-{4-[5-(methoxymethyl)-1,3-benzoxazol-2-yl]phenyl}-2-(2-methylphenoxy)acetamide. $R_f$=0.31 (40% EtOAc/hexanes). LCMS=403.4 $(M+1)^+$. $^1$H NMR ($CDCl_3$, 500 MHz) δ 8.53 (s, 1H), 8.26 (d, J=8.7 Hz, 2H), 7.78 (d, J=8.7 Hz, 2H), 7.72 (s, 1H), 7.55 (d, J=8.5 Hz, 1H), 7.35 (d, J=8.2 Hz, 1H), 7.20-7.26 (m, 2H), 7.00 (t, J=7.5 Hz, 1H), 6.86 (d, J=8.0 Hz, 1H), 4.65 (s, 2H), 4.58 (s, 2H), 3.42 (s, 3H), 2.40 (s, 3H).

Example 336

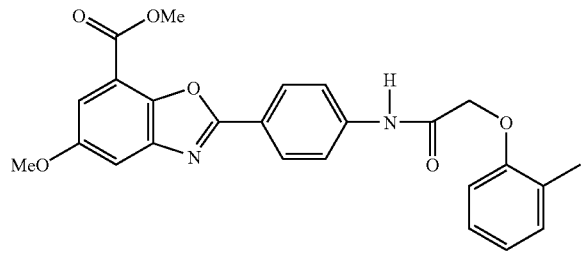

methyl 5-methoxy-2-(4-{[(2-methylphenoxy)acetyl]amino}phenyl)-1,3-benzoxazole-7-carboxylate

Step A: methyl 2-hydroxy-5-methoxy-3-nitrobenzoate

To a solution of methyl 2-hydroxy-5-methoxybenzoate (1 mL, 6.71 mmol) in HOAc (7 mL) a solution of fuming $HNO_3$ (282 μL) in HOAc (2 mL) was added dropwise. During the course of the reaction, a precipitate formed. The precipitate was removed by filtration and washed with $Et_2O$ to afford methyl 2-hydroxy-5-methoxy-3-nitrobenzoate. $R_f$=0.23 (25% EtOAc/hexanes). $^1$H NMR (DMSO, 500 MHz) δ 7.76 (d, J=3.2 Hz, 1H), 7.58 (d, J=3.4 Hz, 1H), 3.91 (s, 3H), 3.80 (s, 3H).

Step B: methyl 3-amino-2-hydroxy-5-methoxybenzoate

To a partial suspension of methyl 2-hydroxy-5-methoxy-3-nitrobenzoate (250 mg, 1.10 mmol) in THF (8 mL) and MeOH (1 mL) was added $PtO_2$ (25 mg, 0.11 mmol). The reaction was placed under and atmosphere of $H_2$. After 1.5 hours, the catalyst was removed by filtration, and the filtrate was concentrated to afford methyl 3-amino-2-hydroxy-5- methoxybenzoate. R$_f$=0.21 (25% EtOAc/hexanes). $^1$H NMR (CDCl$_3$, 500 MHz) δ 10.54 (s, 1H), 6.69 (d, J=2.7 Hz, 1H), 6.52 (d, J=2.5 Hz, 1H), 3.93 (s, 3H), 3.74 (s, 3H).

Step C: methyl 5-methoxy-2-(4-{[(2-methylphenoxy)acetyl]amino}phenyl)-1,3-benzoxazole-7-carboxylate To a solution of methyl 3-amino-2-hydroxy-5-methoxybenzoate (50 mg, 0.254 mmol) in dioxane (5 mL) was added 4-{[(2-methylphenoxy)acetyl]amino}benzoyl chloride (1 mL of a 0.5 M solution in CH$_2$Cl$_2$, 0.5 mmol; synthesized from the corresponding acid with oxalyl chloride). The reaction was heated to 100° C. for 2 hours and then cooled to room temperature. The reaction was diluted with EtOAc (50 mL) and washed with saturated NaHCO$_3$ and brine (15 mL each). The organic layer was dried over Na$_2$SO$_4$, filtered, and concentrated. Purification of the residue by flash column chromatography (50% EtOAc/hexanes) gave partially purified methyl 2-hydroxy-5-methoxy-3-[(4-{[(2-methylphenoxy)acetyl]amino}benzoyl)amino]benzoate. This material was heated to reflux in o-xylene (10 mL) with PPTS (20 mg, 0.08 mmol) using a dean-stark trap. After refluxing overnight, the reaction was diluted with EtOAc (50 mL) and washed with H$_2$O, saturated NaHCO$_3$, and brine (15 mL each). The organic layer was dried over Na$_2$SO$_4$, filtered, and concentrated. Purification of the residue by flash column chromatography (0 to 2% acetone/CH$_2$Cl$_2$) afforded methyl 5-methoxy-2-(4-{[(2-methylphenoxy)acetyl]amino}phenyl)-1,3-benzoxazole-7-carboxylate. R$_f$=0.27 (2% acetone/CH$_2$Cl$_2$). LCMS=447.3 (M+1)$^+$. $^1$H NMR (CD$_2$Cl$_2$, 500 MHz) δ 8.55 (s, 1H), 8.27 (d, J=8.7 Hz, 2H), 7.81 (d, J=8.7 Hz, 2H), 7.53 (d, J=2.7 Hz, 1H), 7.45 (d, J=2.7 Hz, 1H), 7.20-7.25 (m, 2H), 6.99 (t, J=7.2 Hz, 1H), 6.89 (d, J=8.0 Hz, 1H), 4.65 (s, 2H), 4.03 (s, 3H), 3.91 (s, 3H), 2.40 (s, 3H).

Example 337

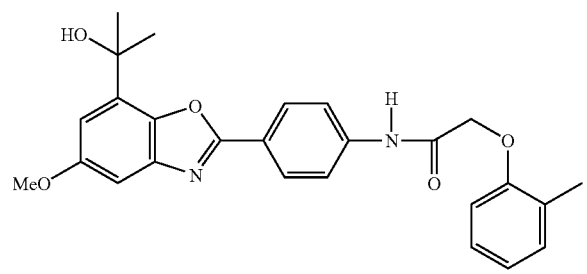

N-{4-[7-(1-hydroxy-1-methylethyl)-5-methoxy-1,3-benzoxazol-2-yl]phenyl}-2-(2-methylphenoxy)acetamide A solution of methyl 5-methoxy-2-(4-{[(2-methylphenoxy)acetyl]amino}phenyl)-1,3-benzoxazole-7-carboxylate (14.8 mg, 0.033 mmol) in THF (1 mL) was cooled to −20° C. MeMgBr (22 µL of a 3 M solution in Et$_2$O) was added. The reaction was monitored by thin layer chromatography, and additional MeMgBr was added until the reaction was complete. The reaction was quenched by pouring it into 30 mL of EtOAc containing 300 µL of HOAc. The organic solution was washed with H$_2$O and brine (10 mL each), dried over Na$_2$SO$_4$, filtered, and concentrated. Purification of the residue by flash column chromatography (5 to 8% acetone/CH$_2$Cl$_2$) afforded N-{4-[7-(1-hydroxy-1-methylethyl)-5-methoxy-1,3-benzoxazol-2-yl]phenyl}-2-(2-methylphenoxy)acetamide. R$_f$=0.18 (5% acetone/CH$_2$Cl$_2$). LCMS=447.4 (M+1)$^+$. $^1$H NMR (DMSO, 500 MHz) δ 10.43 (s, 1H), 8.13 (d, J=8.7 Hz, 2H), 7.86 (d, J=8.9 Hz, 2H), 7.15-7.18 (m, 3H), 7.07 (d, J=2.6 Hz, 1H), 6.86-6.89 (m, 2H), 5.41 (s, 1H), 4.76 (s, 2H), 3.80 (s, 3H), 2.25 (s, 3H), 1.64 (s, 6H).

Intermediate 18

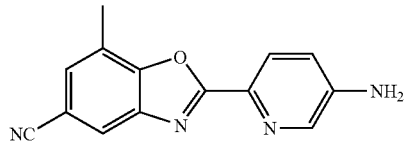

2-(5-aminopyridin-2-yl)-7-methyl-1,3-benzoxazole-5-carbonitrile 6-(5-bromo-7-methyl-1,3-benzoxazol-2-yl)pyridine-3-amine (Example 356, Step B; 50 mg; 0.165 mmol) was treated with tris(dibenzylideneacetone)dipalladium (15.1 mg; 0.0165 mmol), 1,1'-bis(diphenylphosphino)ferrocene (18.2 mg; 0.0329 mmol) and Zn(CN)$_2$ (19.3 mg; 0.165 mmol) as described in Example 355 to afford 2-(5-aminopyridin-2-yl)-7-methyl-1,3-benzoxazole-5-carbonitrile as a yellow solid. LCMS=251.2 (M+1)$^+$. $^1$H NMR (500 MHz, CDCl$_3$): δ 8.32 (d, J=2.5 Hz, 1H), 8.20 (d, J=8.5 Hz, 1H), 7.95 (s, 1H), 7.48 (s, 1H), 7.15 (dd, J=8.5, 2.8 Hz, 1H), 4.23 (br s, 2H), 2.68 (s, 3H).

Example 339

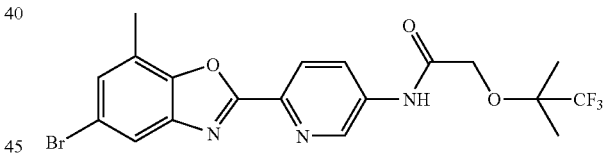

N-[6-(5-bromo-7-methyl-1,3-benzoxazol-2-yl)pyridine-3-yl]-2-(2,2,2-trifluoro-1,1-dimethylethoxy)acetamide Step A: (2,2,2-trifluoro-1,1-dimethylethoxy)acetic acid 1,1,1-trifluoro-2-methylpropan-2-ol (866 µL; 7.92 mol) was treated with NaH (60% in oil; 1.44 g; 35.98 mol) and bromoacetic acid (1.0 g; 7.92 mol) as described in EXAMPLE 7, Step A. $^1$H NMR (500 MHz, CDCl$_3$): δ 4.28 (s, 2H), 1.49 (s, 6H).

Step B: N-[6-(5-bromo-7-methyl-1,3-benzoxazol-2-yl)pyridine-3-yl]-2-(2,2,2-trifluoro-1,1-dimethylethoxy)acetamide The acid chloride of (2,2,2-trifluoro-1,1-dimethylethoxy)acetic acid (Step A; 55 mg; 0.296 mmol) was treated with 6-(5-bromo-7-methyl-1,3-benzoxazol-2-yl)pyridine-3- amine (Example 356, Step B; 60 mg; 0.197 mmol) and diisopropylethylamine (137 µL; 0.788 mmol) as described in Example 354, Step D to afford N-[6-(5-bromo-7-methyl-1,3-benzoxazol-2-yl)pyridine-3-yl]-2-(2,2,2-trifluoro-1,1-dimethylethoxy)acetamide as an off-white solid. LCMS=474.1 (M+2)⁺. ¹H NMR (500 MHz, CDCl₃): δ 8.86 (s, 1H), 8.50-8.47 (m, 2H), 8.38 (d, J=9 Hz, 1H), 7.82 (s, 1H), 7.39 (s, 1H), 4.29 (s, 2H), 2.66 (s, 3H), 1.56 (s, 6H).

Example 340

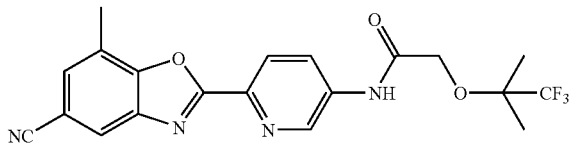

N-[6-(5-cyano-7-methyl-1,3-benzoxazol-2-yl)pyridine-3-yl]-2-(2,2,2-trifluoro-1,1-dimethylethoxy)acetamide The acid chloride of (2,2,2-trifluoro-1,1-dimethylethoxy)acetic acid (Example 339, Step A; 12.3 mg; 0.066 mmol) was treated with 2-(5-aminopyridin-2-yl)-7-methyl-1,3-benzoxazole-5-carbonitrile (INTERMEDIATE 18; 11 mg; 0.044 mmol) and diisopropylethylamine (31 µL; 0.176 mmol) as described in Example 354, Step D to afford N-[6-(5-cyano-7-methyl-1,3-benzoxazol-2-yl)pyridine-3-yl]-2-(2,2,2-trifluoro-1,1-dimethylethoxy)acetamide as an off-white solid. LCMS=419.2 (M+1)⁺. ¹H NMR (500 MHz, CDCl₃): δ 8.86 (d, J=2.3 Hz, 1H), 8.50 (s, 1H), 8.49 (dd, J=8.7, 2.3 Hz, 1H), 8.39 (d, J=8.5 Hz, 1H), 7.99 (s, 1H), 7.52 (s, 1H), 4.28 (s, 2H), 2.70 (s, 3H), 1.54 (s, 6H).

Intermediate 19

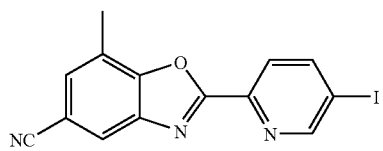

2-(5-iodopyridin-2-yl)-7-methyl-1,3-benzoxazole-5-carbonitrile

To a stirred suspension of 2-(5-aminopyridin-2-yl)-7-methyl-1,3-benzoxazole-5-carbonitrile (INTERMEDIATE 18; 170 mg; 0.68 mmol) in CH₂I₂ (4 mL) was added t-butyl nitrite (162 mL; 1.36 mmol) under an atmosphere of nitrogen. The reaction was heated to 125° C. over 90 min. The reaction mixture was preadsorbed onto silica gel and purified by flash column chromatography (0-100% EtOAc/hexanes gradient; flushed with 10% MeOH/CHCl₃) to afford 2-(5-iodopyridin-2-yl)-7-methyl-1,3-benzoxazole-5-carbonitrile as an orange solid. LCMS=362.1 (M+1)⁺. ¹H NMR (500 MHz, DMSO): δ 9.09 (d, J=1.6 Hz, 1H), 8.50 (dd, J=8.4, 2.0 Hz, 1H), 8.32 (s, 1H), 8.17 (d, J=8.3 Hz, 1H), 7.82 (s, 1H), 2.61 (s, 3H).

Example 341

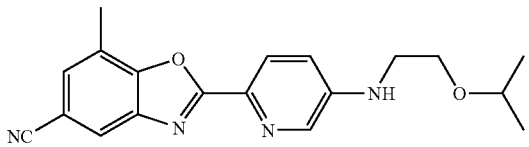

2-{5-[(2-isopropoxyethyl)amino]pyridin-2-yl}-7-methyl-1,3-benzoxazole-5-carbonitrile To an oven-dried tube was added tris(dibenzylideneacetone)dipalladium (3.8 mg; 0.004 mmol), (+/−) BINAP (4.3 mg; 0.007 mmol), sodium tert-butoxide (18.6 mg; 0.194 mmol), 2-aminoethylisopropyl ether (25.5 µL; 0.208 mmol) and a degassed solution of 2-(5-iodopyridin-2-yl)-7-methyl-1,3-benzoxazole-5-carbonitrile (INTERMEDIATE 19; 50 mg; 0.139 mmol) in toluene (2 mL). The reaction was flushed with N₂, sealed, and heated at 140° C. for 24 h. The reaction was partitioned between EtOAc (50 mL) and saturated NH₄Cl (50 mL). The aqueous layer was extracted with EtOAc (3×50 mL) and the combined organic layers were washed with brine (50 mL), dried (MgSO₄), filtered and concentrated under reduced pressure. The crude product was purified by flash column chromatography (0-50% EtOAc/hexanes gradient) and by preparative thin layer chromatography, eluting with 2% MeOH/CHCl₃) to afford 2-{5-[(2-isopropoxyethyl)amino]pyridin-2-yl}-7-methyl-1,3-benzoxazole-5-carbonitrile as a yellow solid. LCMS=337.3 (M+1)⁺. ¹H NMR (500 MHz, CDCl₃): δ 8.28 (d, J=2.3 Hz, 1H), 8.22 (d, J=8.7 Hz, 1H), 7.93 (s, 1H), 7.47 (s, 1H), 7.07 (dd, J=8.6, 2.9 Hz, 1H), 3.74 (t, J=5.2 Hz, 2H), 3.73-3.68 (m, 1H), 3.44 (t, J=5.3 Hz, 2H), 2.69 (s, 3H), 1.26 (s, 3H), 1.25 (s, 3H).

Example 342

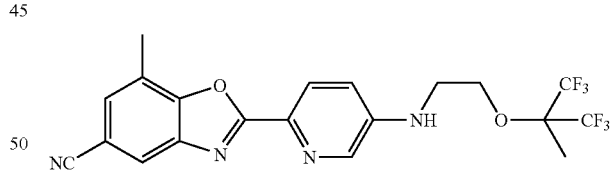

7-methyl-2-[5-({2-[2,2,2-trifluoro-1-methyl-1-(trifluoromethyl)ethoxy]ethyl}amino)pyrindin-2-yl]-1,3-benzoxazole-5-carbonitrile 2-(5-iodopyridin-2-yl)-7-methyl-1,3-benzoxazole-5-carbonitrile (INTERMEDIATE 19; 108 mg; 0.299 mmol) was treated with 2-[2,2,2-trifluoro-1-methyl-1-(trifluoromethyl)ethoxy]ethanamine (Step A; 101 mg; 0.449 mmol), tris(dibenzylideneacetone)dipalladium (8.2 mg; 0.009 mmol), (+/−) BINAP (9.3 mg; 0.015 mmol) and sodium tert-butoxide (40 mg; 0.419 mmol) as described in Example 341 to afford 7-methyl-2-[5-({2-[2,2,2-trifluoro-1-methyl-1-(trifluoromethyl)ethoxy]ethyl}amino)-pyrindin-2-yl]-1,3-benzoxazole-5-carbonitrile as a yellow solid. LCMS=459.3 (M+1)⁺. ¹H NMR (500 MHz, CDCl₃): δ 8.28 (s, 1H), 8.23 (d, J=8.7 Hz, 1H), 7.94 (s, 1H), 7.48 (s, 1H), 7.09 (dd, J=8.7, 2.6 Hz, 1H), 4.61 (br s, 1H), 4.10-3.99 (m, 2H), 3.59-3.56 (m, 2H), 2.69 (s, 3H), 1.67 (s, 3H).

The EXAMPLES in Table 10 were prepared by the general procedures outlined in EXAMPLES 339-342

TABLE 10

| EXAMPLE | R₁ | R₂ | LCMS |
|---|---|---|---|
| 343 | (CH₂O-CH₂-2-CF₃-phenyl) | Br | 522.2 (M + 2)⁺ |
| 344 | (CH₂O-cyclohexyl) | Br | 446.2 (M + 2)⁺ |
| 345 | (CH₂O-CH₂-2-CF₃-phenyl) | CN | 467.2 (M + 1)⁺ |
| 346 | (CH₂O-cyclohexyl) | H | 366.3 (M + 1)⁺ |
| 347 | (CH₂O-cyclohexyl) | CN | 391.3 (M + 1)⁺ |

Example 348

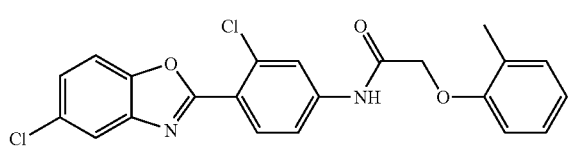

N-[3-chloro-4-(5-chloro-1,3-benzoxazol-2-yl)phenyl]-2-(2-methylphenoxy)acetamide Step A:
3-chloro-4-(5-chloro-1,3-benzoxazol-2-yl)aniline To an oven-dried tube were added 4-amino-2-chlorobenzoic acid (100 mg; 0.58 mmol), boric acid (36 mg; 0.58 mmol), 2-amino-4-chlorophenol (84 mg; 0.58 mmol) and o-xylene (2 mL). The reaction mixture was flushed with N₂, sealed and subjected to microwave irradiation (300 W, 270° C., 40 min). The reaction was cooled, diluted with EtOAc (25 mL) and washed successively with saturated NaHCO₃ (2×25 mL), H₂O (2×25 mL), and brine (25 mL). The organic layer was dried (MgSO₄), filtered, concentrated under reduced pressure and purified by flash column chromatography (0.5-2% MeOH/CHCl₃ gradient) to afford 3-chloro-4-(5-chloro-1,3-benzoxazol-2-yl)aniline as a pale pink solid. LCMS=279.1 (M+1)⁺. ¹H NMR (500 MHz, CDCl₃): δ 8.02 (d, J=8.7 Hz, 1H), 7.80 (d, J=2.0 Hz, 1H), 7.52 (d, J=8.4 Hz, 1H), 7.34 (dd, J=8.6, 2.2 Hz, 1H), 6.86 (d, J=2.3 Hz, 1H), 6.71 (dd, J=8.7, 2.3 Hz, 1H), 4.16 (s, 2H).

Step B: N-[3-chloro-4-(5-chloro-1,3-benzoxazol-2-yl)phenyl]-2-(2-methylphenoxy)-acetamide The acid chloride of (2-methylphenoxy)acetic acid (26 mg; 0.158 mmol) was treated with 3-chloro-4-(5-chloro-1,3-benzoxazol-2-yl)aniline (Step A; 44 mg; 0.158 mmol) and diisopropylethylamine (69 μL; 0.395 mmol) as described in Example 354, Step D to afford N-[3-chloro-4-(5-chloro-1,3-benzoxazol-2-yl)phenyl]-2-(2-methylphenoxy)acetamide as a white solid. LCMS=427.1 (M+1)⁺. ¹H NMR (500 MHz, CDCl₃): δ 8.56 (s, 1H), 8.22 (d, J=8.7 Hz, 1H), 7.99 (d, J=2.3 Hz, 1H), 7.86 (d, J=1.9 Hz, 1H), 7.71 (dd, J=8.7, 1.5 Hz, 1H), 7.58 (d, J=8.5 Hz, 1H), 7.41 (dd, J=8.7, 2.0 Hz, 1H), 7.31-7.25 (m, 2H), 7.05 (t, J=7.4 Hz, 1H), 6.90 (d, J=8.2 Hz, 1H), 4.70 (s, 2H), 2.44 (s, 3H).

Example 349

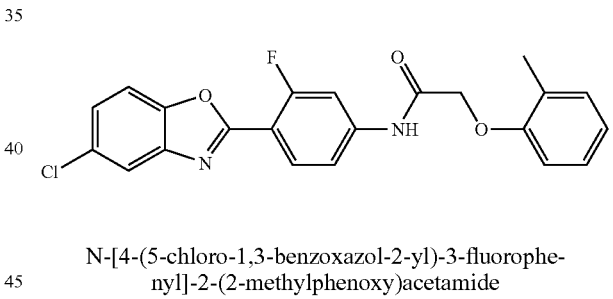

N-[4-(5-chloro-1,3-benzoxazol-2-yl)-3-fluorophenyl]-2-(2-methylphenoxy)acetamide Step A:
4-(5-chloro-1,3-benzoxazol-2-yl)-3-fluoroaniline 4-amino-2-fluorobenzoic acid (200 mg; 1.29 mmol) and 2-amino-4-chlorophenol (223 mg; 1.55 mmol) were treated with polyphosphoric acid (2 mL) as described in Example 354, Step C to afford 4-(5-chloro-1,3-benzoxazol-2-yl)-3-fluoroaniline as a pink solid. LCMS=263.2 (M+1)⁺. ¹H NMR (500 MHz, CDCl₃): δ 8.03 (t, J=8.4 Hz, 1H), 7.77 (d, J=2.1 Hz, 1H), 7.51 (d, J=8.5 Hz, 1H), 7.32 (dd, J=8.5, 2.1 Hz, 1H), 6.59 (dd, J=8.4, 2.3 Hz, 1H), 6.54 (d, J=12.8, 2.3 Hz, 1H), 4.24 (s, 2H).

Step B: N-[4-(5-chloro-1,3-benzoxazol-2-yl)-3-fluorophenyl]-2-(2-methylphenoxy)acetamide The acid chloride of (2-methylphenoxy)acetic acid (100 mg; 0.60 mmol) was treated with 4-(5-chloro-1,3-benzoxazol-2-yl)-3-fluoroaniline (Step A; 189 mg; 0.72 mmol) and triethylamine (101 μL; 0.72 mmol) as described in Example 354, Step D to afford N-[4-(5-chloro-1,3-benzoxazol-2-yl)-3- fluorophenyl]-2-(2-methylphenoxy)acetamide as a pale pink solid. LCMS=411.1 (M+1)+. $^1$H NMR (500 MHz, CDCl$_3$): δ 8.62 (s, 1H), 8.25 (t, J=8.2 Hz, 1H), 7.90 (dd, J=12.6, 2.0 Hz, 1H), 7.83 (d, J=1.9 Hz, 1H), 7.57 (d, J=8.5 Hz, 1H), 7.43 (dd, J=8.7, 2.0 Hz, 1H), 7.39 (dd, J=8.7, 2.0 Hz, 1H), 7.31-7.25 (m, 1H), 7.05 (t, J=7.4 Hz, 1H), 6.90 (d, J=8.0 Hz, 1H), 4.71 (s, 2H), 2.44 (s, 3H).

Example 350

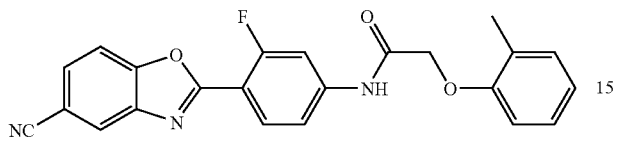

N-[4-(5-cyano-1,3-benzoxazol-2-yl)-3-fluorophenyl]-2-(2-methylphenoxy)acetamide

N-[4-(5-chloro-1,3-benzoxazol-2-yl)-3-fluorophenyl]-2-(2-methylphenoxy)acetamide (Example 349; 40 mg; 0.098 mmol) was treated with tris(dibenzylideneacetone)dipalladium (17.9 mg; 0.0195 mmol), 1,1'-bis(diphenylphosphino)ferrocene (21.6 mg; 0.039 mmol) and Zn(CN)$_2$ (11.5 mg; 0.098 mmol) as described in Example 355 to afford N-[4-(5-cyano-1,3-benzoxazol-2-yl)-3-fluorophenyl]-2-(2-methylphenoxy)-acetamide as a white solid. LCMS=402.2 (M+1)+. $^1$H NMR (500 MHz, CDCl$_3$): δ 8.65 (s, 1H), 8.27 (t, J=8.3 Hz, 1H), 8.17 (s, 1H), 7.93 (dd, J=12.6, 2.1 Hz, 1H), 7.76 (d, J=8.3 Hz, 1H), 7.73 (dd, J=8.5, 1.4 Hz, 1H), 7.45 (dd, J=8.7, 2.0 Hz, 1H), 7.31-7.26 (m, 1H), 7.06 (t, J=7.3 Hz, 1H), 6.90 (8.3 Hz, 1H), 4.71 (s, 2H), 2.45 (s, 3H).

Example 351

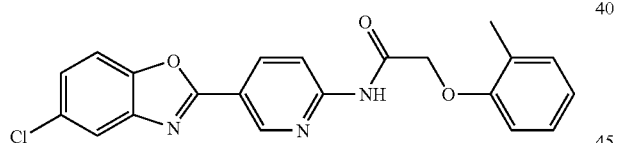

N-[5-(5-chloro-1,3-benzoxazol-2-yl)pyridine-2-yl]-2-(2-methylphenoxy)acetamide

Step A:
5-(5-chloro-1,3-benzoxazol-2-yl)pyridine-2-amine 6-aminonicotinic acid (500 mg; 3.62 mmol) and 2-amino-4-chlorophenol (624 mg; 4.34 mmol) were treated with polyphosphoric acid (5 mL) as described in Example 354, Step C to afford 5-(5-chloro-1,3-benzoxazol-2-yl)pyridine-2-amine as a pale pink solid. LCMS=246.2 (M+1)+. $^1$H NMR (500 MHz, DMSO): δ 8.75 (d, J=2.1 Hz, 1H), 8.07 (dd, J=8.7, 1.9 Hz, 1H), 7.80 (s, 1H), 7.74 (d, J=8.5 Hz, 1H), 7.39 (d, J=8.5 Hz, 1H), 6.91 (s, 1H), 6.60 (d, J=8.9 Hz, 1H).

Step B: N-[5-(5-chloro-1,3-benzoxazol-2-yl)pyridine-2-yl]-2-(2-methylphenoxy)-acetamide The acid chloride of (2-methylphenoxy)acetic acid (30 mg; 0.18 mmol) was treated with 5-(5-chloro-1,3-benzoxazol-2-yl)pyridine-2-amine (Step A; 53 mg; 0.22 mmol) and triethylamine (30 μL; 0.22 mmol) as described in Example 354, Step D to afford N-[5-(5-chloro-1,3-benzoxazol-2-yl)pyridine-2-yl]-2-(2-methylphenoxy)acetamide as a white solid. LCMS=394.1 (M+1)+. $^1$H NMR (500 MHz, CDCl$_3$): δ 9.21 (d, J=1.8 Hz, 1H), 9.19 (s, 1H), 8.58 (dd, J=8.8, 2.2 Hz, 1H), 8.52 (d, J=8.9 Hz, 1H), 7.80 (d, J=2.1 Hz, 1H), 7.57 (d, J=8.7 Hz, 1H), 7.40 (dd, J=8.7, 2.1 Hz, 1H), 7.30-7.23 (m, 1H), 7.03 (t, J=7.4 Hz, 1H), 6.90 (d, J=8.0 Hz, 1H), 4.73 (s, 2H), 2.47 (s, 3H).

Example 352

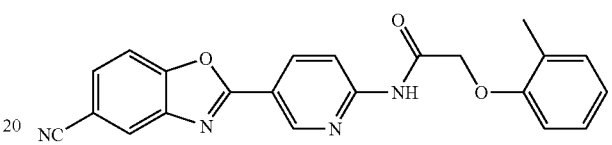

N-[5-(5-cyano-1,3-benzoxazol-2-yl)pyridin-2-yl]-2-(2-methylphenoxy)acetamide

N-[5-(5-chloro-1,3-benzoxazol-2-yl)pyridine-2-yl]-2-(2-methylphenoxy)acetamide (Example 351; 13.3 mg; 0.034 mmol) was treated with tris(dibenzylideneacetone)dipalladium (3.1 mg; 0.0034 mmol), 1,1'-bis(diphenylphosphino)ferrocene (3.8 mg; 0.0068 mmol) and Zn(CN)$_2$ (2.4 mg; 0.020 mmol) as described in Example 355 to afford N-[5-(5-cyano-1,3-benzoxazol-2-yl)pyridin-2-yl]-2-(2-methylphenoxy)acetamide as an off-white solid. LCMS=385.2 (M+1)+. $^1$H NMR (500 MHz, CDCl$_3$): δ 9.23 (d, J=2.1 Hz, 1H), 9.21 (s, 1H), 8.61 (dd, J=8.8, 2.2 Hz, 1H), 8.55 (d, J=8.7 Hz, 1H), 8.14 (s, 1H), 7.75 (d, J=8.4 Hz, 1H), 7.73 (dd, J=8.4, 1.5 Hz, 1H), 7.31-7.24 (m, 1H), 7.05 (t, J=7.5 Hz, 1H), 6.90 (d, J=8.0 Hz, 1H), 4.74 (s, 2H), 2.47 (s, 3H).

Example 353

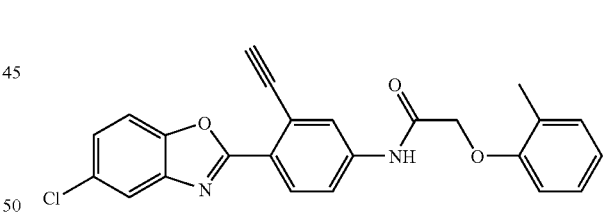

N-[4-(5-chloro-1,3-benzoxazol-2-yl)-3-ethynylphenyl]-2-(2-methylphenoxy)acetamide Step A:
5-amino-2-(5-chloro-1,3-benzoxazol-2-yl)phenol 4-aminosalicylic acid (1.0 g; 6.53 mmol) and 2-amino-4-chlorophenol (1.13 g; 7.84 mmol) were treated with polyphosphoric acid (3 mL) as described in Example 354, Step C to afford 5-amino-2-(5-chloro-1,3-benzoxazol-2-yl)phenol as a brown solid. LCMS=261.1 (M+1)+. $^1$H NMR (500 MHz, DMSO): δ 10.97 (s, 1H), 7.80 (d, J=2.0 Hz, 1H), 7.74 (d, J=8.5 Hz, 1H), 7.65 (d, J=8.7 Hz, 1H), 7.37 (dd, J=8.6, 1.9 Hz, 1H), 6.30 (dd, J=8.7, 2.1 Hz, 1H), 6.19 (d, J=2.1 Hz, 1H), 6.18-6.16 (m, 2H).

Step B: N-[4-(5-chloro-1,3-benzoxazol-2-yl)-3-hydroxyphenyl]-2-(2-methylphenoxy)-acetamide The acid chloride of (2-methylphenoxy)acetic acid (47.4 mg; 0.29 mmol) was treated with 5-amino-2-(5-chloro-1,3-benzoxazol-2-yl)phenol (Step A, 109 mg; 0.34 mmol) and triethylamine (48 µL; 0.34 mmol) as described in Example 354, Step D to afford N-[4-(5-chloro-1,3-benzoxazol-2-yl)-3-hydroxyphenyl]-2-(2-methylphenoxy)-acetamide as a white solid. LCMS=409.1 (M+1)$^+$. $^1$H NMR (500 MHz, CDCl$_3$): δ 11.41 (s, 1H), 8.53 (s, 1H), 8.03 (d, J=8.9 Hz, 1H), 7.74 (d, J=1.9 Hz, 1H), 7.57 (d, J=8.4 hz, 1H), 7.43-7.38 (m, 3H), 7.30-7.24 (m, 2H), 7.04 (t, J=7.4 Hz, 1H), 6.90 (d, J=8.1 Hz, 1H), 4.69 (s, 2H), 2.09 (s, 3H).

Step C: 5-amino-2-(5-chloro-1,3-benzoxazol-2-yl)phenyl trifluoromethanesulfonate To an oven-dried tube were added N-[4-(5-chloro-1,3-benzoxazol-2-yl)-3-hydroxyphenyl]-2-(2-methylphenoxy)acetamide (Step B, 100 mg., 0.245 mmol), N-phenyl trifluoromethanesulfonimide (87.5 mg; 0.245 mmol), K$_2$CO$_3$ (102 mg; 0.735 mmol), and THF (3 mL). The reaction mixture was flushed with N$_2$, sealed and subjected to microwave radiation (200 W, 120° C., 40 min). The resultant mixture was partitioned between EtOAc (15 mL) and H$_2$O (15 mL). The aqueous layer was extracted with EtOAc (2×15 mL) and the combined organic layers were washed with brine (15 mL), dried (MgSO$_4$), filtered, and concentrated under reduced pressure. Purified by flash column chromatography (0-25% EtOAc/hexanes gradient) to afford 5-amino-2-(5-chloro-1,3-benzoxazol-2-yl)phenyl trifluoromethanesulfonate as a white solid. LCMS=541.1 (M+1)$^+$. $^1$H NMR (500 MHz, CDCl$_3$): δ 8.69 (s, 1H), 8.39 (d, J=8.7 Hz, 1H), 8.17 (d, J=1.9 Hz, 1H), 7.85 (d, J=2.1 Hz, 1H), 7.62 (dd, J=8.5, 2.1 Hz, 1H), 7.59 (d, J=8.6 Hz, 1H), 7.43 (dd, J=8.7, 2.1 Hz, 1H), 7.31-7.26 (m, 2H), 7.07 (t, J=7.1 Hz, 1H), 6.91 (d, J=8.0 Hz, 1H), 4.72 (s, 2H), 2.44 (s, 3H).

Step D: N-[4-(5-chloro-1,3-benzoxazol-2-yl)-3-ethynylphenyl]-2-(2-methylphenoxy)-acetamide To an oven-dried tube were added 5-amino-2-(5-chloro-1,3-benzoxazol-2-yl)phenyl trifluoromethanesulfonate (15 mg; 0.028 mmol), tributylethynylstannane (8.4 mg; 0.029 mmol), LiCl (3.5 mg; 0.08 mmol), (PPh$_3$)$_4$Pd (1.6 mg; 0.001 mmol) and THF (1 mL). The reaction mixture was degassed, sealed, and subjected to microwave irradiation (200 W, 120° C., 60 min). The reaction was partitioned between EtOAc (20 mL) and 10% aq. NH$_4$OH (20 mL). The aqueous layer was extracted with EtOAc (3×20 mL) and the combined organic layers were washed with H$_2$O (20 mL) and brine (20 mL), dried (MgSO$_4$), filtered and concentrated under reduced pressure. The crude material was purified by flash column chromatography (0-25% EtOAc/hexanes gradient) to afford N-[4-(5-chloro-1,3-benzoxazol-2-yl)-3-ethynylphenyl]-2-(2-methylphenoxy)acetamide as an off-white solid. LCMS=417.2 (M+1)$^+$. $^1$H NMR (500 MHz, CDCl$_3$): δ 8.55 (s, 1H), 8.26 (d, J=8.7 Hz, 1H), 7.96 (d, J=1.8 Hz, 1H), 7.90 (dd, J=8.6, 2.1 Hz, 1H), 7.84 (d, J=1.8 Hz, 1H), 7.56 (d, J=8.4 Hz, 1H), 7.39 (dd, J=8.7, 1.8 Hz, 1H), 7.31-7.25 (m, 2H), 7.05 (t, J=7.5 Hz, 1H), 6.90 (d, J=8.0 Hz, 1H), 4.72 (s, 2H), 3.52 (s, 1H), 2.45 (s, 3H).

Example 354

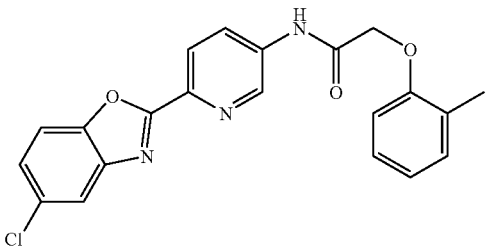

N-[6-(5-chloro-1,3-benzoxazol-2-yl)pyridine-3-yl]-2-(2-methylphenoxy)acetamide

Step A. 6-(methoxycarbonyl)nicotinic acid

To a suspension of 2,5-pyridine dicarboxylic acid (8.4 g, 0.055 mol) in MeOH (100 mL) was added concentrated H$_2$SO$_4$ (3 g), and the resulting mixture was heated under reflux for 2 h. The reaction mixture was allowed to cool and then poured into H$_2$O (500 mL). The resulting precipitate was collected by filtration and washed with H$_2$O (2×40 mL) and dried overnight in a high vacuo oven to afford 6-(methoxycarbonyl)nicotinic acid. LCMS calc.=181.15; found=182.2 (M+1)$^+$.

Step B. methyl 5-[(tert-butoxycarbonyl)amino]pyridine-2-carboxylate

A solution of 6-(methoxycarbonyl)nicotinic acid (1 g, 5.5 mmol), diphenylphosphoryl azide (1.19 mL, 5.5 mmol) and triethylamine (0.77 mL, 5.5 mmol) in tert-butanol (10 mL) was stirred under reflux for 3.5 h. The solvent was evaporated to give a yellow oil which was dissolved in EtOAC (140 mL). The solution was washed successively with 5% aqueous citric acid, H$_2$O, aqueous NaHCO$_3$, brine (30 mL each) and dried over MgSO$_4$. Evaporation of the solvent and trituration with toluene (30 mL) gave the desired product as a pale yellow solid. LCMS calc.=252.26; found=253.2 (M+1)$^+$.

Step C. 6-(5-chloro-1,3-benzoxazol-2-yl)pyridine-3-amine

A suspension of polyphosphoric acid (1 mL), 2-amino-4-chlorophenol (0.114 g, 0.79 mmol) and methyl 5-[(tert-butoxycarbonyl)amino]pyridine-2-carboxylate (0.200 g, 0.79 mmol) was heated at 180° C. for 6 h. The reaction mixture was allowed to cool and then poured into H$_2$O (50 mL). The solution was neutralized with 6N NaOH and extracted with EtOAC (3×70 mL). The combined organic extracts were washed with brine (50 mL), dried over MgSO$_4$, filtered and concentrated. The crude product was purified by silica gel chromatography (15% MeOH/CHCl$_3$) to afford 6-(5-chloro-1,3-benzoxazol-2-yl)pyridine-3-amine as a yellow solid. LCMS calc.=245.66; found=246.2 (M+1)$^+$.

Step D. N-[6-(5-chloro-1,3-benzoxazol-2-yl)pyridine-3-yl]-2-(2-methylphenoxy)acetamide Oxalyl chloride (88 µl, 0.18 mmol, 2.0 M in CH$_2$Cl$_2$) was added to a stirred and cooled solution (0° C.) of (2-methylphenoxy)acetic acid (6.3 mg, 0.038 mmol) in CH$_2$Cl$_2$ (1 mL), under an atmosphere of nitrogen. One drop of anhydrous DMF was added and the mixture was stirred for an additional 15 min before the addition of 6-(5-chloro-1,3-benzoxazol-2-yl)pyridine-3-amine (8.5 mg, 0.035 mmol). The reaction mixture was allowed to warm to ambient temperature and stirred for an additional 11 h. The reaction was diluted with H$_2$O (5 mL) and extracted with EtOAc (3×20 mL). The combined organic extracts were washed with brine (25 mL), dried over MgSO$_4$, filtered and concentrated. The crude product was purified by flash silica gel chromatography (50% EtOAc/hexanes) to afford Example 401. LCMS calc.=393.82; found=394.2 (M+1)$^+$. $^1$H NMR (500 MHz, CDCl$_3$) δ 8.86 (brs, 1H), 8.63 (brs, 1H) 8.54 (dd, J=8.7 and 2.8 Hz, 1H), 8.41 (d, J=8.5 Hz, 1H), 7.83 (d, J=1.8 Hz, 1H), 7.61 (d, J=8.5 Hz, 1H), 7.40 (dd, J=8.7, 2.0 Hz, 1H), 7.26 (m, 1H), 7.04 (m, 1H), 6.91 (d, J=8.0 Hz, 1H), 4.73 (s, 2H), 2.43 (s, 3H).

Example 355

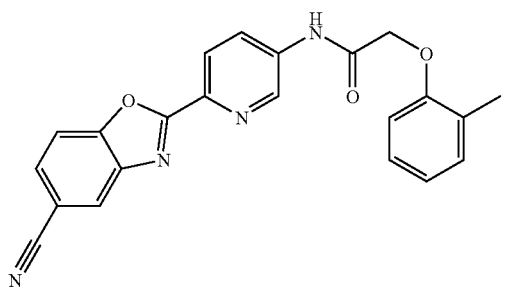

N-[6-(5-cyano-1,3-benzoxazol-2-yl)pyridine-3-yl-2-(2-methylphenoxy)acetamide

A solution of N-[6-(5-chloro-1,3-benzoxazol-2-yl)pyridine-3-yl]-2-(2-methylphenoxy)acetamide (10 mg, 0.025 mmol), tris(dibenzylideneacetone)dipalladium (4.6 mg, 0.005 mmol), 1,1'-bis(diphenylphosphino)ferrocene (5.5 mg, 0.01 mmol) and Zn(CN)$_2$ (3.0 mg, 0.025 mmol) in dimethylacetamide (1 mL) was degassed, flushed with N$_2$ and subjected to microwave irradiation (60 W, 200° C., 60 min). The reaction mixture was diluted with EtOAc (10 mL) and water (10 mL). The aqueous layer was extracted with EtOAc (2×10 mL) and the combined organic extracts were washed with brine (10 mL), dried (Na$_2$SO$_4$) and concentrated under reduced pressure to afford the crude product. This was purified by silica-gel flash chromatography (0-40% EtOAc in hexanes gradient) to afford N-[6-(5-cyano-1,3-benzoxazol-2-yl)pyridine-3-yl-2-(2-methylphenoxy)acetamide as a colorless solid. LCMS calc.=384.39; found=385.2 (M+1)$^+$. $^1$H NMR (500 MHz, CDCl$_3$) δ 10.73 (s, 1H), 9.03 (s, 1H), 8.39 (s, 2H), 8.08 (d, J=8.5 Hz, 1H), 7.96 (dd, J=8.4, 1.6 Hz, 1H), 7.21 (m, 2H), 6.93 (m, 2H), 4.84 (s, 2H), 2.28 (s, 3H).

Example 356

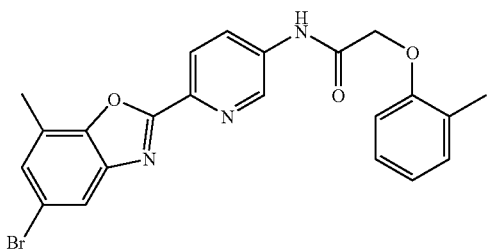

N-[6-(5-bromo-7-methyl-1,3-benzoxazol-2-yl)pyridine-3-yl]-2-(2-methylphenoxy)acetamide Step A. 5-[(tert-butoxycarbonyl)amino]pyridine-2-carboxylic acid A mixture of methyl 5-[(tert-butoxycarbonyl)amino]pyridine-2-carboxylate (0.200 g, 0.79 mmol), 1N NaOH (1.58 mL, 1.58 mmol), H$_2$O (4.1 mL) and EtOH (2.9 mL) was stirred at room temperature for 72 h. The mixture was concentrated to ca. 5 mL total volume, acidified to pH 4.0 with 2N HCl, and then chilled in a refrigerator for 1 h. The resulting precipitate was collected by filtration, washed with H$_2$O (5 mL) and dried overnight in a high vacuo oven to afford 5-[(tert-butoxycarbonyl)amino]pyridine-2-carboxylic acid. LCMS calc.=237.25; found=198.2 (M-40)$^+$.

Step B. 6-(5-bromo-7-methyl-1,3-benzoxazol-2-yl)pyridine-3-amine

A solution of oxalyl chloride (0.22 mL, 2 M in CH$_2$Cl$_2$, 0.45 mmol) was added to a suspension of 5-[(tert-butoxycarbonyl)amino]pyridine-2-carboxylic acid (59 mg, 0.25 mmol) in CH$_2$Cl$_2$ (3 mL) followed by a few drops of DMF at room temperature under N$_2$. The reaction was stirred at room temperature for 4 h after which time the suspension dissolved. The reaction mixture was concentrated under reduced pressure and azeotroped with toluene (10 mL). The crude acid chloride was dissolved in THF (2 mL) and added dropwise to a solution of 2-amino-4-bromophenol (50 mg, 0.25 mmol) in THF (2 mL) under N$_2$. The reaction was diluted with EtOAc (50 mL) and water (50 mL) and the aqueous layer was extracted with EtOAc (2×50 mL). The combined organic extracts were washed with brine (50 mL), dried (Na$_2$SO$_4$) and concentrated under reduced pressure to afford the crude amide product. A mixture of the crude amide and pyridinium p-toluenesulfonate (0.82 mg, 0.016 mmol) in o-xylene (15 mL) was heated at reflux under a Dean-Stark apparatus overnight under N$_2$. The reaction was diluted with EtOAc (15 mL) and washed successively with saturated NaHCO$_3$ (10 mL), water (10 mL) and brine (10 mL), dried (Na$_2$SO$_4$) and concentrated under reduced pressure to afford the crude product. This was purified by flash column chromatography (0-50% EtOAc in hexanes gradient) to afford 6-(5-bromo-7-methyl-1,3-benzoxazol-2-yl)pyridine-3-amine as a colorless solid. LCMS calc.=304.14; found=306.1 (M+2)$^+$. $^1$H NMR (500 MHz, DMSO) δ 8.32 (s, 1H), 8.10 (d, J=2.5 Hz, 1H), 8.02 (d, J=8.5 Hz, 1H), 7.76 (brs, 1H), 7.06 (dd, J=8.5, 2.8 Hz, 2H). 6.25 (brs, 2H), 2.51 (s, 3H).

Step C. N-[6-(5-bromo-7-methyl-1,3-benzoxazol-2-yl)pyridine-3-yl]-2-(2-methylphenoxy)acetamide 6-(5-Bromo-7-methyl-1,3-benzoxazol-2-yl)pyridine-3-amine (12 mg, 0.04 mmol) was treated with the acid chloride derived from (2-methylphenoxy)acetic acid (6.9 mg, 0.041 mmol) as described in Example 354, Step D to afford N-[6-(5-bromo-7-methyl-1,3-benzoxazol-2-yl)pyridine-3-yl]-2-(2-methylphenoxy)acetamide as a white solid. LCMS calc.=452.30; found=454.1 (M+2)$^+$. $^1$H NMR (500 MHz, CDCl$_3$) δ 8.87 (d, J=2.6 Hz, 1H), 8.66 (brs, 1H), 8.54 (dd, J=8.7, 2.5 Hz, 1H), 8.42 (d, J=8.7 Hz, 1H), 7.82 (br s, 1H), 7.39 (brs, 1H). 7.27 (m, 1H), 7.07 (t, J=7.5 Hz, 1H), 6.92 (d, J=8.7 Hz, 1H), 4.77 (s, 2H), 2.66 (s, 3H), 2.50 (s, 3H).

Example 357

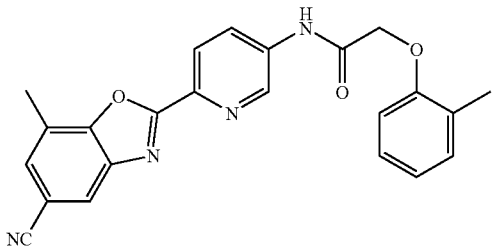

N-[6-(5-cyano-7-methyl-1,3-benzoxazol-2-yl)pyridine-3-yl]-2-(2-methylphenoxy)acetamide N-[6-(5-bromo-7-methyl-1,3-benzoxazol-2-yl)pyridine-3-yl]-2-(2-methylphenoxy)acetamide (7.0 mg, 0.0155 mmol) was treated with tris(dibenzylideneacetone)dipalladium (1.4 mg, 0.0155 mmol), 1,1'-bis(diphenylphosphino) ferrocene (1.72 mg, 0.0031 mmol) and Zn(CN)$_2$ (1.82 mg, 0.0155 mmol) as described in EXAMPLE 355 to afford N-[6-(5-cyano-7-methyl-1,3-benzoxazol-2-yl)pyridine-3-yl]-2-(2-methylphenoxy)acetamide as a white solid. LCMS calc.=398.41; found=399.2 (M+1)$^+$. $^1$H NMR (500 MHz, CDCl$_3$) δ 8.90 (d, J=2.3 Hz, 1H), 8.68 (brs, 1H), 8.58 (dd, J=8.7, 2.5 Hz, 1H), 8.44 (d, J=8.5 Hz, 1H), 8.02 (br s, 1H), 7.55 (brs, 1H), 7.29 (m, 1H), 7.08 (t, J=7.5 Hz, 1H), 6.93 (d, J=8.7 Hz, 1H), 4.75 (s, 2H), 2.74 (s, 3H), 2.45 (s, 3H).

Example 358

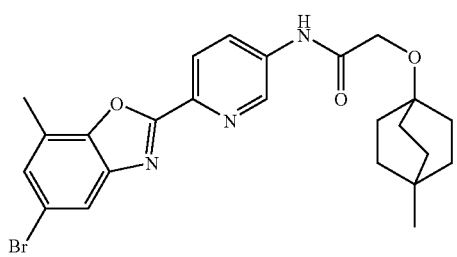

N-[6-(5-bromo-7-methyl-1,3-benzoxazol-2-yl)pyridine-3-yl]-2-[(4-methylbicyclo[2,2,2]oct-1-yl)oxy]acetamide 6-(5-Bromo-7-methyl-1,3-benzoxazol-2-yl)pyridine-3-amine (30 mg, 0.10 mmol) was treated with the acid chloride derived from [(4-methylbicyclo[2,2,2]oct-1-yl)oxy]acetic acid (25 mg, 0.125 mmol) as described in EXAMPLE 354, Step D to afford N-[6-(5-bromo-7-methyl-1,3-benzoxazol-2-yl)pyridine-3-yl]-2-[(4-methylbicyclo[2,2,2]oct-1-yl)oxy]acetamide as a clear glass. LCMS calc.=484.39; found=486.2 (M+2)$^+$. $^1$H NMR (500 MHz, CDCl$_3$) δ 8.82 (d, J=2.7 Hz, 1H), 8.68 (brs, 1H), 8.53 (dd, J=8.7, 2.7 Hz, 1H), 8.40 (d, J=8.7 Hz, 1H), 7.81 (br s, 1H), 7.38 (brs, 1H). 7.40 (brs, 1H), 4.09 (s, 2H), 2.65 (s, 3H), 2.50 (s, 3H), 1.80-1.76 (m, 6H), 1.65-1.59 (m, 9H), 0.87 (s, 3H).

Example 359

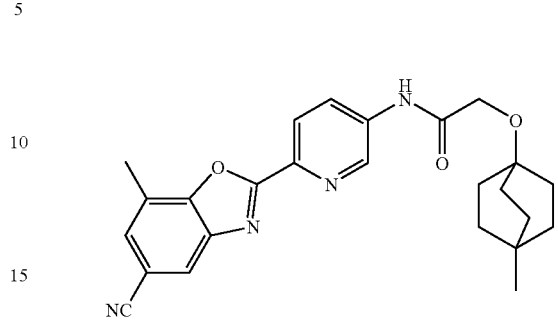

N-[6-(5-cyano-7-methyl-1,3-benzoxazol-2-yl)pyridine-3-yl]-2-[(4-methylbicyclo[2,2,2]oct-1-yl)oxy]acetamide N-[6-(5-bromo-7-methyl-1,3-benzoxazol-2-yl)pyridine-3-yl]-2-[(4-methylbicyclo[2,2,2]oct-1-yl)oxy]acetamide (21 mg, 0.043 mmol) was treated with tris(dibenzylideneacetone)dipalladium (4.0 mg, 0.0043 mmol), 1,1'-bis(diphenylphosphino) ferrocene (4.8 mg, 0.0086 mmol) and Zn(CN)$_2$ (5.05 mg, 0.043 mmol) as described in Example 355 to afford N-[6-(5-cyano-7-methyl-1,3-benzoxazol-2-yl)pyridine-3-yl]-2-[(4-methylbicyclo[2,2,2]oct-1-yl)oxy]acetamide as a white solid. LCMS calc.=430.49; found=431.3 (M+1)$^+$.

Example 360

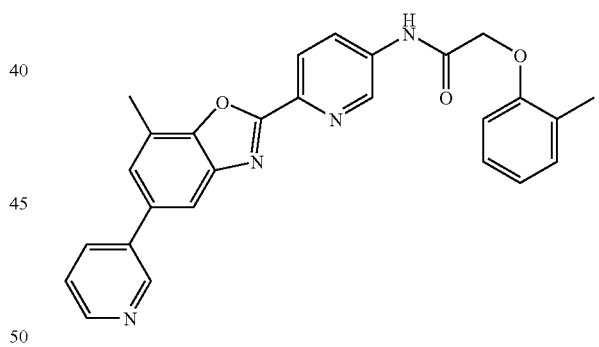

2-(2-methylphenoxy)-N-[6-(7-methyl-5-pyridin-3-yl-1,3-benzoxazol-2-yl)pyridine-3-yl]acetamide N-[6-(5-bromo-7-methyl-1,3-benzoxazol-2-yl)pyridine-3-yl]-2-(2-methylphenoxy)acetamide (20 mg, 0.044 mmol), was treated with 3-pyridyl boronic acid (16.2 mg, 0.132 mmol), tetrakistriphenylphoshine palladium (0) (6.10 mg, 0.0053 mmol) and sodium carbonate (38 mg) as described in Example 216 to afford 2-(2-methylphenoxy)-N-[6-(7-methyl-5-pyridin-3-yl-1,3-benzoxazol-2-yl)pyridine-3-yl]acetamide as a white solid. LCMS calc.=450.49; found=451.3 (M+2)$^+$. $^1$H NMR (500 MHz, CDCl$_3$) δ 8.95 (brs, 1H), 8.90 (d, J=2.5 Hz, 1H), 8.90 (brs, 2H), 8.57 (dd, J=8.5, 2.3 Hz, 1H), 8.47 (d, J=8.5 Hz, 1H), 7.98-7.60 (m, 1H), 7.87 (brs, 1H). 7.72-7.68 (m, 1H), 7.54-7.50 (m, 1H), 7.48-7.42 (m, 1H), 7.32-7.29 (m, 1H), 7.11 (t, J=7.1 Hz, 1H), 6.94 (d, J=8.0 Hz, 1H), 4.75 (s, 2H), 2.78 (s, 3H), 2.48 (s, 3H).

Example 361

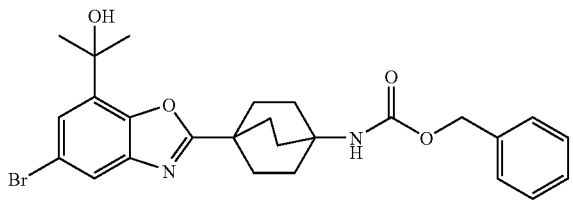

benzyl {4-[5-bromo-7-(1-hydroxy-1-methylethyl)-1,3-benzoxazol-2-yl]bicycle[2,2,2]oct-1-yl}carbamate Step A. methyl 4-{[(benzyloxy)carbonyl]amino}bicyclo[2,2,2]octane-1-carboxylate 4-(methoxycarbonyl)bicyclo[2,2,2]octane-1-carboxylic acid (0.500 g, 2.36 mmol) was treated with diphenylphosphoryl azide (0.510 mL, 2.36 mmol), triethylamine (0.33 mL, 2.36 mmol) and BnOH (1.47 mL, 14.2 mmol) as described in Example 354, Step B to give methyl 4-{[(benzyloxy) carbonyl]amino}bicyclo[2,2,2]octane-1-carboxylate. LCMS calc.=317.38 found=318.4 (M+1)$^+$.

Step B. 4-{[(benzyloxy)carbonyl]amino}bicyclo[2,2,2]octane-1-carboxylic acid

Methyl 4-{[(benzyloxy) carbonyl]amino}bicyclo[2,2,2]octane-1-carboxylate (1.56 g, 4.92 mmol) was dissolved in MeOH/H$_2$O (95:5) (11.4 mL: 0.6 mL) and treated with solid KOH (0.83 g, 14.76 mmol). The resultant solution was heated at 60° C. for 12 h. The mixture was concentrated under reduced pressure, diluted with H$_2$O (20 mL) and extracted with EtOAc (40 mL). The aqueous phase was separated and re-extracted with EtOAc (3×30 mL). The combined organic extracts were washed with brine (50 mL), dried (MgSO$_4$), filtered and concentrated under reduced pressure. The crude product was triturated with hexanes (3×30 mL) to afford 4-{[(benzyloxy)carbonyl]amino}bicyclo[2,2,2]octane-1-carboxylic acid as a white solid. LCMS calc.=303.35 found=304.3 (M+1)$^+$. $^1$H NMR (500 MHz, CDCl$_3$) δ 7.42-7.22 (m, 5H), 5.18 (s, 2H), 4.60 (brs, 1H), 2.02-1.82 (m, 14H).

Step C. benzyl[4-(7-acetyl-5-bromo-1,3-benzoxazol-2-yl)bicyclo[2,2,2]oct-1-yl]carbamate 4-{[(benzyloxy)carbonyl]amino}bicyclo[2,2,2]octane-1-carboxylic acid was treated with oxalyl chloride (1.03 mL, 2 M in CH$_2$Cl$_2$, 2.06 mmol), DMF (3 drops), 1-(3-amino-5-bromo-2-hydroxyphenyl)ethanone (261 mg, 1.1 mmol) and pyridinium p-toluenesulfonate (309 mg, 1.23 mmol) as described in Example 356, Step B to afford benzyl[4-(7-acetyl-5-bromo-1,3-benzoxazol-2-yl)bicyclo[2,2,2]oct-1-yl] carbamate (141 mg, 28%), as a colorless solid. LCMS calc.=497.38; found=499.2 (M+2)$^+$. $^1$H NMR (500 MHz, CDCl$_3$) δ 8.20-8.00 (m, 2H), 7.45-7.35 (m, 5H), 5.21 (s, 2H), 4.70 (brs, 1H), 2.25-2.20 (m, 7H), 2.15-2.00 (m, 7H).

Step D: benzyl{4-[5-bromo-7-(1-hydroxy-1-methylethyl)-1,3-benzoxazol-2-yl]bicycle[2,2,2]oct-1-yl}carbamate Benzyl[4-(7-acetyl-5-bromo-1,3-benzoxazol-2-yl)bicyclo[2,2,2]oct-1-yl]carbamate (70 mg, 0.140 mmol) was treated with methyl magnesium chloride (3.0 M solution in THF, 71 RL, 0.21 mmol) as described in Example 218 to afford benzyl{4-[5-bromo-7-(1-hydroxy-1-methylethyl)-1,3-benzoxazol-2-yl]bicyclo[2,2,2]oct-1-yl}carbamate as a colorless oil. LCMS calc.=513.42; found=515.2 (M+2)$^+$. $^1$H NMR (500 MHz, CDCl$_3$) δ 7.72 (d, J=1.8 Hz, 1H), 7.61 (d, J=2.1 Hz, 1H) 7.42-7.32 (m, 5H), 5.18 (brs, 2H), 4.66 (brs, 1H), 2.20-2.18 (m, 7H), 2.12-2.00 (m, 7H), 1.65 (s, 6H).

Example 362

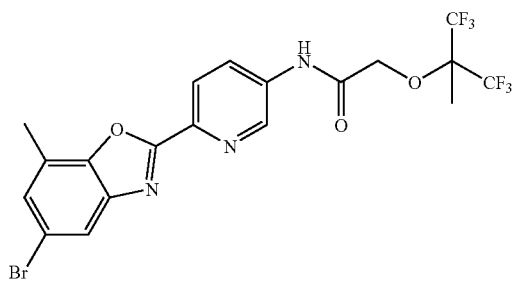

N-[6-(5-bromo-7-methyl-1,3-benzoxazol-2-yl)pyridine-3-yl]-2-[2,2,2-trifluoro-1-methyl-1-(trifluoromethyl)ethoxy]acetamide Step A. 2-bromo-N-[6-(5-bromo-7-methyl-1,3-benzoxazol-2-yl)pyridine-3-yl]acetamide 6-(5-Bromo-7-methyl-1,3-benzoxazol-2-yl)pyridine-3-amine (70 mg, 0.23 mmol) was treated with bromoacetic acid (35 mg, 0.25 mmol), oxalyl chloride (0.3 mL, 0.58 mmol) and triethylamine (35 μL, 0.25 mmol) in a procedure analogous to that described in EXAMPLE 7, Step A to afford 2-bromo-N-[6-(5-bromo-7-methyl-1,3-benzoxazol-2-yl)pyridine-3-yl]acetamide as a yellow oil. LCMS calc.=425.07, found=426.0.

Step B. N-[6-(5-bromo-7-methyl-1,3-benzoxazol-2-yl)pyridine-3-yl]-2-[2,2,2-trifluoro-1-methyl-1-(trifluoromethyl)ethoxy]acetamide 2-Bromo-N-[6-(5-bromo-7-methyl-1,3-benzoxazol-2-yl)pyridine-3-yl]acetamide (13 mg, 0.03 mmol) was treated with hexafluoro-2-methyl isopropanol (34 mg, 0.19 mmol) and potassium carbonate (26 mg, 0.19 mmol) as described in Example 1 to afford N-[6-(5-bromo-7-methyl-1,3-benzoxazol-2-yl)pyridine-3-yl]-2-[2,2,2-trifluoro-1-methyl-1-(trifluoromethyl)ethoxy]acetamide as a white solid. LCMS calc.=526.23; found=528.2 (M+2)$^+$. $^1$H NMR (500 MHz, CDCl$_3$) δ 8.85-8.80 (m, 1H), 8.42-8.38 (m, 2H), 7.80 (s, 1H), 7.40 (s, 1H), 4.60 (s, 1H), 4.42 (s, 1H), 2.60 (s, 3H), 1.25 (s, 3H).

Example 363

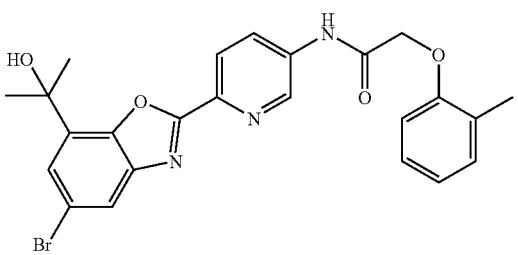

N-{6-[5-bromo-7-(1-hydroxy-1-methylethyl)-1,3-benzoxazol-2-yl]pyridine-3yl}-2 (2-methylphenoxy)acetamide Step A. 1-[2-(5-aminopyridin-2-yl)-5-bromo-1,3-benzoxazol-7-yl]ethanone 5-[tert-butoxycarbonyl)amino]pyridine-2-carboxylic acid (1.0 g, 4.20 mmol), was treated with oxalyl chloride (3.78 mL of a 2.0M solutionin CH$_2$Cl$_2$, 7.56 mmol, 1.8 eq.) 1-(3-amino-5-bromo-2-hydroxyphenyl)ethanone (1.16 g, 5.04 mmol) and p-toluenesulfonic acid (1.26 g, 5.04 mmol) as detailed in Example 356, Step B to afford 1-[2-(5-aminopyridin-2-yl)-5-bromo-1,3-benzoxazol-7-yl]ethanone. LCMS calc.=332.15; found=334.2 (M+2)$^+$.

Step B. N-[6-(7-acetyl-5-bromo-1,3-benzoxazol-2-yl]-2-(2-methylphenoxy)acetamide

[2-(5-aminopyridin-2-yl)-5-bromo-1,3-benzoxazol-7-yl]ethanone (42 mg, 0.13 mmol) was treated with the acid chloride derived from (2-methylphenoxy)acetic acid (26 mg, 0.16 mmol) as described in Example 354, Step D to afford N-[6-(7-acetyl-5-bromo-1,3-benzoxazol-2-yl]-2-(2-methylphenoxy)acetamide as a white solid. LCMS calc.=480.31; found=482.2 (M+2)$^+$. $^1$H NMR (500 MHz, CDCl$_3$) δ 8.87 (d, J=2.3 Hz, 1H), 8.69 (brs, 1H), 8.61 (dd, J=8.7, 2.5 Hz, 1H), 8.42 (t, J=8.7 Hz, 1H), 8.18 (d, J=1.8 Hz, 1H), 8.14 (d, J=2.1 Hz, 1H), 7.29-7.26 (m, 1H), 7.08 (t, J=7.3 Hz, 1H). 6.93 (d, J=8.0 Hz, 1H), 4.74 (s, 2H), 2.97 (s, 3H), 2.46 (s, 3H).

Step C: N-{6-[5-bromo-7-(1-hydroxy-1-methylethyl)-1,3-benzoxazol-2-yl]pyridine-3-yl}-2-(2-methylphenoxy)acetamide N—[6-(7-acetyl-5-bromo-1,3-benzoxazol-2-yl]-2-(2-methylphenxoy)acetamide (10 mg, 0.021 mmol) was treated with methyl magnesium bromide (3.0 M in THF, 42 RL, 0.125 mmol) as described in Example 218 to afford N-{6-[5-bromo-7-(1-hydroxy-1-methylethyl)-1,3-benzoxazol-2-yl]pyridine-3-yl}-2-(2-methylphenoxy)acetamide. LCMS calc.=496.35; found=498.2 (M+2)$^+$. $^1$H NMR (500 MHz, CDCl$_3$) δ 10.72 (brs, 1H), 9.00 (s, 1H), 8.40-8.30 (m, 2H), 7.95 (d, J=1.8 Hz, 1H), 7.67 (d, J=2.1, 1H), 7.22-7.15 (m, 2H), 6.86-6.82 (m, 2H), 4.83 (s, 2H), 2.28 (s, 3H), 1.68 (s, 6H).

Example 364

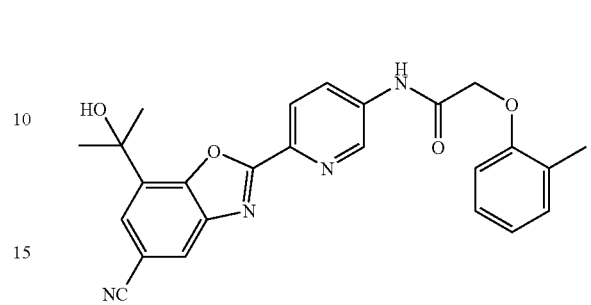

N-{6-[5-cyano-7-(1-hydroxy-1-methylethyl)-1,3-benzoxazol-2-yl]pyridine-3-yl}-2-(2-methylphenoxy)acetamide N-{6-[5-bromo-7-(1-hydroxy-1-methylethyl)-1,3-benzoxazol-2-yl]pyridine-3-yl}-2-(2-methylphenoxy)acetamide (3.0 mg, 0.006 mmol) was treated with tris(dibenzylideneacetone) dipalladium (0.7 mg, 0.0008 mmol), 1,1'-bis(diphenylphosphino) ferrocene (0.9 mg, 0.0016 mmol) and Zn(CN)$_2$ (0.94 mg, 0.008 mmol) as described in Example 355 to afford N-{6-[5-cyano-7-(1-hydroxy-1-methylethyl)-1,3-benzoxazol-2-yl]pyridine-3-yl}-2-(2-methylphenoxy)acetamide as a white solid. LCMS calc.=442.47; found=443.2 (M+1)$^+$. $^1$H NMR (500 MHz, CDCl$_3$) δ 8.87 (brs, 1H), 8.70 (s, 1H), 8.59 (dd, J=8.7, 2.5 Hz, 1H), 8.40 (d, J=8.7 Hz, 1H), 8.08 (d, J=1.4 Hz, 1H), 7.92 (d, J=1.6 Hz, 1H). 7.28-7.26 (m, 1H), 7.07 (t, J=7.6 Hz, 1H), 6.92 (d, J=8.2 Hz, 1H), 4.74 (s, 2H), 2.45 (s, 3H), 1.90 (s, 6H).

Intermediate 20

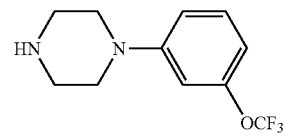

1-[3-(Trifluoromethoxy)phenyl]piperazine

To bis-(2-chloroethyl)amine hydrochloride (0.2 g, 1.12 mmol) was added 3-triflioromethoxy aniline (0.3 g, 1.68 mmol). The reaction was heated at 190° C. for 5 min in a microwave reactor. The residue was neutralized with saturated sodium bicarbonate solution. Aqueous layer was extracted with EtOAc (3×). The combined organic phase was dried over MgSO$_4$ and concentrated. The residue was purified on 2×1000 micron preparative thin layer chromatography plates eluting with 10% methanol in dichloromethane to give the title compound. $^1$H NMR (500 MHz, CDCl$_3$) δ 7.2 (m, 1H), 6.8 (d, 2H, J=10.3 Hz), 6.71 (s, 1H), 6.68 (d, 2H), 3.18 (m, 4H), 3.04 (m, 4H). LC/MS 247 (M+1); HPLC 2.04 min. The INTERMEDIATES in Table 11 were prepared according to the general procedure outlined in INTERMEDIATE 20.

TABLE 11

| INTERMEDIATE | R | MS (M + 1) |
|---|---|---|
| 21 | 3-OCF₃-phenyl | 247 |
| 22 | 2-F, 5-CF₃-phenyl | 249 |
| 23 | 3-biphenyl | 239 |
| 24 | 3,4,5-trifluorophenyl | 217 |
| 25 | 4-F, 3-CF₃-phenyl | 249 |
| 26 | 2-F, 4-CF₃, 5-F-phenyl | 267 |
| 27 | 2-F, 4-CF₃-phenyl | 249 |
| 28 | 4-OCF₃-phenyl | 247 |
| 29 | 4-CF₃-pyridin-2-yl | 232 |
| 30 | 6-CF₃-pyridin-2-yl | 232 |

Intermediate 31

To (S)-2-methyl piperazine (0.150 g, 1.5 mmol) was added 4-bromobenzotrifluoride (0.225 g, 1.0 mmol), dichloro-bis (tri-o-tolyphosphine) palladium (II) (0.236 g, 0.3 mmol), and sodium t-butoxide (0.144 g, 1.5 mmol), and toluene (2 mL) sequentially. After nitrogen was bubbled through the mixture for 15 minutes, the reaction was heated to 100° C. The reaction was stirred at 100° C. for 2 hr. The reaction was filtered through celite and concentrated under reduced pressure. The residue was then purified on a 1000 micron preparative thin layer chromatography plate eluting with 5% MeOH in dichloromethane to yield the title compound as an oil. ¹H NMR (500 MHz, CDCl₃) δ 7.5 (d, 2H, J=8.7 Hz), 6.95 (d, 2H, J=8.7 Hz), 3.71 (d, 2H, J=10 Hz), 3.20 (m, 1H), 3.04 (m, 2H), 2.85 (m, 1H), 2.48 (m, 1H), 1.24 (d, 3H, J=7.2 Hz). LC/MS 247 (M+1); HPLC 2.41 min.

Intermediate 32

The title compound was prepared essentially following the same procedures for the synthesis of INTERMEDIATE 31, except that (R)-2-methyl piperazine was used in place of (S)-2-methyl piperazine. 1H NMR (500 MHz, CDCl₃) δ 7.5 (d, 2H, J=8.7 Hz), 6.9 (d, 2H, J=8.7 Hz), 3.7 (d, 2H, J=00 Hz), 3.20 (m, 1H), 3.1 (m, 2H), 2.9 (m, 1H), 2.5 (m, 1H), 1.25 (d, 3H, J=7.2 Hz). LC/MS 247 (M+1); HPLC 2.38 min.

Intermediate 33

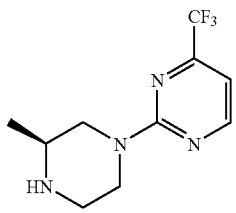

2-[(3S)-3-methylpiperazin-1-yl]-4-(trifluoromethyl) pyrimidine

To (S)-2-methyl piperazine (0.100 g, 1.0 mmol) in ethanol (2.5 mL) was added triethyl amine (211 μL, 1.5 mmol) followed by 2-chloro-4-(trifluoromethyl)-pyrimidine (0.121 μL, 1.0 mmol). The reaction was stirred in the microwave at 150° C. for 5 minutes under 50 W of power. After cooling to room temperature, white solid began to precipitate. The solid was filtered, and liquid was concentrated under reduced pressure. The residue was then purified on a 1000 micron preparative thin layer chromatography plate eluting with 10% MeOH in dichloromethane to yield the title compound as an off-white solid. 1H NMR (500 MHz, CDCl$_3$) δ 8.55 (d, 1H, J=4.8 Hz), 6.85 (d, 1H, J=4.8 Hz), 4.75-4.81 (m, 2H), 3.31-3.44 (m, 2H), 2.85-3.17 (m, 3H), 1.42 (d, 3H, J=6.1 Hz). LC/MS 247 (M+1); HPLC 1.31 min.

Intermediate 34

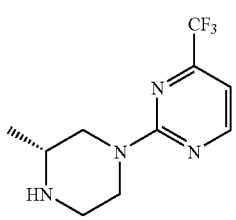

2-[(3R)-3-methylpiperazin-1-yl]-4-(trifluoromethyl) pyrimidine

The title compound was prepared essentially following the same procedures for the synthesis of INTERMEDIATE 33, except that (R)-2-methyl piperazine was used in place of (S)-2-methyl piperazine. 1H NMR (500 MHz, CDCl$_3$) δ 8.50 (d, 1H, J=4.8 Hz), 6.76 (d, 1H, J=4.8 Hz), 4.63-4.74 (m, 2H), 3.12-3.15 (m, 1H), 2.99-3.05 (m, 1H), 2.84-2.92 (m, 2H), 2.64-2.68 (m, 1H), 1.19 (d, 3H, J=6.4 Hz). LC/MS 247 (M+1); HPLC 2.01 min.

Example 365

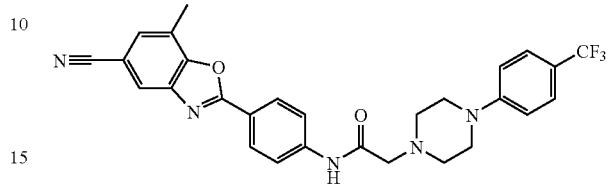

N-[4-(5-Cyano-7-methyl-1,3-benzoxazole-2-yl)phenyl]-2-[4-[4-(trifluoromethyl)phenyl]piperazin-1-yl] acetamide Step A: 2-Bromo-N-[4-(5-Cyano-7-methyl-1,3-benzoxazole-2-yl)phenyl]acetamide To a solution of 2-(4-aminophenyl)-7-methyl-1,3-benzoxazole-5-carbonitrile (INTERMEDIATE 6, 0.500 g, 2.00 mmol) in dichloromethane (150 mL) at 0° C. was added diisopropylethylamine (0.418 mL, 2.40 mmol) followed by bromoacetyl bromide (0.209 mL, 2.40 mmol) at 0° C. The reaction was gradually warmed 0° C. to room temperature over a 6 h period. After evaporation of solvent, the residue was partitioned between ethyl acetate and saturated aqueous sodium bicarbonate solution. Aqueous layer was extracted three times with ethyl acetate. The combined organic phase was washed with brine, dried over magnesium sulfate and concentrated to give 693 mg of the title compound as a solid. $^1$H NMR (500 MHz, CDCl$_3$) δ 8.40 (s, 1H), 8.30 (d, 2H, J=2.3 Hz), 7.92 (s, 1H), 7.81 (d, 2H, J=2.0 Hz), 7.47 (s, 1H), 4.10 (s, 2H), 2.65 (s, 3H); LC/MS 370 (M+1); HPLC A 3.39 min.

Step B: N-[4-(5-Cyano-7-methyl-1,3-benzoxazole-2-yl)phenyl]-2-{4-[4-(trifluoromethyl)phenyl]-piperazin-1-yl}acetamide To a solution of 2-bromo-N-[4-(5-cyano-7-methyl-1,3-benzoxazole-2-yl)phenyl]acetamide (0.025 g, 0.068 mmol, from Step A) in dimethylformamide (0.5 mL) was added 1-(4-trifluoromethylphenyl)piperazine (0.016 g, 0.068 mmol) followed by triethylamine (0.019 ml, 0.136 mmol) at 60° C. The solution was stirred at 60° C. for 1 hr. After concentration under reduced pressure the residue was purified on a 1000 micron preparative thin layer chromatography plate eluting with 5% methanol in dichloromethane to give the title compound as a solid. $^1$H NMR (500 MHz, DMSO) δ 10.19 (s, 1H), 8.18 (d, 2H, J=7.1 Hz), 8.16 (s, 1H), 7.92 (d, 2H, J=9 Hz), 7.71 (s, 1H), 7.5 (d, 2H, J=9 Hz), 7.09 (d, 2H, J=8.7 Hz), 3.37 (m, 4H), 3.28 (s, 2H), 2.69 (m, 4H), 2.57 (s, 3H). LC/MS: 530 (M+1); HPLC A 3.38 min.

The EXAMPLES in Table 12 were prepared according to the general procedure outlined in EXAMPLE 365

TABLE 12

[Structure: 5-cyano-7-methylbenzoxazole connected to phenyl-NH-C(O)-CH2-piperazine-N-R6]

| EXAMPLE | R6 | MS (M + 1) |
|---------|----|-----------|
| 366 | —C(O)O-tBu | 476 |
| 367 | 2-isopropylphenyl | 494 |
| 368 | 2,6-dichlorophenyl | 520 |
| 369 | 2,6-dimethylphenyl | 480 |
| 370 | 2-chlorophenyl | 486 |
| 371 | 2,4-dichlorophenyl | 520 |
| 372 | phenyl | 452 |
| 373 | 3-(trifluoromethyl)phenyl | 520 |

TABLE 12-continued

| EXAMPLE | R6 | MS (M + 1) |
|---------|----|-----------|
| 374 | —S(O)2—CH2—phenyl | 530 |
| 375 | 2-fluorophenyl | 470 |
| 376 | 4-fluorophenyl | 470 |
| 377 | 2-(trifluoromethyl)phenyl | 520 |
| 378 | 3,5-bis(trifluoromethyl)phenyl | 588 |
| 379 | 4-biphenyl | 528 |
| 380 | cyclohexyl | 458 |
| 381 | 2-methoxyphenyl | 482 |

TABLE 12-continued

[Structure: 7-methyl-5-cyano-benzoxazole linked to phenyl-NH-C(O)-CH2-piperazine-N-R6]

| EXAMPLE | R6 | MS (M + 1) |
|---------|-----|------------|
| 382 | 4-CF3-phenyl | 520 |
| 383 | 2-NO2-5-CF3-phenyl | 565 |
| 384 | 3-Cl-phenyl | 486 |
| 385 | 3,4-diCl-phenyl | 520 |
| 386 | 3-OCF3-phenyl | 536 |
| 387 | 2,4-diF-phenyl | 488 |
| 388 | 2-F-5-CF3-phenyl | 538 |
| 389 | 3,4-diF-phenyl | 488 |
| 390 | 4-NO2-3-CF3-phenyl | 565 |
| 391 | 5-F-2-SO2Me-phenyl | 548 |
| 392 | 3,4,5-triF-phenyl | 506 |
| 393 | 4-Cl-3-CF3-phenyl | 554 |
| 394 | 4-F-3-CF3-phenyl | 538 |
| 395 | CH(phenyl)(4-Cl-phenyl) | 576 |
| 396 | CH2-phenyl | 466 |
| 397 | 2,5-diF-4-CF3-phenyl | 556 |

TABLE 12-continued
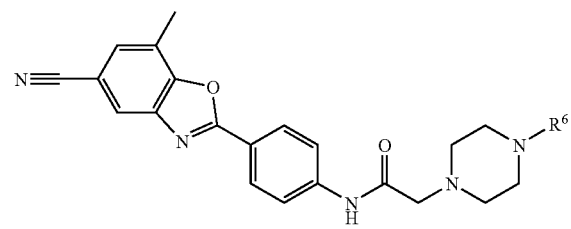
| EXAMPLE | R⁶ | MS (M + 1) |
|---|---|---|
| 398 | 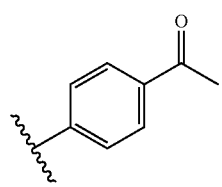 | 494 |
| 399 | 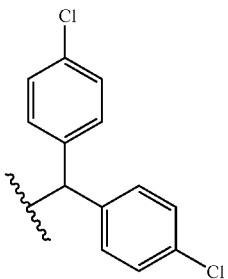 | 610 |
| 400 | 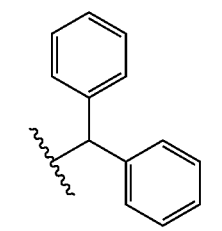 | 542 |
| 401 | 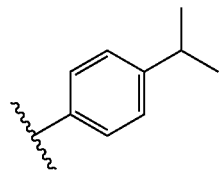 | 494 |
| 402 | 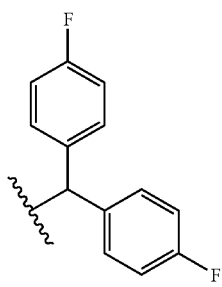 | 578 |
| 403 | 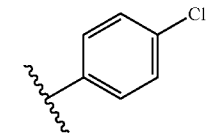 | 486 |
| 404 | 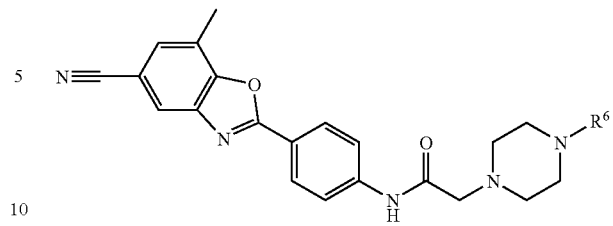 | 538 |
| 405 | 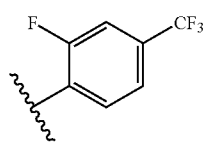 | 482 |
| 406 | 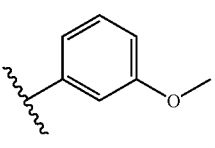 | 482 |
| 407 | 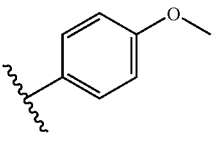 | 536 |
| 408 | 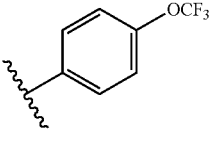 | 570 |
| 409 | 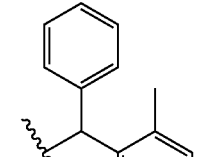 | 556 |
| 410 | 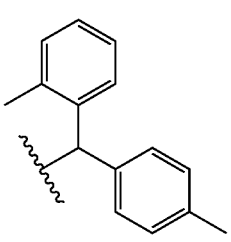 | 570 |

TABLE 12-continued
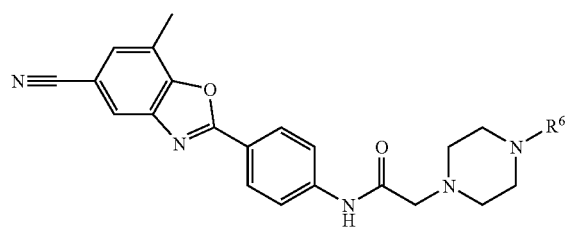
| EXAMPLE | R⁶ | MS (M + 1) |
|---|---|---|
| 411 | 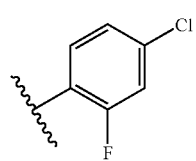 | 504 |
| 412 | 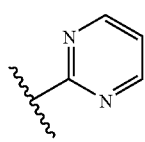 | 454 |
| 413 | 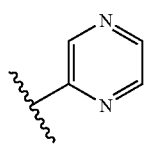 | 454 |
| 414 | 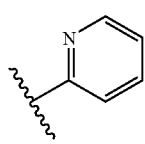 | 453 |
| 415 | 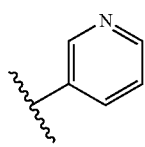 | 453 |
| 416 | 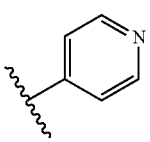 | 453 |
| 417 | 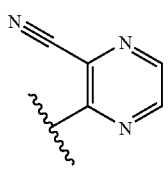 | 479 |
| 418 | 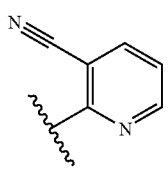 | 478 |
TABLE 12-continued
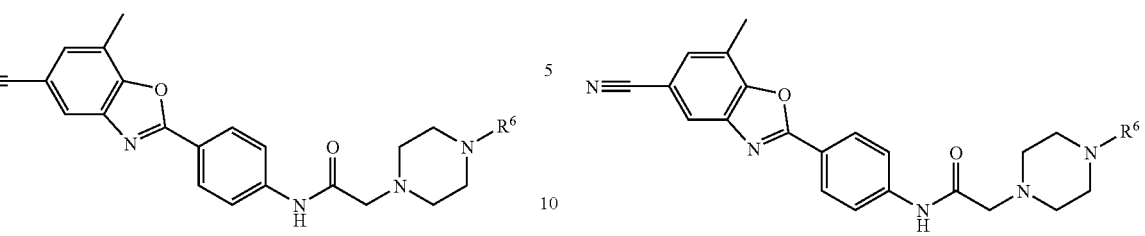
| EXAMPLE | R⁶ | MS (M + 1) |
|---|---|---|
| 419 | 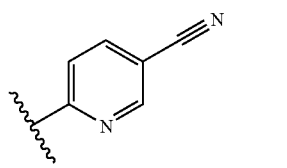 | 478 |
| 420 | 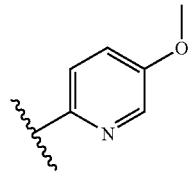 | 483 |
| 421 | 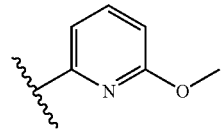 | 483 |
| 422 | 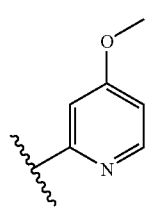 | 483 |
| 423 | 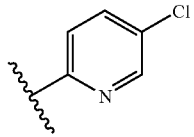 | 487 |
| 424 | 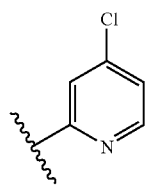 | 487 |
| 425 | 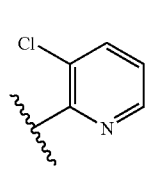 | 487 |

TABLE 12-continued
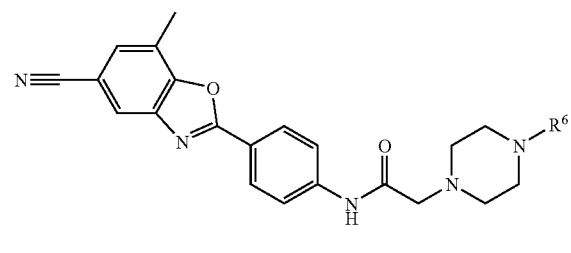
| EXAMPLE | R⁶ | MS (M + 1) |
|---|---|---|
| 426 | 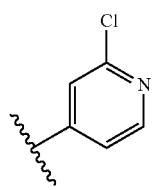 | 487 |
| 427 | 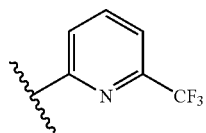 | 521 |
| 428 | 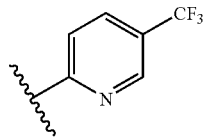 | 521 |
| 429 | 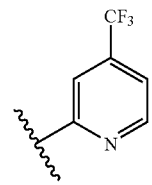 | 521 |
| 430 |  | 521 |
| 431 | 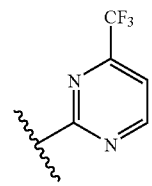 | 522 |
| 432 | 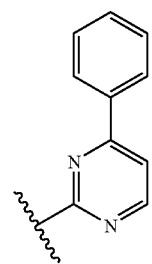 | 530 |
TABLE 12-continued
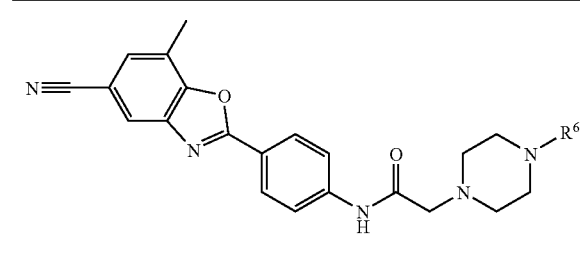
| EXAMPLE | R⁶ | MS (M + 1) |
|---|---|---|
| 433 | | 482 |
| 434 | | 467 |
| 435 | | 467 |
| 436 | | 502 |
| 437 | | 503 |
| 438 | | 503 |
| 439 | | 503 |

TABLE 12-continued
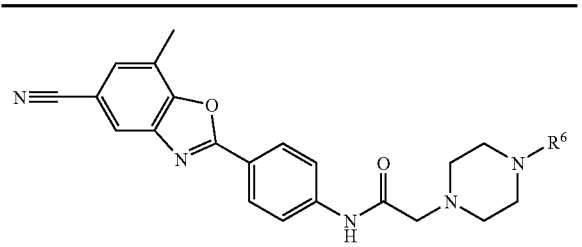
| EXAMPLE | R⁶ | MS (M + 1) |
|---|---|---|
| 440 | 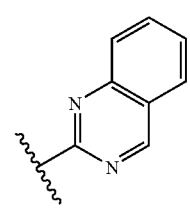 | 504 |
| 441 | 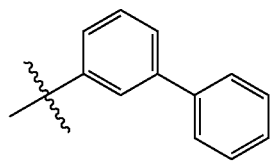 | 528 |
The EXAMPLES in Table 13 were prepared according to the general procedure outlined in Example 365, Step B using the appropriately substituted cyclic amine.
TABLE 13
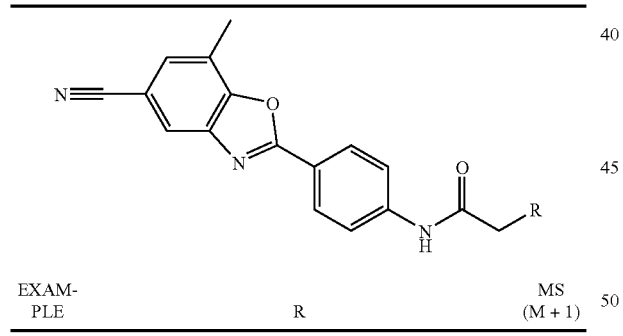
| EXAMPLE | R | MS (M + 1) |
|---|---|---|
| 442 | 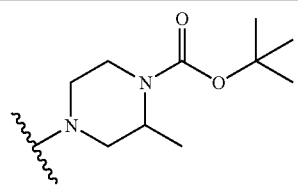 | 491 |
| 443 | 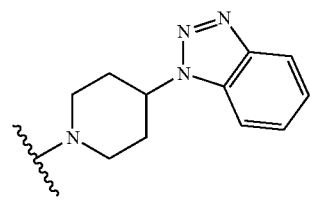 | 492 |
TABLE 13-continued
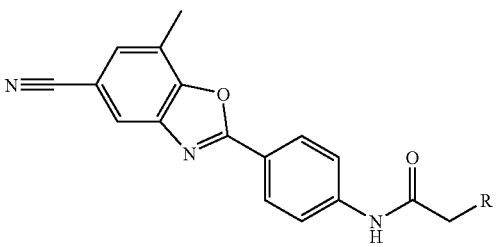
| EXAMPLE | R | MS (M + 1) |
|---|---|---|
| 444 | 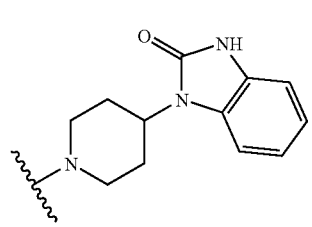 | 507 |
| 445 | 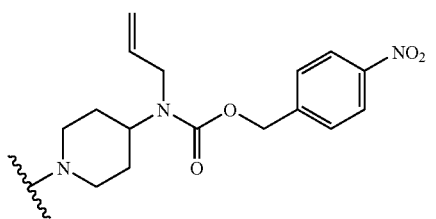 | 609 |
| 446 | 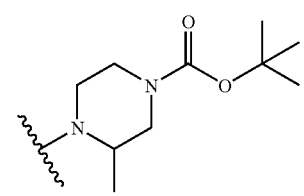 | 490 |
| 447 | 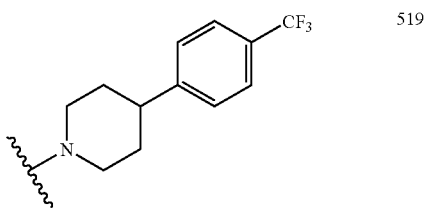 | 519 |
| 448 | 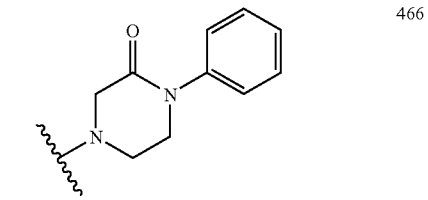 | 466 |
| 449 | 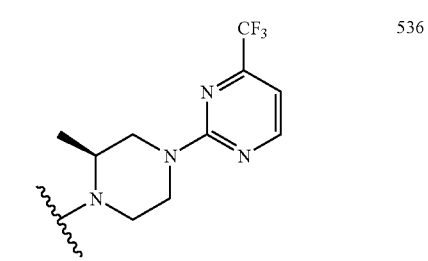 | 536 |

TABLE 13-continued

| EXAMPLE | R | MS (M + 1) |
|---|---|---|
| 450 | (S)-3-methyl-4-(4-(trifluoromethyl)pyrimidin-2-yl)piperazin-1-yl | 536 |
| 451 | 4,4-difluoropiperidin-1-yl | 411 |
| 452 | 3,3-difluoropyrrolidin-1-yl | 397 |
| 453 | 2-(trifluoromethyl)-5,6-dihydro-[1,2,4]triazolo[1,5-a]pyrazin-7(8H)-yl | 482 |
| 454 | 2-isopropyl-5,6-dihydro-[1,2,4]triazolo[1,5-a]pyrazin-7(8H)-yl | 456 |
| 455 | 2-butyl-5,6-dihydro-[1,2,4]triazolo[1,5-a]pyrazin-7(8H)-yl | 470 |
| 456 | 2-phenyl-5,6-dihydro-[1,2,4]triazolo[1,5-a]pyrazin-7(8H)-yl | 490 |
| 457 | 2-benzyl-5,6-dihydro-[1,2,4]triazolo[1,5-a]pyrazin-7(8H)-yl | 504 |
| 458 | 2-(trifluoromethyl)-6,7-dihydroimidazo[1,2-a]pyrazin-7(8H)-yl | 481 |

TABLE 13-continued

| EXAMPLE | R | MS (M+1) |
|---|---|---|
| 459 | (1-methyl-3-(trifluoromethyl)-5,6-dihydro-[1,2,4]triazolo[4,3-a]pyrazin-7(8H)-yl) | 496 |
| 460 | (8-(2-(dimethylamino)-2-oxoethyl)-3-(trifluoromethyl)-5,6-dihydro-[1,2,4]triazolo[4,3-a]pyrazin-7(8H)-yl) | 567 |
| 461 | ((S)-3-methyl-4-(4-(trifluoromethyl)pyrimidin-2-yl)piperazin-1-yl) | 536 |
| 462 | ((R)-3-methyl-4-(4-(trifluoromethyl)pyrimidin-2-yl)piperazin-1-yl) | 536 |
| 463 | (4-(2-ethyl-4,5,6,7-tetrahydropyrazolo[1,5-a]pyridin-3-yl)piperidin-1-yl) | 522 |
| 464 | (1'-(methylsulfonyl)spiro[indoline-3,4'-piperidin]) | 555 |
| 465 | (spiro[benzo[b]thiophene-1,4'-piperidin]) | 494 |
| 466 | (4-cyclohexyl-4-(ethoxycarbonyl)piperidin-1-yl) · TFA | 528 |
| 467 | (4-(tert-butylcarbamoyl)-4-cyclohexylpiperidin-1-yl) · TFA | 555 |
| 468 | (1'-acetylspiro[indoline-3,4'-piperidin]) | 519 |

TABLE 13-continued

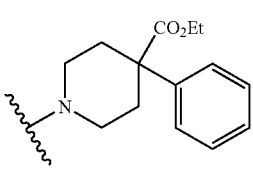

| EXAMPLE | R | MS (M + 1) |
|---|---|---|
| 469 | 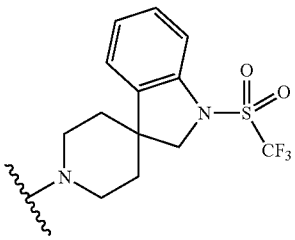 · TFA | 522 |
| 470 | 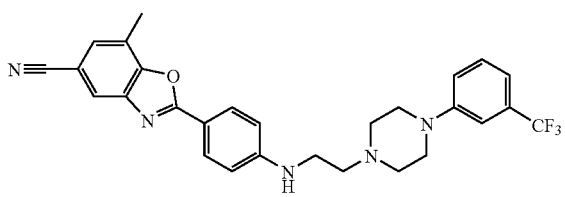 | 609 |

Example 471

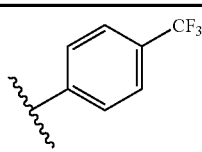

N-[4-(5-Cyano-7-methyl-1,3-benzoxazole-2-yl)phenyl]-2-{4-[3-(trifluoromethyl)phenyl]piperazin-1-yl}

Step A: N-methoxy-N-methyl-2-{4-3-(trifluoromethyl)phenyl]piperazin-1-yl}acetamide To 3-trifluoromethylphenyl piperazine (0.4 ml, 2.17 mmol) was added 2-chloro-N-methoxy-n-methyl acetamide (0.36 g, 2.6 mmol), potassium carbonate (0.36 g, 2.6 mmol), and sodium iodide (0.153 g, 1.02 mmol), and acetonitrile (25 ml) sequentially. The reaction was stirred at 45° C. for 3 hr and then concentrated under reduced pressure. The residue was dissolved in dichloromethane and washed with water. The combined organic phase was dried over magnesium sulfate and concentrated. The residue was purified by flash column chromatography, eluting with 75% ethyl acetate and hexanes to give the title compound. $^1$H NMR (500 MHz, CDCl$_3$) δ7.36 (m, 1H), 7.14 (s, 1H), 7.08 (d, 2H, J=13.7 Hz), 3.76 (s, 3H), 3.43 (s, 2H), 3.32 (m, 4H), 3.23 (s, 3H), 2.78 (m, 4H) LC/MS 332 (M+1); HPLC 2.80 min.

Step B: {4-[3-(Trifluoromethyl)phenyl]piperazin-1-yl}-acetaldehyde

N-methoxy-N-methyl-2-{4-3-(trifluoromethyl)phenyl]piperazin-1-yl}acetamide (from Step A, 0.34 ml, 1.02 mmol) was dissolved in toluene (16 mL) and tetrahydrofuran (14 mL). The solution was cooled to −45° C. under a nitrogen atmosphere. To this solution was added RedAl (1.02 ml, 3.06 mmol) at −45° C. After stirring at −45° C. for 2 hours, the reaction was quenched with saturated Rochelle's Salt solution and then diluted in with dichloromethane, 2N—HCl, and saturated aqueous sodium bicarbonate solution. The mixture was extracted with ethyl acetate. The combined organic layers were washed with brine, dried over magnesium sulfate and concentrated under reduced pressure. The reside was then purified by flash column chromatography eluting with 75% ethyl acetate in hexanes to yield the title compound as a clear oil. $^1$H NMR (500 MHz, CDCl$_3$) δ 9.77 (s, 1H), 7.33 (m, 1H), 7.12 (s, 1H), 7.0 (m, 2H), 3.44 (s, 2H), 3.28 (m, 4H), 2.74 (m, 4H). LC/MS 273 (M+1); HPLC 1.8 min.

Step C: N-[4-(5-Cyano-7-methyl-1,3-benzoxazole-2-yl)phenyl]-2-{4-[3-(trifluoromethyl)phenyl]piperazin-1-yl}

To a solution of {4-[3-(trifluoromethyl)phenyl]piperazin-1-yl}-acetaldehyde (0.05 g, 0.18) in dichloroethane (2 ml) was added 2-(4-aminophenyl)-7-methyl-1,3-benzoxazole-5-carbonitrile (Intermediate 1, 0.045 g, 0.18 mmol) followed by sodium triacetoxyborohydride (0.078 g, 0.36 mmol) and 4-Å molecular sieves (0.025 g). After the addition of a catalytic amount of acetic acid (1 drop) the reaction was stirred at room temperature overnight. The reaction was concentrated under reduced pressure. Methanol was added to the residue and allowed to stir for 15 min. After concentration under reduced pressure the residue was partitioned between dichloromethane and saturated aqueous sodium bicarbonate solution. The organic layer was washed with brine, dried over magnesium sulfate, and concentrated under reduced pressure. The residue was purified on 2×1000 micron preparative thin layer chromatography plates, eluting with 50% Ethyl Acetate, hexanes to yield the title compound. $^1$H NMR (500 MHz, DMSO) δ 8.01 (s, 1H), 7.95 (d, 2H, J=8.7 Hz), 7.62 (s, 1H), 7.41 (m, 1H), 7.23 (d, 1H, J=10.3 Hz), 7.16 (s, 1H), 7.06 (d, 1H, J=7.6 Hz) 6.79 (d, 2H, J=8.9 Hz), 3.29 (s, 2H), 3.25 (m, 4H), 2.60 (m, 6H), 2.55 (2, 3H). LC/MS 506 (M+1); HPLC 2.97 min.

Examples listed in Table 14 were prepared essentially following the procedures outlined for Example 108.

TABLE 14

| Example | R$^6$ | MS (M + 1) |
|---|---|---|
| 472 | CF$_3$-phenyl | 505 |

TABLE 14-continued

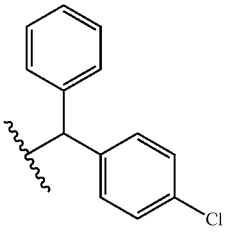

| Example | R⁶ | MS (M + 1) |
|---------|----|-----------| 
| 473 | | 562 |

Example 474

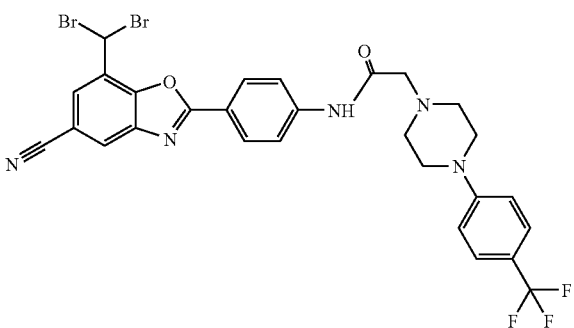

N-{4-[5-cyano-7-(dibromomethyl)-1,3-benzoxazol-2-yl]phenyl}-2-{4-[4-(trifluoromethyl)phenyl]piperazin-1-yl}acetamide Step A: 2-bromo-N-{4-[5-cyano-7-(dibromomethyl)-1,3-benzoxazol-2-yl]phenyl}acetamide A mixture of 124 mg of tert-butyl {4-[5-cyano-7-(dibromomethyl)-1,3-benzoxazol-2-yl]phenyl}carbamate (EXAMPLE 205, Step B) and 1 ml TFA in 2 ml dichloromethane was stirred for ca 1 hour and concentrated azeotroping with toluene. The residue was dissolved in 5 ml THF and 43 μl of bromoacetyl bromide and 170 μl of diisopropylethyl amine were added. After stirring at room temperature for ca. 3 hours, another 43 μl of bromoacetyl bromide were added and the reaction temperature was increased to 40° C. After ca. 2 hours the reaction mixture was concentrated and the product purified by flash column chromatography on a Biotage Horizon, 25M Si column, eluting with 1 column volume of dichloromethane, followed by a linear gradient of EtOAc in dichloromethane from 0% to 100% over 10 column volumes to provide the title compound. Mass spectrum (ESI) 526.1 (M+1); 528.2 (M+3); 530 (M+5); 532.0 (M+7). ¹H NMR (400 MHz, CDCl₃): δ 4.08 (s, 2H); 7.04 (s, 1H); 7.80 (d, J=8.8 Hz, 2H); 7.94 (d, J=1.4 Hz, 1H); 8.02 (d, J=1.4 Hz, 1H); 8.31 (m, 3H).

Step B: N-{4-[5-cyano-7-(dibromomethyl)-1,3-benzoxazol-2-yl]phenyl}-2-{4-[4-(trifluoromethyl)phenyl]piperazin 1-yl}acetamide A mixture of 97 mg of 2-bromo-N-{4-[5-cyano-7-(dibromomethyl)-1,3-benzoxazol-2-yl]phenyl}acetamide (Step A), 51 mg of 1-(4-trifluoromethylphenyl)piperazine, and 63 μl of diisopropylethyl amine in 5 ml of THF was stirred under nitrogen at room temperature for ca. 2.5 hours, concentrated, and purified by flash column chromatography on a Biotage Horizon, 25M Si column, eluting with 1 column volume of dichloromethane, followed by a linear gradient of EtOAc in dichloromethane from 0% to 100% over 10 column volumes to provide the title compound. Mass spectrum (ESI) 676.3 (M+1); 678.3 (M+3); 680.3 (M+5). ¹H NMR (500 MHz, CDCl₃: δ 2.84 (t, J=4.9 Hz, 4H); 3.28 (s, 2H); 3.40 (t, J=4.9 Hz, 4H); 6.97 (d, J=8.7 Hz, 2H); 7.04 (s, 1H); 7.52 (d, J=8.7 Hz, 2H); 7.82 (d, J=8.7 Hz, 2H); 7.93 (d, J=0.9 Hz, 1H); 8.00 (s, 1H); 8.28 (d, J=8.7 Hz, 2H); 9.37 (s, 1H)

Example 475

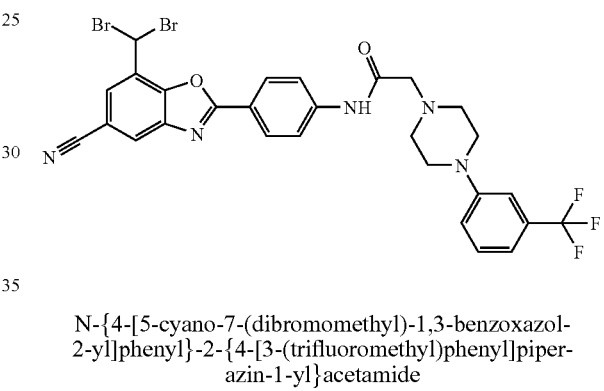

N-{4-[5-cyano-7-(dibromomethyl)-1,3-benzoxazol-2-yl]phenyl}-2-{4-[3-(trifluoromethyl)phenyl]piperazin-1-yl}acetamide The title compound was prepared from 2-bromo-N-{4-[5-cyano-7-(dibromomethyl)-1,3-berzoxazol-2-yl]phenyl}acetamide (EXAMPLE 474, Step A) and 1-(3-trifluoromethylphenyl)piperazine by a procedure analogous to that described in EXAMPLE 474, Step B. Mass spectrum (ESI) 676.2 (M+1); 678.2 (M+3); 680.3 (M+5). ¹H NMR (500 MHz, CDCl₃): δ 2.85 (m, 4H); 3.29 (s, 2H); 3.36 (m, 4H); 7.04 (s, 1H); 7.10-7.15 (br m, 3H); 7.39 (m, 1H); 7.82 (d, J=8.7 Hz, 2H); 7.94 (s, 1H); 8.00 (d, J=1.4 Hz, 1H); 8.28 (d, J=8.7 Hz, 2H); 9.34 (s, 1H).

Example 476

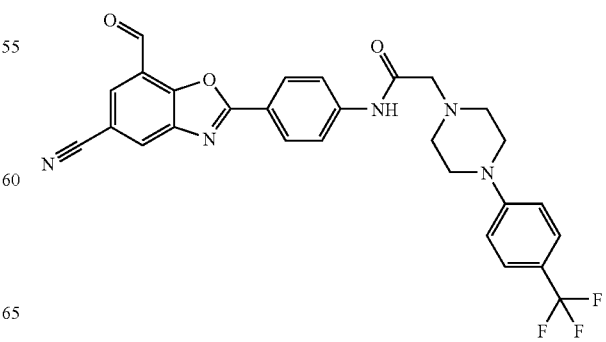

187

N-[4-(5-cyano-7-formyl-1,3-benzoxazol-2-yl)phenyl]-2-{4-[4-(trifluoromethyl)phenyl]piperazin-1-yl}acetamide A solution of 21 mg of N-{4-[5-cyano-7-(dibromomethyl)-1,3-benzoxazol-2-yl]phenyl}-2-{4-[4-(trifluoromethyl)phenyl]piperazin-1-yl}acetamide (EXAMPLE 474) in 1 ml of pyridine was heated at 100° C. overnight under nitrogen. Water was added and, after stirring for a few minutes, the mixture was extracted 3 times with ethyl acetate. The combined organics were washed with brine, dried over sodium sulfate, concentrated, and purified by flash column chromatography on a Biotage Horizon, 25M Si column, eluting with 1 column volume of dichloromethane, followed by a linear gradient of EtOAc in dichloromethane from 0% to 100% over 10 column volumes to provide the title compound. Mass spectrum (ESI) 534.4 (M+1). $^1$H NMR (500 MHz, CD$_3$OD): selected peaks δ 6.03 (s, 1H); 7.06 (d, J=8.9 Hz, 2H); 7.48 (d, J=8.5 Hz, 2H); 7.84 (s, 1H); 7.89 (d, J=8.7 Hz, 2H); 8.08 (s, 1H); 8.26 (d, J=8.6 Hz, 2H).

Example 477

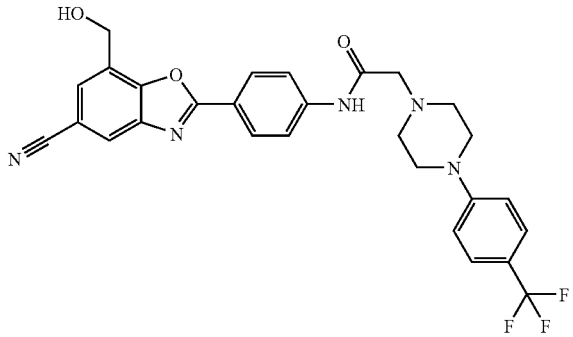

N-{4-[5-cyano-7-(hydroxymethyl)-1,3-benzoxazol-2-yl]phenyl}-2-{4-[4-(trifluoromethyl)phenyl]piperazin-1-yl}acetamide The title compound was prepared from N-[4-(5-cyano-7-formyl-1,3-benzoxazol-2-yl)phenyl]-2-{4-[4-(trifluoromethyl)phenyl]piperazin-1-yl}acetamide (EXAMPLE 476) and NaBH$_4$ by a procedure analogous to that described in EXAMPLE 207. Mass spectrum (ESI) 536.4 (M+1). $^1$H NMR (500 MHz, DMSO-d$_6$): δ 2.68 (m, 4H); 3.27 (s, 2H); 3.36 (m, 4H); 4.87 (d, J=6.0 Hz, 2H); 5.65 (t, J=5.8 Hz, 1H); 7.07 (d, J=8.9 Hz, 2H); 7.50 (d, J=8.7 Hz, 2H); 7.78 (s, 1H); 7.93 (d, J=8.7 Hz, 2H); 8.20 (d, J=8.7 Hz, 2H); 8.25 (s, 1H); 10.19 (s, 1H).

Example 478

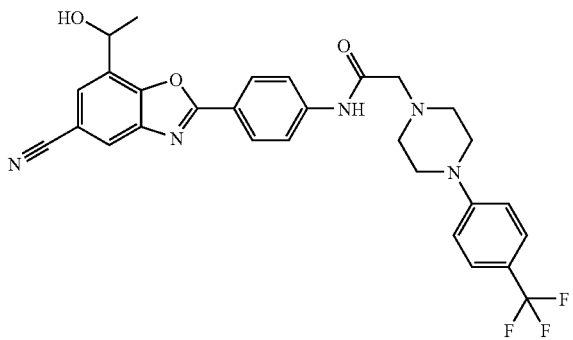

188

N-{4-[5-cyano-7-(1-hydroxyethyl)-1,3-benzoxazol-2-yl]phenyl}-2-{4-[4-(trifluoromethyl)phenyl]piperazin-1-yl}acetamide The title compound was prepared from N-[4-(5-cyano-7-formyl-1,3-benzoxazol-2-yl)phenyl]-2-{4-[4-(trifluoromethyl)phenyl]piperazin-1-yl}acetamide (EXAMPLE 476) and methylmagnesium bromide by a procedure analogous to that described in EXAMPLE 208. Mass spectrum (ESI) 550.5 (M+1). $^1$H NMR (500 MHz, CDCl$_3$): δ 1.71 (d, J=6.7 Hz, 3H); 2.83 (m, 4H); 3.27 (s, 2H); 3.39 (m, 4H); 5.42 (q, J=6.6 Hz, 1H); 6.96 (d, J=9.0 Hz, 2H); 7.51 (d, J=9.0 Hz, 2H); 7.75 (m, 3H); 7.93 (s, 1H); 8.20 (d, J=8.7 Hz, 2H); 9.34 (s, 1H).

Example 479

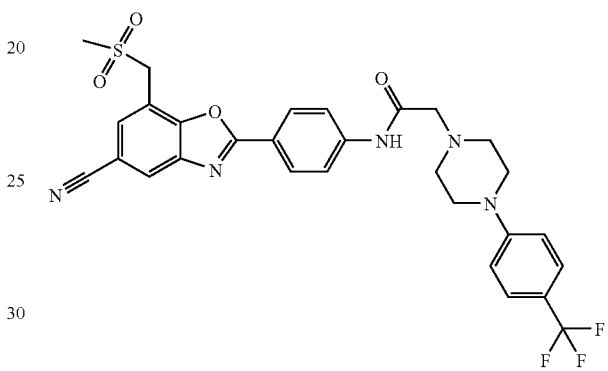

N-(4-{5-cyano-7-[(methylsulfonyl)methyl]-1,3-benzoxazol-2-yl}phenyl)-2-{4-[4-(trifluoromethyl)phenyl]piperazin-1-yl}acetamide A mixture of 25 mg of N-{4-[5-cyano-7-(dibromomethyl)-1,3-benzoxazol-2-yl]phenyl}-2-{4-[4-(trifluoromethyl)phenyl]piperazin-1-yl}acetamide (EXAMPLE 474), 13 mg of MeSO$_2$Na, and 7.8 mg of NaHCO$_3$ in DMA/water (1.6 ml/0.4 ml) was heated under nitrogen at 90° C. overnight. Added water and extracted mixture 4 times with ethyl acetate. The combined organics were washed with brine, dried over sodium sulfate, concentrated, and purified by flash column chromatography on a Biotage Horizon, 25M Si column, eluting with 1 column volume of dichloromethane, followed by a linear gradient of EtOAc in dichloromethane from 0% to 100% over 10 column volumes. The product was repurified 3 times by thin layer chromatography, eluting with 20% EtOAC in dichloromethane; RP HPLC, Waters XTerra C8 5 □m 19×50 mm column, eluting with a linear gradient of MeCN (0.1% TFA) in water (0.1% TFA) from 10% to 100% over 5.25 min at 20 ml/min; and thin layer chromatography eluting with 2% NH$_3$ (2M solution in MeOH) in dichloromethane to provide the title compound. Mass spectrum (ESI) 598.4 (M+1). $^1$H NMR (500 MHz, CDCl$_3$): δ 2.83 (m, 4H); 2.96 (s, 3H); 3.28 (s, 2H); 3.39 (m, 4H); 4.64 (s, 2H); 6.96 (d, J=8.7

Hz, 2H); 7.52 (d, J=8.7 Hz, 2H); 7.73 (d, J=0.9 Hz, 1H); 7.80 (d, J=8.7 Hz, 2H); 8.07 (s, 1H); 8.23 (d, J=8.7 Hz, 2H); 9.36 (s, 1H).

Example 480

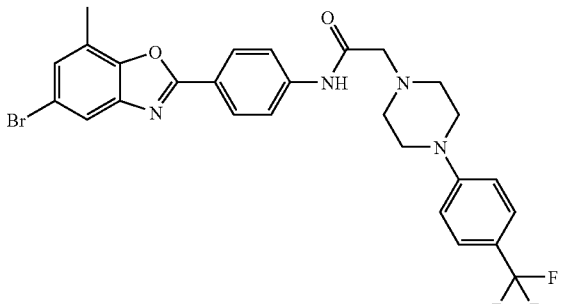

N-[4-(5-bromo-7-methyl-1,3-benzoxazol-2-yl)phenyl]-2-{4-[4-(trifluoromethyl)phenyl]piperazin-1-yl}acetamide Step A: 2-bromo-N-[4-(5-bromo-7-methyl-1,3-benzoxazol-2-yl)phenyl]acetamide A mixture of 291 mg of 4-(5-bromo-7-methyl-1,3-benzoxazol-2-yl)aniline (INTERMEDIATE 6, Step D), 167 μl of bromoacetyl bromide, and 352 μl of diisopropylethyl amine in 5 ml of THF was stirred at room temperature under nitrogen for 1 hour. The mixture was concentrated, preadsorbed on silica gel, and purified by flash column chromatography on a Biotage Horizon, 25M Si column, eluting with 1 column volume of $CH_2Cl_2$, followed by a linear gradient of EtOAc in $CH_2Cl_2$ from 0% to 100% over 10 column volumes to provide the title compound. Mass spectrum (ESI) 423.2 (M+1); 425.2 (M+3); 427.2 (M+5).
$^1$H NMR (400 MHz, CDCl$_3$): δ 2.57 (s, 3H); 4.07 (s, 2H); 7.29 (s, 1H); 7.71 (m, 3H); 8.26 (m, 3H).

Step B: N-[4-(5-bromo-7-methyl-1,3-benzoxazol-2-yl)phenyl]-2-{4-[4-(trifluoromethyl)phenyl]piperazin-1-yl}acetamide The title compound was prepared from 2-bromo-N-[4-(5-bromo-7-methyl-1,3-benzoxazol-2-yl)phenyl]acetamide (Step A) and 1-(4-trifluoromethylphenyl)piperazine by a procedure analogous to that described in EXAMPLE 474, Step B. Mass spectrum (ESI) 573 (M+1); 575.4 (M+3). $^1$H NMR (500 MHz, CDCl$_3$): δ 2.56 (s, 3H); 2.83 (br s, 4H); 3.27 (s, 2H); 3.39 (m, 4H); 6.96 (d, J=8.7 Hz, 2H); 7.27 (s, 1H); 7.51 (d, J=8.6 Hz, 2H); 7.69 (s, 1H); 7.76 (d, J=8.7 Hz, 2H); 8.22 (d, J=8.7 Hz, 2H); 9.31 (br s, 1H).

Example 481

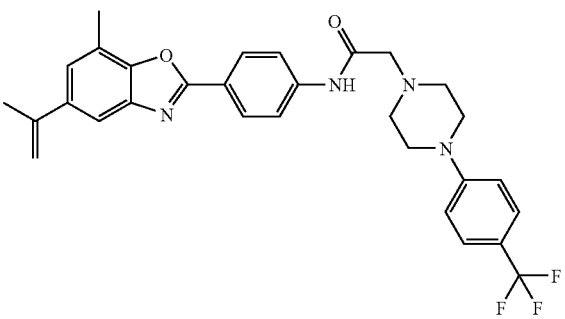

N-[4-(5-isopropenyl-7-methyl-1,3-benzoxazol-2-yl)phenyl]-2-{4-[4-(trifluoromethyl)phenyl]piperazin-1-yl}acetamide A mixture of 40 mg of N-[4-(5-bromo-7-methyl-1,3-benzoxazol-2-yl)phenyl]-2-{4-[4-(trifluoromethyl)phenyl]piperazin-1-yl}acetamide (EXAMPLE 480), 30 mg of isopropenylboronic acid, 74 mg of $Na_2CO_3$, and 8.1 mg of Pd(PPh$_3$)$_4$ in DME/water (2 ml/0.2 ml) was refluxed under nitrogen overnight. Added aqueous sodium bicarbonate to the mixture and extracted 3 times with ethyl acetate. The combined organics were washed with brine, dried over sodium sulfate, concentrated, and purified by thin layer chromatography (2×1000 μm plates) eluting with 10% EtOAc in dichloromethane to provide the title compound. Mass spectrum (ESI) 535.4 (M+1). $^1$H NMR (500 MHz, CDCl$_3$): δ 2.21 (s, 3H); 2.59 (s, 3H); 2.83 (m, 4H); 3.27 (s, 2H); 3.39 (m, 4H); 5.11 (s, 1H); 5.78 (s, 1H); 6.97 (d, J=8.7 Hz, 2H); 7.29 (s, 1H); 7.52 (d, J=8.5 Hz, 2H); 7.65 (s, 1H); 7.76 (d, J=8.5 Hz, 2H); 8.24 (d, J=8.7 Hz, 2H); 9.28 (s, 1H).

Example 482

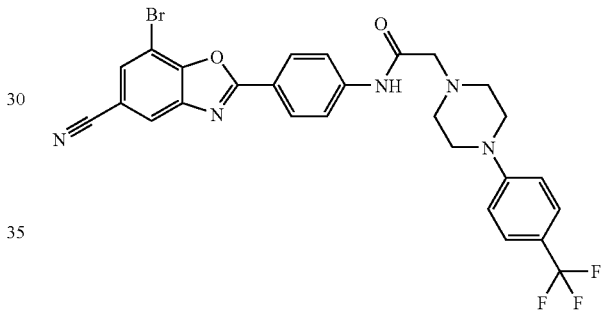

N-[4-(7-bromo-5-cyano-1,3-benzoxazol-2-yl)phenyl]-2-{4-[4-(trifluoromethyl)phenyl]piperazin-1-yl}acetamide Step A: 3-bromo-4-hydroxy-5-nitrobenzonitrile To a solution of 2.00 g of 3,5-dibromo-4-hydroxybenzonitrile in 150 ml of AcOH under nitrogen were added 994 mg of sodium nitrite and the resulting mixture was stirred for 2 days at room temperature. The mixture was poured into 200 ml of ice/water, added another 400 ml of water and extracted 5 times with ethyl acetate. The combined organics were washed 2 times with brine, dried over sodium sulfate, and concentrated to provide the title compound. $^1$H NMR (500 MHz, CDCl$_3$): δ 8.12 (d, J=2 Hz, 1H); 8.45 (d, J=1.9 Hz, 1H); 11.50 (s, 1H).

Step B: 3-amino-5-bromo-4-hydroxybenzonitrile

A mixture of 2.02 g of 3-bromo-4-hydroxy-5-nitrobenzonitrile (Step A) and 9.39 g of tin chloride dihydrate in 180 ml of ethanol was stirred at room temperature under nitrogen for 3 days. The mixture was concentrated under reduced pressure and ethyl acetate and saturated sodium bicarbonate were added slowly while stirring to avoid foaming. The biphasic mixture was filtered through a fritted funnel, the layers were separated, and the aqueous was extracted 4 times with EtOAc.

The organics were washed with brine, dried and concentrated to provide the title compound. Mass spectrum (ESI) 213 (M+1); 215.1 (M+3).

Step C: 7-bromo-2-(4-nitrophenyl)-1,3-benzoxazole-5-carbonitrile

The title compound was prepared from 3-amino-5-bromo-4-hydroxybenzonitrile (Step B) and 4-nitrobenzoyl chloride by a procedure analogous to that described in INTERMEDIATE 6, Step C. $^1$H NMR (500 MHz, DMSO-$d_6$): δ 8.33 (s, 1H); 8.46 (s, 4H); 8.55 (s, 1H).

Step D: 2-(4-aminophenyl)-7-bromo-1,3-benzoxazole-5-carbonitrile

The title compound was prepared from 7-bromo-2-(4-nitrophenyl)-1,3-benzoxazole-5-carbonitrile (Step C) by a procedure analogous to that described in INTERMEDIATE 6, Step D. Mass spectrum (ESI) 314 (M+1); 316.2 (M+3).

Step E: 2-bromo-N-[4-(7-bromo-5-cyano-1,3-benzoxazol-2-yl)phenyl]acetamide

The title compound was prepared from 2-(4-aminophenyl)-7-bromo-1,3-benzoxazole-5-carbonitrile (Step D) and bromoacetyl bromide by a procedure analogous to that described in EXAMPLE 480, Step A. Mass spectrum (ESI) 434.1 (M+1); 436.2 (M+3); 438.1 (M+5).

Step F: N-[4-(7-bromo-5-cyano-1,3-benzoxazol-2-yl)phenyl]-2-{4-[4-(trifluoromethyl)phenyl]piperazin-1-yl}acetamide The title compound was prepared from 2-bromo-N-[4-(7-bromo-5-cyano-1,3-benzoxazol-2-yl)phenyl]acetamide (Step E) and 1-(4-trifluoromethylphenyl)piperazine by a procedure analogous to that described in EXAMPLE 474, Step B. Mass spectrum (ESI) 584.1 (M+1). $^1$H NMR (400 MHz, CDCl$_3$): δ 2.84 (m, 4H); 3.28 (s, 2H); 3.40 (m, 4H); 6.97 (d, J=8.7 Hz, 2H); 7.52 (d, J=8.7 Hz, 2H); 7.80 (m, 3H); 7.97 (d, J=1.2 Hz, 1H); 8.27 (d, J=8.7 Hz, 2H); 9.36 (s, 1H).

The following compounds were prepared by essentially the same procedure as EXAMPLE 481:

TABLE 15

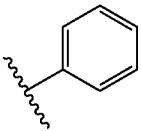

| EXAMPLE | R$_1$ | R$_2$ | MS (M + 1) |
|---|---|---|---|
| 483 | phenyl | CN | 582.4 |
| 484 | isopropenyl | CN | 546.5 |
| 485 | pyridin-3-yl | CN | 83.3 |
| 486 | Me | pyridin-3-yl | 572.2 |
| 487 | pyrimidin-5-yl | CN | 584.5 |
| 488 | 3-fluorophenyl | CN | 600.4 |
| 489 | 2-fluorophenyl | CN | 600.5 |

Example 490

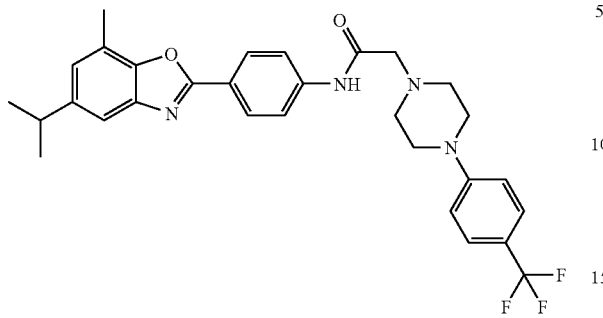

N-[4-(5-isopropyl-7-methyl-1,3-benzoxazol-2-yl)phenyl]-2-{4-[4-(trifluoromethyl)phenyl]piperazin-1-yl}acetamide The title compound was prepared from N-[4-(5-isopropenyl-7-methyl-1,3-benzoxazol-2-yl)phenyl]-2-{4-[4-(trifluoromethyl)phenyl]piperazin-1-yl}acetamide (EXAMPLE 481) by a procedure analogous to that described in INTERMEDIATE 6, Step D. Mass spectrum (ESI) 537.3 (M+1). $^1$H NMR (500 MHz, CDCl$_3$): δ 1.30 (d, J=6.9 Hz, 6H); 2.57 (s, 3H); 2.82 (m, 4H); 3.00 (septet, J=6.9 Hz, 1H); 3.26 (s, 2H); 3.38 (m, 4H); 6.96 (d, J=8.7 Hz, 2H); 7.01 (s, 1H); 7.43 (s, 1H); 7.51 (d, J=8.7 Hz, 2H); 7.75 (d, J=8.7 Hz, 2H); 8.23 (d, J=8.7 Hz, 2H); 9.27 (s, 1H).

Example 491

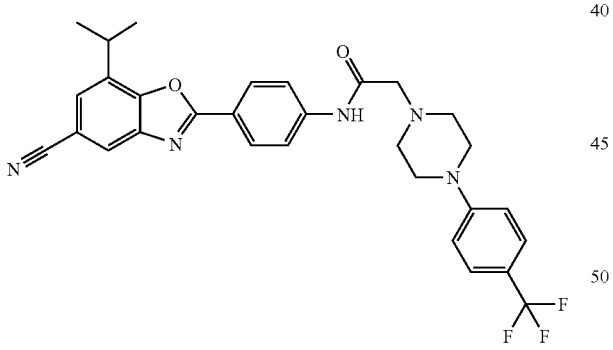

N-[4-(5-cyano-7-isopropyl-1,3-benzoxazol-2-yl)phenyl]-2-{4-[4-(trifluoromethyl)phenyl]piperazin-1-yl}acetamide The title compound was prepared from N-[4-(5-cyano-7-isopropenyl-1,3-benzoxazol-2-yl)phenyl]-2-{4-[4-(trifluoromethyl)phenyl]piperazin-1-yl}acetamide (EXAMPLE 484) by a procedure analogous to that described in INTERMEDIATE 6, Step D. Mass spectrum (ESI) 548.5 (M+1). $^1$H NMR (500 MHz, CDCl$_3$: δ 1.45 (d, J=6.8 Hz, 6H); 2.83 (m, 4H); 3.28 (s, 2H); 3.39 (m, 4H); 3.46 (septet, J=6.9 Hz, 1H); 6.97 (d, J=8.7 Hz, 2H); 7.47 (d, J=1.1 Hz, 1H); 7.52 (d, J=8.7 Hz, 2H); 7.79 (d, J=8.9 Hz, 2H); 7.89 (d, J=1.3 Hz, 1H); 8.24 (d, J=8.7 Hz, 2H); 9.33 (s, 1H).

Example 492

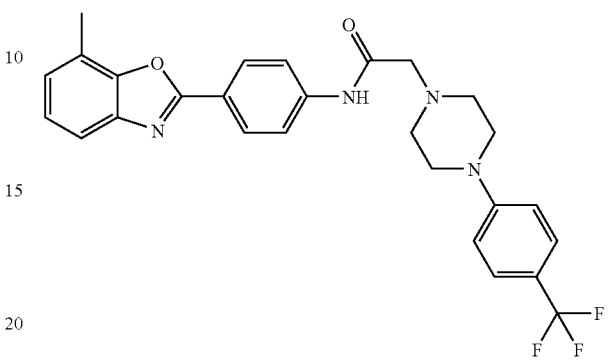

N-[4-(7-methyl-1,3-benzoxazol-2-yl)phenyl]-2-{4-[4-(trifluoromethyl)phenyl]piperazin-1-yl}acetamide To a solution of 20 mg of N-[4-(5-bromo-7-methyl-1,3-benzoxazol-2-yl)phenyl]-2-{4-[4-(trifluoromethyl)phenyl]piperazin-1-yl}acetamide (EXAMPLE 480) in 2 ml of THF under nitrogen were added 20 μl of isopropylmagnesium chloride. The resulting solution was stirred for ca. 25 min at room temperature, cooled to −78° C. and 82 μl of t-BuLi was added followed immediately by 5 drops of acetone. Removed the dry ice bath after ca. 30 minutes and stirred the reaction mixture at room temperature overnight, concentrated, and purified by thin layer chromatography (on a 1000 μm plate) eluting with 10% EtOAc in dichloromethane to provide the title compound as the major product. Mass spectrum (ESI) 495.4 (M+1). $^1$H NMR (500 MHz, CDCl$_3$): δ 2.83 (m, 4H); 3.27 (s, 2H); 3.39 (m, 4H); 6.96 (d, J=8.7 Hz, 2H); 7.14 (d, J=7.4 Hz, 1H); 7.23 (d, J=7.8 Hz, 1H); 7.52 (d, J=8.7 Hz, 2H); 7.58 (d, J=8.0 Hz, 1H); 7.76 (d, J=8.7 Hz, 2H); 8.25 (d, J=8.5 Hz, 2H); 9.28 (s, 1H).

Example 493

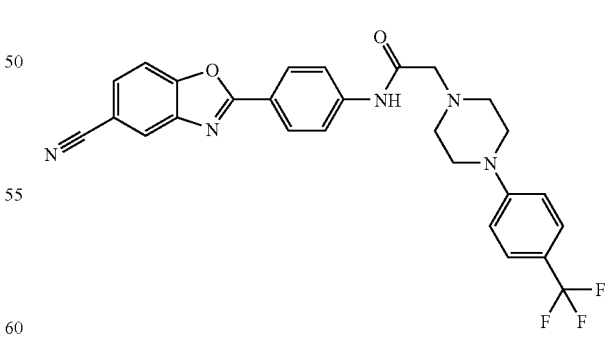

N-[4-(5-cyano-1,3-benzoxazol-2-yl)phenyl]-2-{4-[4-(trifluoromethyl)phenyl]piperazin-1-yl}acetamide The title compound was the major product from the reaction of N-[4-(7-bromo-5-cyano-1,3-benzoxazol-2-yl)phenyl]-2-

{4-[4-(trifluoromethyl)phenyl]piperazin-1-yl}acetamide (EXAMPLE 482) with n-BuLi, and benzaldehyde by a procedure analogous to that described in EXAMPLE 492. Mass spectrum (ESI) 506.3 (M+1). $^1$H NMR (400 MHz, CDCl$_3$): δ 2.83 (m, 4H); 3.28 (s, 2H); 3.39 (m, 4H); 6.97 (d, J=8.8 Hz, 2H); 7.52 (d, J=8.7 Hz, 2H); 7.66 (m, 2H); 7.79 (d, J=8.7 Hz, 2H); 8.05 (s, 1H); 8.24 (d, J=8.8 Hz, 2H); 9.35 (s, 1H).

Example 494

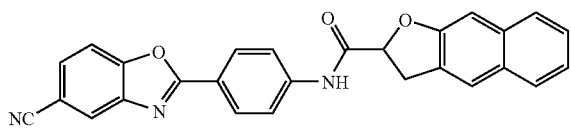

N-[4-(5-cyano-1,3-benzoxazol-2-yl)phenyl]-2,3-dihydronaphtho[2,3-b]furan-2-carboxamide Following the procedure described in EXAMPLE 8, Step B, 26 mg of 2,3-dihydronaphtho[2,3-b]furan-2-carboxylic acid, 100 µL of 2M oxalyl chloride solution, 19 µL of diisopropylethylamine, and 25 mg of 2-(4-aminophenyl)-1,3-benzoxazole-5-carbonitrile (INTERMEDIATE 3) were used to make the title compound. Mass spectrum (ESI) 432.2 (M+1). $^1$H NMR (500 MHz, DMSO): δ 10.65, (s, 1H), 8.37 (s, 1H), 8.20 (d, J=8.5 Hz, 2H), 7.98 (m, 3H), 7.89 (m, 2H), 7.82 (d, J=9 Hz, 1H), 7.70 (d, J=8.5 Hz, 1H), 7.52 (m, 1H), 7.36 (m, 1H), 7.28 (d, J=9 Hz, 1H), 5.59 (dd, J=6.5, 10 Hz, 1H), 3.85 (m, 1H) 3.70 (m, 1H).

The following compounds were prepared according to the procedure outlined in EXAMPLE 481:

TABLE 16

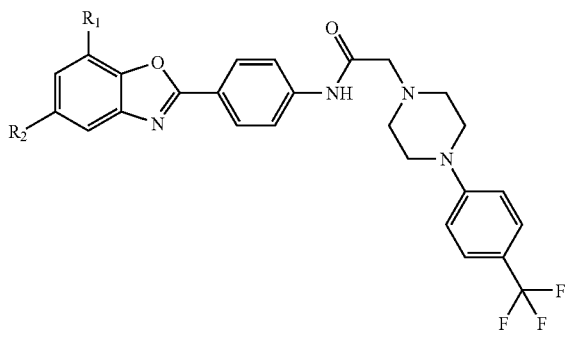

| EXAMPLE | R$_1$ | R$_2$ | MS (M + 1) |
|---|---|---|---|
| 495 | cyclopropyl | CN | 546.1 |
| 496 | vinyl | CN | 532.0 |

TABLE 16-continued

| EXAMPLE | R$_1$ | R$_2$ | MS (M + 1) |
|---|---|---|---|
| 497 | 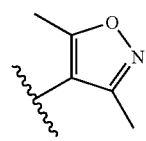 dimethylisoxazolyl | CN | 601.2 |
| 498 | 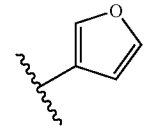 furanyl | CN | 572.3 |
| 499 | 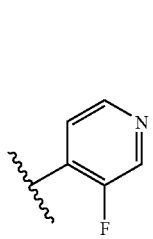 fluoropyridyl | CN | 601.0 |

Example 500

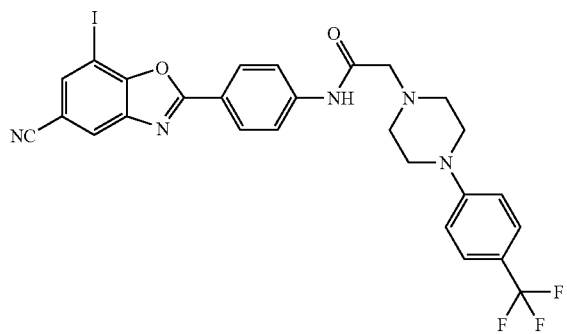

N-[4-(5-cyano-7-iodo-1,3-benzoxazol-2-yl)phenyl]-2-[4-[4-(trifluoromethyl)phenyl]piperazin-1-yl]acetamide The title compound was prepared by a procedure analogous to that described in EXAMPLE 482. Mass spectrum (ESI) 632.2 (M+1).

Example 501

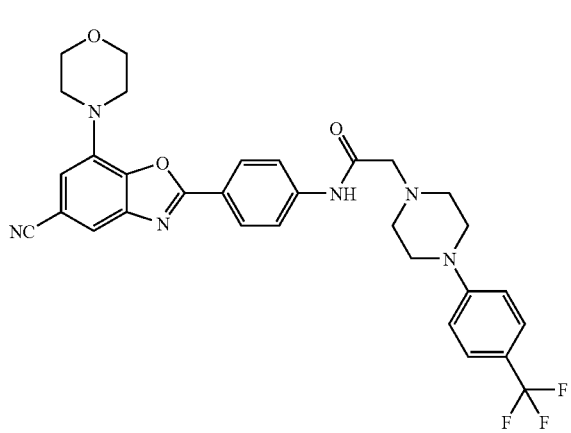

N-[4-(5-cyano-7-morpholin-4-yl-1,3-benzoxazol-2-yl)phenyl]-2-{4-[4-(trifluoromethyl)phenyl]piperazin-1-yl}acetamide A mixture of N-[4-(5-cyano-7-iodo-1,3-benzoxazol-2-yl)phenyl]-2-{4-[4-(trifluoromethyl)phenyl]piperazin-1-yl}acetamide (EXAMPLE 500) (25 mg, 0.040 mmol), morpholine (7 µl, 0.080 mmol), NaOtBu (6 mg, 0.060 mmol), Pd₂(dba)₃ (4 mg, 0.0040 mmol), and BINAP (5 mg, 0.0080 mmol) in toluene (2 ml) was heated at 90° C. for 4 days, concentrated and purified by thin layer chromatography to afford the title compound. Mass spectrum (ESI) 591.3 (M+1).

Example 502

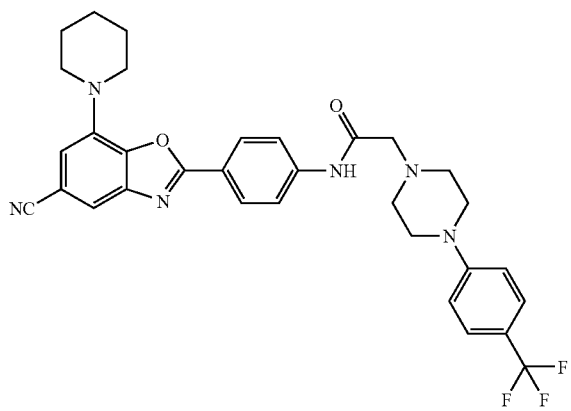

N-[4-(5-cyano-7-piperidin-1-yl-1,3-benzoxazol-2-yl)phenyl]-2-{4-[4-(trifluoromethyl)phenyl]piperazin-1-yl}acetamide The title compound was prepared by a procedure analogous to that described in EXAMPLE 501. Mass spectrum (ESI) 589.3 (M+1).

Example 503

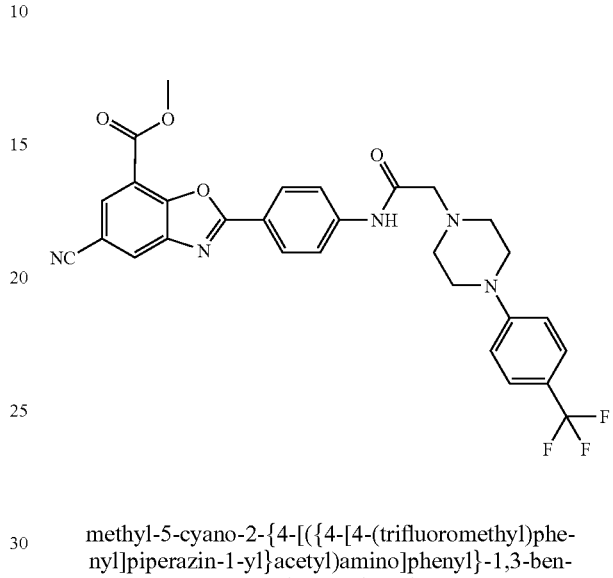

methyl-5-cyano-2-{4-[({4-[4-(trifluoromethyl)phenyl]piperazin-1-yl}acetyl)amino]phenyl}-1,3-benzoxazole-7-carboxylate A mixture of N-[4-(7-bromo-5-cyano-1,3-benzoxazol-2-yl)phenyl]-2-{4-[4-(trifluoromethyl)phenyl]piperazin-1-yl}acetamide (EXAMPLE 482) (622 mg), palladium acetate (47.6 mg), triethylamine (1.09 ml), and 1,3-bis(diphenylphosphino)propane (101 mg) in DMF/MeOH (5 ml/5 ml) was stirred for 16 hours at 60° C. under 50 psi of CO, then, concentrated and purified by flash column chromatography to afford the title compound. Mass spectrum (ESI) 564.1 (M+1).

Example 504

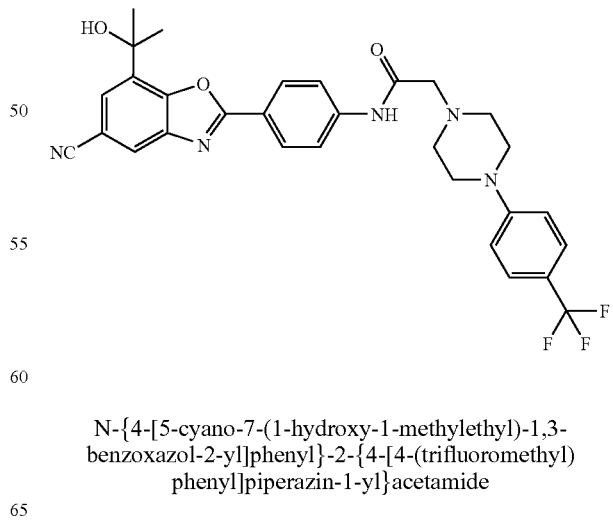

N-{4-[5-cyano-7-(1-hydroxy-1-methylethyl)-1,3-benzoxazol-2-yl]phenyl}-2-{4-[4-(trifluoromethyl)phenyl]piperazin-1-yl}acetamide To a mixture of methyl-5-cyano-2-{4-[({4-[4-(trifluoromethyl)phenyl]piperazin-1-yl}acetyl)amino]phenyl}-1,3-benzoxazole-7-carboxylate (EXAMPLE 503) (105 mg) in 4 ml THF under nitrogen was added 465 μl of MeMgBr (1.4M in toluene/THF 75/25) and the resulting solution was stirred for 10 minutes, then, added 1 ml MeOH and concentrated. Added water to the residue and extracted 3 times with EtOAc. The combined organics were washed with brine, dried over sodium sulfate, and concentrated. The residue was purified by flash column chromatography using a Biotage Horizon, 25M Si column, eluting with 1 CV of DCM, followed by a linear gradient of EtOAc in DCM from 0% to 100% over 10 CV to afford the title compound. Mass spectrum (ESI) 564.1 (M+1).

Example 505

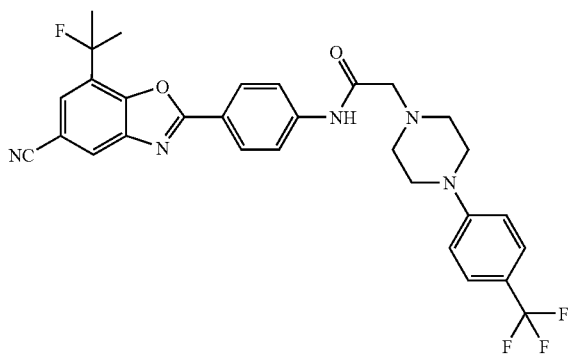

N-{4-[5-cyano-7-(1-fluoro-1-methylethyl)-1,3-benzoxazol-2-yl]phenyl}-2-{4-[4-(trifluoromethyl)phenyl]piperazin-1-yl}acetamide To a mixture of N-{4-[5-cyano-7-(1-hydroxy-1-methylethyl)-1,3-benzoxazol-2-yl]phenyl}-2-{4-[4-(trifluoromethyl)phenyl]piperazin-1-yl}acetamide (EXAMPLE 504) in DCM under nitrogen was added 90 μl of DAST and the resulting mixture was stirred for 2 days. Added another 20 μl of DAST and 2 ml DCM and stirred for 2 more days. Added sat. aq. sodium bicarbonate, and extracted the aqueous layer 3 times with DCM. The combined organics were washed with brine, dried over sodium sulfate, and concentrated. The residue was purified by flash column chromatography using a Biotage Horizon, 25M Si column, eluting with 1 CV of DCM, followed by a linear gradient of EtOAc in DCM from 0% to 50% over 10 CV to afford the title compound. Mass spectrum (ESI) 566.0 (M+1).

Example 506

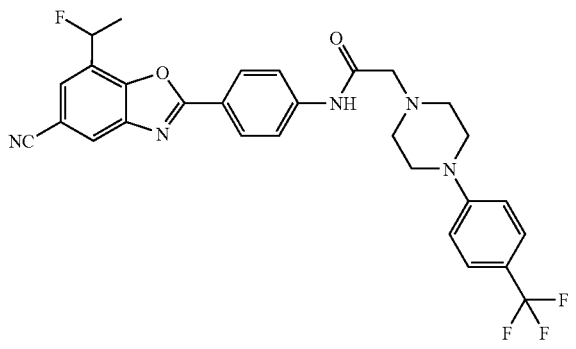

N-{4-[5-cyano-7-(1-fluoroethyl)-1,3-benzoxazol-2-yl]phenyl}-2-{4-[4-(trifluoromethyl)phenyl]piperazin-1-yl}acetamide The title compound was prepared from N-{4-[5-cyano-7-(1-hydroxyethyl)-1,3-benzoxazol-2-yl]phenyl}-2-{4-[4-(trifluoromethyl)phenyl]piperazin-1-yl}acetamide (EXAMPLE 478) by a procedure analogous to that described in EXAMPLE 505. Mass spectrum (ESI) 552.0 (M+1).

Intermediate 35

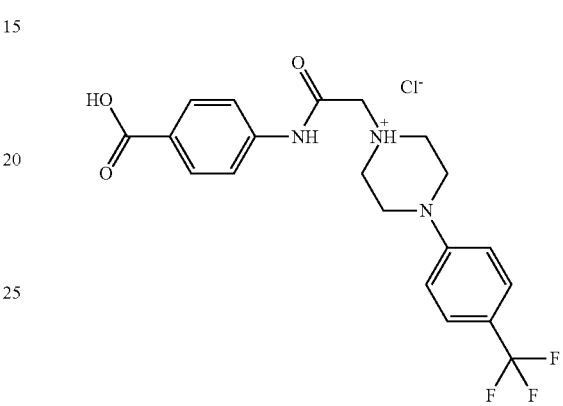

1-{2-[(4-carboxyphenyl)amino]-2-oxoethyl}-4-[4-(trifluoromethyl)phenyl]piperazin-1-ium chloride Step A: methyl 4-[(bromoacetyl)amino]benzoate The title compound was prepared from bromoacetyl bromide and methyl 4-aminobenzoate by a procedure analogous to that described in EXAMPLE 482, Step E. Mass spectrum (ESI) 273.8 (M+3).

Step B: methyl-4-[({4-[4-(trifluoromethyl)phenyl]piperazin-1-yl}acetyl)amino]benzoate The title compound was prepared from methyl 4-[(bromoacetyl)amino]benzoate (Step A) and 1-(4-trifluoromethylphenyl)piperazine by a procedure analogous to that described in EXAMPLE 482, Step F. Mass spectrum (ESI) 422.0 (M+3).

Step C: 1-{2-[(4-carboxyphenyl)amino]-2-oxoethyl}-4-[4-(trifluoromethyl)phenyl]piperazin-1-ium chloride A mixture of methyl-4-[({4-[4-(trifluoromethyl)phenyl]piperazin-1-yl}acetyl)amino]benzoate (Step B) (5.59 g) and lithium hydroxide monohydrate (5.58 g) in THF/MeOH/water (60 ml/30 ml/30 ml) was stirred at RT overnight, concentrated, and partitioned between 1M HCl and EtOAc. The precipitating solids were filtered and dried in vacuo to afford the title compound. Mass spectrum (ESI) 408.2 (M+1).

Example 507

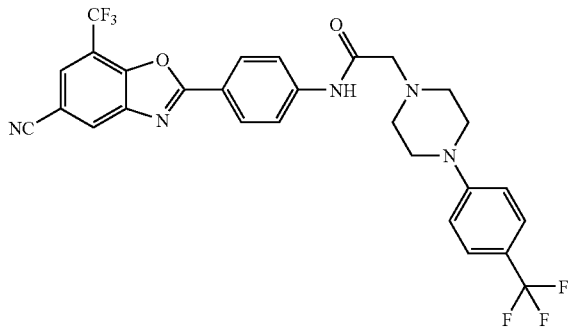

N-{4-[5-cyano-7-(trifluoromethyl)-1,3-benzoxazol-2-yl]phenyl}-2-{4-[4-(trifluoromethyl)phenyl]piperazin-1-yl}acetamide Step A: 4-hydroxy-3-(trifluoromethyl)benzonitrile The title compound was prepared from 4-methoxy-3-(trifluoromethyl)benzonitrile by a procedure analogous to that described in INTERMEDIATE 36, Step C. Mass spectrum (ESI) 186.1 (M−1).

Step B: 4-hydroxy-3-nitro-5-(trifluoromethyl)benzonitrile

The title compound was prepared from 4-hydroxy-3-(trifluoromethyl)benzonitrile (Step A) by a procedure analogous to that described in INTERMEDIATE 36, Step A. Mass spectrum (ESI) 231.0 (M−1).

Step C: 3-amino-4-hydroxy-5-(trifluoromethyl)benzonitrile

The title compound was prepared from 4-hydroxy-3-nitro-5-(trifluoromethyl)benzonitrile (Step B) by a procedure analogous to that described in INTERMEDIATE 36, Step D. Mass spectrum (ESI) 203.0 (M+1).

Step D: N-{4-[5-cyano-7-(trifluoromethyl)-1,3-benzoxazol-2-yl]phenyl}-2-{4-[4-(trifluoromethyl)phenyl]piperazin-1-yl}acetamide The title compound was prepared from 3-amino-4-hydroxy-5-(trifluoromethyl)benzonitrile (Step C) and 1-{2-[(4-carboxyphenyl)amino]-2-oxoethyl}-4-[4-(trifluoromethyl)phenyl]piperazin-1-ium chloride (INTERMEDIATE 35) by a procedure analogous to that described in INTERMEDIATE 37, Step A. Mass spectrum (ESI) 574.0 (M+1).

Example 508

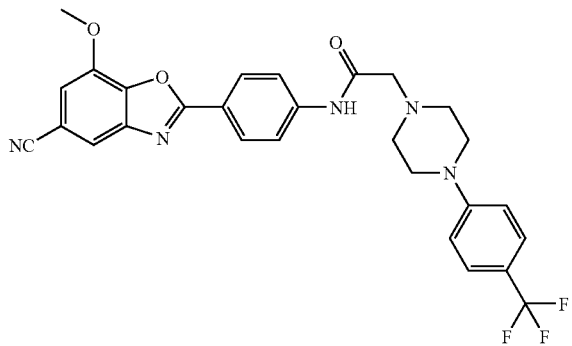

N-[4-(5-cyano-7-methoxy-1,3-benzoxazol-2-yl)phenyl]-2-{4-[4-(trifluoromethyl)phenyl]piperazin-1-yl}acetamide The title compound was prepared from 4-hydroxy-3-methoxybenzonitrile and 1-{2-[(4-carboxyphenyl)amino]-2-oxoethyl}-4-[4-(trifluoromethyl)phenyl]piperazin-1-ium chloride (INTERMEDIATE 35) by a procedure analogous to that described in EXAMPLE 507. Mass spectrum (ESI) 536.0 (M+1).

Intermediate 36

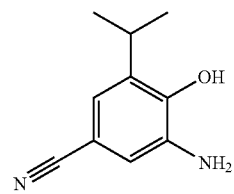

3-amino-4-hydroxy-5-isopropylbenzonitrile

Step A: 3-bromo-4-methoxy-5-nitrobenzonitrile 3-bromo-4-methoxybenzonitrile (5.22 g, 24.62 mmol) was added to chilled (ice bath) stirring fuming nitric acid (10 ml, 201 mmol). The ice bath was removed and the reaction mixture was stirred for 2 hours at RT. Added EtOAc and washed the organic layer twice with water, followed by brine. Dried the organic layer over sodium sulfate, filtered, and the solvent was evaporated under reduced pressure to afford the title compound, which was carried on without further purification.

Step B: 3-isopropenyl-4-methoxy-5-nitrobenzonitrile

To a mixture of 3-bromo-4-methoxy-5-nitrobenzonitrile (Step A) (6.26 g, 24.35 mmol) in DME (61 ml) was added water (16 ml), isopropenylboronic acid (6.28 g, 73.1 mmol), potassium carbonate (10.10 g, 73.1 mmol), and tetrakis(triphenylphosphine)palladium (0) (0.281 g, 0.244 mmol). The resulting mixture was heated to reflux overnight under nitrogen, then, concentrated. Added water to the residue and extracted 3 times with EtOAc. The combined organics were washed with brine, dried over sodium sulfate, filtered, and the solvent was evaporated under reduced pressure. The residue was purified by flash column chromatography using a Horizon Biotage, 65i Si column, eluting with 1 CV of hexanes, followed by a linear gradient of EtOAc in hexanes from 0% to 100% over 10 CV to afford the title compound as a red oil.

Step C: 4-hydroxy-3-isopropenyl-5-nitrobenzonitrile

A mixture of 3-isopropenyl-4-methoxy-5-nitrobenzonitrile (StepB) (5.06 g, 23.19 mmol) and pyridine hydrochloride (10 g, 87 mmol) was placed in an oil bath at 200° C. for 4 minutes. Cooled reaction to RT, added 1M HCl, and extracted 3 times with EtOAc. The combined organics were washed with brine, dried over sodium sulfate, filtered, and the solvent was evaporated under reduced pressure. The residue was purified by flash column chromatography using a Horizon Biotage, 65i Si column, eluting with 1 CV of 1% EtOAc in hexanes, followed by a linear gradient of EtOAc in hexanes from 1% to 100% over 10 CV to afford the title compound. Mass spectrum (ESI) 203.1 (M−1).

Step D: 3-amino-4-hydroxy-5-isopropylbenzonitrile

To a solution of 4-hydroxy-3-isopropenyl-5-nitrobenzonitrile (Step C) (4.135 g, 20.25 mmol) in EtOAc (100 ml) was added 1.2 g of Pd/C and the resulting mixture was degassed and flushed with nitrogen, then, degassed and flushed with hydrogen using a double balloon. The reaction was stirred under hydrogen for 14 hours, then, diluted with EtOAc, filtered through a pad of celite and concentrated. The residue was purified by flash column chromatography using a Horizon Biotage, 65i Si column, eluting with 1 CV of DCM, followed by a linear gradient of EtOAc in DCM from 0% to 50% over 10 CV. It was then repurified by flash column chromatography using a Horizon Biotage, 65i Si column, eluting with 1 CV of 5% EtOAc in hexanes, followed by a linear gradient of EtOAc in hexanes from 5% to 100% over 10 CV to afford the title compound. Mass spectrum (ESI) 177.4 (M+1).

Intermediate 37

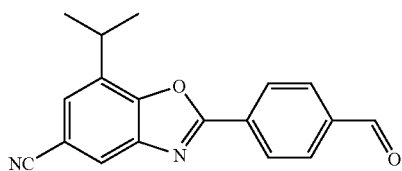

2-(4-formylphenyl)-7-isopropyl-1,3-benzoxazole-5-carbonitrile

Step A: 7-isopropyl-2-(4-vinylphenyl)-1,3-benzoxazole-5-carbonitrile

To a solution of 4-vinylbenzoic acid (1.50 g, 10.12 mmol) in DCM (30 ml) under nitrogen was added oxalyl chloride (2M solution in DCM) (10.12 ml, 20.25 mmol) followed by two drops of DMF and the resulting mixture was stirred at RT under nitrogen for 1 hour, then, concentrated in vacuo, added 1,4-dioxane (50 ml), 3-amino-4-hydroxy-5-isopropylbenzonitrile (INTERMEDIATE 36) (1.784 g, 10.12 mmol), and the resulting solution was refluxed overnight, then, concentrated. The residue was taken up in toluene (100 ml), added p-toluenesulfonic acid monohydrate (0.193 g, 1.012 mmol), and refluxed for ca. 6 hours. The reaction mixture was concentrated and triturated with methanol. Filtered solids washing with methanol to afford the title compound. Mass spectrum (ESI) 289.4 (M+1).

Step B: 2-(4-formylphenyl)-7-isopropyl-1,3-benzoxazole-5-carbonitrile

A yellow solution of 7-isopropyl-2-(4-vinylphenyl)-1,3-benzoxazole-5-carbonitrile (Step A) (109 mg, 0.378 mmol) in DCM (20 ml) was cooled to −78° C. and purged with oxygen for several minutes. Then it was purged with ozone till the color of the reaction turned to steel blue (less than 5 min.). Purged reaction mixture with oxygen till the blue color disappeared, followed by purging with nitrogen. Quenched reaction with 1 ml of dimethylsulfide followed by 200 mg (2 eq.) of triphenylphosphine. The resulting mixture was stirred at RT for 2.5 hours, concentrated, and triturated with hot MeOH. After cooling to RT the solids were filtered and dried to afford the title compound. Mass spectrum (ESI) 291.2 (M+1).

Intermediate 38

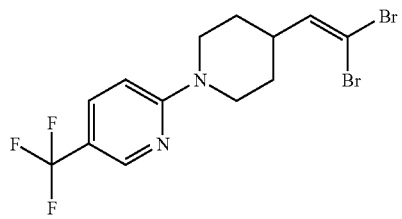

2-[4-(2,2-dibromovinyl)piperidin-1-yl]-5-(trifluoromethyl)pyridine

Step A: {1-[5-(trifluoromethyl)pyridin-2-yl]piperidin-4-yl}methanol

A mixture of 4-piperidinemethanol (705 mg, 6.12 mmol) and 2-bromo-5-(trifluoromethyl)pyridine (1383 mg, 6.12 mmol) in DBU (5 ml) was placed in a 100° C. oil bath and stirred at this temperature for 20 minutes. The reaction mixture was cooled and purified by flash column chromatography using a Horizon Biotage, 40M Si column, eluting with 2 CV of DCM, followed by a linear gradient of EtOAc in DCM from 0% to 100% over 10 CV to afford the title compound. Mass spectrum (ESI) 261.5 (M+1).

Step B: 1-[5-(trifluoromethyl)pyridin-2-yl]piperidine-4-carbaldehyde

To a solution of {1-[5-(trifluoromethyl)pyridin-2-yl]piperidin-4-yl}methanol (Step A) (971 mg, 3.73 mmol) in DCM (20 ml) at 0° C. under nitrogen was added Dess-Martin periodinane (1741 mg, 4.10 mmol). The ice bath was removed and the resulting solution was allowed to warm to RT overnight.

Added 2M aqueous sodium hydroxide and extracted the aqueous layer 3 times with dichloromethane. The combined organics were washed with brine, dried over sodium sulfate, filtered, and the solvent was evaporated under reduced pressure. The crude was purified by flash column chromatography using a Horizon Biotage, 40M Si column, eluting with 2 CV of hexanes, followed by a linear gradient of EtOAc in hexanes from 0% to 50% over 10 CV to afford the title compound. Mass spectrum (ESI) 258.8 (M+1).

Step C: 2-[4-(2,2-dibromovinyl)piperidin-1-yl]-5-(trifluoromethyl)pyridine

To a solution of triphenylphosphine (1654 mg, 6.30 mmol) in toluene (8 ml) at −25° C., under nitrogen, was added potassium t-butoxide (707 mg, 6.30 mmol) followed by fast dropwise addition of bromoform. The resulting mixture was stirred maintaining the temperature between −18° C. and −25° C. for 1 hour. A solution of 1-[5-(trifluoromethyl)pyridin-2-yl]piperidine-4-carbaldehyde (Step B) (407 mg, 1.576 mmol) in toluene (8 ml) was then added fast, dropwise, maintaining the same temperature range. The reaction mixture was then stirred at RT overnight. Added ether and filtered the solids washing with ether. The filtrate was concentrated and purified by flash column chromatography using a Horizon Biotage, 40M Si column, eluting with 2 CV of hexanes, followed by a linear gradient of DCM in hexanes from 0% to 30% over 10 CV, and a linear gradient of DCM in hexanes from 30% to 60% over 12 CV to afford the title compound. Mass spectrum (ESI) 412.9 (M+1); 414.9 (M+3).

Examples 509 and 510

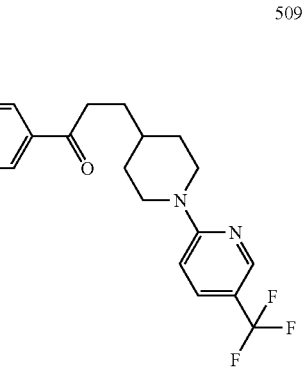

509

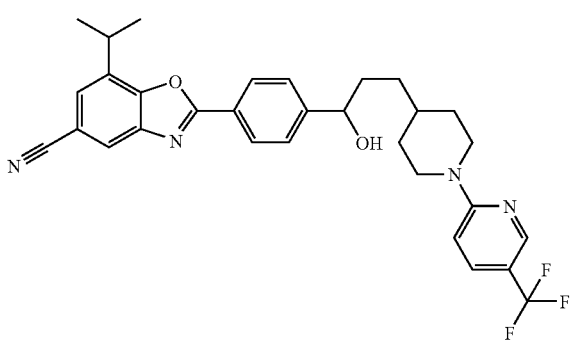

510

Example 509

7-isopropyl-2-[4-(3-{1-[5-(trifluoromethyl)pyridin-2-yl]piperidin-4-yl}propanoyl)phenyl]-1,3-benzoxazole-5-carbonitrile Example 510

2-[4-(1-hydroxy-3-{1-[5-(trifluoromethyl)pyridin-2-yl]piperidin-4-yl}propyl)phenyl]-7-isopropyl-1,3-benzoxazole-5-carbonitrile Step A: 2-[4-(1-hydroxy-3-{1-[5-(trifluoromethyl)pyridin-2-yl]piperidin-4-yl}prop-2-yn-1-yl)phenyl]-7-isopropyl-1,3-benzoxazole-5-carbonitrile To a solution of 2-[4-(2,2-dibromovinyl)piperidin-1-yl]-5-(trifluoromethyl)pyridine (INTERMEDIATE 38) (605 mg, 1.461 mmol) in THF (10 ml) at −78° C. was added dropwise n-butyllithium (1.6M in hexane) (1.826 ml, 2.92 mmol). The resulting mixture was stirred for 1 hour at this temperature, then, a solution of 2-(4-formylphenyl)-7-isopropyl-1,3-benzoxazole-5-carbonitrile (INTERMEDIATE 37) (424 mg, 1.461 mmol) in THF (30 ml) was added in portions. The reaction mixture was allowed to warm to RT overnight, then, quenched with water and extracted 3 times with EtOAc. The combined organics were washed with brine, dried over sodium sulfate, filtered, and the solvent was evaporated under reduced pressure. The residue was purified by flash column chromatography using a Horizon Biotage, 40M Si column, eluting with 2 CV of DCM, followed by a linear gradient of EtOAc in DCM from 0% to 40% over 10 CV to afford the title compound. Mass spectrum (ESI) 545.2 (M+1).

Step B: 7-isopropyl-2-[4-(3-{1-[5-(trifluoromethyl)pyridin-2-yl]piperidin-4-yl}prop-2-ynoyl)phenyl]-1,3-benzoxazole-5-carbonitrile To a solution of 2-[4-(1-hydroxy-3-{1-[5-(trifluoromethyl)pyridin-2-yl]piperidin-4-yl}prop-2-yn-1-yl)phenyl]-7-isopropyl-1,3-benzoxazole-5-carbonitrile (Step A) (34 mg, 0.062 mmol) in DCM (3 ml) at RT under nitrogen was added Dess-Martin periodinane (29.1 mg, 0.069 mmol) and the resulting mixture was stirred at RT overnight. Added 2M NaOH and extracted the aqueous layer 3 times with dichloromethane. The combined organics were washed with brine, dried over sodium sulfate, filtered, and the solvent was evaporated under reduced pressure. The crude was purified by TLC eluting with 80:20 hexanes/EtOAc to afford the title compound. Mass spectrum (ESI) 543.2 (M+1).

Step C: 7-isopropyl-2-[4-(3-{1-[5-(trifluoromethyl)pyridin-2-yl]piperidin-4-yl}propanoyl)phenyl]-1,3-benzoxazole-5-carbonitrile and 2-[4-(1-hydroxy-3-{1-[5-(trifluoromethyl)pyridin-2-yl]piperidin-4-yl}propyl)phenyl]-7-isopropyl-1,3-benzoxazole-5-carbonitrile To a solution of 7-isopropyl-2-[4-(3-{1-[5-(trifluoromethyl)pyridin-2-yl]piperidin-4-yl}prop-2-ynoyl)phenyl]-1,3-benzoxazole-5-carbonitrile (Step B) (18 mg, 0.033 mmol) in EtOAc (6 ml) was added 18 mg of 10% Pd/C and the resulting mixture was degassed and flushed with nitrogen, then, degassed and flushed with hydrogen using a double balloon. The mixture was stirred under hydrogen overnight, then, diluted with EtOAc, filtered through a celite pad, and concentrated. The residue was purified by TLC eluting with 92:8

DCM/EtOAc to afford the pure title compounds. EXAMPLE 509: Mass spectrum (ESI) 547.3 (M+1). EXAMPLE 510: Mass spectrum (ESI) 549.3 (M+1).

Example 511

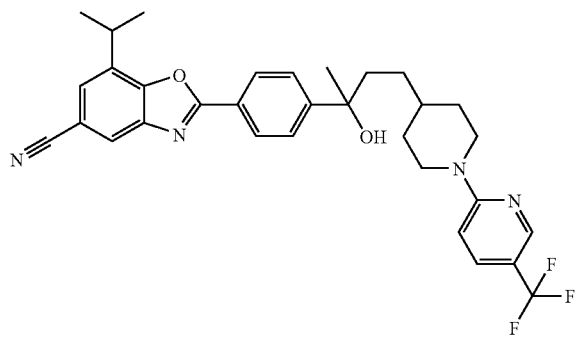

2-[4-(1-hydroxy-1-methyl-3-{1-[5-(trifluoromethyl) pyridin-2-yl]piperidin-4-yl}propyl)phenyl]-7-isopropyl-1,3-benzoxazole-5-carbonitrile To a stirred solution of 7-isopropyl-2-[4-(3-{1-[5-(trifluoromethyl)pyridin-2-yl]piperidin-4-yl}propanoyl)phenyl]-1, 3-benzoxazole-5-carbonitrile (EXAMPLE 509) (20 mg, 0.037 mmol) in THF (2 ml) at RT under nitrogen was added methylmagnesium bromide (1.4M solution in toluene/THF) (0.131 ml, 0.183 mmol). The resulting solution was stirred for 35 minutes, then, added water and extracted 3 times with ethyl acetate. The combined organics were washed with brine, dried over sodium sulfate, filtered, and the solvent was evaporated under reduced pressure. The residue was purified by TLC eluting with 60:40 hexanes/EtOAc, then, repurified by RP HPLC on a Gilson, Kromasil KR100—5C18 100×21.2 mm column, eluting with a gradient of MeCN (0.1% TFA) in water (0.1% TFA) from 10% to 100% over 12 minutes, at 20 ml/min, to afford the title compound as the TFA salt. Mass spectrum (ESI) 563.3 (M+1).

Example 512

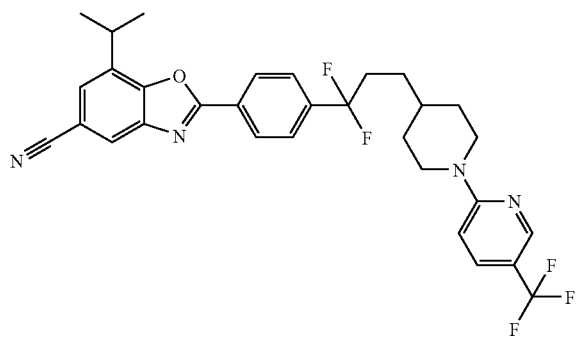

2-[4-(1,1-difluoro-3-{1-[5-(trifluoromethyl)pyridin-2-yl]piperidin-4-yl}propyl)phenyl]-7-isopropyl-1,3-benzoxazole-5-carbonitrile To a stirred solution of 7-isopropyl-2-[4-(3-{1-[5-(trifluoromethyl)pyridin-2-yl]piperidin-4-yl}propanoyl)phenyl]-1, 3-benzoxazole-5-carbonitrile (EXAMPLE 509) (30 mg, 0.055 mmol) in DCM (2 ml) at RT under nitrogen was added DAST (0.036 ml, 0.274 mmol). Stirred the resulting solution overnight at RT. LC/MS showed only SM. Transferred to a microwave vial and washed flask with 2 ml DCM. Added a total of 500 μl of DAST and heated with microwaves for 2 hours 20 minutes at 100° C. Added 2M aqueous sodium hydroxide and extracted the aqueous layer 3 times with ethyl acetate. The combined organics were washed with brine, dried over sodium sulfate, filtered, and the solvent was evaporated under reduced pressure. The residue was purified by TLC eluting with 80:20 hexanes/EtOAc, then, repurified by mass-directed RP HPLC, Waters SunFire Prep C18, 5 micron, 19×100 mm column, eluting with a gradient of MeCN (0.1% TFA) in water (0.1% TFA) from 10% to 100% over 12 minutes, at 20 mL/min, to afford the title compound as the TFA salt. Mass spectrum (ESI) 569.3 (M+1).

Example 513

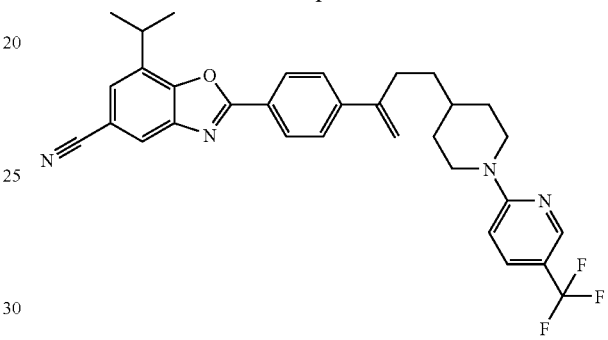

7-isopropyl-2-[4-(1-methylene-3-{1-[5-(trifluoromethyl)pyridin-2-yl]piperidin-4-yl}propyl)phenyl]-1, 3-benzoxazole-5-carbonitrile To a mixture of 7-isopropyl-2-[4-(3-{1-[5-(trifluoromethyl) pyridin-2-yl]piperidin-4-yl}propanoyl)phenyl]-1,3-benzoxazole-5-carbonitrile (EXAMPLE 509) (30 mg, 0.055 mmol) and methyltriphenylphosphonium iodide (44.4 mg, 0.110 mmol) in THF (0.9 ml), under nitrogen at RT, was added potassium t-butoxide (1M in THF) (0.110 ml, 0.110 mmol). The resulting mixture was stirred at RT for 40 minutes, then, diluted with EtOAc and filtered through a small silica plug washing with EtOAc. The residue was purified by flash column chromatography using a Horizon Biotage, 25M Si column, eluting with 2 CV of hexanes, followed by a linear gradient of EtOAc in hexanes from 0% to 30% over 10 CV to afford the title compound. Mass spectrum (ESI) 545.3 (M+1).

Example 514

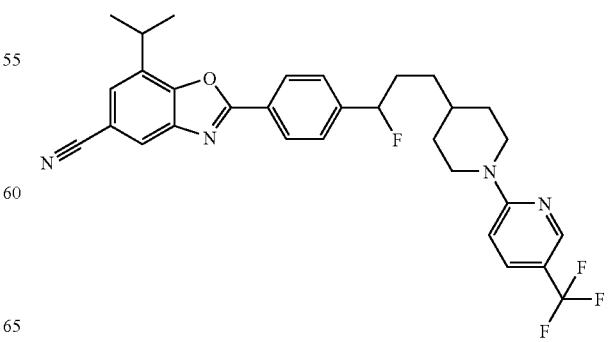

2-[4-(1-fluoro-3-{1-[5-(trifluoromethyl)pyridin-2-yl]
piperidin-4-yl}propyl)phenyl]-7-isopropyl-1,3-ben-
zoxazole-5-carbonitrile To a stirred solution of 2-[4-(1-hydroxy-3-{1-[5-(trifluorom-
ethyl)pyridin-2-yl]piperidin-4-yl}propyl)phenyl]-7-isopro-
pyl-1,3-benzoxazole-5-carbonitrile (EXAMPLE 510) (22
mg, 0.040 mmol) in DCM (2 ml) at RT, under nitrogen, was
added DAST (0.100 ml, 0.757 mmol). The resulting solution
was stirred for 2.5 hours, then, purified by TLC eluting twice
with 80:20 hexanes/EtOAc to afford the title compound.
Mass spectrum (ESI) 551.3 (M+1).

Intermediate 39

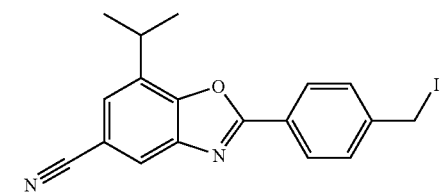

2-[4-(iodomethyl)phenyl]-7-isopropyl-1,3-benzox-
azole-5-carbonitrile

Step A: 2-[4-(chloromethyl)phenyl]-7-isopropyl-1,3-
benzoxazole-5-carbonitrile

A mixture of 3-amino-4-hydroxy-5-isopropylbenzonitrile
(INTERMEDIATE 36) 200 mg, 1.135 mmol) and 4-(chlo-
romethyl)benzoyl chloride (215 mg, 1.135 mmol) in 1,4-
dioxane (10 ml) was refluxed for 55 minutes, then concen-
trated, diluted with toluene (20 ml), added p-toluenesulfonic
acid monohydrate (21.59 mg, 0.113 mmol), and refluxed
overnight. The resulting mixture was concentrated and tritu-
rated with methanol to afford the title compound. Mass spec-
trum (ESI) 311.2 (M+1).

Step B: 2-[4-(iodomethyl)phenyl]-7-isopropyl-1,3-
benzoxazole-5-carbonitrile

A solution of 2-[4-(chloromethyl)phenyl]-7-isopropyl-1,3-
benzoxazole-5-carbonitrile (Step A) (229 mg, 0.737 mmol)
and sodium iodide (1104 mg, 7.37 mmol) in acetone (50 ml)
(solution at reflux) was heated at reflux for 4.5 hours, then,
concentrated in vacuo. 120 ml of hot DCM were added and
the solids were filtered washing with DCM. Dried the solids
in vacuo to afford the title compound. Mass spectrum (ESI)
402.98 (M+1).

Example 515

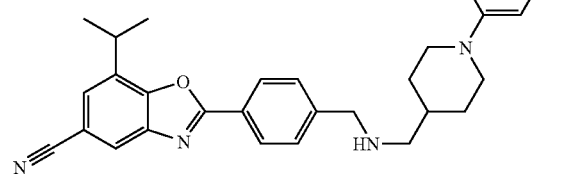

7-isopropyl-2-(4-{[({1-[4-(trifluoromethyl)phenyl]
piperidin-4-yl}methyl)amino]methyl}phenyl)-1,3-
benzoxazole-5-carbonitrile Step A: 1-{1-[4-(trifluoromethyl)phenyl]piperidin-4-
yl}methanamine A mixture of 4-(boc-aminomethyl)piperidine (300 mg, 1.400
mmol), 1-bromo-4-(trifluoromethyl)benzene (0.216 ml,
1.540 mmol), tris(dibenzylideneacetone)dipalladium (0)
(38.5 mg, 0.042 mmol), BINAP (52.3 mg, 0.084 mmol), and,
sodium t-butoxide (202 mg, 2.100 mmol) in toluene (5 ml)
was refluxed overnight. EtOAc and 1M HCl were added to the
reaction mixture and stirred at 50° C. for 2 hours. The reaction
mixture was then extracted 2 times with EtOAc and the organ-
ics were discarded. The aqueous layer was made basic with
5M NaOH and extracted 3 times with EtOAc. The combined
organics were dried over sodium sulfate and concentrated to
provide the title compound. Mass spectrum (ESI) 259.2
(M+1).

Step B: 7-isopropyl-2-(4-{[({1-[4-(trifluoromethyl)
phenyl]piperidin-4-yl}methyl)amino]
methyl}phenyl)-1,3-benzoxazole-5-carbonitrile A mixture of 1-{1-[4-(trifluoromethyl)phenyl]piperidin-4-
yl}methanamine (Step A) (32 mg, 0.124 mmol), 2-[4-(io-
domethyl)phenyl]-7-isopropyl-1,3-benzoxazole-5-carboni-
trile (INTERMEDIATE 39) (40 mg, 0.099 mmol), and
potassium carbonate (21.5 mg, 0.156 mmol) in DMF (1.5 ml)
was heated at 100° C. under nitrogen for 4 days. The reaction
mixture was concentrated, added water and extracted 3 times
with EtOAc. The combined organics were washed with brine,
dried over sodium sulfate, filtered, and the solvent was evapo-
rated under reduced pressure. The residue was purified by
flash column chromatography using a Horizon Biotage, 25M
Si column, eluting with 1 CV of DCM, followed by a linear
gradient of EtOAc in DCM from 0% to 100% over 10 CV, and
10 CV of EtOAc, and repurified by mass-directed RP HPLC,
Waters XBridge Prep C18, 19×100 mm column, eluting with
a gradient of MeCN (0.1% TFA) in water (0.1% TFA) from
10% to 100% over 12 minutes, to afford the title compound as
the TFA salt. Mass spectrum (ESI) 533.2 (M+1).

Example 516

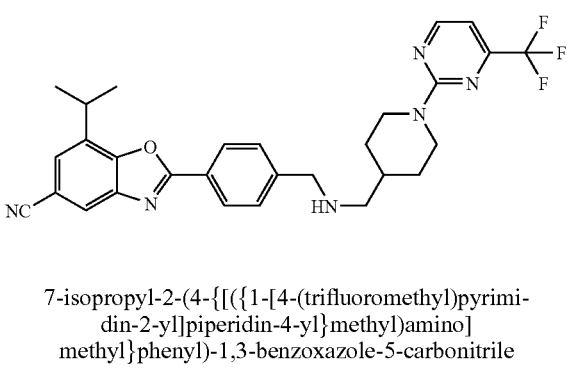

7-isopropyl-2-(4-{[({1-[4-(trifluoromethyl)pyrimi-
din-2-yl]piperidin-4-yl}methyl)amino]
methyl}phenyl)-1,3-benzoxazole-5-carbonitrile The title compound was prepared from 2-[4-(chloromethyl)
phenyl]-7-isopropyl-1,3-benzoxazole-5-carbonitrile
INTERMEDIATE 39, Step A) and 1-{1-[4-(trifluoromethyl)

pyrimidin-2-yl]piperidin-4-yl}methenamine by a procedure analogous to that described in EXAMPLE 515. Mass spectrum (ESI) 535.2 (M+1).

Example 517

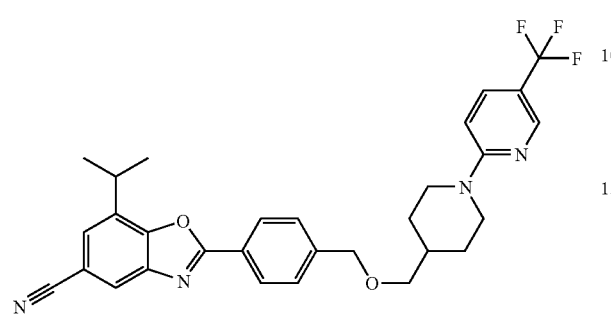

7-isopropyl-2-{4-[({1-[5-(trifluoromethyl)pyridin-2-yl]piperidin-4-yl}methoxy)methyl]phenyl}-1,3-benzoxazole-5-carbonitrile Step A: t-butyl-4-({[4-(5-cyano-7-isopropyl-1,3-benzoxazol-2-yl)benzyl]oxy}methyl)piperidine-1-carboxylate To a solution of 1-boc-4-piperidinemethanol (60 mg, 0.279 mmol) in THF (5 ml) at RT was added sodium hydride (60% in mineral oil) (15 mg, 0.375 mmol) under nitrogen and the resulting mixture was stirred for 35 minutes, then, 2-[4-(iodomethyl)phenyl]-7-isopropyl-1,3-benzoxazole-5-carbonitrile (INTERMEDIATE 39) (100 mg, 0.249 mmol) was added and the resulting mixture was stirred overnight, concentrated in vacuo and purified twice by flash column chromatography, then by TLC eluting 4 times with 80:20 hexanes/EtOAc to afford the title compound. Mass spectrum (ESI) 490.2 (M+1).

Step B: 7-isopropyl-2-{4-[(piperidin-4-ylmethoxy)methyl]phenyl}-1,3-benzoxazole-5-carbonitrile To a solution of t-butyl-4-({[4-(5-cyano-7-isopropyl-1,3-benzoxazol-2-yl)benzyl]oxy}methyl)piperidine-1-carboxylate (Step A) (40 mg, 0.082 mmol) in DCM (2 ml) at RT was added TFA (1 ml, 12.98 mmol) and the resulting solution was stirred for ca 15 minutes at RT and concentrated. The residue was purified by flash column chromatography using a Horizon Biotage, 25M Si column, eluting with 1 L of 10% ammonia (2M solution in methanol) in DCM to afford the title compound.

Step C: 7-isopropyl-2-{4-[({1-[5-(trifluoromethyl)pyridin-2-yl]piperidin-4-yl}methoxy)methyl]phenyl}-1,3-benzoxazole-5-carbonitrile A mixture of 7-isopropyl-2-{4-[(piperidin-4-ylmethoxy)methyl]phenyl}-1,3-benzoxazole-5-carbonitrile (Step B) (15 mg, 0.039 mmol) and 2-bromo-5-(trifluoromethyl)pyridine (8.70 mg, 0.039 mmol) in DBU (1 ml) was placed in a 100° C. oil bath and stirred (turned into solution) at this temperature for 1.75 hours. The reaction mixture was cooled to RT and purified by flash column chromatography using a Horizon Biotage, 25M Si column, eluting with 720 ml of 5% EtOAc in DCM to afford the title compound. Mass spectrum (ESI) 535.2 (M+1).

Example 518

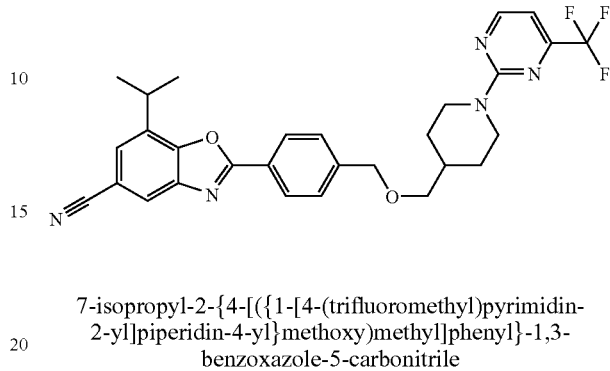

7-isopropyl-2-{4-[({1-[4-(trifluoromethyl)pyrimidin-2-yl]piperidin-4-yl}methoxy)methyl]phenyl}-1,3-benzoxazole-5-carbonitrile The title compound was prepared from 7-isopropyl-2-{4-[(piperidin-4-ylmethoxy)methyl]phenyl}-1,3-benzoxazole-5-carbonitrile (EXAMPLE 517, Step B) and 2-chloro-4-(trifluoromethyl)pyrimidine by a procedure analogous to that described in EXAMPLE 517, Step C. Mass spectrum (ESI) 536.2 (M+1).

Intermediate 40

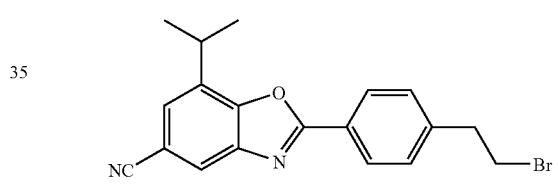

2-[4-(2-bromoethyl)phenyl]-7-isopropyl-1,3-benzoxazole-5-carbonitrile

The title compound was prepared from 3-amino-4-hydroxy-5-isopropylbenzonitrile (INTERMEDIATE 36) and 4-(2-bromoethyl)benzoic acid by a procedure analogous to that described in INTERMEDIATE 37, Step A. Mass spectrum (ESI) 370.96 (M+3).

Example 519

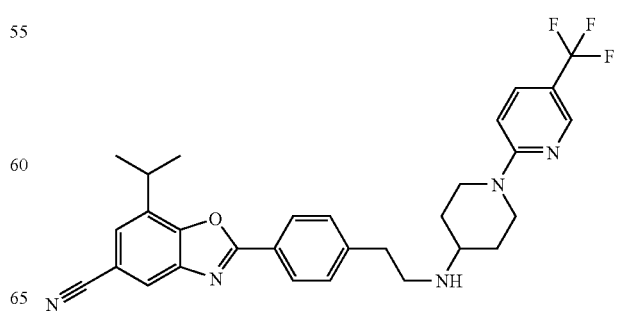

7-isopropyl-2-{4-[2-({1-[5-(trifluoromethyl)pyridin-2-yl]piperidin-4-yl}amino)ethyl]phenyl}-1,3-benzoxazole-5-carbonitrile Step A: tert-butyl {1-[5-(trifluoromethyl)pyridin-2-yl]piperidin-4-yl}carbamate A mixture of tert-butyl piperidin-4-ylcarbamate (500 mg, 2.497 mmol) and 2-bromo-5-(trifluoromethyl)pyridine (564 mg, 2.497 mmol) in DBU (5 ml) was placed in a 100° C. oil bath and stirred (turned into solution) at this temperature for 20 minutes. The reaction mixture was cooled to RT and purified by flash column chromatography using a Horizon Biotage, 40M Si column, eluting with 2 CV of DCM, followed by a linear gradient of EtOAc in DCM from 0% to 100% over 10 CV to collect the title compound. Mass spectrum (ESI) 346.1 (M+1).

Step B: 1-[5-(trifluoromethyl)pyridin-2-yl]piperidin-4-amine

A solution of tert-butyl {1-[5-(trifluoromethyl)pyridin-2-yl]piperidin-4-yl}carbamate (Step A) (0.794 g, 2.299 mmol) and TFA (10 ml, 130 mmol) in DCM (20 ml) was stirred at RT overnight, then, concentrated, added aqueous sodium hydrogen carbonate and extracted 3 times with ethyl acetate. The combined organics were washed with brine, dried over sodium sulfate, filtered, and the solvent was evaporated under reduced pressure to afford the title compound. Mass spectrum (ESI) 246.1 (M+1).

Step C: 7-isopropyl-2-{4-[2-({1-[5-(trifluoromethyl)pyridin-2-yl]piperidin-4-yl}amino)ethyl]phenyl}-1,3-benzoxazole-5-carbonitrile A solution of 2-[4-(2-bromoethyl)phenyl]-7-isopropyl-1,3-benzoxazole-5-carbonitrile (INTERMEDIATE 40) (77 mg, 0.209 mmol), 1-[5-(trifluoromethyl)pyridin-2-yl]piperidin-4-amine (Step B) (77 mg, 0.314 mmol), and DIPEA (0.073 ml, 0.417 mmol) in DMF (2 ml) was stirred under nitrogen at 50° C. for 3 days. Sat. aq. sodium bicarbonate was added and extracted 3 times with EtOAc. The combined organics were washed with brine, dried over sodium sulfate, filtered, and the solvent was evaporated under reduced pressure. The residue was purified by FCC using a Horizon Biotage, 25M Si column, eluting with 11 CV of EtOAc, followed by 11 CV of MeOH to afford the title compound. Mass spectrum (ESI) 534.2 (M+1).

Intermediate 41

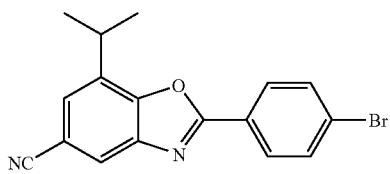

2-(4-bromophenyl)-7-isopropyl-1,3-benzoxazole-5-carbonitrile

The title compound was prepared from 3-amino-4-hydroxy-5-isopropylbenzonitrile (INTERMEDIATE 36) and 4-bromobenzoyl chloride by a procedure analogous to that described in INTERMEDIATE 37, Step A. Mass spectrum (ESI) 342.9 (M+3).

Example 520

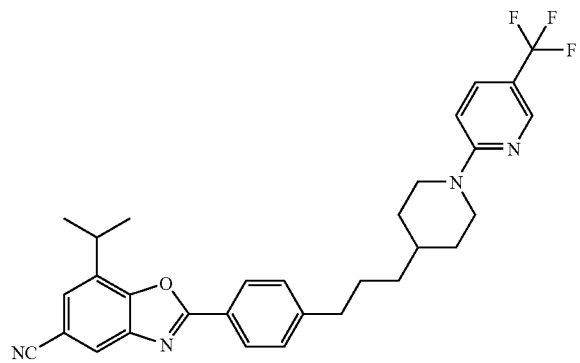

7-isopropyl-2-[4-(3-{1-[5-(trifluoromethyl)pyridin-2-yl]piperidin-4-yl}propyl)phenyl]-1,3-benzoxazole-5-carbonitrile Step A: t-butyl 4-[3-(trimethylsilyl)prop-2-yn-1-yl]piperidine-1-carboxylate The title compound was prepared from t-butyl 4-(2-oxoethyl)piperidine-1-carboxylate by a procedure analogous to that described in INTERMEDIATE 38, Step C and EXAMPLES 509, 510, Step A.

Step B: t-bytyl-4-{3-[4-(5-cyano-7-isopropyl-1,3-benzoxazol-2-yl)phenyl]prop-2-yn-1-yl}piperidine-1-carboxylate A mixture of palladium (II) acetate (27.1 mg, 0.040 mmol), 1,3-bis(2,4,6-trimethylphenyl)imidazolium chloride (27.4 mg, 0.080 mmol), and cesium carbonate (873 mg, 2.68 mmol) in DMA (5 ml) was stirred at RT under nitrogen for 15 minutes. 2-(4-bromophenyl)-7-isopropyl-1,3-benzoxazole-5-carbonitrile (INTERMEDIATE 41) (457 mg, 1.339 mmol) was added followed by a solution of t-butyl 4-[3-(trimethylsilyl)prop-2-yn-1-yl]piperidine-1-carboxylate (Step A) (435 mg, 1.473 mmol) in DMA (6 ml). The resulting mixture was heated at 80° C. overnight. Added sat. aq. sodium bicarbonate to the reaction mixture and extracted 3 times with EtOAc. The combined organics were washed with brine, dried over sodium sulfate, filtered, and the solvent was evaporated under reduced pressure. Purified by flash column chromatography using a Horizon Biotage, 40M Si column, eluting with 1 CV of 2% EtOAc in hexanes, followed by a linear gradient of EtOAc in hexanes from 2% to 100% over 10 CV to afford the title compound. Mass spectrum (ESI) 428.1 (M+1 minus t-Bu).

Step C: 7-isopropyl-2-[4-(3-piperidin-4-ylprop-1-yn-1-yl)phenyl]-1,3-benzoxazole-5-carbonitrile A solution of t-bytyl-4-{3-[4-(5-cyano-7-isopropyl-1,3-benzoxazol-2-yl)phenyl]prop-2-yn-1-yl}piperidine-1-carboxylate (Step B) (53 mg, 0.110 mmol) and TFA (200 µL, 2.60 mmol) in DCM (2 ml) was stirred at RT for 1 hour, then, concentrated, added aqueous sodium hydrogen carbonate and extracted 3 times with ethyl acetate. The combined organics were washed with brine, dried over sodium sulfate, filtered, and the solvent was evaporated under reduced pressure to afford the title compound. Mass spectrum (ESI) 384.2 (M+1).

Step D: 7-isopropyl-2-[4-(3-{1-[5-(trifluoromethyl) pyridin-2-yl]piperidin-4-yl}prop-1-yn-1-yl)phenyl]-1,3-benzoxazole-5-carbonitrile A solution of 7-isopropyl-2-[4-(3-piperidin-4-ylprop-1-yn-1-yl)phenyl]-1,3-benzoxazole-5-carbonitrile (Step C) (19 mg, 0.050 mmol) and 2-bromo-5-(trifluoromethyl)pyridine (25 mg, 0.111 mmol) in DBU (1 ml) was stirred at 40° C. for 2.5 hours, then, at RT for 3 days. It was then purified by flash column chromatography using a Horizon Biotage, 25M Si column, eluting with 120 ml of DCM, followed by 720 ml of 5% EtOAc in DCM to afford the title compound. Mass spectrum (ESI) 529.2 (M+1).

Step E: 7-isopropyl-2-[4-(3-{1-[5-(trifluoromethyl) pyridin-2-yl]piperidin-4-yl}propyl)phenyl]-1,3-benzoxazole-5-carbonitrile To a solution of 7-isopropyl-2-[4-(3-{1-[5-(trifluoromethyl) pyridin-2-yl]piperidin-4-yl}prop-1-yn-1-yl)phenyl]-1,3-benzoxazole-5-carbonitrile (Step D) (26 mg, 0.049 mmol) in EtOAc (3 ml)/THF (3 ml) was added 26 mg of 10% Pd/C and the resulting mixture was degassed and flushed with nitrogen, following by degassing and flushing with hydrogen using a double balloon. It was stirred under hydrogen overnight, then, flushed with nitrogen, diluted with EtOAc, filtered, and concentrated. The residue was purified by flash column chromatography using a Horizon Biotage, 25M Si column, eluting with 1 CV of 2% EtOAc in hexanes, followed by a linear gradient of EtOAc in hexanes from 2% to 100% over 10 CV to afford the title compound. Mass spectrum (ESI) 533.2 (M+1).

Example 521

Added another 3 ml of THF and the chunky mixture was stirred for 30 minutes. A solution of {1-[5-(trifluoromethyl) pyridin-2-yl]piperidin-4-yl}methanol (INTERMEDIATE 38, Step A) (200 mg, 0.768 mmol) and thioacetic acid (0.110 ml, 1.537 mmol) in THF (3 ml) was added dropwise. The resulting mixture was stirred at 0° C. for 1 hour, then, at RT for 1 hour. It was then concentrated and purified twice by flash column chromatography eluting, first with EtOAc in hexanes, then, with DCM to afford the title compound. Mass spectrum (ESI) 319.7 (M+1).

Step B: 7-isopropyl-2-(4-{[({1-[5-(trifluoromethyl) pyridin-2-yl]piperidin-4-yl}methyl)thio] methyl}phenyl)-1,3-benzoxazole-5-carbonitrile To a solution of S—({1-[5-(trifluoromethyl)pyridin-2-yl]piperidin-4-yl}methyl)ethanethioate (Step A) (60 mg, 0.188 mmol) in THF (2 ml) at RT under nitrogen was added sodium methoxide (0.5 M solution in MeOH) (0.415 ml, 0.207 mmol). After 1 hr 20 minutes added 2-[4-(chloromethyl)phenyl]-7-isopropyl-1,3-benzoxazole-5-carbonitrile (INTERMEDIATE 39, Step A) (46.9 mg, 0.151 mmol) followed by DIPEA (0.100 ml, 0.574 mmol). The reaction mixture was stirred at RT overnight, concentrated, and purified by flash column chromatography using a Horizon Biotage, 25M Si column, eluting with 2 CV of hexanes, followed by a linear gradient of EtOAc in hexanes from 0% to 70% over 10 CV to afford the title compound. Mass spectrum (ESI) 551.2 (M+1).

Example 522

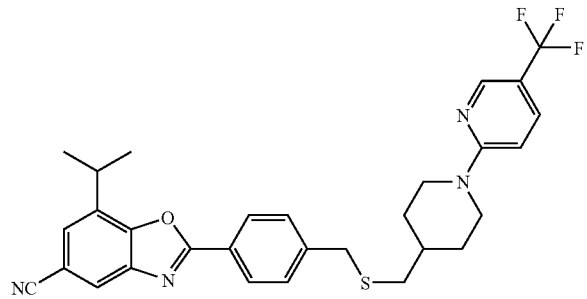

7-isopropyl-2-{4-[2-({1-[5-(trifluoromethyl)pyridin-2-yl]piperidin-4-yl}thio)ethyl]phenyl}-1,3-benzoxazole-5-carbonitrile The title compound was prepared from piperidin-4-ol, 2-bromo-5-(trifluoromethyl)pyridine, and 2-[4-(2-bromoethyl)phenyl]-7-isopropyl-1,3-benzoxazole-5-carbonitrile (INTERMEDIATE 39) by a procedure analogous to that described in INTERMEDIATE 38, Step A and EXAMPLE 521. Mass spectrum (ESI) 551.2 (M+1).

Intermediate 42

7-isopropyl-2-(4-{[({1-[5-(trifluoromethyl)pyridin-2-yl]piperidin-4-yl}methyl)thio]methyl}phenyl)-1,3-benzoxazole-5-carbonitrile Step A: S—({1-[5-(trifluoromethyl)pyridin-2-yl] piperidin-4-yl}methyl)ethanethioate To a solution of triphenylphosphine (403 mg, 1.537 mmol) in THF (1 ml) at 0° C. was added DIAD (0.299 ml, 1.537 mmol) under nitrogen and the resulting mixture was stirred at 0° C.

2-(4-iodophenyl)-7-isopropyl-1,3-benzoxazole-5-carbonitrile

The title compound was prepared from 3-amino-4-hydroxy-5-isopropylbenzonitrile (INTERMEDIATE 36) and 4-iodobenzoyl chloride by a procedure analogous to that described in INTERMEDIATE 37, Step A. Mass spectrum (ESI) 388.9 (M+1).

Example 523

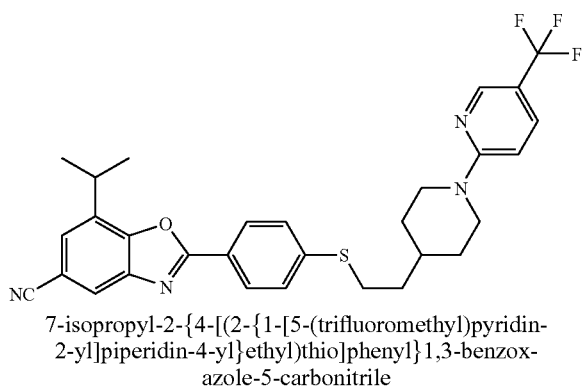

7-isopropyl-2-{4-[(2-{1-[5-(trifluoromethyl)pyridin-2-yl]piperidin-4-yl}ethyl)thio]phenyl}-1,3-benzoxazole-5-carbonitrile To a solution of S-(2-{1-[5-(trifluoromethyl)pyridin-2-yl]piperidin-4-yl}ethyl)ethanethioate (prepared from 2-piperidin-4-ylethanol and 2-bromo-5-(trifluoromethyl)pyridine by a procedure analogous to that described in INTERMEDIATE 38, Step A and EXAMPLE 521, Step A) (59.9 mg, 0.180 mmol) in THF (2 ml) was added sodium methoxide (0.5M solution in methanol) (0.397 ml, 0.199 mmol) and the resulting solution was stirred under nitrogen for 1 hour, then, concentrated. To a mixture of the thiol in toluene (1.5 ml) was added NaHMDS (0.6M in toluene) (0.301 ml, 0.180 mmol) and DME (1.5 ml) (to help with solubility). In a separate flask had been mixed palladium acetate (10 mg, 0.015 mmol), 2-(4-iodophenyl)-7-isopropyl-1,3-benzoxazole-5-carbonitrile (INTERMEDIATE 42) (50 mg, 0.129 mmol), and (R)-Tol-BINAP (13 mg, 0.019 mmol) in toluene (1 ml). After 20 minutes the catalyst mixture was added to the one above, washing the flask with toluene (1 ml). The resulting mixture was heated to 100° C. overnight under nitrogen, then, cooled to RT, diluted with EtOAc, and washed with 2M aqueous sodium hydroxide, followed by brine. The aqueous layers were combined and extracted one more time with EtOAc. Then, the combined organic layers were dried over sodium sulfate, filtered, and the solvent was evaporated under reduced pressure. The residue was purified by FCC using a Horizon Biotage, 25M Si column, eluting with 3 CV of hexanes, followed by a linear gradient of EtOAc in hexanes from 0% to 80% over 10 CV to afford the title compound. Mass spectrum (ESI) 551.2 (M+1).

Intermediate 43

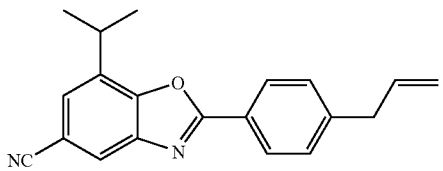

2-(4-allylphenyl)-7-isopropyl-1,3-benzoxazole-5-carbonitrile

To a solution of the 4-allylbenzoic acid (649 mg) in 150 mL of methylene chloride was added 6.0 mL of a 2M solution of oxalyl chloride. To this was added ~30 uL of DMF. After stirring for 15 minutes, acyl chloride formation was complete. The solution was concentrated in vacuo and the residue was taken up in 80 mL of dioxane and added to a solution of 705 mg of the 3-amino-4-hydroxy-5-isopropylbenzonitrile (INTERMEDIATE 36) in 70 mL of dioxane. To this mixture was immediately added 4.18 mL of Hunig's base. The mixture was heated to 50° C. for 1 hour, whereupon LC/MS analysis showed complete formation of desired acylated product along with a very small formation of the bis-acylated amino phenol. This mixture was concentrated in vacuo and the residue was dissolved in 400 mL of toluene. This was fitted with a Dean Stark trap and reflux condenser and heated to reflux for 12 hours. LC/MS showed ~80% product formation along with 20% of the bisacylated intermediate. Further heating for 8 hours more resulted in no change, so the reaction was worked up by concentration of the solution in vacuo and the filtering of the residue through a plug of silica gel. The residue, after concentration in vacuo, was purified via column chromatography to afford the title compound. Mass spectrum (ESI) 303.1 (M+1). $^1$H NMR (500 MHz, CDCl$_3$) δ: 8.19 (d, J=8.3 Hz, 2H1H), 7.90 (d, J=1.4 Hz, 1H), 7.47 (d, J=1.3 Hz, 1H), 7.39 (d, J=8.2 Hz, 1H), 5.99 (m, 1H), 5.14 (dd, J=17.5, 1.6 Hz, 1H), 5.13 (dd, J=8.6, 1.6 Hz, 1H), 3.50 (d, J=6.8 Hz, 2H), 3.46 (sept, J=7.1 Hz, 1H), 1.45 (d, J=7.1 Hz, 6H).

Intermediate 44

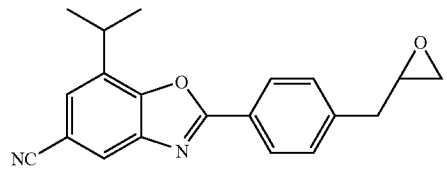

7-isopropyl-2-[4-(oxiran-2-ylmethyl)phenyl]-1,3-benzoxazole-5-carbonitrile

To a mixture of 2-(4-allylphenyl)-7-isopropyl-1,3-benzoxazole-5-carbonitrile (723 mg) (INTERMEDIATE 43) and acetonitrile (252 uL) in methylene chloride was slowly added hydrogen peroxide (406 uL) (which was pre-treated with K$_2$HPO$_4$ prior to adding to adjust its pH to ~7). The biphasic mixture was then stirred at room temp under N$_2$ for 24 hours. Analysis of the crude mixture showed ~80% product formation. The reaction was then concentrated in vacuo and the residue purified by column chromatography, FCC Horizon 288 0% EtOAc in hexanes (1 column vol) to 50% EtOAc (over 10 column volumes), then held at 50% EtOAc for 5 column volumes, to afford the title compound. Mass spectrum (ESI) 319.1 (M+1). $^1$H NMR (500 MHz, CDCl$_3$) δ: 8.21 (d, J=8.0 Hz, 2H), 7.91 (d, J=1.3 Hz, 1H), 7.48 (d, J=1.3 Hz, 1H), 7.46 (d, J=8.3 Hz, 2H), 3.46 (sept, J=7.1 Hz, 1H), 3.22

(m, 1H), 3.02 (dd, J=14.6, 4.6 Hz, 1H), 2.94 (dd, J=14.8, 6.2 Hz, 1H), 2.849 (t, J=4.6 Hz, 1H), 2.58 (dd, J=4.8, 2.2 Hz, 1H), 1.45 (d, J=7.1 Hz, 6H).

Example 524

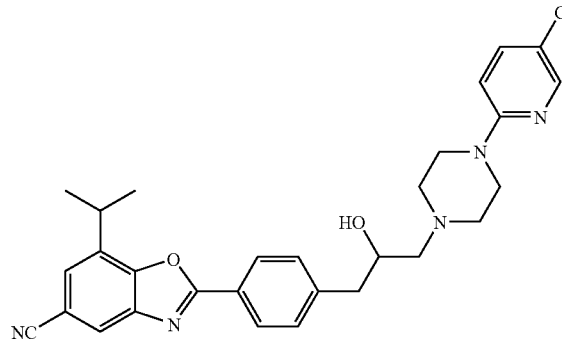

2-[4-(2-hydroxy-3-{4-[5-(trifluoromethyl)pyridin-2-yl]piperazin-1-yl}propyl)phenyl]-7-isopropyl-1,3-benzoxazole-5-carbonitrile A mixture of 7-isopropyl-2-[4-(oxiran-2-ylmethyl)phenyl]-1,3-benzoxazole-5-carbonitrile (INTERMEDIATE 44) (33 mg) and 1-[5-(trifluoromethyl)pyridin-2-yl]piperazine (26 mg) in ethanol (5 mL) was stirred at 90° C. under N₂ for 5 hours. The mixture was then concentrated in vacuo and the resultant solid was purified via prep-plate TLC (R$_f$=0.42 in 2:1 hexane:EtOAc) to provide the title compound as an off-white solid. Mass spectrum (ESI) 550.3 (M+1). $^1$H NMR (500 MHz, CDCl₃) δ: 8.39 (s, 1H), 7.91 (d, J=1.3 Hz, 1H), 8.20 (d, J=8.0 Hz, 2H), 7.91 (s, 1H), 7.62 (dd, J=8.9, 2.0 Hz, 1H), 7.48 (s, 1H), 7.46 (d, J=8.0 Hz, 2H), 6.63 (d, J=8.9 Hz, 1H), 4.04 (m, 1H), 3.65 (m, 4H), 3.45 (sept, J=6.9 Hz, 1H), 2.91 (m, 4H), 2.48 (m, 4H), 2.94 (dd, J=14.8, 6.2 Hz, 1H), 1.45 (d, J=7.1 Hz, 6H).

Following the procedure described in EXAMPLE 524, the compounds listed in Table 17 were prepared:

TABLE 17

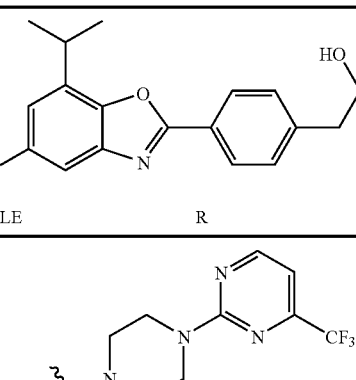

| EXAMPLE | R | MS (M + 1) |
|---|---|---|
| 525 | 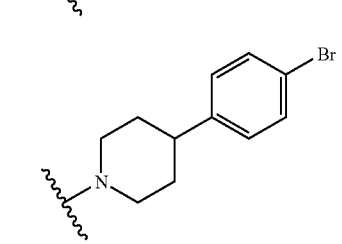 (4-CF₃-phenyl-piperazinyl) | 549.3 |

TABLE 17-continued

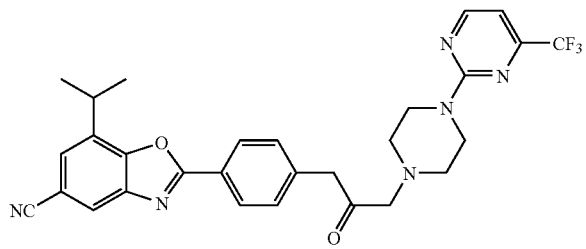

| EXAMPLE | R | MS (M + 1) |
|---|---|---|
| 526 | 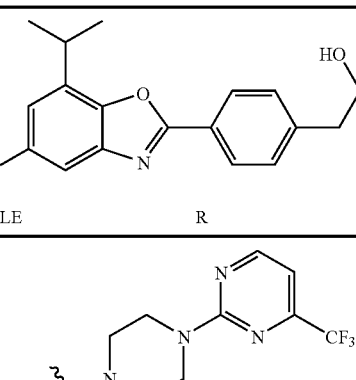 (4-CF₃-pyrimidin-2-yl-piperazinyl) | 551.4 |
| 527 | 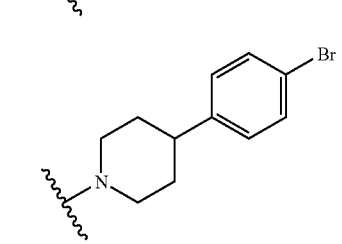 (4-Br-phenyl-piperidinyl) | 559.9 |

Example 528

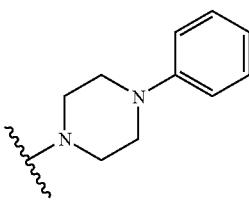

7-isopropyl-2-[4-(2-oxo-3-{4-[4-(trifluoromethyl)pyrimidin-2-yl]piperazin-1-yl}propyl)phenyl]-1,3-benzoxazole-5-carbonitrile To a mixture of 20% w/w of PCC in basic alumina (216 mg) in 4 mL of methylene chloride was added 2-[4-(2-hydroxy-3-{4-[4-(trifluoromethyl)pyrimidin-2-yl]piperazin-1-yl}propyl)phenyl]-7-isopropyl-1,3-benzoxazole-5-carbonitrile (EXAMPLE 526) (55 mg). The reaction was stirred at room temp for 24 h, the reaction was checked by LC/MS which showed ~55% conversion to the desired product after 12 h and no increase in conversion after this. Purification was accomplished via FLEX HPLC (Cromasil 100×20 mm C18 column, solvent gradient: 10-90% acetonitrile in water (0.1% TFA)) providing a minor fraction that was pure product. This was concentrated in vacuo, taken up in 5 mL ethyl acetate and washed with 5 mL sat. NaHCO₃. The organic layer was then filtered and concentrated in vacuo to provide the title compound. Mass spectrum (ESI) 549.2 (M+1). $^1$H NMR (500 MHz, CDCl₃) δ: 8.48 (d, J=4.8 Hz, 1H), 8.23 (d, J=8.3 Hz, 2H), 7.92 (d, J=1.4 Hz, 1H), 7.49 (s, 1H), 7.45 (d, J=8.3 Hz, 2H), 6.76 (d, J=4.8 Hz, 1H), 3.92 (m, 6H), 3.45 (sept, J=6.9 Hz, 1H), 3.31 (s, 2H), 2.55 (t, J=5.0 Hz, 4H) 1.45 (d, J=6.9 Hz, 6H).

Example 529

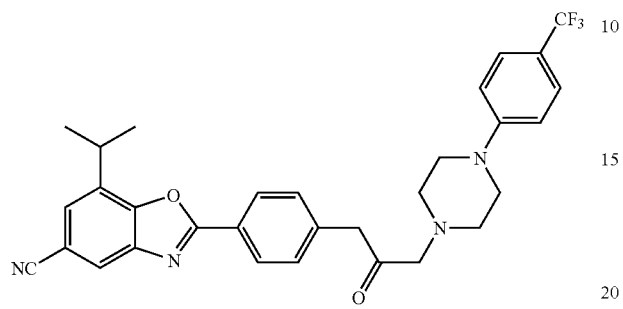

7-isopropyl-2-[4-(2-oxo-3-{4-[4-(trifluoromethyl) phenyl]piperazin-1-yl}propyl)phenyl]-1,3-benzoxazole-5-carbonitrile To a mixture of 20% w/w of PCC in basic alumina (216 mg) in 4 mL of methylene chloride was added 2-[4-(2-hydroxy-3-{4-[4-(trifluoromethyl)phenyl]piperazin-1-yl}propyl)phenyl]-7-isopropyl-1,3-benzoxazole-5-carbonitrile (EXAMPLE 525) (55 mg). The reaction was stirred at room temp for 24 h. Purification was accomplished via FLEX HPLC (Cromasil 100×20 mm C18 column, solvent gradient: 10-90% acetonitrile in water (0.1% TFA)) providing a minor fraction that was pure product. This was concentrated in vacuo, taken up in 5 mL ethyl acetate and washed with 5 mL sat. NaHCO$_3$. The organic layer was then filtered and concentrated in vacuo to provide the title compound. Mass spectrum (ESI) 547.3 (M+1). $^1$H NMR (500 MHz, CDCl$_3$) δ: 8.23 (d, J=8.0 Hz, 2H), 7.91 (s, 1H), 7.46 (m, 5H), 6.92 (d, J=9.0 Hz, 2H), 3.92 (s, 2H), 3.44 (sept, J=6.9 Hz, 1H), 3.33 (m, 6H), 2.62 (m, 4H) 1.45 (d, J=7.1 Hz, 6H).

Example 530

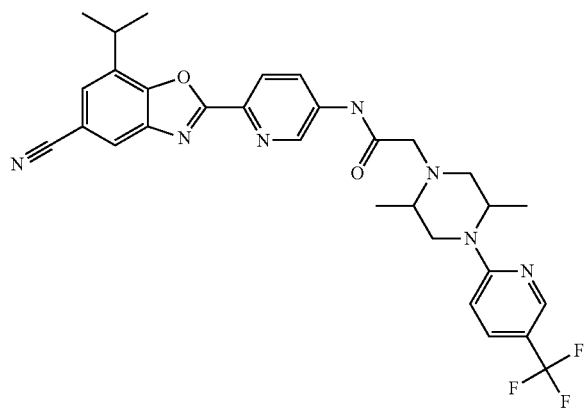

N-[6-(5-cyano-7-isopropyl-1,3-benzoxazol-2-yl) pyridin-3-yl]-2-{2,5-dimethyl-4-[5-(trifluoromethyl) pyridin-2-yl]piperazin-1-yl}acetamide Step A: 7-Isopropyl-1,3-benzoxazole-5-carbonitrile A solution of 3-amino-4-hydroxy-5-isopropylbenzonitrile (400 mg, 2.27 mmol, from INTERMEDIATE 36) in trimethyl orthoformate (111 mL, 100 mmol) was heated to 110° C. for 72 h. After the solution was cooled to room temperature, concentration, followed by flash chromatography on biotage silica gel column (mobile phase 0-30% ethyl acetate/hexanes for 10 column volumes and 30% for 5 column volumes) afforded the title compound as an off-white solid. LC/MS: m/z 187.0 (M+1).

Step B: 2,5-Dimethyl-1-[5-(trifluoromethyl)pyridin-2-yl]piperazine

To a solution of trans-2,5-dimethylpiperazine (2.14 g, 18.7 mmol) and 2-chloro-5-(trifluoromethyl)pyridine (1.70 g, 9.36 mmol) in DMF was added potassium carbonate (1.94 g, 14.05 mmol). The reaction was heated at 120° C. for 24 h. Concentration, followed by flash chromatography on a Biotage silica gel column (mobile phase gradient of 50% to 100% ethyl acetate in hexanes over 10 column volumes, followed by a gradient of 10% to 50% methanol in dichloromethane over 5 column volumes) afforded the title compound as a brown oil. LC/MS: m/z 260 (M+1).

Step C: tert-Butyl-2,5-dimethyl-4-[5-(trifluoromethyl)pyridin-2-yl]piperazine-1-carboxylate To a solution of 2,5-dimethyl-1-[5-(trifluoromethyl)pyridin-2-yl]piperazine (1.19 g, 4.59 mmol, from Step B) in dichloromethane (15 mL) was added di-tert-butyl dicarbonate (1.00 g, 4.59 mmol), followed by N,N-diisopropylethyl amine (0.963 mL, 5.51 mmol). The reaction was stirred at room temperature for 1 h. The mixture was partitioned b/t dichloromethane and saturated sodium bicarbonate solution, extracted with dichloromethane (3×), washed w/brine, dried over magnesium sulfate, filtered and concentrated. Flash chromatography on a Biotage silica gel column (mobile phase gradient of 0% to 25% ethyl acetate in hexanes over 10 column volumes) afforded 1.2531 grams of a mixture of trans enantiomers. Chiral separation on the normal phase Gilson via an OD chiral column using 2.5% of isopropanol in heptane afforded 524.8 mg of the faster-eluting enantiomer and 505.3 mg of the slower-eluting enantiomer. LC/MS (faster eluting): m/z 304 (M+1-t-butyl), m/z 260 (M+1-Boc); LC/MS (slower eluting): m/z 304 (M+1-t-butyl), m/z 260 (M+1-Boc).

Step D: 2,5-Dimethyl-1-[5-(trifluoromethyl)pyridin-2-yl]piperazine hydrochloride To a solution of tert-Butyl-2,5-dimethyl-4-[5-(trifluoromethyl)pyridin-2-yl]piperazine-1-carboxylate (524.8 mg, 1.46 mmol, the faster-eluting enantiomer from Step C) in MeOH (3.0 mL) was added saturated hydrochloric acid in methanol (3.0 mL). The reaction stirred at room temperature for 1 h. Concentration afforded the title compound as a white solid. $^1$H NMR (500 MHz, CD$_3$OD) δ 8.42 (s, 1H), 7.97 (dd, 1H, J=2.3, 9.1 Hz), 7.17 (d, 1H, J=9.1), 4.84 (br s, 1H), 4.30 (dd, 1H, J=2.7, 14.8 Hz), 3.91-3.85 (m, 1H), 3.50 (dd, 1H, J=3.6, 14.6 Hz), 3.62 (dd, 1H, J=5.3, 13.5 Hz), 1.40-1.48 (m, 6H).

Step E: 2-Bromo-N-(6-bromopyridin-3-yl)acetamide

To a solution of 3-amino-6-bromopyridine (5.32 g, 30.78 mmol) in dichloromethane at 0° C. was added by N,N-diisopropylethyl amine (6.23 mL, 36.9 mmol), followed by bromoacetyl bromide (3.23 mL, 36.9 mmol). The mixture was heated from 0° C. to room temperature over 18 h. Starting material remained, so more bromoacetyl bromide (3.23 mL, 36.9 mmol) was added, and the reaction stirred at room temperature for an additional 3 h. The mixture was partitioned between ethyl acetate and saturated sodium bicarbonate solution, extracted with ethyl acetate (3×), washed w/brine, dried over magnesium sulfate, filtered and concentrated. Flash chromatography on a Biotage silica gel column (mobile phase gradient of 5% to 30% ethyl acetate in hexanes) afforded the title compound as a white solid. LC/MS: m/z 295 (M+1), m/z 297 (M+3).

Step F: N-(6-bromopyridin-3-yl)-2-{2,5-dimethyl-4-[5-(trifluoromethyl)pyridin-2-yl]piperazin-1-yl}acetamide To a solution of 2,5-dimethyl-1-[5-(trifluoromethyl)pyridin-2-yl]piperazine hydrochloride (80.0 mg, 0.241 mmol, Step D) in DMF was added 2-bromo-N-(6-bromopyridin-3-yl)acetamide (70.8 mg, 0.241 mmol, Step E). The mixture was stirred at 60° C. for 2 h. Concentration in vacuo, followed by flash chromatography on a Biotage silica column (mobile phase gradient of 5%-50% ethyl acetate in hexanes) afforded the title compound as a white solid. LC/MS: mz/z 473 (M+1).

Step G: N-[6-(5-cyano-7-isopropyl-1,3-benzoxazol-2-yl)pyridin-3-yl]-2-{2,5-dimethyl-4-[5-(trifluoromethyl)pyridin-2-yl]piperazin-1-yl}acetamide In a procedure similar to, but slightly modified from, that described in the literature (B. Sezen and D. Sames, Org. Lett., 2003, 5, 3607), palladium (II) acetate (1.81 mg, 0.008 mmol), 1,3-bis(2,4,6-trimethylphenyl)imidazolium chloride (5.49 mg, 0.016 mmol), and tripotassium phosphate (3.42 mg, 0.016 mmol, Step D) were combined in dioxane (0.250 mL) and stirred in a sealed tube filled with argon at room temperature for 10 minutes. To the mixture was added 7-isopropyl-1,3-benzoxazole-5-carbonitrile (30.0 mg, 0.161 mmol, Step A), cesium carbonate (63.0 mg, 0.193 mmol), copper (I) iodide (6.14 mg, 0.032 mmol), and N-(6-bromopyridin-3-yl)-2-{2,5-dimethyl-4-[5-(trifluoromethyl)pyridin-2-yl]piperazin-1-yl}acetamide (91 mg, 0.193 mmol, Step F), along with another 0.250 mL dioxane. The reaction tube was filled again with argon and heated at 120° C. for 7 h. The reaction mixture was cooled to room temperature, partitioned between ethyl acetate and saturated sodium bicarbonate solution, extracted with ethyl acetate (3×), washed with brine, dried over magnesium sulfate, filtered and concentrated. Prep TLC in 75% ethyl acetate/hexanes afforded the title compound as a tan solid. LC/MS: m/z 578 (M+1).

Example 531

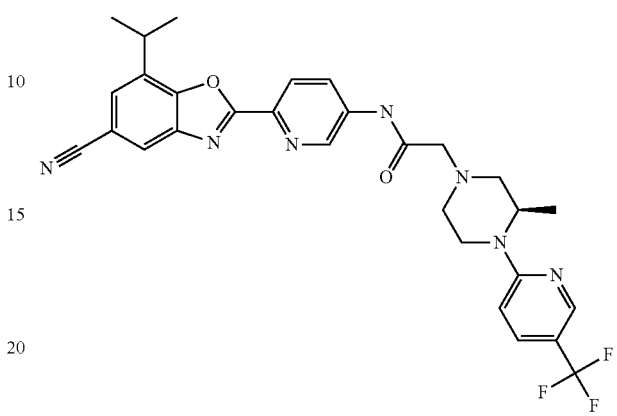

N-[6-(5-cyano-7-isopropyl-1,3-benzoxazol-2-yl)pyridin-3-yl]-2-{(3R)-3-methyl-4-[5-(trifluoromethyl)pyridin-2-yl]piperazin-1-yl}acetamide Step A: 5-[(tert-Butoxycarbonyl)amino]pyridine-2-carboxylic acid To a solution of 5-aminopyridine-2-carboxylic acid (4.50 g, 32.6 mmol), prepared from 5-aminopyridine-2-carbonitrile using a procedure analogous to that described in the literature (R. T. Shuman et al., J. Org. Chem., 1973, 38, 2049), in 180 mL of methanol: dichloromethane:tetrahydrofuran (16:1:1) was added di-tert-butyl dicarbonate (10.67 g, 48.9 mmol), followed by N,N-diisopropylethyl amine (5.68 mL, 32.6 mmol). The reaction mixture was stirred at room temperature for 168 h. Concentration was followed by acidification by 1N potassium bisulfate to pH=2. The aqueous solution was extracted with ethyl acetate (3×), washed with brine, dried over magnesium sulfate, and concentrated to give the title compound as a white solid. LC-MS: m/z 239 (M+1).

Step B: tert-Butyl-5-amino-N-(5-cyano-2-hydroxy-3-isopropylphenyl)pyridine-2-carboxylate To a solution of 5-[(tert-Butoxycarbonyl)amino]pyridine-2-carboxylic acid (600 mg, 2.52 mmol, Step A) suspended in dichloromethane (10 mL) was added oxalyl chloride (0.331 mL, 3.78 mmol) and DMF (0.010 mL, 0.126 mmol), respectively. The reaction mixture stirred at room temperature for 2 h. The reaction mixture was concentrated and co-evaporated with toluene (3×20 mL) and diluted w/1,4-dioxane (10 mL). To the solution was added 3-amino-4-hydroxy-5-isopropyl-benzonitrile (533 mg, 3.02 mmol, from INTERMEDIATE 36). After heating at reflux for 18 h, the mixture was partitioned between ethyl acetate and water, extracted with ethyl acetate (3×), washed with brine, dried over magnesium sulfate, filtered and concentrated. Flash chromatography on a Biotage silica gel column (mobile phase gradient of 5% to 50% ethyl acetate/hexanes) afforded the title compound as a tan solid. LC/MS: m/z 397 (M+1), m/z 341 (M+1-t-butyl), m/z 297 (M+1-Boc).

Step C: 2-(5-aminopyridin-2-yl)-7-isopropyl-1,3-benzoxazole-5-carbonitrile

To a solution of tert-Butyl-5-amino-N-(5-cyano-2-hydroxy-3-isopropylphenyl)pyridine-2-carboxylate (375 mg, 0.946 mmol, Step B) in toluene was added p-toluenesulfonic acid monohydrate (540 mg, 2.84 mmol) and heated to reflux for 7 h. After cooling to room temperature, saturated sodium bicarbonate solution was added, and the mixture was extracted with ethyl acetate (3x). The combined organic fractions were washed with brine, dried over magnesium sulfate, filtered, and concentrated. Flash chromatography on a Biotage silica gel column (mobile phase gradient 50%-100% ethyl acetate/hexanes over 10 column volumes, followed by 100% ethyl acetate over 10 column volumes) afforded the title compound as a white powder. LC/MS: nm/z 279 (M+1).

Step D: 2-bromo-N-[6-(5-cyano-7-isopropyl-1,3-benzoxazol-2-yl)pyridin-3-yl]acetamide To a solution of 2-(5-aminopyridin-2-yl)-7-isopropyl-1,3-benzoxazole-5-carbonitrile (77 mg, 0.277 mmol, Step C) in dichloromethane (15 mL) was added N,N-diisopropylethyl amine (0.058 mL, 0.322 mmol). The mixture was cooled to 0° C. Bromoacetyl bromide (0.029 mL, 0.332 mmol) was added dropwise, and the reaction mixture stirred and warmed to room temperature over 18 h. The mixture was concentrated and partitioned between ethyl acetate and saturated sodium bicarbonate solution. The crude mixture was then extracted with ethyl acetate (3x), washed with brine, dried over magnesium sulfate, filtered and concentrated to afford the title compound as a tan solid. LC/MS: m/z 400 (M+1).

Step E: tert-Butyl (3R)-3-methylpiperazine-1-carboxylate

To a solution of R-2-methylpiperazine (800 mg, 7.99 mmol) in dichloromethane (40 mL) was added di-tert-butyl dicarbonate (1.743 g, 7.99 mmol), followed by N,N-diisopropylethyl amine (1.674 mL, 9.58 mmol). The reaction mixture stirred at room temperature for 3 days. The mixture was partitioned between dichloromethane and saturated sodium bicarbonate solution, extracted with dichloromethane (3x), washed with brine, dried over magnesium sulfate, filtered and concentrated to afford the title compound. $^1$H NMR (500 MHz, CDCl$_3$) δ 3.77-4.20 (m, 2H), 2.85-3.05 (m, 1H), 2.65-2.83 (m, 2H), 2.30-2.50 (m, 1H), 1.55-1.75 (m, 1H), 1.43-1.55 (m, 9H), 1.04 (d, 3H, J=6.4 Hz).

Step F: tert-Butyl (3R)-3-methyl-4-[5-(trifluoromethyl)pyridin-2-yl]piperazine-1-carboxylate To a solution of tert-butyl (3R)-3-methylpiperazine-1-carboxylate (500 mg, 2.50 mmol, Step E) and 2-chloro-5-(trifluoromethyl)pyridine (453 mg, 2.50 mmol) in DMF was added potassium carbonate (518 mg, 3.74 mmol). The reaction was heated at 120° C. for 72 h. Concentration, followed by reverse phase separation on the Gilson (mobile phase gradient of 90% water/acetonitrile to 10% water/acetonitrile) afforded the title compound as a white solid. LC/MS: nm/z 246 (M+1-Boc).

Step G: (2R)-2-Methyl-1-[5-(trifluoromethyl)pyridin-2-yl]piperazine

A solution of tert-Butyl (3R)-3-methyl-4-[5-(trifluoromethyl)pyridin-2-yl]piperazine-1-carboxylate (110 mg, 0.319 mmol, from Step F) in saturated hydrochloric acid in methanol (3 mL) was stirred at room temperature for 1 h. Concentration, followed by prep TLC on silica gel (mobile phase 80:15:1 dichloromethane:methanol: ammonium hydroxide) afforded the title compound as a clear oil. LC/MS: m/z 246 (M+1).

Step H: N-[6-(5-cyano-7-isopropyl-1,3-benzoxazol-2-yl)pyridin-3-yl]-2-{(3R)-3-methyl-4-[5-(trifluoromethyl)pyridin-2-yl]piperazin-1-yl}acetamide To a solution of 2-bromo-N-[6-(5-cyano-7-isopropyl-1,3-benzoxazol-2-yl)pyridin-3-yl]acetamide (30.4 mg, 0.076 mmol, from Step D) and (2R)-2-Methyl-1-[5-(trifluoromethyl)pyridin-2-yl]piperazine (17 mg, 0.069 mmol, from Step G) in DMF (0.5 mL) was added triethyl amine (0.012 mL, 0.083 mmol). The mixture was stirred at 60° C. for 1 h. Concentration, followed by Prep TLC (mobile phase 75% ethyl acetate/hexanes) afforded the title compound as a white solid. LC/MS: m/z 564 (M+1).

The following compounds were prepared using procedures analogous to those described for the synthesis of EXAMPLES 530 and 531.

TABLE 18

| EXAMPLE | Description | X | R | MS m/z (M + H) |
|---|---|---|---|---|
| 532 | Mixture of trans enantiomers | CH | 4-CF$_3$-pyrimidin-2-yl | 579 |
| 533 | From slower eluting Boc-protected piperazine trans enantiomer on the OJ chiral column | CH | 4-CF$_3$-pyrimidin-2-yl | 579 |
| 534 | From faster eluting Boc-protected piperazine trans enantiomer on the OD chiral column | N | 4-CF$_3$-pyridin-2-yl | 579 |

We claim:
1. A compound having Formula Ia, or a pharmaceutically acceptable salt thereof,

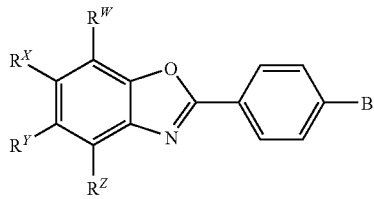

wherein $R^X$ and $R^Z$ are each H;
$R^W$ is selected from the group consisting of (a) $C_1$-$C_5$alkyl which is optionally substituted with 1-9 substituents independently selected from 1-7 halogens and 1-2 groups independently selected from —CN, —OH, —OCH$_3$, —OCF$_3$ and —N(R$^9$)$_2$, (b) $C_{2-5}$ alkenyl optionally substituted with 1-5 halogens; (c) —C(=O)OC$_{1-3}$alkyl optionally substituted with 1-5 halogens; (d) —C(=O)C$_1$-C$_3$alkyl which is optionally substituted with 1-7 halogens, (e) —C(=O)H, (f) —NO$_2$, (g) —OC$_1$-C$_3$ alkyl which is optionally substituted with 1-7 halogens, (h) C$_3$-C$_6$cycloalkyl, (i) phenyl, (j) a 5-6 membered saturated or partly unsaturated heterocyclic ring having 1-3 heteroatoms independently selected from N, S and O, and (k) a 5-7 membered heteroaromatic ring having 1-3 heteroatoms independently selected from N, S, and O, wherein said C$_3$-C$_6$cycloalkyl, phenyl, 5-6 membered saturated or partly unsaturated heterocyclic ring, and 5-7 membered heteroaromatic ring are optionally substituted with 1-5 substituents independently selected from halogen, CH$_3$, CF$_3$, —OCH$_3$, and —OCF$_3$;
$R^Y$ is selected from the group consisting of Br, —OCH$_3$, —CN, and pyridyl;
x is an integer from 0-2;
B is selected from the group consisting of:
—N(R$^9$)(C(=O))DR$^3$,
—N(R$^9$)(C(=O))DR$^7$,
—N(R$^9$)(C(=O))R$^3$,
—N(R$^9$)(C(=O))R$^7$,
—N(R$^9$)(C(=O))OCH$_2$R$^3$,
—N(R$^9$)D(C(=O))R$^7$,
—N(R$^9$)DR$^3$,
—N(R$^9$)D$^2$R$^7$,
—OD$^2$R$^3$,
—SD$^2$R$^3$,
—C(=O)CH$_2$CH$_2$R$^4$,
-D$^2$(C(=O))R$^7$,
-D$^2$R$^3$, and
D$^2$R$^7$;
D is a difunctional group selected from C$_1$-C$_7$alkylene, C$_2$-C$_5$alkenylene, and C$_2$-C$_5$alkynylene, wherein said alkylene group optionally has one difunctional group O, S, —NH— or —N(C$_1$-C$_3$alkyl)-between two carbon atoms of D, and said alkylene, alkenylene, and alkynylene groups are optionally substituted with 1-9 substituents independently selected from 1-7 halogens and optionally 1-2 OH groups;
D$^2$ is a difunctional group selected from C$_2$-C$_7$alkylene and C$_2$-C$_5$alkynylene, wherein said alkylene group optionally has one difunctional group O, S, —NH— or —N(C$_1$-C$_3$alkyl)-between two carbon atoms of the alkylene group other than carbonyl, and said alkylene and alkynylene groups are optionally substituted with 1-9 substituents independently selected from (a) 1-7 halogens, (b) 1-2 substituents independently selected from —N(R$^9$)$_2$, —CN, —NO$_2$, —OC$_1$-C$_3$ alkyl optionally substituted with 1-3 halogens, —C(=O)OH, —C(=O)H, —C(=O)OC$_1$-C$_5$alkyl optionally substituted with 1-7 halogens, —C(=O)C$_1$-C$_5$alkyl optionally substituted with 1-7 halogens, —C(=O)N(R$^9$)$_2$, (c) 1-2 -OH groups, and (d) an oxo group on a carbon atom between two other carbon atoms of the alkylene group;
$R^3$ is selected from the group consisting of R$^4$, -T-R$^4$, and —R$^5$;
$R^7$ is selected from the group consisting of —OC$_1$-C$_7$alkyl, —CH$_2$S(O)$_2$C$_1$-C$_7$alkyl, C$_5$-C$_{10}$alkyl, —NR$^9$C$_1$-C$_7$alkyl, —NR$^9$C(=O)OC$_1$-C$_7$alkyl, —OC(=O)OC$_1$-C$_7$alkyl and —OSi(R$^8$)$_3$, wherein the C$_5$-C$_{10}$alkyl and C$_1$-C$_7$alkyl groups of R$^7$ are optionally substituted with 1-9 halogens and are optionally substituted with one group selected from —N(R$^9$)$_2$, —N(R$^9$)C(=O)OC$_1$-C$_7$alkyl, —N(R$^9$)C(=O)C$_1$-C$_7$alkyl, and —OH, wherein the C$_1$-C$_7$alkyl groups of the —N(R$^9$)C(=O)OC$_1$-C$_7$alkyl and —N(R$^9$)C(=O)C$_1$-C$_7$alkyl substituents on R$^7$ are optionally substituted with 1-9 halogens;
T is selected from —O—, —N(R$^9$)—, and —S—;
Each R$^8$ group is independently selected from C$_1$-C$_5$alkyl, which is optionally substituted with 1-7 halogens;
$R^4$ is a cyclic group selected from the group consisting of
(a) C$_3$-C$_8$Cycloalkyl which optionally comprises 1-2 double bonds;
(b) Bicyclic C$_6$-C$_{12}$Cycloalkyl optionally comprising 1-2 double bonds;
(c) A 4-8 membered saturated or partly unsaturated heterocyclic ring having 1-2 ring members independently selected from —O— and —N(R$^6$)—, said heterocyclic ring being connected to the left hand part of Formula I through a carbon atom of the heterocyclic ring, wherein said heterocyclic ring is optionally fused to an aromatic ring selected from phenyl and naphthyl or to a C$_5$-C$_7$Cycloalkyl;
(d) An aromatic ring selected from phenyl and naphthyl; and
(e) A 5-7 membered heteroaromatic ring having 1-3 heteroatoms independently selected from N, S, and O, and optionally having one —C(=O)— group as a ring member, said heteroaromatic ring being connected to the left hand part of formula I through a carbon atom of the heteroaromatic ring, wherein said heteroromatic group is optionally fused to an aromatic ring selected from phenyl and naphthyl;
Wherein said cyclic groups R$^4$ defined in (a)-(e), including optional fused rings, are optionally substituted with 1-7 substitutents independently selected from halogen, C$_1$-C$_5$alkyl, —OC$_1$-C$_5$alkyl, phenyl, —NO$_2$, —C(=O)C$_1$-C$_5$alkyl, —C(=O)OC$_1$-C$_5$alkyl, —C(=O)OH, and —NR$^9$C(=O)C$_1$-C$_5$alkyl, wherein C$_1$-C$_5$alkyl and OC$_1$-C$_5$alkyl in all uses are optionally substituted with 1-9 halogens, and said phenyl is optionally substituted with 1-5 substituents independently selected from halogen, CH$_3$, CF$_3$, —OCH$_3$, and —OCF$_3$;
$R^5$ is a saturated or partly unsaturated 5-8 membered monocyclic heterocyclic group or a saturated or partly unsaturated 6-10 membered bicyclic heterocyclic group, wherein said heterocyclic group has a heteroatom N connected to the left hand side of Formula I and optionally has a second heteroatom selected from O, S, and —N(R$^6$)—, wherein said heterocyclic group optionally has 1-2 double bonds and an optional carbonyl group and is optionally fused to a cyclic group selected from phenyl and a 5-7 membered heteroaromatic ring having 1-3 heteroatoms independently selected from O, N, and S, or is optionally connected through a spiro linkage of a carbon atom to a 5-6 membered cycloalkyl ring or to a 5-7 membered heterocyclic ring having one heteroatom selected from 0, N and $S(O)_x$, said cycloalkyl and heterocyclic ring optionally having one double bond and optionally being fused to a phenyl ring; wherein $R^5$ including the rings optionally fused to $R^5$ or connected to $R^5$ through a spiro linkage is optionally substituted with 1-9 halogen atoms and is optionally substituted with 1-3 substituents independently selected from $C_1$-$C_5$alkyl; —$OC_1$-$C_5$alkyl; —$NO_2$; —$N(R^9)C(=O)OCH_2$-phenyl; —$S(O)_2C_1$-$C_3$alkyl; $C_3$-$C_6$cycloalkyl; —$CO_2H$; —$C(=O)C_1$-$C_3$alkyl; —$C(=O)OC_1$-$C_3$alkyl; —$C(=O)N(R^9)_2$; —$C_1$-$C_3$alkyleneN$(R^9)_2$; $C_1$-$C_3$alkyleneC(=O)N$(R^9)_2$; phenyl; —$C_1$-$C_3$alkylenePhenyl; a 5-10 membered heteroaromatic monocyclic or fused bicyclic group having 1-3 heteroatoms independently selected from N, O, and S; a 5-6 membered saturated or partly unsaturated heterocyclic ring having 1-3 heteroatoms independently selected from N, O, and S, optionally having a carbonyl group, optionally having one double bond, and optionally being fused to a phenyl ring; and a 5-6-membered heteroaromatic ring having 1-2 heteroatoms independently selected from N, S, and O, said heteroaromatic ring being fused to a 5-7 membered cycloalkyl or to a saturated or partly unsaturated heterocycle having 1-2 heteroatoms independently selected from N, S, and O; wherein all of said alkyl groups that are included in substituent groups on $R^5$ are optionally substituted with 1-9 halogens, and all of said phenyl groups that are substituents on $R^5$ or that are included in substituents on $R^5$ are optionally substituted with 1-5 substituents independently selected from halogen, —CN, —$NO_2$, $CH_3$, $CF_3$, —$OCH_3$, and —$OCF_3$;

$R^6$ is selected from the group consisting of $C_1$-$C_7$alkyl, —C(=O)$OC_1$-$C_7$alkyl, —C(=O)$C_1$-$C_7$alkyl, —$S(O)_x$phenyl, —$S(O)_x$ $C_1$-$C_7$alkyl, —C(=O)N$(R^9)_2$, —C(=O)Phenyl, —C(=O)OPhenyl, —$C_1$-$C_3$alkylene C(=O)$OC_1$-$C_6$alkyl, —$C_1$-$C_5$alkylene-$OC_1$-$C_5$alkyl, —C(=O)$C_3$-$C_7$cycloalkyl, —C(=O)$OC_3$-$C_7$cycloalkyl, and a cyclic group selected from (a) phenyl, (b) naphthyl, (c) biphenyl, (d) $C_3$-$C_8$cycloalkyl, (e) a saturated or partially unsaturated monocyclic or bicyclic 5-10 membered heterocycle having 1-2 heteroatoms independently selected from N, O, and S, said heterocycle optionally having 1-2 double bonds, and (f) a monocyclic or bicyclic 5-12 membered heteroaromatic group having 1-4 heteroatoms independently selected from N, S, and O and optionally having 1-2 carbonyl groups, wherein in all instances, each alkyl, alkenyl and alkynyl group included in $R^6$ is optionally substituted with 1-10 halogens and is also optionally substituted with 1-2 groups independently selected from phenyl, OH, biphenyl, —Ophenyl, and —$OC_1$-$C_3$alkylene-phenyl, wherein said phenyl substituents on the alkyl, alkenyl and alkynyl groups of $R^6$ are optionally substituted with 1-5 substituent groups independently selected from halogen, $CH_3$, $CF_3$, —$OCF_3$, —$NO_2$ and —$OCH_3$, and when $R^6$ is a cyclic group selected from (a) phenyl, (b) naphthyl, (c) biphenyl, (d) $C_3$-$C_8$cycloalkyl, (e) a saturated or partially unsaturated monocyclic or bicyclic 5-10 membered heterocycle having 1-2 heteroatoms independently selected from N, O, and S, said heterocycle optionally having 1-2 double bonds, and (f) a cyclic or bicyclic 5-12 membered heteroaromatic group having 1-4 heteroatoms independently selected from N, S, and O and optionally having 1-2 carbonyl groups, said cyclic group $R^6$ is optionally substituted with 1-3 groups independently selected from $C_1$-$C_5$alkyl, —$OC_1$-$C_5$alkyl, —C(=O)$C_1$-$C_3$alkyl, —$S(O)_xC_1$-$C_3$alkyl, phenyl, halogen, —CN, and —$NO_2$, said $C_1$-$C_5$alkyl and —$OC_1$-$C_5$alkyl being optionally substituted with 1-7 halogens; and $R^9$ is selected from the group consisting of H, $C_1$-$C_5$alkyl, $C_2$-$C_5$alkenyl, and $C_2$-$C_5$alkynyl, wherein said $C_1$-$C_5$alkyl, $C_2$-$C_5$alkenyl, and $C_2$-$C_5$alkynyl are optionally substituted with 1-9 halogens;

With the proviso (I) that when the group $R^W$ or $R^Y$ is —$OCH_3$; then B is not —N(H)C(=O)$(CH_2)_5$NH(C(=O))$CF_3$ or —N(H)C(=O)CH(NH$_2$)($C_4$alkyl);

And with the further proviso (II) that when the group $R^W$ is —$OCH_3$, halogen, $C_1$-$C_4$alkyl, or —$NH_2$, or $R^Y$ is —$OCH_3$ or Br, then B is not —NHC(=O)phenyl, —NHC(=O)cyclobutyl, —NHC(=O)(CH=CH)(1,4-furyl)phenyl, —NHC(=O)(1,4-furyl)phenyl, —NHC(=O)(CH$_2$)(CH$_2$) 1,2,4-oxadiazolyl)phenyl, —NHC(=O)(cyclopentyl)phenyl, or NHC(=O)biphenyl, wherein phenyl in all instances is optionally substituted with 1-2 substituents independently selected from halogen, methoxy, and C1-4alkyl.

2. The compound of claim 1 having formula Ib, or a pharmaceutically acceptable salt thereof:

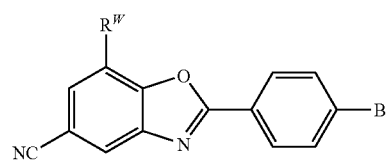

Ib wherein $R^W$ is selected from the group consisting of (a) (b) $C_1$-$C_5$alkyl which is optionally substituted with 1-9 substituents independently selected from 1-7 halogens and 1-2 groups independently selected from —CN, —OH, —$OCH_3$, —$OCF_3$ and —$N(R^9)_2$, (c) $C_{2-5}$ alkenyl optionally substituted with 1-5 halogens; (d) —C(=O)$OC_{1-3}$alkyl optionally substituted with 1-5 halogens; (e) —C(=O)$C_1$-$C_3$alkyl which is optionally substituted with 1-7 halogens, (f) —C(=O)H, (g) —$NO_2$, (h) —$OC_1$-$C_3$ alkyl which is optionally substituted with 1-7 halogens, (i) $C_3$-$C_6$cycloalkyl, (j) phenyl, (k) a 5-6 membered saturated or partly unsaturated heterocyclic ring having 1-3 heteroatoms independently selected from N, S and O, and (1) a 5-7 membered heteroaromatic ring having 1-3 heteroatoms independently selected from N, S, and O, wherein said $C_3$-$C_6$cycloalkyl, phenyl, 5-6 membered saturated or partly unsaturated heterocyclic ring, and 5-7 membered heteroaromatic ring are optionally substituted with 1-5 substituents independently selected from halogen, $CH_3$, $CF_3$, —$OCH_3$, and —$OCF_3$; and $R^9$ is independently selected from H and $CH_3$.

3. The compound of claim 1, or a pharmaceutically acceptable salt thereof, wherein:

B is selected from the group consisting of:
—(NH)(C(=O))$CH_2R^3$,
—(NH)(C(=O))$CH_2CH_2R^3$, —(NH)(C(=O))CH$_2$—O—(CH$_2$)$_3$R$^7$,
—(NH)(C(=O))OCH$_2$R$^4$,
—C$_2$-C$_4$alkyleneR$^3$, wherein —C$_2$-C$_4$alkylene optionally has one difunctional group O, S, —NH—, or —N(CH$_3$)— between two carbon atoms and is optionally substituted with 1-8 substituents independently selected from (a) 1-7 halogens, (b) 1-2 substituents independently selected from —N(R$^9$)$_2$, —CN, —OC$_1$-C$_3$ alkyl optionally substituted with 1-3 halogens, —C(=O)OH, —C(=O)H, —C(=O)OC$_1$-C$_5$alkyl optionally substituted with 1-7 halogens, —C(=O)C$_1$-C$_5$alkyl optionally substituted with 1-7 halogens, —C(=O)N(R$^9$)$_2$, (c) 1-2-OH groups, and (d) an oxo group on a carbon atom between two other carbon atoms of the alkylene group;
—C$_2$-C$_4$alkyleneR$^7$, wherein —C$_2$-C$_4$alkylene optimally has one difunctional group O, S, —NH—, or —N(CH$_3$)— between two carbon atoms and is optionally substituted with 1-8 substituents independently selected from (a) 1-7 halogens, (b) 1-2 substituents independently selected from —N(R$^9$)$_2$, —CN, —C(=O)OH, —C(=O)H, —C(=O)OC$_1$-C$_5$alkyl optionally substituted with 1-7 halogens, —C(=O)C$_1$-C$_5$alkyl optionally substituted with 1-7 halogens, —C(=O)N(R$^9$)$_2$, (c) 1-2-OH groups, and (d) an oxo group on a carbon atom between two other carbon atoms of the alkylene group;
—C≡CH$_2$R$^3$,
—C≡CH$_2$R$^7$,
—NHCH$_2$CH$_2$R$^3$,
—NHCH(CF$_3$)CH$_2$R$^7$,
—NHCH$_2$C(=O)R$^5$,
—CH(OH)CH(OH)C(=O)OC$_1$-C$_4$alkyl; and
Each R$^9$ is independently selected from H and CH$_3$.

4. The compound of claim 3, or a pharmaceutically acceptable salt thereof, wherein:
R$^3$ is selected from the group consisting of R$^4$, —OR$^4$, and —R$^5$;
R$^4$ is a cyclic group selected from the group consisting of:
(a) Cyclohexyl,
(b) 2-quinolyl,
(c) 1-isoquinolyl,
(d) phenyl,
(e) 2-tetrahydropyranyl, (f)
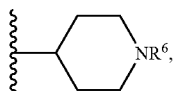

(g)
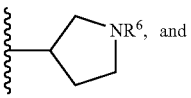

(h)
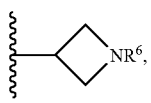

wherein R$^4$ is optionally substituted with 1-3 substituents independently selected from —CH$_3$, —CF$_3$, —OCH$_3$, —OCF$_3$, and halogen;

R$^5$ is selected from the group consisting of:

(a)
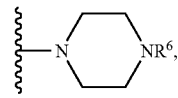

(b)
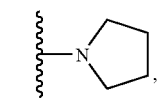

(c)
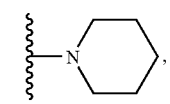

(d)
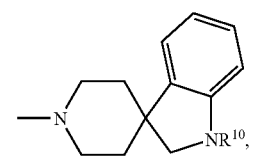

(e)
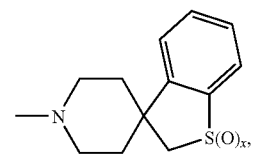

(f)
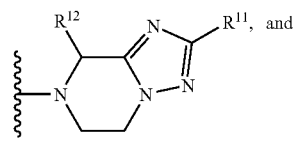

(g)
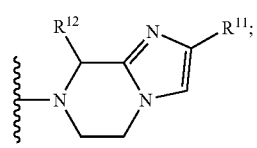

wherein R$^{10}$ is selected from the group consisting of —SO$_2$CF$_3$, —SO$_2$CH$_3$, and —C(=O)CH$_3$;
R$^{11}$ is selected from the group consisting of H, C$_1$-C$_5$alkyl, phenyl, and benzyl, wherein C$_1$-C$_5$alkyl is optionally substituted with 1-3 halogens, and wherein phenyl and benzyl are optionally substituted with 1-3 groups independently selected from halogen, —CH$_3$, —CF$_3$, —OCH$_3$, and —OCF$_3$;
R$^{12}$ is selected from the group consisting of H, C$_1$-C$_3$alkyl which is optionally substituted with 1-3 halogens, and —CH$_2$C(=O)N(R$^9$)$_2$;
wherein when R$^5$ is (a) or (d)-(g), then R$^5$ is optionally substituted with 1-3 substituent groups independently selected from halogen, —CH$_3$, —CF$_3$, —OCH$_3$, and —OCF$_3$; and when R$^5$ is (b) or (c), then R$^5$ is optionally substituted with 1-2 substituents independently selected from halogen, cyclohexyl, phenyl, —C(=O)N(R$^9$)C$_2$-C$_5$alkyl, —C(=O)OC$_1$-C$_4$alkyl, benzotriazole, pyrazolotetrahydropyridine, and —N(C$_2$-C$_3$alkenyl)(C(=O))O-benzyl, wherein alkyl and alkenyl are optionally substitued with 1-3 halogens, and phenyl and the phenyl of benzyl are optionally substituted with 1-3 halogens and 1 group selected from —CH$_3$, —CF$_3$, —OCH$_3$, —OCF$_3$, and —NO$_2$;

x is an integer from 0-2;

R$^6$ is selected from the group consisting of:
(a) phenyl,
(b) pyrimidinyl,
(c) pyrazinyl,
(d) pyridyl,
(e) naphthyl,
(f) C$_3$-C$_6$cycloalkyl,
(g) CH(phenyl)$_2$,
(h) —C(=O)OC$_1$-C$_5$alkyl,
(i) —C(=O)C$_1$-C$_5$alkyl,
(j) —SO$_2$C$_1$-C$_3$alkylene-phenyl,
(k) —SO$_2$C$_1$-C$_5$alkyl,
(l) —C(=O)OC$_3$-C$_5$alkylene-OH,
(m) —C(=O)OC$_3$-C$_5$alkylene-Obenzyl,
(n) —C(=O)O-phenyl,
(o) —C(=O)O-benzyl,
(p) —C(=O)N(R$^9$)C$_1$-C$_5$alkyl,
(q) —C(=O)OC$_5$-C$_6$cycloalkyl,
(r) —CH$_2$C(=O)OC$_1$-C$_5$alkyl,
(s) C$_1$-C$_3$alkylene-phenyl, and
(t) C$_4$-C$_6$alkyl,
wherein alkyl, alkylene, and cycloalkyl groups are optionally substituted with 1-3 halogens; phenyl, the phenyl groups of benzyl, and naphthyl are optionally substituted with 1-3 substituents independently selected from (i) halogen, (ii) C$_1$-C$_3$ alkyl optionally substituted with 1-3 halogens, (iii) —OCF$_3$, (iv) —OCH$_3$, (v) —NO$_2$, (vii) phenyl, (viii) —CN, (ix) —C(=O)CH$_3$ and (x) —SO$_2$CH$_3$; and pyridyl, pyrimidinyl and pyrazinyl are optionally substituted with 1-3 substituents independently selected from halogen, —CH$_3$, —CF$_3$, —OCH$_3$, —OCF$_3$, —NO$_2$, —CN, and phenyl; and R$^7$ is selected from the group consisting of —OC$_3$-C$_5$alkyl and —N(R$^9$)C(=O)OC$_3$-C$_5$alkyl, wherein each alkyl group is optionally substituted with 1-3 halogens.

5. The compound of claim 2, or a pharmaceutically acceptable salt thereof, wherein B is selected from the group consisting of:
(a) —NHC(=O)CH2OR$^4$,
(b) —NHC(=O)CH2R$^3$,
(c) —NHCH2CH2R$^3$,
(d) —SCH2CH2R$^3$,
(e) —C(=O)CH2CH2R$^4$,
(f) —CH2CH2CH2R$^3$, wherein the propylene chain is optionally substituted with 1-2 halogens, one —OH group, or a methylene group (=CH$_2$),
(g) —CH2TCH2R$^3$,
(h) —CH2C(=O)CH2R$^3$, and
(i) —CH2CH2TR$^4$;

T is selected from the group consisting of 0, —NH—, and S;

R$^3$ is selected from R$^4$ and R$^5$;

R$^4$ is selected from the group consisting of 4-piperidinyl having an R$^6$ substitutent on the N, cyclohexyl, and phenyl, wherein 4-piperidinyl is optionally substituted with 1-2 substitutents independently selected from F, CH3, and CF3, and phenyl and cyclohexyl are optionally substituted with 1-3 substitutents independently selected from halogen, CH3, CF3, OCH3, and OCF3;

R$^5$ is selected from the group consisting of 1-pyrrolidinyl, 1-piperidinyl, and 1-piperazinyl, wherein the N at the 4-position of 1-piperazinyl is substituted with R$^6$, and the pyrrolidinyl, piperidinyl, and piperazinyl groups are optionally substituted with 1-2 substitutents independently selected from F, CH$_3$, and CF$_3$; and R$^6$ is selected from the group consisting of (a) —C(=O)OC1-C5alkyl, (b) —C(=O)C1-C3alkyl optionally substituted with 1-3F, (c) phenyl, (d) pyridyl, and (e) pyrimidinyl, wherein pyridyl, pyrimidinyl, and phenyl are optionally substituted with 1-3 groups independently selected from halogen, CH3, CF3, OCH3, and OCF3, and optionally one phenyl.

6. The compound of claim 5, wherein R$^W$ is selected from the group consisting of —OCH$_3$, —OCF$_3$, —C(=O)OCH$_3$, C1-C3alkyl, and C2-C3alkenyl, wherein C1-C3alkyl and C2-C3alkenyl are each optionally substituted with 1-3 halogens and one —OH.

7. The compound of claim 1 or a pharmaceutically acceptable salt thereof, selected from the structures below:

Ex 7

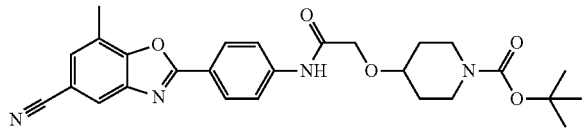

Ex 10

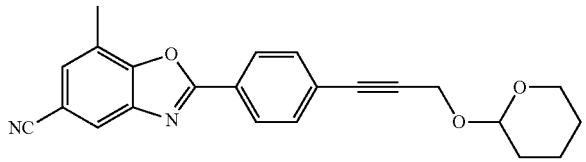

Ex 11

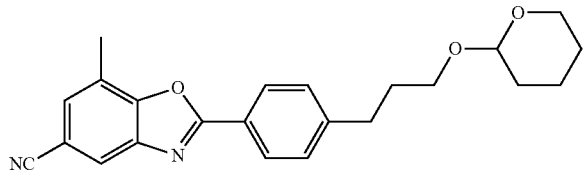

Ex 12

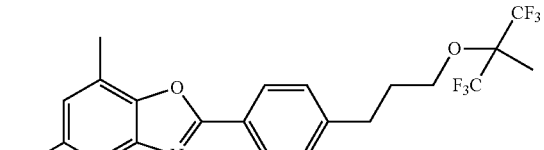

-continued
Ex 16
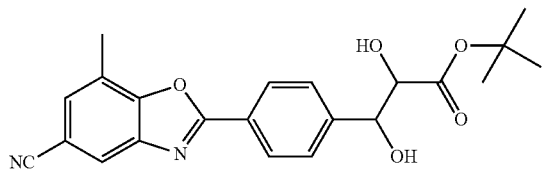
Ex 19
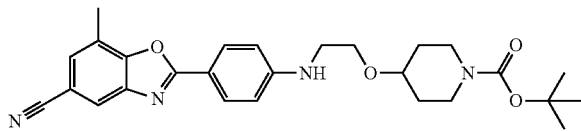
Ex 21
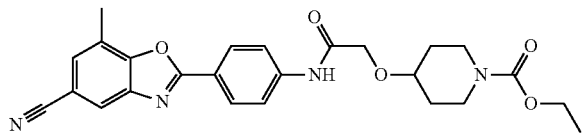
Ex 22
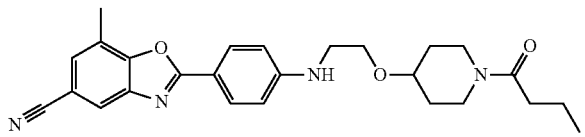
Ex 23
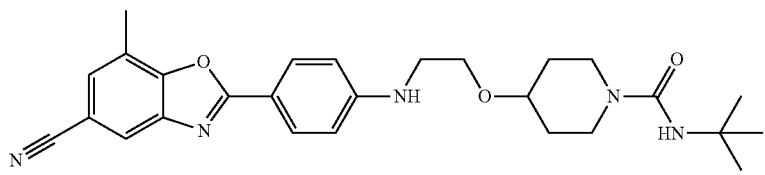
Ex 24
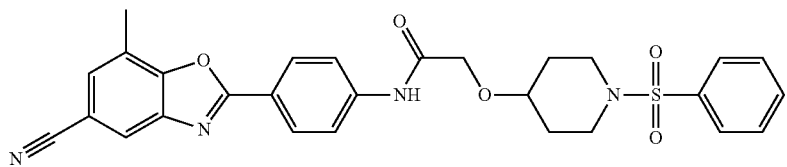
Ex 25
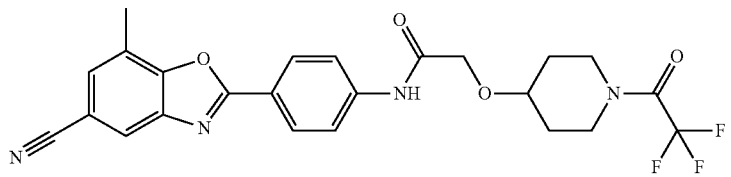
Ex 26
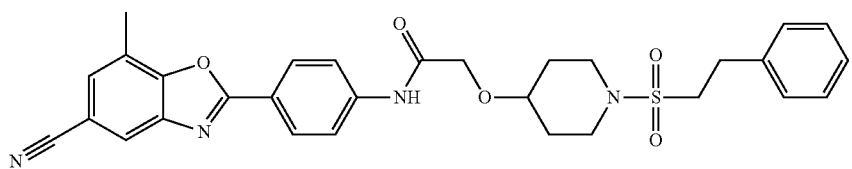
Ex 27
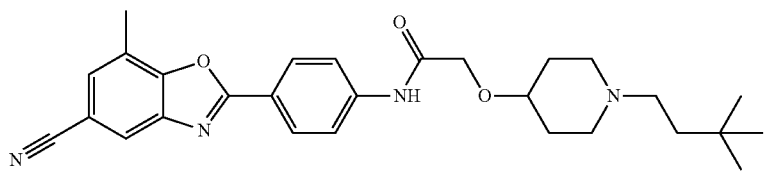
Ex 28
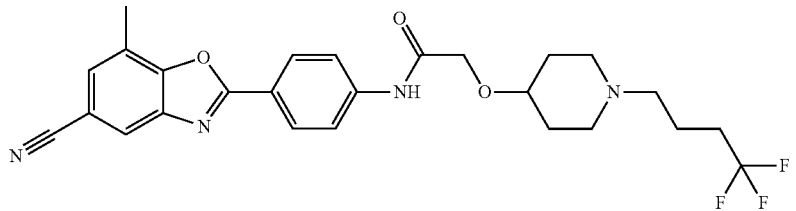

-continued
Ex 29
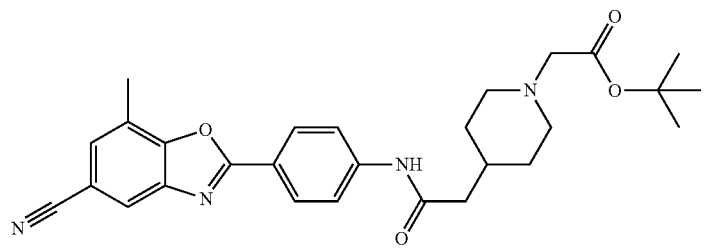
Ex 30
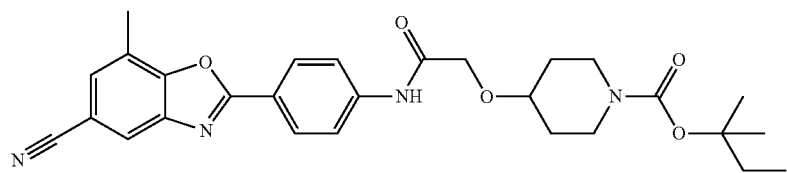
Ex 31
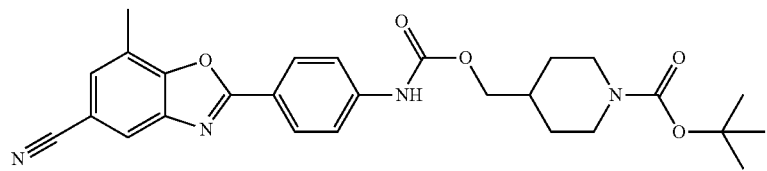
Ex 32
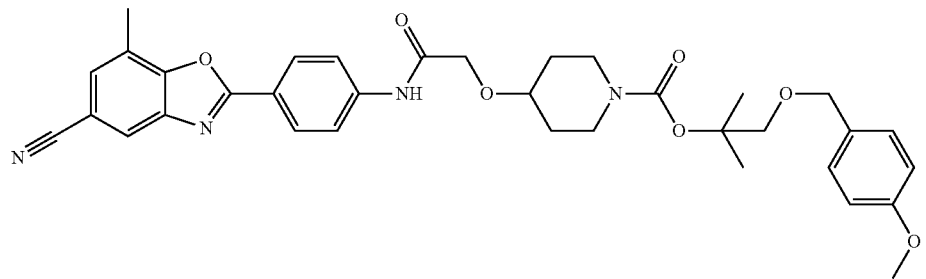
Ex 33
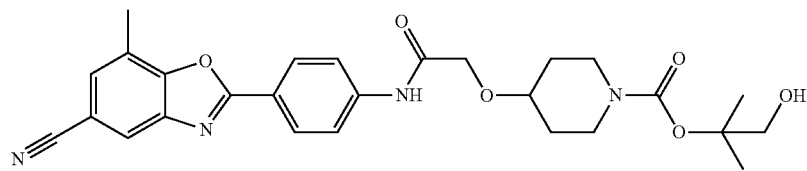
Ex 34
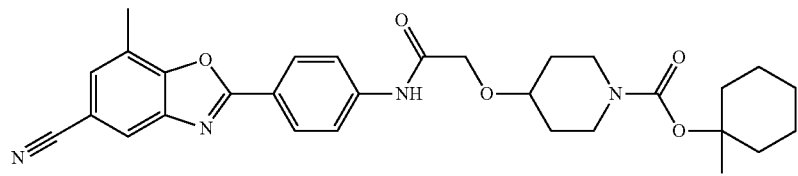
Ex 35
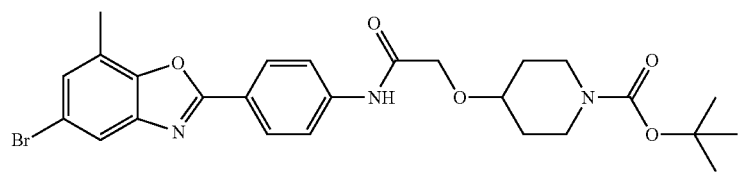
Ex 205
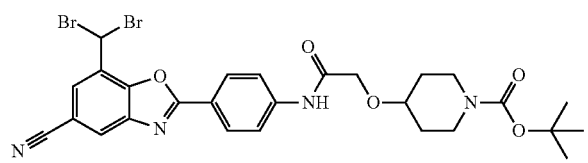
Ex 206
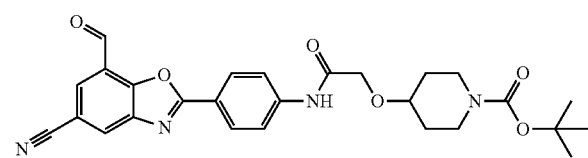

-continued
Ex 207
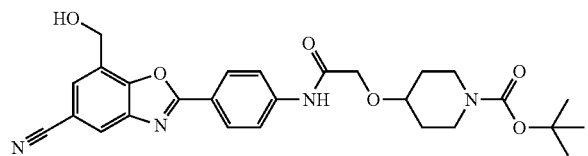
Ex 208
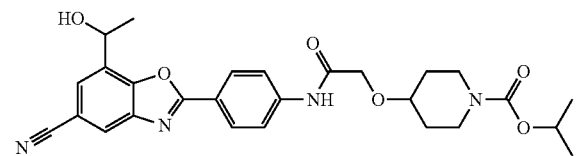
Ex 209
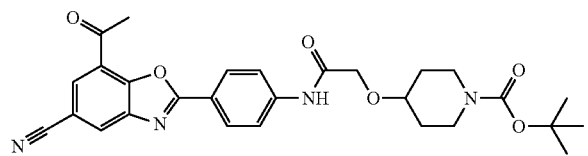
Ex 210
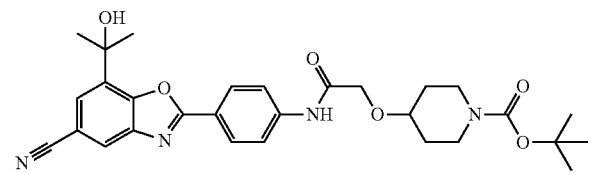
Ex 211
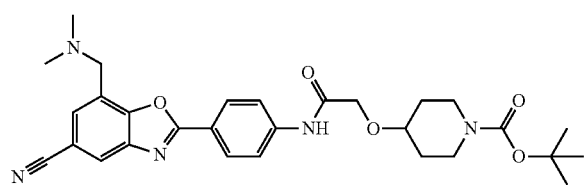
Ex 212
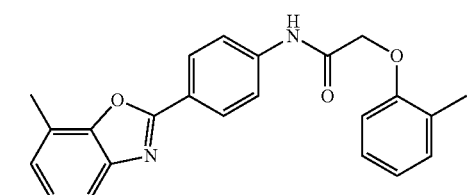
Ex 218
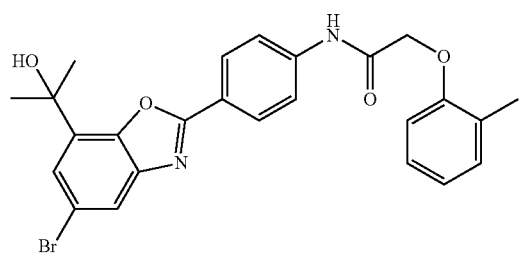
Ex 229
Ex 234
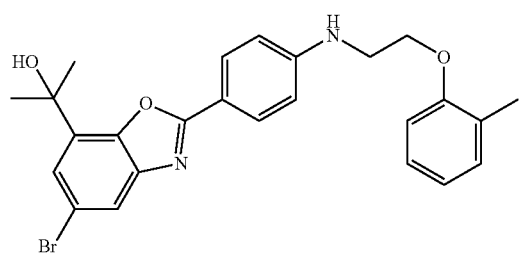
Ex 235
Ex 236
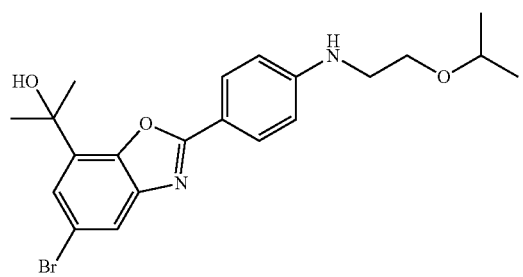
Ex 237
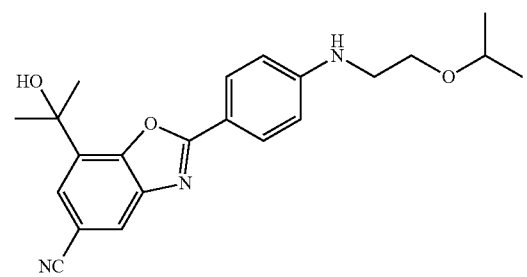

-continued
Ex 238
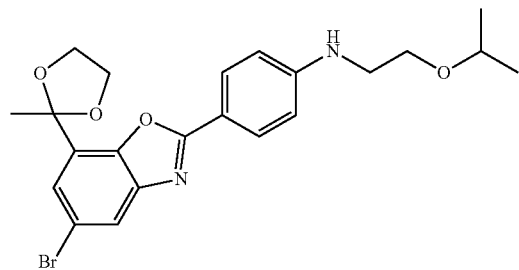
Ex 292
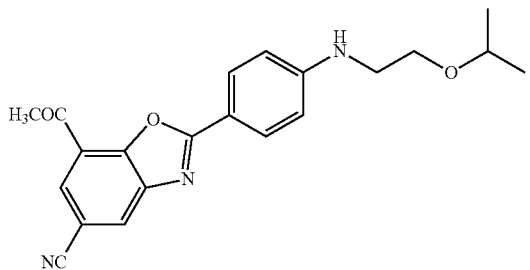
Ex 336
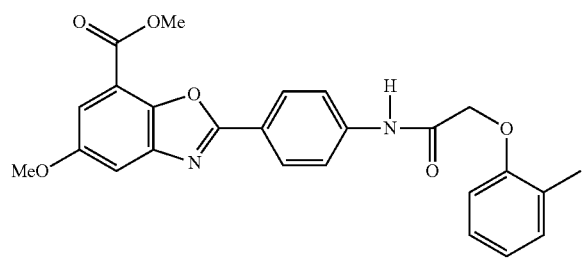
Ex 337
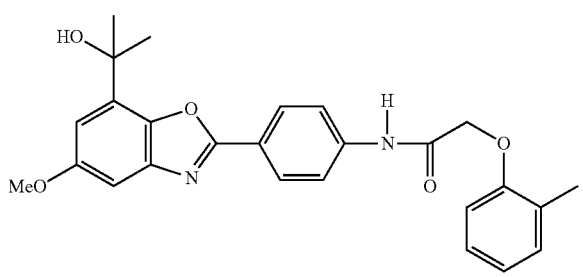
Ex 365
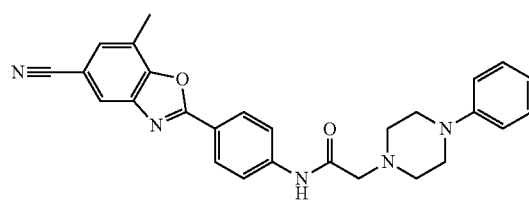
Ex 471
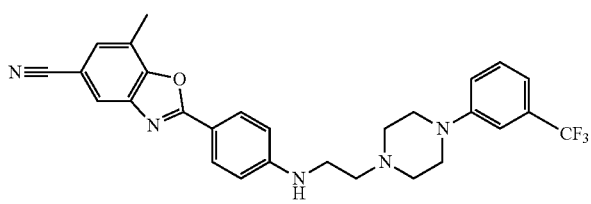
Ex 474
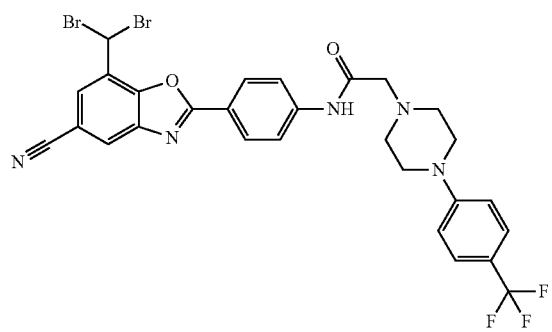
Ex 475
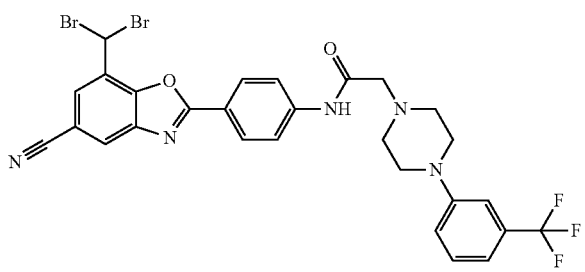
Ex 476
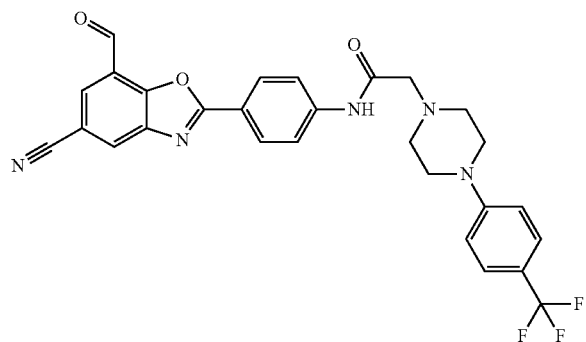
Ex 477
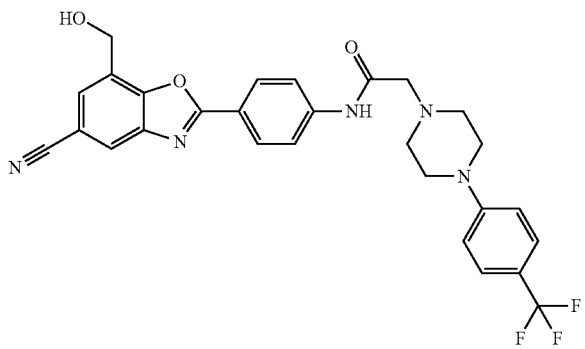

-continued
Ex 478
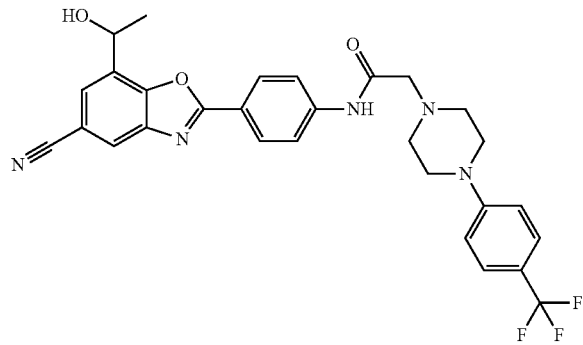
Ex 480
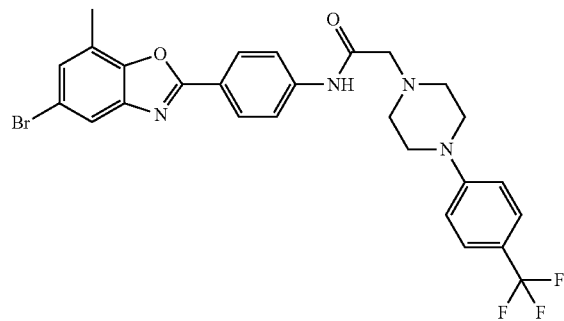
Ex 491
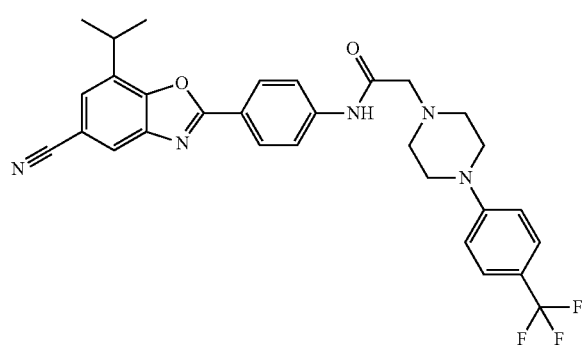
Ex 501
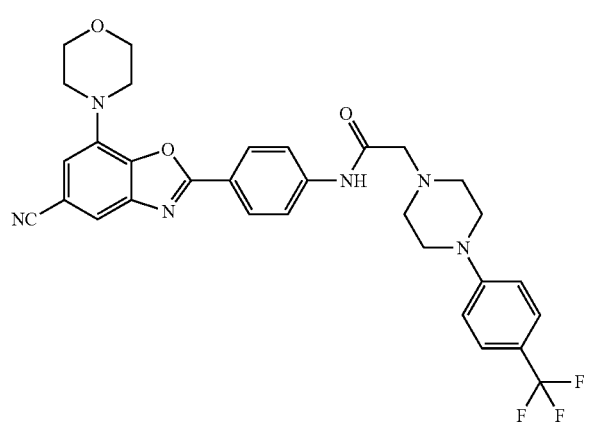
Ex 502
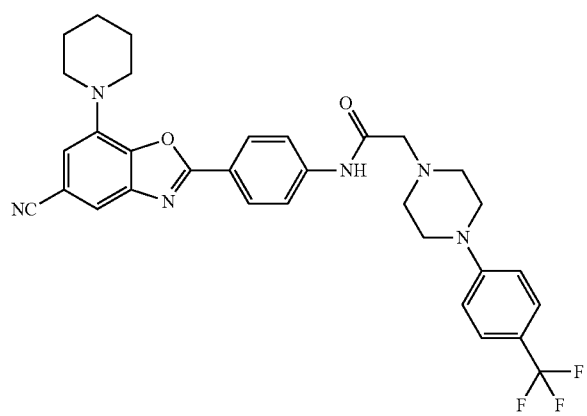
Ex. 503
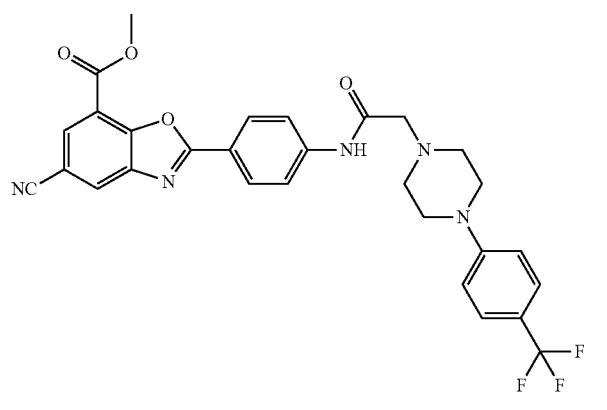
Ex 504
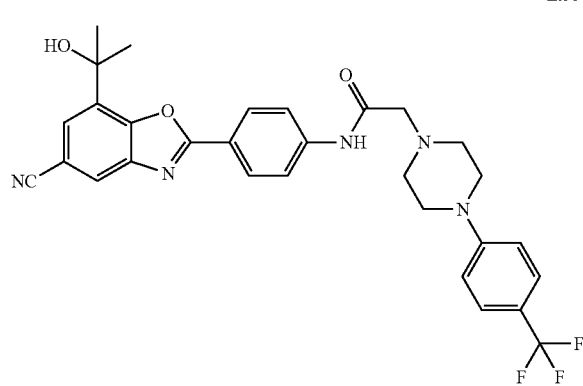
Ex. 505
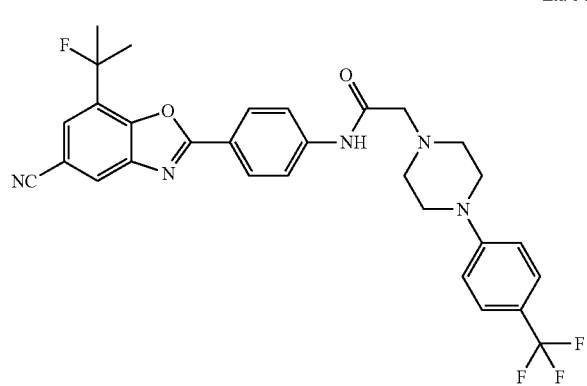

-continued
Ex. 506
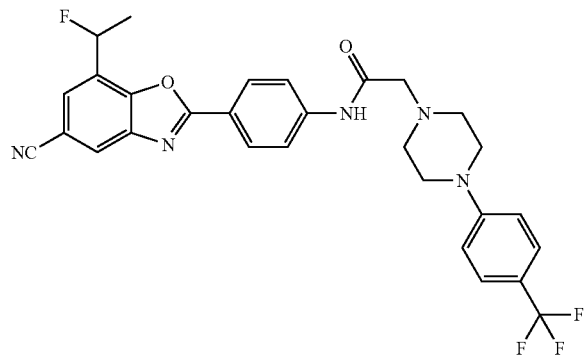
Ex. 507
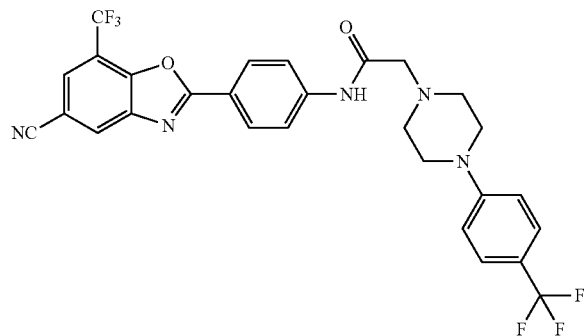
Ex. 508
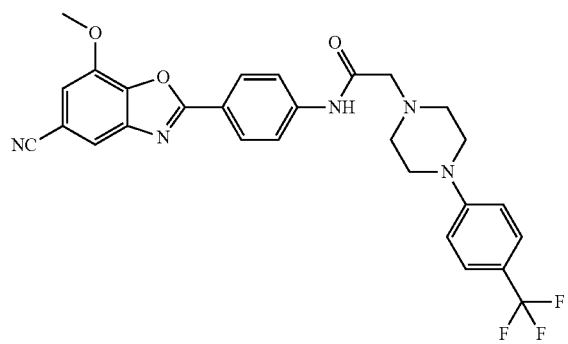
Ex. 509
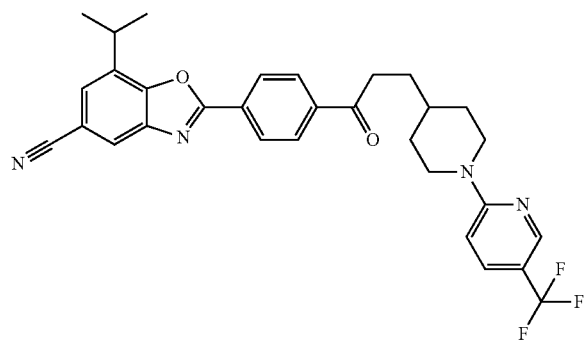
Ex. 510
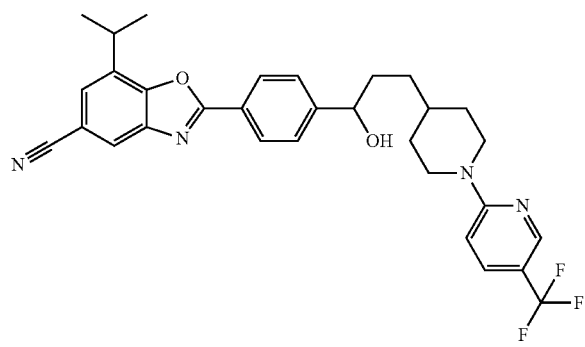
Ex. 511
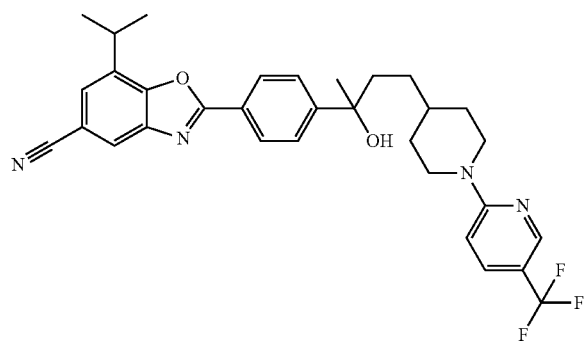
Ex. 512
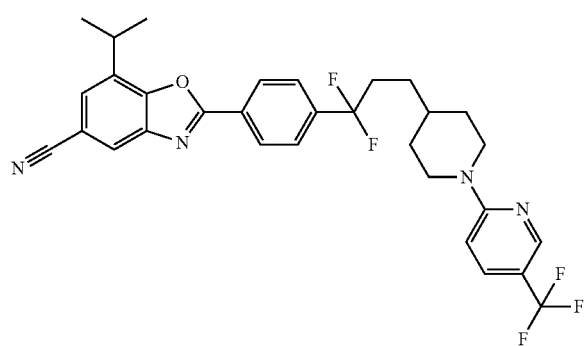
Ex. 514
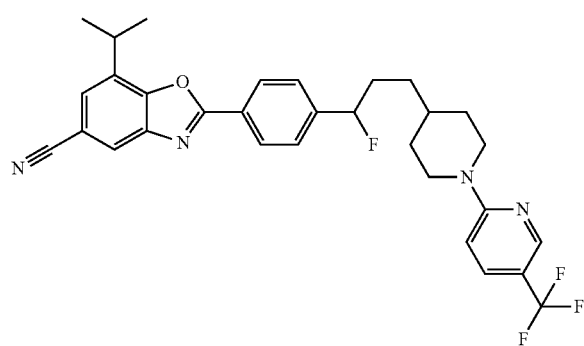

-continued
Ex. 515
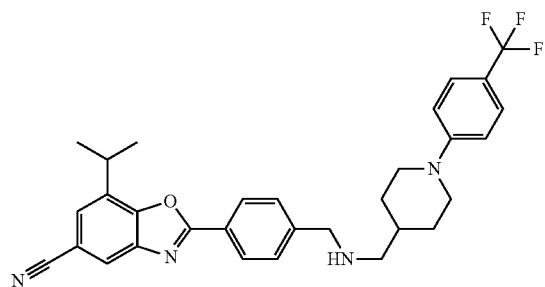
Ex. 516
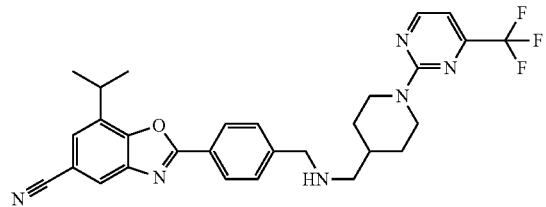
Ex. 517
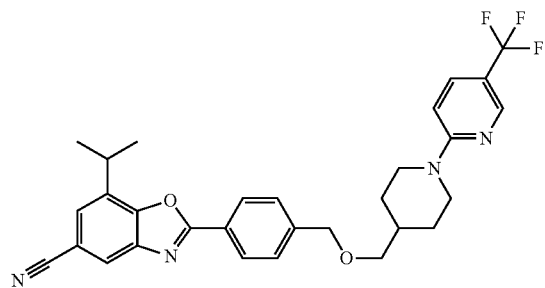
Ex. 518
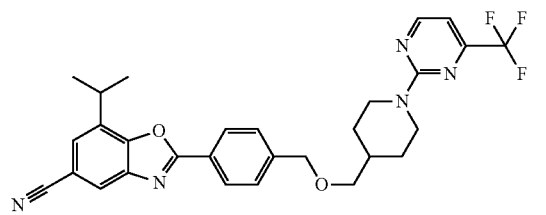
Ex. 519
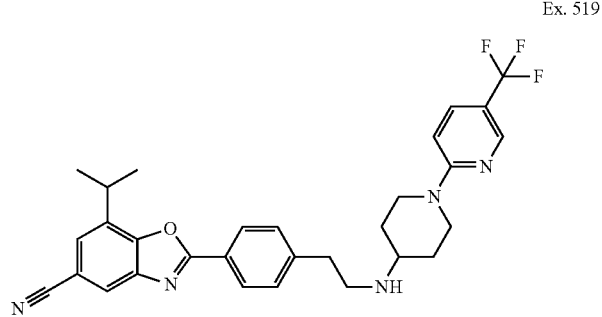
Ex. 520
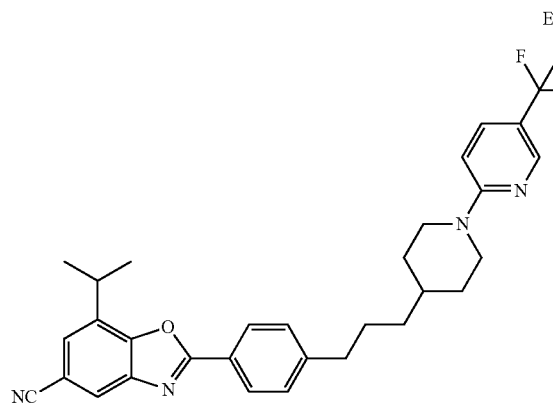
Ex. 521
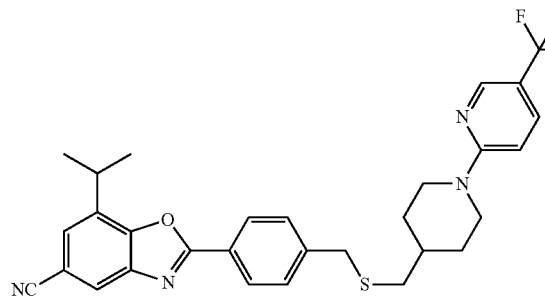
Ex. 522
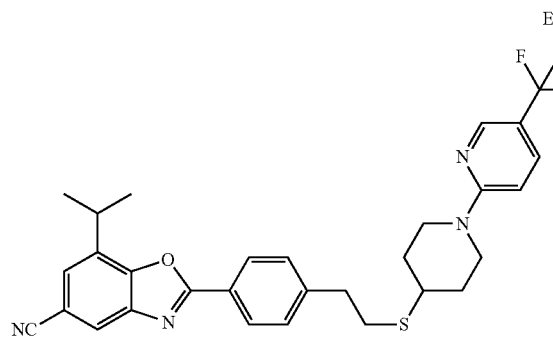

-continued
Ex. 523
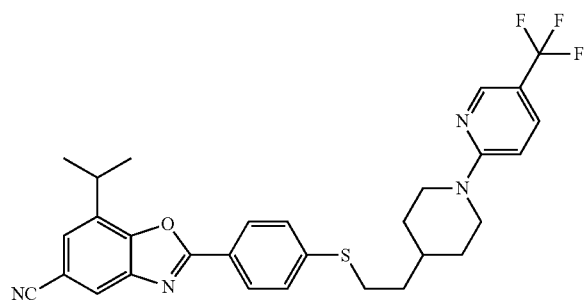
Ex. 524
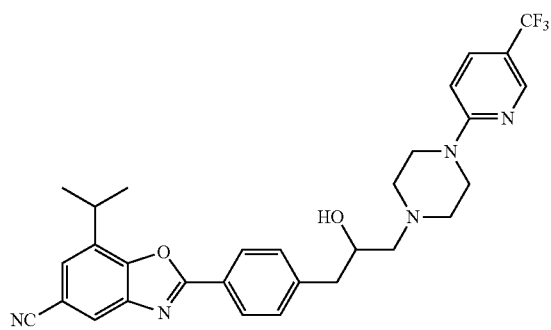
Ex. 528
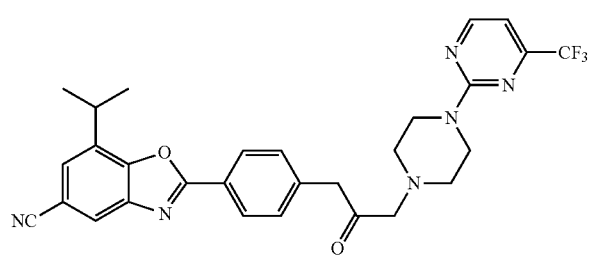
Ex. 529
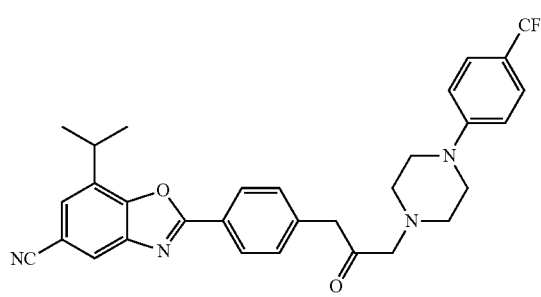
8. The compound of claim 1, or a pharmaceutically acceptable salt thereof, selected from the structures below:
TABLE 1
| EX | R₁ | R₂ | R₃ |
|---|---|---|---|
| 157 | (pyrrolidine-O-Boc) | CH₃ | CN |
| 158 | (pyrrolidine-O-Boc) | CH₃ | CN |
| 159 | (azetidine-O-Boc) | CH₃ | CN |
| 160 | (-CH₂-O-(CH₂)₃-NH-Boc) | CH₃ | CN |
TABLE 1-continued
| EX | R₁ | R₂ | R₃ |
|---|---|---|---|
| 161 | (piperidine-N-CO-OMe) | CH₃ | CN |
| 162 | (piperidine-N-Boc) | CH₃ | CN |
| 163 | (piperidine-N-Boc) | CH₃ | CN |

TABLE 2
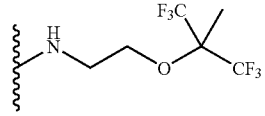
| EX | R₁ | R₂ | R₃ |
|---|---|---|---|
| 184 | 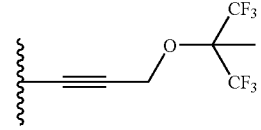 | CH₃ | CN |
| 185 | 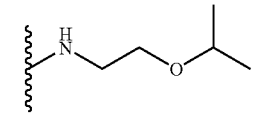 | CH₃ | CN |
| 187 | 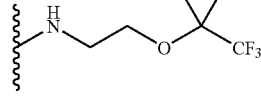 | CH₃ | Br |
| 188 | 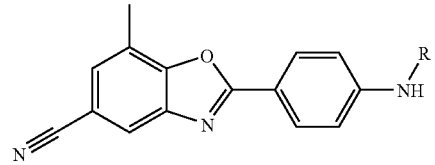 | CH₃ | Br |
TABLE 3
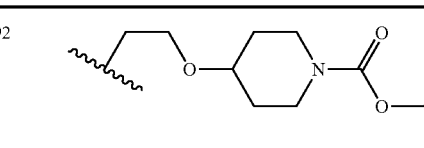
| Ex | R |
|---|---|
| 189 | 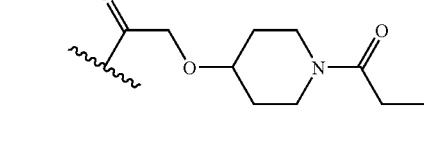 |
| 190 | 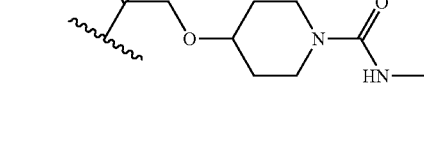 |
| 191 | 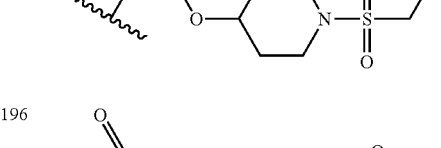 |
TABLE 3-continued
| Ex | R |
|---|---|
| 192 |  |
| 193 | 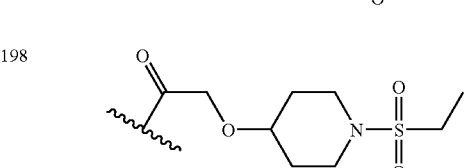 |
| 194 | 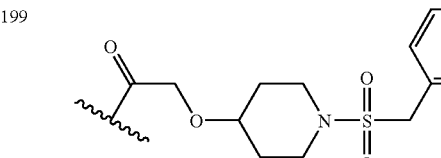 |
| 195 |  |
| 196 | 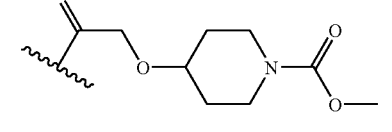 |
| 197 | 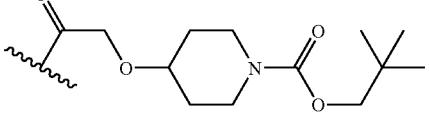 |
| 198 | 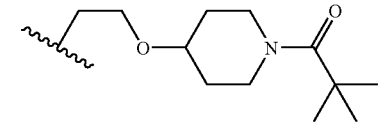 |
| 199 | |

TABLE 3-continued
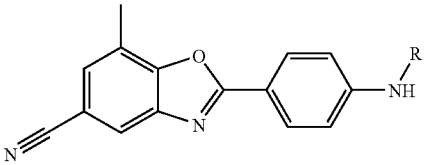
| Ex | R |
|---|---|
| 200 | 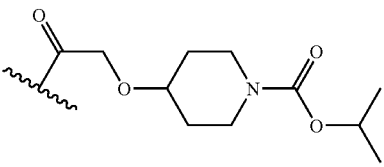 |
| 201 | 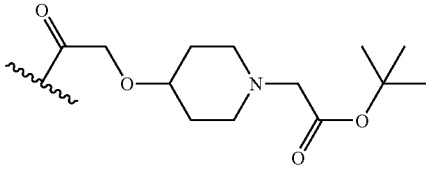 |
TABLE 5
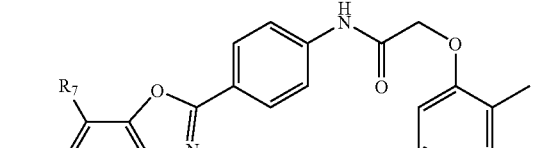
| Ex | R4 | R5 | R6 | R7 |
|---|---|---|---|---|
| 258 | H | Br | H | COCH3 |
| 262 | H | 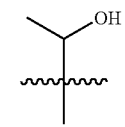 | H | CH3 |
| 270 | H | Br | H | 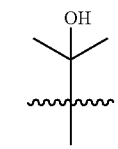 |
| 271 | H | Br | H | 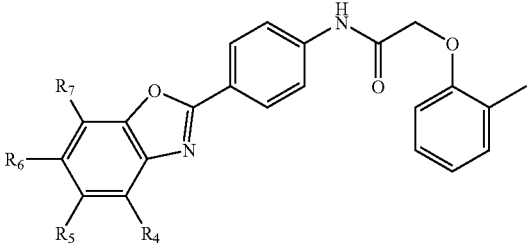 |
| 272 | H | Br | H | 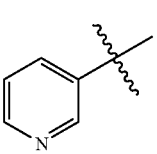 |
TABLE 5-continued
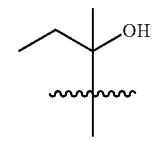
| Ex | R4 | R5 | R6 | R7 |
|---|---|---|---|---|
| 276 | H | CN | H | CH3 |
| 282 | H | CN | H | COCH3 |
| 283 | H | CN | H | 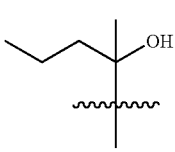 |
| 284 | H | CN | H | 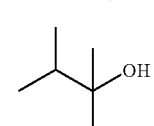 |
| 285 | H | CN | H | 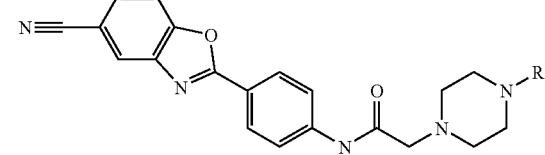 |
| 286 | H | CN | H | 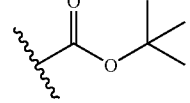 |
| 287 | H | CN | H |  |
TABLE 12
| Ex | R6 |
|---|---|
| 366 |  |

TABLE 12-continued
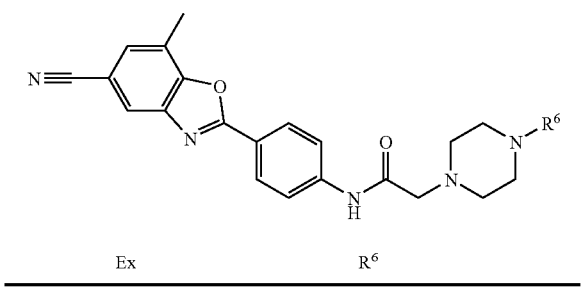
| Ex | R6 |
|---|---|
| 367 | 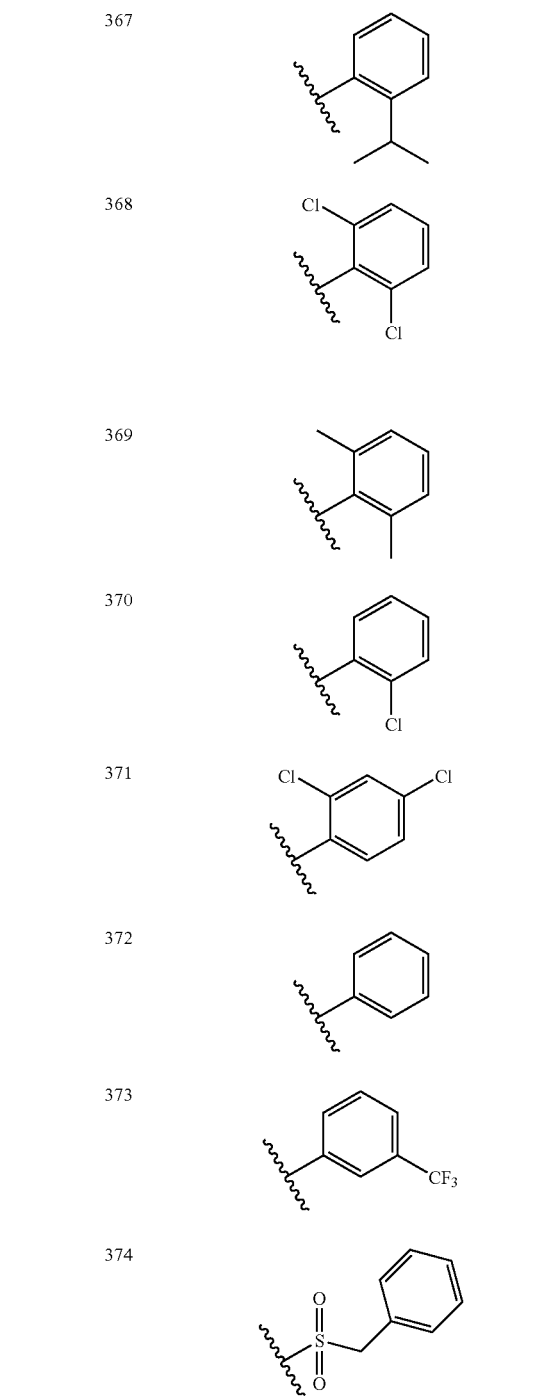 |
| 368 | |
| 369 | |
| 370 | |
| 371 | |
| 372 | |
| 373 | |
| 374 | |
TABLE 12-continued
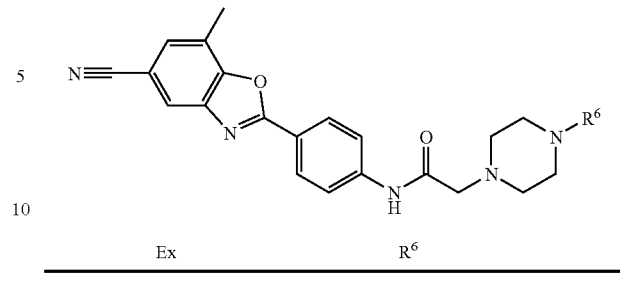
| Ex | R6 |
|---|---|
| 375 | 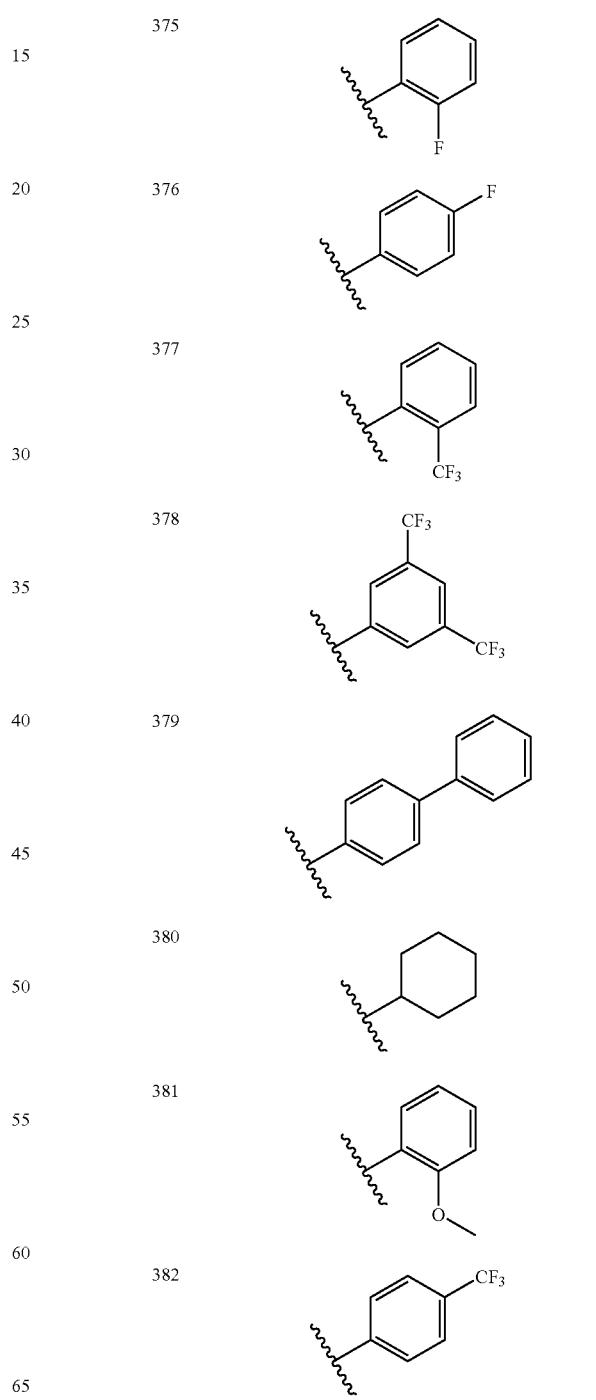 |
| 376 | |
| 377 | |
| 378 | |
| 379 | |
| 380 | |
| 381 | |
| 382 | |

TABLE 12-continued

| Ex | R⁶ |
|---|---|
| 383 | 2-nitro-4-(trifluoromethyl)phenyl |
| 384 | 3-chlorophenyl |
| 385 | 3,4-dichlorophenyl |
| 386 | 3-(trifluoromethoxy)phenyl |
| 387 | 2,4-difluorophenyl |
| 388 | 2-fluoro-5-(trifluoromethyl)phenyl |
| 389 | 3,4-difluorophenyl |
| 390 | 4-nitro-3-(trifluoromethyl)phenyl |
| 391 | 5-fluoro-2-(methylsulfonyl)phenyl |
| 392 | 3,4,5-trifluorophenyl |
| 393 | 4-chloro-3-(trifluoromethyl)phenyl |
| 394 | 4-fluoro-3-(trifluoromethyl)phenyl |
| 395 | (4-chlorophenyl)(phenyl)methyl |
| 396 | benzyl |
| 397 | 2,5-difluoro-4-(trifluoromethyl)phenyl |
| 398 | 4-acetylphenyl |

TABLE 12-continued
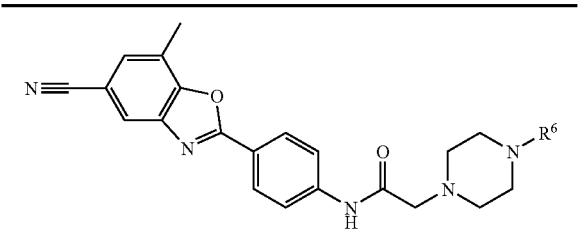
| Ex | R6 |
|---|---|
| 399 | 4-Cl,4-Cl-diphenylmethyl |
| 400 | diphenylmethyl |
| 401 | 4-isopropylphenyl |
| 402 | 4-F,4-F-diphenylmethyl |
| 403 | 4-chlorophenyl |
| 404 | 2-F,4-CF3-phenyl |
TABLE 12-continued
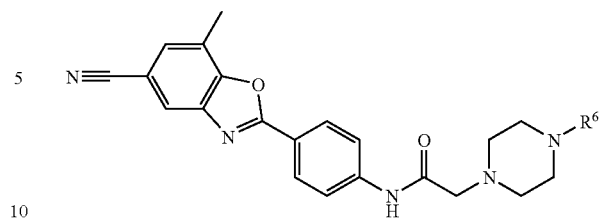
| Ex | R6 |
|---|---|
| 405 | 3-methoxyphenyl |
| 406 | 4-methoxyphenyl |
| 407 | 4-OCF3-phenyl |
| 408 | (2,5-dimethylphenyl)(phenyl)methyl |
| 409 | (2-methylphenyl)(phenyl)methyl |
| 410 | (2-methylphenyl)(4-methylphenyl)methyl |
| 411 | 4-Cl,2-F-phenyl |

TABLE 12-continued
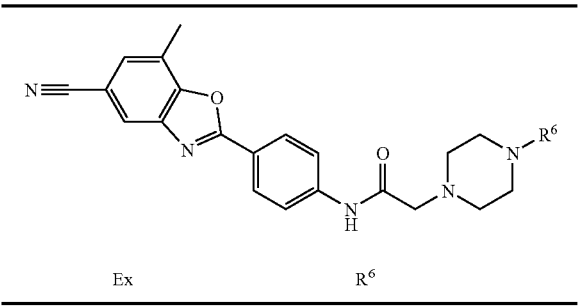
| Ex | R⁶ |
|---|---|
| 412 | 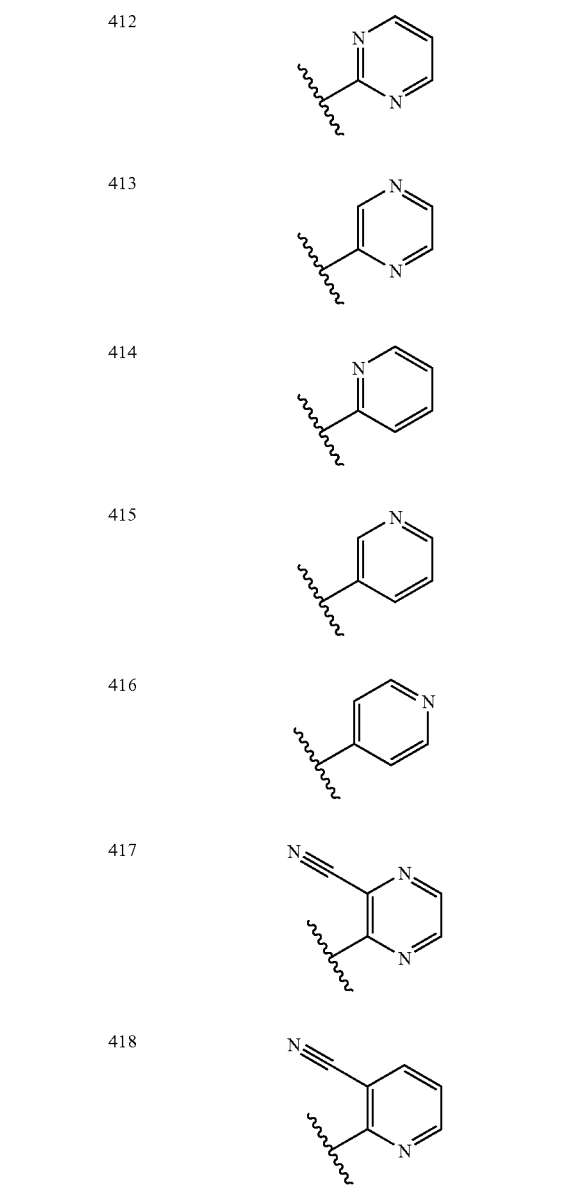 |
| 413 | |
| 414 | |
| 415 | |
| 416 | |
| 417 | |
| 418 | |
| 419 | 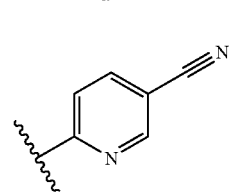 |
TABLE 12-continued
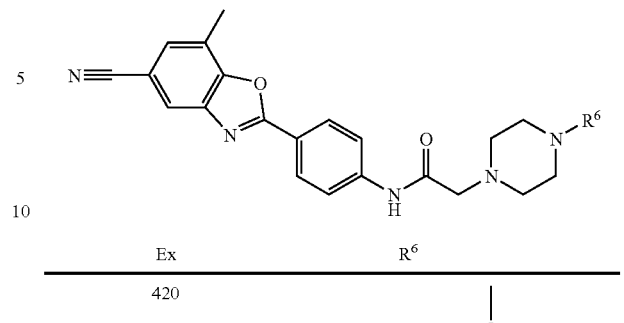
| Ex | R⁶ |
|---|---|
| 420 | 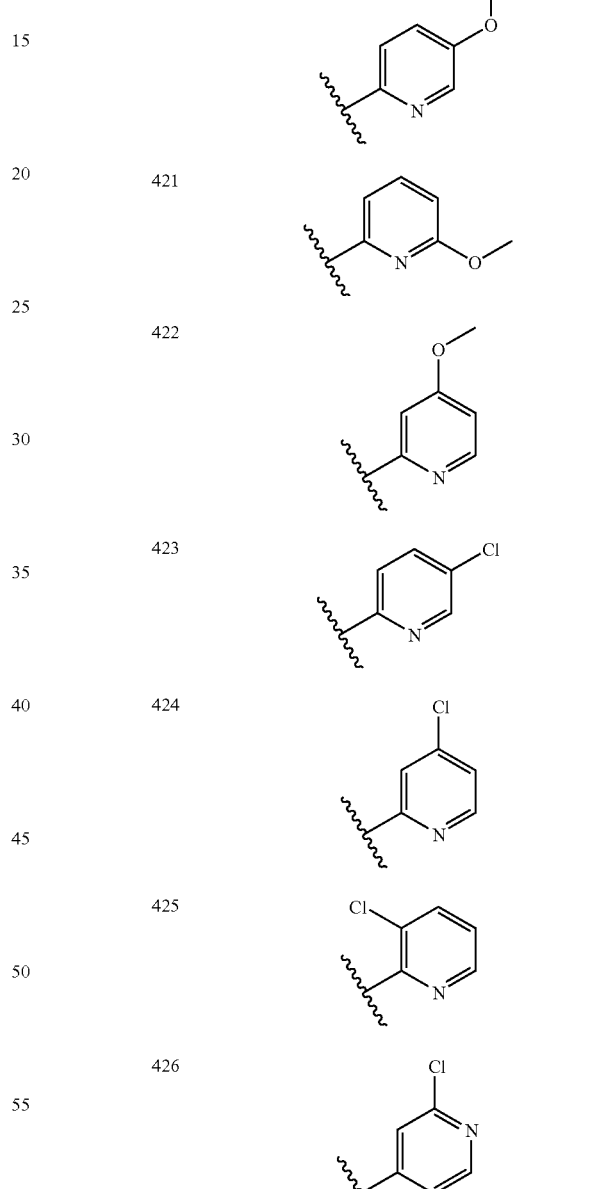 |
| 421 | |
| 422 | |
| 423 | |
| 424 | |
| 425 | |
| 426 | |
| 427 | 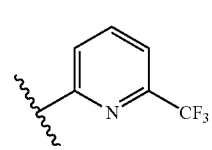 |

TABLE 12-continued

| Ex | R⁶ |
|---|---|
| 428 | 5-(trifluoromethyl)pyridin-2-yl |
| 429 | 4-(trifluoromethyl)pyridin-2-yl |
| 430 | 3-(trifluoromethyl)pyridin-2-yl |
| 431 | 4-(trifluoromethyl)pyrimidin-2-yl |
| 432 | 4-phenylpyrimidin-2-yl |
| 433 | 4,6-dimethylpyrimidin-2-yl |
| 434 | 4-methylpyridin-2-yl |
| 435 | 6-methylpyridin-2-yl |
| 436 | naphthalen-1-yl |
| 437 | isoquinolin-1-yl |
| 438 | isoquinolin-3-yl |
| 439 | quinolin-2-yl |
| 440 | quinazolin-2-yl |
| 441 | biphenyl-3-yl |

TABLE 13
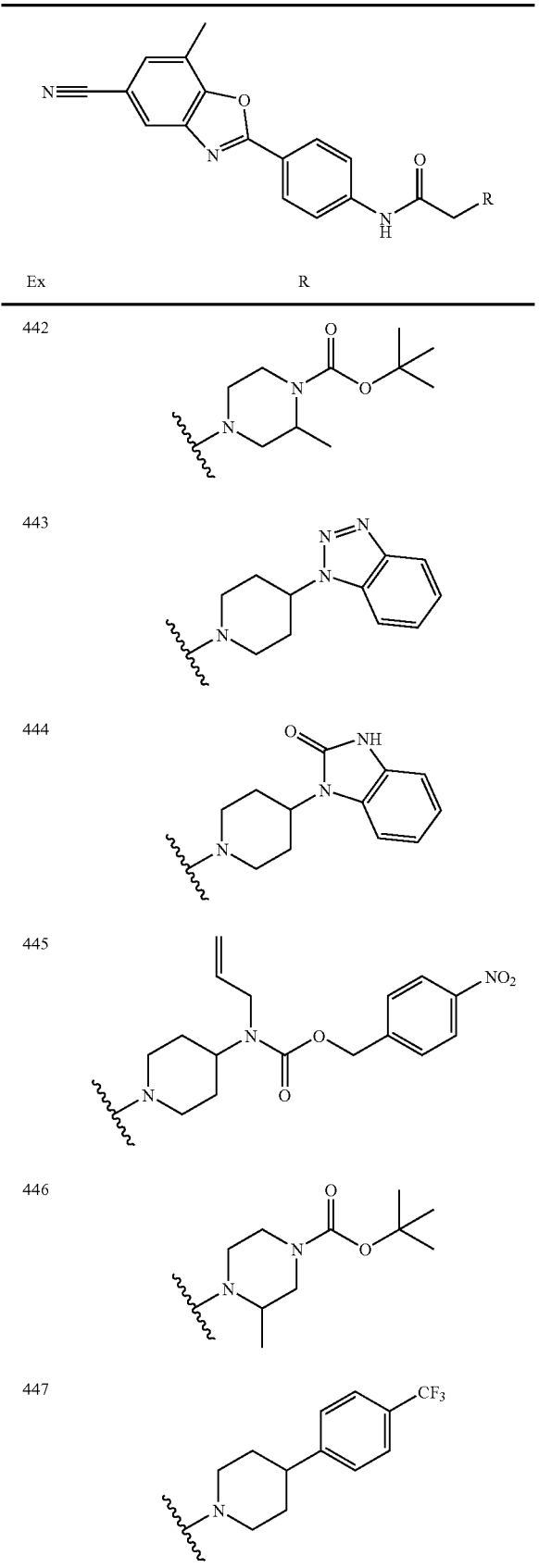
TABLE 13-continued
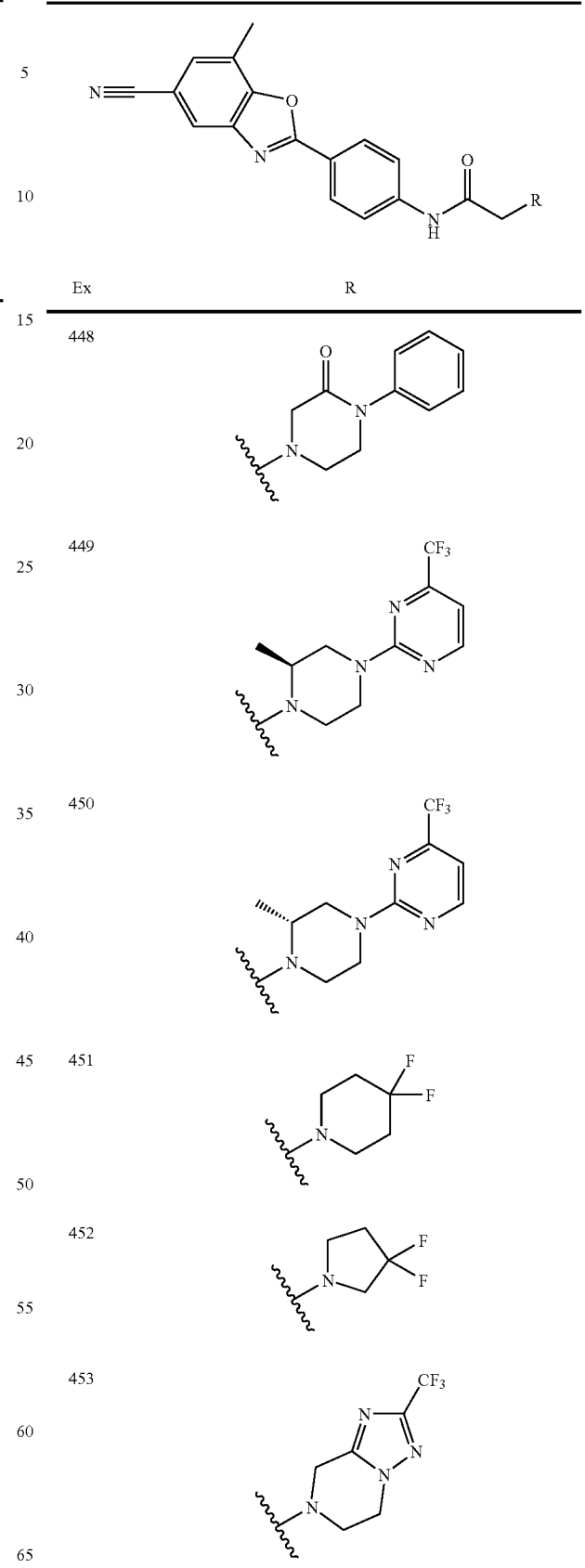

US 8,334,290 B2
TABLE 13-continued
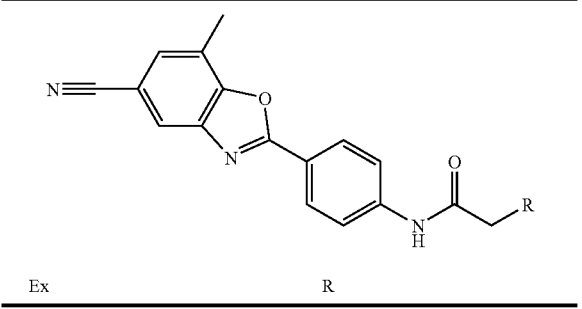
| Ex | R |
|---|---|
| 454 | 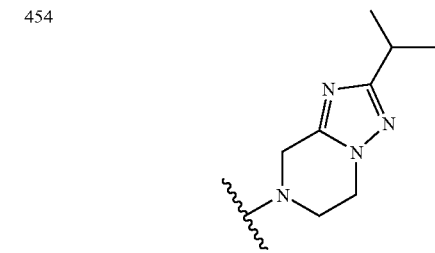 |
| 455 | 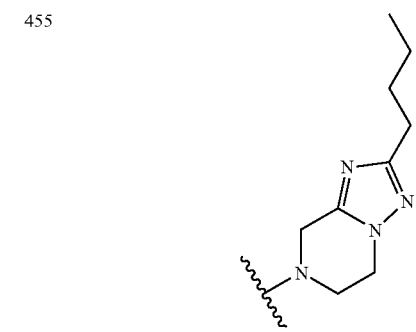 |
| 456 | 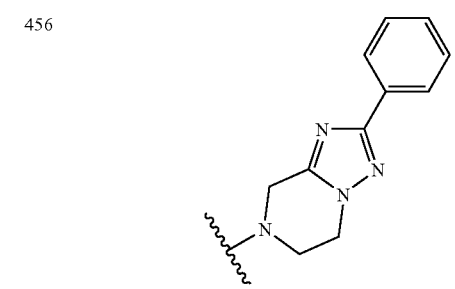 |
| 457 | 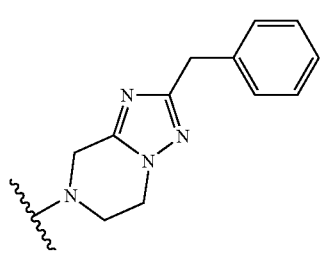 |
| 458 | 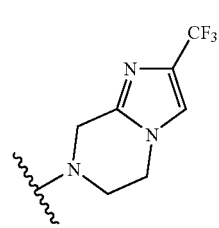 |
TABLE 13-continued
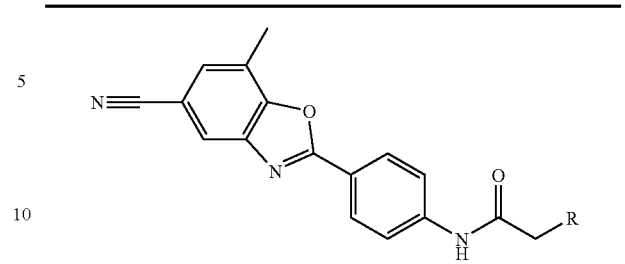
| Ex | R |
|---|---|
| 459 | 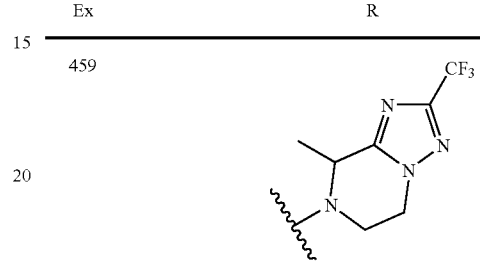 |
| 460 | 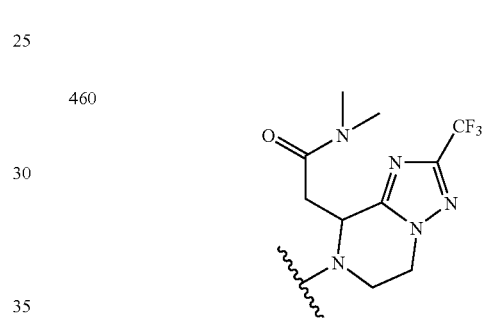 |
| 461 | 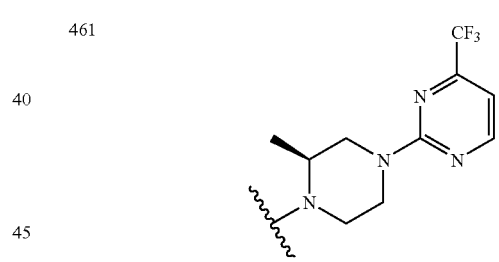 |
| 462 | 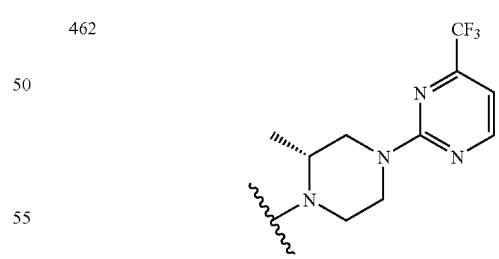 |
| 463 | 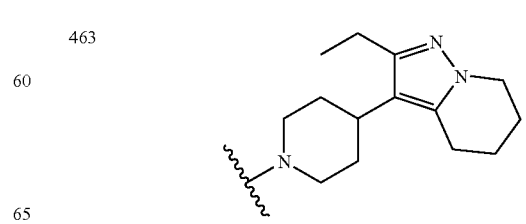 |

TABLE 13-continued

| Ex | R |
|---|---|
| 464 | (spiroindoline-piperidine with N-SO2Me) |
| 465 | (spiro benzothiophene-piperidine) |
| 466 | (4-cyclohexyl-4-CO2Et piperidine · TFA) |
| 467 | (4-cyclohexyl-4-C(O)NH-tBu piperidine · TFA) |
| 468 | (spiroindoline-piperidine with N-acetyl) |
| 469 | (4-phenyl-4-CO2Et piperidine · TFA) |
| 470 | (spiroindoline-piperidine with N-SO2CF3) |

TABLE 14

| Ex | R6 |
|---|---|
| 472 | 4-(trifluoromethyl)benzyl |
| 473 | (4-chlorophenyl)(phenyl)methyl |

TABLE 15

Core structure: 7-R1, 5-R2-benzoxazole linked to phenyl-NH-C(O)-CH2-piperazine-[4-(trifluoromethyl)phenyl]

| Ex | R₁ | R₂ |
|---|---|---|
| 483 | phenyl | CN |
| 484 | isopropenyl (2-methylprop-1-en-1-yl) | CN |
| 485 | pyridin-3-yl | CN |
| 486 | Me | pyridin-3-yl |
| 487 | pyrimidin-5-yl | CN |
| 488 | 3-fluorophenyl | CN |
| 489 | 2-fluorophenyl | CN |

TABLE 16

Core structure: same as Table 15

| EXAMPLE | R₁ | R₂ |
|---|---|---|
| 495 | cyclopropylmethyl | CN |
| 496 | allyl | CN |
| 497 | 3,5-dimethylisoxazol-4-yl | CN |
| 498 | furan-3-yl | CN |
| 499 | 3-fluoropyridin-4-yl | CN |

TABLE 17

Core structure: 7-isopropyl-5-cyano-benzoxazole-2-yl linked to phenyl-CH2-CH(OH)-CH2-R

| EXAMPLE | R |
|---|---|
| 525 | 4-[4-(trifluoromethyl)phenyl]piperazin-1-yl |

TABLE 17-continued

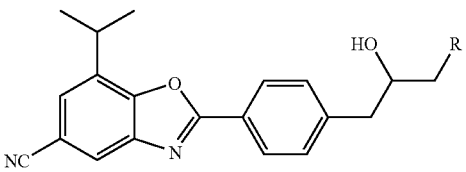

| EXAMPLE | R |
|---|---|
| 526 | 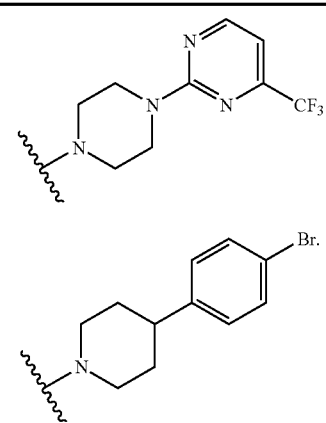 |
| 527 | |

9. A pharmaceutical composition comprising the compound of claim 1, or a pharmaceutically acceptable salt thereof, and a pharmaceutically acceptable carrier.

10. A pharmaceutical composition comprising the compound of claim 1, or a pharmaceutically acceptable salt thereof, a pharmaceutically acceptable carrier, and one or more active ingredients selected from the group consisting of:

(a) PPAR gamma agonists and partial agonists;
(b) biguanides;
(c) protein tyrosine phosphatase-1B (PTP-1B) inhibitors;
(d) dipeptidyl peptidase IV (DP-IV) inhibitors;
(e insulin;
(f) sulfonylureas;
(g) α-glucosidase inhibitors;
(h) one or more compounds selected from the group consisting of (a) HMG-CoA reductase inhibitors; (b) bile acid sequestrants; (c) niacin, nicotinyl alcohol, nicotinamide, and nicotinic acid or a salt thereof; (d) PPARα agonists; (e) cholesterol absorption inhibitors; (f) acyl CoA:cholesterol acyltransferase (ACAT) inhibitors; (g) phenolic anti-oxidants, and (h) a microsomal triglyceride transfer protein (MTP)/ApoB secretion inhibitor;
(i) PPARα/γdual agonists;
(j) PPARδ agonists;
(k) antiobesity compounds
(l) ileal bile acid transporter inhibitors;
(m) anti-inflammatory agents;
(n) glucagon receptor antagonists;
(o) GLP-1,
(p) and GIP-1.

11. A method of treating atherosclerosis or raising HDL in a patient in need of treatment comprising the administration of a therapeutically effective amount of the compound of claim 1 or a pharmaceutically acceptable salt thereof.

12. A method of treating atherosclerosis or raising HDL in a patient in need of treatment comprising the administration of a therapeutically effective amount of the compound of claim 2, or a pharmaceutically acceptable salt thereof.

* * * * *